United States Patent
Marshall et al.

(10) Patent No.: US 10,933,069 B2
(45) Date of Patent: Mar. 2, 2021

(54) COMPOUNDS, COMPOSITIONS, AND METHODS FOR TREATMENT OF DISEASES INVOLVING ACIDIC OR HYPOXIC DISEASED TISSUES

(71) Applicant: Cybrexa 1, Inc., New Haven, CT (US)

(72) Inventors: Daniel Richard Marshall, New Haven, CT (US); Johanna Marie Csengery, New Haven, CT (US); Dalton King, New Haven, CT (US); Robert A. Volkmann, Mystic, CT (US); Yana Reshetnyak, Kingston, RI (US); Oleg Andreev, Kingston, RI (US); Don Engleman, Kingston, RI (US)

(73) Assignee: Cybrexa 1, Inc., New Haven, CT (US)

( * ) Notice: Subject to any disclaimer, the term of this patent is extended or adjusted under 35 U.S.C. 154(b) by 0 days.

(21) Appl. No.: 16/240,438

(22) Filed: Jan. 4, 2019

(65) Prior Publication Data

US 2019/0209580 A1    Jul. 11, 2019

Related U.S. Application Data

(60) Provisional application No. 62/758,264, filed on Nov. 9, 2018, provisional application No. 62/613,931, filed on Jan. 5, 2018.

(51) Int. Cl.

| | | |
|---|---|---|
| *A61K 38/00* | (2006.01) | |
| *A61K 31/55* | (2006.01) | |
| *C07D 403/06* | (2006.01) | |
| *C12N 9/10* | (2006.01) | |
| *C07D 487/16* | (2006.01) | |
| *C07D 295/092* | (2006.01) | |
| *C07D 235/18* | (2006.01) | |
| *C07D 231/56* | (2006.01) | |
| *C07D 401/10* | (2006.01) | |
| *A61K 47/64* | (2017.01) | |
| *C07D 401/06* | (2006.01) | |
| *C07D 403/04* | (2006.01) | |
| *A61P 9/00* | (2006.01) | |
| *A61K 47/54* | (2017.01) | |
| *A61P 25/28* | (2006.01) | |
| *A61P 35/00* | (2006.01) | |
| *A61K 31/4184* | (2006.01) | |
| *A61K 31/454* | (2006.01) | |
| *A61K 31/5025* | (2006.01) | |
| *A61K 31/5375* | (2006.01) | |
| *A61K 45/06* | (2006.01) | |

(52) U.S. Cl.
CPC .......... *A61K 31/55* (2013.01); *A61K 31/4184* (2013.01); *A61K 31/454* (2013.01); *A61K 31/5025* (2013.01); *A61K 31/5375* (2013.01); *A61K 47/549* (2017.08); *A61K 47/64* (2017.08); *A61K 47/6425* (2017.08); *A61P 9/00* (2018.01); *A61P 25/28* (2018.01); *A61P 35/00* (2018.01); *C07D 231/56* (2013.01); *C07D 235/18* (2013.01); *C07D 295/092* (2013.01); *C07D 401/06* (2013.01); *C07D 401/10* (2013.01); *C07D 403/04* (2013.01); *C07D 403/06* (2013.01); *C07D 487/16* (2013.01); *C12N 9/1077* (2013.01); *C12Y 204/0203* (2013.01); *A61K 45/06* (2013.01)

(58) Field of Classification Search
None
See application file for complete search history.

(56) References Cited

U.S. PATENT DOCUMENTS

| | | |
|---|---|---|
| 6,100,283 A | 8/2000 | Griffin et al. |
| 6,310,082 B1 | 10/2001 | Griffin et al. |
| 6,495,541 B1 | 12/2002 | Webber et al. |
| 6,548,494 B1 | 4/2003 | Webber et al. |
| 6,696,437 B1 | 2/2004 | Lubisch et al. |
| 7,151,102 B2 | 12/2006 | Martin et al. |
| 7,196,085 B2 | 3/2007 | Martin et al. |
| 7,449,464 B2 | 11/2008 | Martin et al. |
| 7,692,006 B2 | 4/2010 | Menear |
| 7,781,596 B1 | 8/2010 | Lubisch et al. |
| 8,067,613 B2 | 11/2011 | Gandhi |
| 8,071,623 B2 | 12/2011 | Jones et al. |
| 8,076,451 B2 | 12/2011 | Reshetnyak et al. |
| 8,697,736 B2 | 4/2014 | Penning et al. |
| 8,703,909 B2 | 4/2014 | Reshetnyak et al. |
| 9,289,508 B2 | 3/2016 | Reshetnyak et al. |
| 9,676,823 B2 | 6/2017 | Reshetnyak et al. |
| 9,814,781 B2 | 11/2017 | Reshetnyak et al. |
| 2012/0039990 A1 | 2/2012 | Reshetnyak et al. |
| 2012/0045524 A1 | 2/2012 | Wernet et al. |

(Continued)

FOREIGN PATENT DOCUMENTS

| | | |
|---|---|---|
| CN | 109232719 | 1/2019 |
| WO | WO 2000/042040 | 7/2000 |

(Continued)

OTHER PUBLICATIONS

Weerakkody et al, PNAS, Apr. 9, 2013, 110:15:5834-5839 (Year: 2013).*

Karabadzhak et al, ACS Chem. Biol., 2014, 9:2545-5553 (Year: 2014).*

Adiyala et al, "Development of pyrrolo [2,1-c][1,4] benzodiazepine β-glucoside prodrugs for selective therapy of cancer," Bioorganic Chemistry, 2018, 76, 288-293.

(Continued)

*Primary Examiner* — Satyanarayana R Gudibande
(74) *Attorney, Agent, or Firm* — Fish & Richardson P.C.

(57) ABSTRACT

Compounds for treatment of diseases having acidic or hypoxic diseased tissues and pharmaceutical compositions comprising the compounds, as well as methods for making and using the compounds and compositions.

29 Claims, 6 Drawing Sheets

Specification includes a Sequence Listing.

(56) References Cited

U.S. PATENT DOCUMENTS

| | | | |
|---|---|---|---|
| 2016/0303254 A1 | 10/2016 | Kolakowski et al. | |
| 2017/0267727 A1 | 9/2017 | Thevenin et al. | |
| 2018/0221500 A1 | 8/2018 | Reshetnyak et al. | |

FOREIGN PATENT DOCUMENTS

| | | | | |
|---|---|---|---|---|
| WO | WO2001/41534 | | 6/2001 | |
| WO | WO2003/080047 | | 10/2003 | |
| WO | WO 2004/087713 | | 10/2004 | |
| WO | WO-2004087713 | A1 * | 10/2004 | ............... A61P 9/10 |
| WO | WO 2005/012305 | | 2/2005 | |
| WO | WO 2005/012524 | | 2/2005 | |
| WO | WO 2005/053662 | | 6/2005 | |
| WO | WO 2006/033003 | | 3/2006 | |
| WO | WO 2006/033006 | | 3/2006 | |
| WO | WO 2006/033007 | | 3/2006 | |
| WO | WO-2006033007 | A2 * | 3/2006 | .............. A61P 35/00 |
| WO | WO2006/078816 | | 7/2006 | |
| WO | WO 2008/114114 | | 9/2008 | |
| WO | WO 2011/098971 | | 8/2011 | |
| WO | WO2012/047354 | | 4/2012 | |
| WO | WO2015095755 | | 6/2015 | |
| WO | WO 2015/108986 | | 7/2015 | |
| WO | WO 2016/028689 | | 2/2016 | |
| WO | WO2017/199042 | | 11/2017 | |
| WO | WO2017/210608 | | 12/2017 | |
| WO | WO 2018/227132 | | 12/2018 | |

OTHER PUBLICATIONS

Anderson and Cui, "Protease-Sensitive Nanomaterials for Cancer Therapeutics and Imaging," Ind. Eng. Chem Res., 2017, 56:5761-5777.
Atzrodt et al, "The Renaissance of H/D Exchange,"Angew. Chem. Int. Ed., 2007, 46:7744-7765.
Berge et al, "Pharmaceutical Salts," Journal of Pharamceutical Sciences, Jan. 1977, pp. 1-19.
Caculitan et al, "Cathepsin B is Dispensable for Cellular Processing of Cathepsin B-Cleavable Antibody—Drug Conjugates," Cancer Res. 2017, 77(24), 7027-7037.
Choi et al, "Protease-Activated Drug Development," Theranostics, 2012, 2:2:156-178.
Dahan, "Dipeptidyl Peptidase IV as a Potential Target for Selective Prodrug Activation and Chemotherapeutic Action in Cancers," A., Mol. Pharmaceutics, 2014, 11:4385-4394.
Diez-Torrubia et al, "Application of the Dipeptidyl Peptidase IV (DPPIV/CD26) Based Prodrug Approach to Different Amine-Containing Drugs," A., ChemMedChem 2012, 7:618-628.
Diez-Torrubia et al, "Dipeptidyl Peptidase IV (DPPIV/CD26)-Based Prodrugs of Hydroxy-Containing Drugs," A., J. Med. Chem. 2010, 53:559-572.
Fan et al, "Going Beyond Common Drug Metabolizing Enzymes: Case Studies of Biotransformation Involving Aldehyde Oxidase, g-Glutamyl Transpeptidase, Cathepsin B, Flavin-Containing Monooxygenase, and ADP-Ribosyltransferase," Drug Metabolism and Disposition, 2016, 44:1253-1261.
Garcia-Aparicio, "Design and Discovery of a Novel Dipeptidyl-peptidase IV (CD26)-Based Prodrug Approach," C., J. Med. Chem., 2006, 49:5339-5351.
Grinda et al, "A self-immolative dendritic glucuronide prodrug of doxorubicin," M. Med. Chem. Commun., 2012, 3:68-70.
Herceg et al, Design, synthesis and in vitro evaluation of β-glucuronidase-sensitive prodrug of 5-aminolevulinic acid for photodiagnosis of breast cancer cells Biorganic Chemistry, 2018, 78, 372-380.
Kalafatovic et al, "MMP-9 triggered self-assembly of doxorubicin nanofiber depots halts tumor growth," Biomaterials, 2016, 98:192-202.

Karabadzhak et al, "pHLIP-FIRE, a Cell Insertion-Triggered Fluorescent Probe for Imaging Tumors Demonstrates Targeted Cargo Delivery In Vivo," ACS Chem. Biol., 2014, 9:2545-5553.
Kerekes et al, "Aurora Kinase Inhibitors Based on the Imidazo[1,2-a]pyrazine Core: Fluorine and Deuterium Incorporation Improve Oral Absorption and Exposure," J. Med. Chem. 2011, 54, 201-210.
Kim & Yoo, "Matrix metalloproteinase-inspired suicidal treatments of diabetic ulcers with siRNA-decorated nanofibrous meshes," Gene Therapy, 2013, 20, 378-385.
Kolakowski et al, "The Methylene Alkoxy Carbamate Self-Immolative Unit: Utilization for the Targeted Delivery of Alcohol-Containing Payloads with Antibody—Drug Conjugates," Angew. Chem. Int. Ed., 2016, 55, 7948-7951.
Merrifield, "Solid Phase Peptide Synthesis. I. The Synthesis of a Tetrapeptide," J.A.C.S., 1963, 85:2149-2154.
Nguyen et al, "A Novel Soluble Peptide with pH-Responsive Membrane Insertion," Biochemistry, 2015, 54:6567-6575.
Pacher & Szabo, Role of Poly(ADP-ribose) polymerase 1 (PARP-1) in Cardiovascular Diseases: The Therapeutic Potential of PARP Inhibitors, Cardiovasc Drug Rev. 2007; 25(3): 235-260.
Peturssion et al., "Protecting Groups in Carbohydrate Chemistry," J. Chem. Educ., 1997, 74:11:1297-1303.
Reagan-Shaw et al., "Dose translation from animal to human studies revisited," FASEB J., 2008: 22:3:659-661.
Simplicio, "Prodrugs for Amines," A. L., Molecules, 2008, 13:519-547.
Weerakkody et al, "Family of pH (low) insertion peptides for tumor targeting," PNAS, Apr. 9, 2013, 110:15:5834-5839.
Wickstrom et al, "Melflufen—a peptidase-potentiated alkylating agent in clinical trials," M., Oncotarget, 2017, 8:66641-66655.
Xu et al, "Design, synthesis and biological evaluation of deuterated nintendanib for improving pharamcokinetic properties," J. Label Compd. Radiopharm., 2015, 58:308-312.
Yang et al, "Enzyme-mediated hydrolytic activation of prodrugs," Acta Pharamaceutica Sinica, 2011, 1(3):143-159.
Yao et al, "MMP-Responsive 'Smart' Drug Delivery and Tumor Targeting," Trends in Pharmacological Sciences, Aug. 2018, 39:766-781.
Zhong et al, "Cathepsin B-cleavable doxorubicin prodrugs for targeted cancer therapy (Review)," International Journal of Oncology, 2013, 42:373-383.
Mistry et al, "Clinical Advances of Hypoxia-Activated Prodrugs in Combination With Radiation Therapy," International Journal of Radiation: Oncology Biology Physics, 2017, 98:5:1183-1196.
PCT International Search Report and Written Opinion in International Appln. No. PCT/US2019/012413, dated Mar. 26, 2019, 19 pages.
Moshinikova et al., "Antiproliferative Effect of pHLIP-Amanitin," Biochemistry, Jan. 2013, 52:1171-1178.
PCT International Preliminary Report on Patentability in International Appln. No. PCT/US2019/012413, dated Jul. 16, 2020, 8 pages.
Son et al., "Therapeutic Effect of pHLIPmediated CEACAM6 Gene Silencing in Lung Adenocarcinoma," Scientific Reports, Sep. 2019, 9(1):11607.
Vasquez-Montes et al., "Divalent Cations and Lipid Composition Modulate Membrane Insertion and Cancer-Targeting Action of pHLIP," Journal of Molecular Biology, 2019, 45 pages.
Wyatt et al., "Peptides of pHLIP family for targeted intracellular and extracellular delivery of cargo molecules to tumors," Proceedings of the National Academy of Sciences, Mar. 2018, 115(12):E2811-E2818.
Aiello et al., "Abstract #63: Development of tumor-targeted PARP inhibitors for the treatment of solid cancers," Poster, Presented at Proceedings of the 30th EORTC-NCI-AACR Symposium, Dublin, Ireland, Nov. 13, 2018, 1 page.
"Cheng et al., ""MicroRNA silencing for cancer therapy targeted to the tumor microenvironment,"" Nature, 2015, 518:107-110".

* cited by examiner

SEQUENCE LISTING

```
<160> NUMBER OF SEQ ID NOS: 311

<210> SEQ ID NO 1
<211> LENGTH: 28
<212> TYPE: PRT
<213> ORGANISM: Artificial Sequence
<220> FEATURE:
<223> OTHER INFORMATION: synthetic peptide

<400> SEQUENCE: 1

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Cys Gly
            20                  25

<210> SEQ ID NO 2
<211> LENGTH: 35
<212> TYPE: PRT
<213> ORGANISM: Artificial Sequence
<220> FEATURE:
<223> OTHER INFORMATION: synthetic peptide

<400> SEQUENCE: 2

Ala Glu Gln Asn Pro Ile Tyr Trp Ala Arg Tyr Ala Asp Trp Leu Phe
```

```
1               5                   10                  15
Thr Thr Pro Leu Leu Leu Asp Leu Ala Leu Leu Val Asp Ala Asp
            20                  25                  30

Glu Cys Gly
        35

<210> SEQ ID NO 3
<211> LENGTH: 32
<212> TYPE: PRT
<213> ORGANISM: Artificial Sequence
<220> FEATURE:
<223> OTHER INFORMATION: synthetic peptide

<400> SEQUENCE: 3

Ala Asp Asp Gln Asn Pro Trp Arg Ala Tyr Leu Asp Leu Leu Phe Pro
1               5                   10                  15

Thr Asp Thr Leu Leu Asp Leu Leu Trp Asp Ala Asp Glu Cys Gly
            20                  25                  30

<210> SEQ ID NO 4
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: acetylated

<400> SEQUENCE: 4

Ala Ala Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Lys Cys Gly
        35

<210> SEQ ID NO 5
<211> LENGTH: 37
<212> TYPE: PRT
<213> ORGANISM: Artificial Sequence
<220> FEATURE:
<223> OTHER INFORMATION: synthetic peptide

<400> SEQUENCE: 5

Ala Ala Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys
        35

<210> SEQ ID NO 6
<211> LENGTH: 39
<212> TYPE: PRT
<213> ORGANISM: Unknown
<220> FEATURE:
<223> OTHER INFORMATION: Description of Unknown: pH-sensitive membrane
      polypeptide

<400> SEQUENCE: 6

Ala Ala Glu Gln Asn Pro Ile Tyr Trp Trp Ala Arg Tyr Ala Asp Trp
1               5                   10                  15
```

```
Leu Phe Thr Thr Pro Leu Leu Leu Asp Leu Ala Leu Leu Val Asp
                20                  25                  30

Ala Asp Glu Gly Thr Cys Gly
            35

<210> SEQ ID NO 7
<211> LENGTH: 35
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 7

Ala Glu Gln Asn Pro Ile Tyr Trp Ala Arg Tyr Ala Asp Trp Leu Phe
1               5                   10                  15

Thr Thr Pro Leu Leu Leu Asp Leu Ala Leu Leu Val Asp Ala Asp
            20                  25                  30

Glu Gly Thr
        35

<210> SEQ ID NO 8
<211> LENGTH: 36
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 8

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr
        35

<210> SEQ ID NO 9
<211> LENGTH: 35
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 9

Ala Glu Gln Asn Pro Ile Tyr Trp Ala Arg Tyr Ala Asp Trp Leu Phe
1               5                   10                  15

Thr Thr Pro Leu Leu Leu Asp Leu Ala Leu Leu Val Asp Ala Asp
            20                  25                  30

Glu Gly Thr
        35

<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Ala Glu Gln Asn Pro Ile Tyr Trp Ala Arg Tyr Ala Asp Trp Leu
```

```
                1               5                  10                  15
Phe Thr Thr Pro Leu Leu Leu Leu Asp Leu Ala Leu Leu Val Asp Ala
                    20                  25                  30

Asp Glu Gly Thr Cys Gly
            35

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                    20                  25                  30

Asp Glu Gly Thr Cys Gly
            35

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                    20                  25                  30

Asp Glu Gly Thr Gly
            35

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                    20                  25                  30

Asp Glu Gly Thr
            35

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr
            35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Lys Cys Gly
            35

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Cys Thr
            35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
                20                  25                  30

Asp Glu Gly Thr Gly
            35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

-continued

```
Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
            20                  25                  30

Asp Glu Gly Thr Gly
        35

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
            20                  25                  30

Asp Glu Gly Thr
        35

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 22

Ala Ala Glu Gln Asn Pro Ile Tyr Trp Ala Arg Tyr Ala Asp Trp Leu
1               5                   10                  15

Phe Thr Thr Ala Leu Leu Leu Asp Leu Ala Leu Leu Val Asp Ala
            20                  25                  30

Asp Glu Gly Thr
        35

<210> SEQ ID NO 23
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Ala Glu Gln Asn Pro Ile Tyr Trp Ala Arg Tyr Ala Asp Trp Leu
1               5                   10                  15

Phe Thr Thr Pro Leu Leu Leu Glu Leu Ala Leu Leu Val Asp Ala
            20                  25                  30

Asp Glu Gly Thr
        35

<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Ala Glu Gln Asn Pro Ile Tyr Trp Ala Arg Tyr Ala Glu Trp Leu
1               5                   10                  15

Phe Thr Thr Pro Leu Leu Leu Asp Leu Ala Leu Leu Val Asp Ala
            20                  25                  30

Asp Glu Gly Thr
        35

<210> SEQ ID NO 25
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Ala Glu Gln Asn Pro Ile Ile Tyr Trp Ala Arg Tyr Ala Asp Trp
1               5                   10                  15

Leu Phe Thr Asp Leu Pro Leu Leu Leu Asp Leu Leu Ala Leu Leu
            20                  25                  30

Val Asp Ala Asp Glu Gly Thr
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 26

Gly Glu Gln Asn Pro Ile Tyr Trp Ala Gln Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr Cys Gly
        35

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
        35

<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 30
<211> LENGTH: 38
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 30

Gly Gly Glu Gln Asn Pro Ile Tyr Trp Ala Arg Tyr Ala Trp Asp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Ala Glu Gln Asn Pro Ile Tyr Trp Ala Arg Tyr Ala Asp Trp Leu
1               5                   10                  15

Phe Thr Thr Gly Leu Leu Leu Leu Asp Leu Ala Leu Leu Val Asp Ala
            20                  25                  30

Asp Glu Gly Thr
        35

<210> SEQ ID NO 32
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Gly Cys Thr
        35

<210> SEQ ID NO 34
<211> LENGTH: 37
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 34

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 35
<211> LENGTH: 37
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 36

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 37
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 37

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 38
<211> LENGTH: 34
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 38

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Lys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp Cys Gly
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu Cys Gly
```

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Lys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 45
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Thr Glu Asp Ala Asp Val Leu Leu Ala Leu Asp Leu Leu Leu Leu Pro
1               5                   10                  15

Thr Thr Phe Leu Trp Asp Ala Tyr Arg Ala Trp Tyr Pro Asn Gln Glu
            20                  25                  30

Cys Ala

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Glu Gln Asn Pro Ile Tyr Trp Ala Arg Tyr Ala Asp Trp Leu Phe
1               5                   10                  15

Thr Thr Pro Cys Leu
            20

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Cys Glu Gln Asn Pro Ile Tyr Trp Ala Arg Tyr Ala Asp Trp Leu
1               5                   10                  15

Phe Thr Thr Pro Leu
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Glu Gln Asn Pro Ile Tyr Phe Ala Arg Tyr Ala Asp Trp Leu Phe
1               5                   10                  15

Thr Thr Pro Leu
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Glu Asp Gln Asn Pro Trp Ala Arg Tyr Ala Asp Leu Leu Phe Pro
1               5                   10                  15

Thr Thr Leu Ala Trp
            20

```
<210> SEQ ID NO 52
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Cys Glu Asp Gln Asn Pro Trp Ala Arg Tyr Ala Asp Leu Leu Phe
1               5                   10                  15

Pro Thr Thr Leu Ala Trp
            20

<210> SEQ ID NO 53
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 54
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ala Cys Glu Glu Gln Asn Pro Trp Ala Arg Tyr Ala Glu Leu Leu Phe
1               5                   10                  15

Pro Thr Thr Leu Ala Trp
            20

<210> SEQ ID NO 55
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Cys Glu Glu Gln Asn Pro Trp Ala Arg Tyr Ala Glu Trp Leu Phe
1               5                   10                  15

Pro Thr Thr Leu Leu Leu Leu Glu
            20

<210> SEQ ID NO 56
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Cys Glu Glu Gln Asn Pro Trp Ala Arg Tyr Leu Glu Trp Leu Phe
```

```
                1               5                   10                  15
Pro Thr Glu Thr Leu Leu Leu Glu Leu
                20                  25

<210> SEQ ID NO 57
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr
            35

<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Thr
            35

<210> SEQ ID NO 59
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 60
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ala Glu Gln Asn Pro Ile Tyr Trp Ala Arg Tyr Ala Asp Trp Leu Phe
1               5                   10                  15
```

Thr Thr Pro Leu Leu Leu Leu Asp Leu Ala Leu Leu Val Asp Ala Asp
            20                  25                  30

Glu Gly Cys Thr
        35

<210> SEQ ID NO 61
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 62
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 63
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 64
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Lys Glu Gln Asn Pro Ile Tyr Trp Ala Arg Tyr Ala Asp Trp Leu
1               5                   10                  15

```
Phe Thr Thr Pro Leu Leu Leu Leu Asp Leu Ala Leu Leu Val Asp Ala
            20                  25                  30

Asp Glu Cys Thr
            35

<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ala Ala Glu Gln Asn Pro Ile Tyr Trp Ala Arg Tyr Ala Asp Trp Leu
1               5                   10                  15

Phe Thr Thr Ala Leu Leu Leu Asp Leu Ala Leu Leu Val Asp Ala
            20                  25                  30

Asp Glu Gly Thr
            35

<210> SEQ ID NO 66
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Cys Ala Glu Gln Asn Pro Ile Tyr Trp Ala Arg Tyr Ala Asp Trp
1               5                   10                  15

Leu Phe Thr Thr Gly Leu Leu Leu Asp Leu Ala Leu Leu Val Asp
            20                  25                  30

Ala Asp Glu Gly Thr
            35

<210> SEQ ID NO 67
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 68
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Glu Gln Asn Pro Ile Tyr Phe Ala Arg Tyr Ala Asp Trp Leu Phe
1               5                   10                  15
```

Thr Thr Pro Leu Leu Leu Asp Leu Ala Leu Leu Val Asp Ala Asp
            20                  25                  30

Glu Gly Thr
        35

<210> SEQ ID NO 69
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Glu Gln Asn Pro Ile Tyr Phe Ala Arg Tyr Ala Asp Phe Leu Phe
1               5                   10                  15

Thr Thr Pro Leu Leu Leu Asp Leu Ala Leu Leu Trp Asp Ala Asp
            20                  25                  30

Glu Thr

<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Lys Glu Asp Gln Asn Pro Tyr Trp Ala Arg Tyr Ala Asp Trp Leu
1               5                   10                  15

Phe Thr Thr Pro Leu Leu Leu Asp Leu Ala Leu Leu Val Asp Gly
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Ala Cys Glu Asp Gln Asn Pro Tyr Trp Ala Arg Tyr Ala Asp Trp Leu
1               5                   10                  15

Phe Thr Thr Pro Leu Leu Leu Asp Leu Ala Leu Leu Val Asp Gly
            20                  25                  30

<210> SEQ ID NO 72
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Glu Asp Gln Asn Pro Tyr Trp Ala Arg Tyr Ala Asp Trp Leu Phe
1               5                   10                  15

Thr Thr Pro Leu Leu Leu Asp Leu Ala Leu Leu Val Asp Gly
            20                  25                  30

<210> SEQ ID NO 73

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu Cys Gly
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Ala Lys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ala Lys Glu Asp Gln Asn Asp Pro Tyr Trp Ala Arg Tyr Ala Asp Trp
1               5                   10                  15

Leu Phe Thr Thr Pro Leu Leu Leu Leu Asp Leu Ala Leu Leu Val Gly
            20                  25                  30

<210> SEQ ID NO 77
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Thr Glu Asp Ala Asp Val Leu Leu Ala Leu Asp Leu Leu Leu Leu Pro
1               5                   10                  15
```

Thr Thr Phe Leu Trp Asp Ala Tyr Arg Ala Trp Tyr Pro Asn Gln Glu
            20                  25                  30

Cys Ala

<210> SEQ ID NO 78
<211> LENGTH: 36
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 78

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Glu Gln Asn Pro Ile Tyr Trp Ala Arg Tyr Ala Asp Trp Leu Phe
1               5                   10                  15

Thr Thr Pro Cys Leu
            20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Cys Glu Gln Asn Pro Ile Tyr Trp Ala Arg Tyr Ala Asp Trp Leu
1               5                   10                  15

Phe Thr Thr Pro Leu
            20

<210> SEQ ID NO 82

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Cys Glu Gln Asn Pro Ile Tyr Phe Ala Arg Tyr Ala Asp Trp Leu
1               5                   10                  15

Phe Thr Thr Pro Leu
            20

<210> SEQ ID NO 83
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25

<210> SEQ ID NO 84
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Cys Glu Glu Gln Asn Pro Trp Arg Ala Tyr Leu Glu Leu Leu Phe
1               5                   10                  15

Pro Thr Glu Thr Leu Leu Leu Glu Leu Leu Trp
            20                  25

<210> SEQ ID NO 85
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25

<210> SEQ ID NO 86
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Asp Asn Asn Asn Pro Trp Arg Ala Tyr Leu Asp Leu Leu Phe Pro
1               5                   10                  15
```

Thr Asp Thr Leu Leu Leu Asp Trp
            20

<210> SEQ ID NO 87
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Cys Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 88
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 89
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Cys Glu Glu Gln Asn Pro Trp Ala Arg Tyr Ala Glu Trp Leu Phe
1               5                   10                  15

Pro Thr Thr Leu Leu Leu Leu Glu
            20

<210> SEQ ID NO 90
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Cys Glu Asp Gln Asn Pro Trp Ala Arg Tyr Ala Asp Leu Leu Phe
1               5                   10                  15

Pro Thr Thr Leu Ala Trp
            20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Ala Cys Glu Asp Gln Asn Pro Trp Ala Arg Tyr Ala Glu Leu Leu Phe
1               5                   10                  15

Pro Thr Thr Leu Trp
            20

<210> SEQ ID NO 92
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Glu Asp Gln Asn Pro Trp Ala Arg Tyr Ala Asp Leu Leu Phe Pro
1               5                   10                  15

Thr Thr Leu Trp
            20

<210> SEQ ID NO 93
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 94
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

<210> SEQ ID NO 95
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Asp Asp Glu Asp Asn Pro Ile Tyr Trp Ala Arg Tyr Ala His Trp

```
                1               5                   10                  15
Leu Phe Thr Thr Pro Leu Leu Leu His Gly Ala Leu Leu Val Asn
                20                  25                  30

Ala Asp Glu Cys Thr
        35

<210> SEQ ID NO 96
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
                20                  25                  30

Ala Asn Glu Cys Thr
        35

<210> SEQ ID NO 97
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Asp Asp Glu Asp Asn Pro Ile Tyr Trp Ala Arg Tyr Ala Asp Trp
1               5                   10                  15

Leu Phe Thr Thr Pro Leu Leu Leu His Gly Ala Leu Leu Val Asp
                20                  25                  30

Ala Asp Glu Cys Thr
        35

<210> SEQ ID NO 98
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ala Cys Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
                20                  25                  30

Asp Glu Gly Thr Gly
        35

<210> SEQ ID NO 99
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99
```

```
Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Thr
        35

<210> SEQ ID NO 100
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 101
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 102
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
        35

<210> SEQ ID NO 103
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103
```

Gly Gly Glu Gln Asn Pro Ile Tyr Trp Ala Arg Tyr Ala Trp Asp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 104
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ala Ala Glu Gln Asn Pro Ile Tyr Trp Ala Arg Tyr Ala Glu Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 105
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Ala Glu Gln Asn Pro Ile Tyr Trp Ala Arg Tyr Ala Glu Trp Leu
1               5                   10                  15

Phe Thr Thr Pro Leu Leu Leu Leu Glu Leu Ala Leu Leu Val Asp Ala
                20                  25                  30

Asp Glu Gly Thr Cys Gly
            35

<210> SEQ ID NO 106
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 107
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 108
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 109
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 110
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
                20                  25                  30

Asp Glu Gly Thr Gly
            35

<210> SEQ ID NO 111
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 111

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 112
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 113
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 114
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 115
<211> LENGTH: 37
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 115

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

<210> SEQ ID NO 116
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 117
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr Cys Gly
        35

<210> SEQ ID NO 118
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ala Ala Glu Gln Asn Pro Ile Tyr Trp Ala Arg Tyr Ala Glu Trp Leu
1               5                   10                  15

Phe Thr Thr Pro Leu Leu Leu Leu Glu Leu Ala Leu Leu Val Asp Ala
            20                  25                  30

Asp Glu Gly Thr Cys Gly
        35

<210> SEQ ID NO 119
<211> LENGTH: 39
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 119

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr Lys Cys Gly
        35

<210> SEQ ID NO 120
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 120

Gly Gly Glu Gln Asn Pro Ile Tyr Trp Ala Gln Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 121
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 121

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 122
<211> LENGTH: 38
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 122

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 123
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 123

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
            35

<210> SEQ ID NO 124
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
            35

<210> SEQ ID NO 125
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
            35

<210> SEQ ID NO 126
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
            20                  25                  30

Asp Glu Gly Thr Gly
            35

<210> SEQ ID NO 127
<211> LENGTH: 38
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 127

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 128
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 129
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gly Gly Glu Gln Asn Pro Ile Tyr Trp Ala Gln Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 130
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 131
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ala Ala Glu Gln Asn Pro Ile Tyr Trp Ala Arg Tyr Ala Asp Trp Leu
1               5                   10                  15

Phe Thr Asp Leu Pro Leu Leu Leu Asp Leu Leu Ala Leu Leu Val
            20                  25                  30

Asp Ala Asp Glu Gly Thr
        35

<210> SEQ ID NO 132
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
        35

<210> SEQ ID NO 133
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
            20                  25                  30

Asp Glu Gly Thr Cys Gly
        35

<210> SEQ ID NO 134
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Ala Ala Glu Gln Asn Pro Ile Tyr Trp Ala Arg Tyr Ala Asp Trp Leu
1               5                   10                  15

Phe Thr Thr Gly Leu Leu Leu Leu Asp Leu Ala Leu Leu Val Asp Ala
            20                  25                  30

Asp Glu Gly Thr
        35

<210> SEQ ID NO 135
```

<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 136
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 137
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gly Gly Glu Gln Asn Pro Ile Tyr Trp Ala Gln Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 138
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

```
<210> SEQ ID NO 139
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
                20                  25                  30

Asp Glu Gly Thr Cys Gly
            35

<210> SEQ ID NO 140
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 140

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Lys Cys Gly
            35

<210> SEQ ID NO 141
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 141

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
                20                  25                  30

Asp Glu Gly Thr Lys Cys Gly
            35

<210> SEQ ID NO 142
<211> LENGTH: 38
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Cys(phalloidin)

<400> SEQUENCE: 142

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
            35

<210> SEQ ID NO 143
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Cys(phalloidin)

<400> SEQUENCE: 143

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
            35

<210> SEQ ID NO 144
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
            35

<210> SEQ ID NO 145
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
```

```
                20                  25                  30

Asp Glu Thr
        35

<210> SEQ ID NO 146
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 147
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 148
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 149
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Asp Asp Glu Asp Asn Pro Ile Tyr Trp Ala Arg Tyr Ala His Trp
1               5                   10                  15
```

```
Leu Phe Thr Thr Pro Leu Leu Leu Leu His Gly Ala Leu Leu Val Asn
            20                  25                  30

Ala Asp Glu Cys Thr
        35

<210> SEQ ID NO 150
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 151
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 152
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Cys(phalloidin)

<400> SEQUENCE: 152

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 153
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 153
```

Ala Ala Glu Gln Asn Pro Ile Tyr Trp Ala Arg Tyr Ala Asp Trp Leu
1               5                   10                  15

Phe Thr Thr Pro Leu Leu Leu Glu Leu Ala Leu Leu Val Asp Ala
            20                  25                  30

Asp Glu Gly Thr Lys Cys Gly
        35

```
<210> SEQ ID NO 154
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 154
```

Ala Ala Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Lys Cys Gly
        35

```
<210> SEQ ID NO 155
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155
```

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asp
            20                  25                  30

Ala Asp Glu Cys Thr
        35

```
<210> SEQ ID NO 156
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156
```

Asp Asp Asp Glu Asp Asn Pro Ile Tyr Trp Ala Arg Tyr Ala His Trp

```
                1               5                   10                  15
Leu Phe Thr Thr Pro Leu Leu Leu Leu Asp Gly Ala Leu Leu Val Asp
                20                  25                  30

Ala Asp Glu Cys Thr
            35

<210> SEQ ID NO 157
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
                20                  25                  30

Ala Asp Glu Cys Thr
            35

<210> SEQ ID NO 158
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
                20                  25                  30

Ala Asn Glu Cys Thr
            35

<210> SEQ ID NO 159
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
                20                  25                  30

Ala Asp Glu Cys Thr
            35

<210> SEQ ID NO 160
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160
```

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 161
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

<210> SEQ ID NO 162
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 163
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 164
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30

Ala Asn Glu Cys Thr
        35

<210> SEQ ID NO 165
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30

Ala Asn Glu Cys Thr
        35

<210> SEQ ID NO 166
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30

Ala Asp Glu Cys Thr
        35

<210> SEQ ID NO 167
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Asp Asp Glu Asp Asn Pro Ile Tyr Trp Ala Arg Tyr Ala Asp Trp
1               5                   10                  15

Leu Phe Thr Thr Pro Leu Leu Leu His Gly Ala Leu Leu Val Asp
            20                  25                  30

Ala Asp Glu Cys Thr
        35

<210> SEQ ID NO 168
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
            35

<210> SEQ ID NO 169
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
            35

<210> SEQ ID NO 170
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 171
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
            35

<210> SEQ ID NO 172
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 172

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 173
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 174
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

<210> SEQ ID NO 175
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 176
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

Asp Asp Asp Glu Asp Asn Pro Ile Tyr Trp Ala Arg Tyr Ala His Trp
1               5                   10                  15

Leu Phe Thr Thr Pro Leu Leu Leu Leu Asp Gly Ala Leu Leu Val Asp
            20                  25                  30

Ala Asp Glu Cys Thr
        35

<210> SEQ ID NO 177
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 178
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 179
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 180
<211> LENGTH: 37
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 180

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30

Ala Asn Glu Cys Thr
        35

<210> SEQ ID NO 181
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Ala Ala Glu Gln Asn Pro Ile Tyr Trp Ala Arg Tyr Ala Asp Trp Leu
1               5                   10                  15

Phe Thr Thr Gly Leu Leu Leu Asp Leu Ala Leu Leu Val Asp Ala
            20                  25                  30

Asp Glu Gly Thr
        35

<210> SEQ ID NO 182
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Gly Glu Gln Asn Pro Ile Tyr Trp Ala Arg Tyr Ala Trp Asp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 183
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gly Gly Glu Gln Asn Pro Ile Tyr Trp Ala Arg Tyr Asp Ala Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 184
<211> LENGTH: 38
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 184

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 185
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 186
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 187
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gly Gly Glu Gln Asn Pro Ile Tyr Trp Ala Arg Tyr Ala Asp Trp Leu
1               5                   10                  15

Phe Thr Thr Pro Leu Leu Leu Leu Leu Asp Ala Leu Leu Val Asp Ala
            20                  25                  30

Asp Glu Gly Thr Cys Gly
        35

<210> SEQ ID NO 188
<211> LENGTH: 38
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 188

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
            35

<210> SEQ ID NO 189
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
            35

<210> SEQ ID NO 190
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
            35

<210> SEQ ID NO 191
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gly Gly Glu Gln Asn Pro Ile Tyr Trp Ala Gln Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
            35

<210> SEQ ID NO 192
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 193
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 194
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 195
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 196
```

```
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gly Gly Glu Gln Asn Pro Ile Tyr Trp Ala Gln Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 197
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 198
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gly Gly Glu Gln Asn Pro Ile Tyr Trp Ala Gln Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 199
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35
```

-continued

```
<210> SEQ ID NO 200
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Gly Gly Glu Gln Asn Pro Ile Tyr Trp Ala Gln Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 201
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 202
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
                20                  25                  30

Asp Glu Gly Thr Lys Cys Gly
            35

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(rhodamine)
<220> FEATURE:
<221> NAME/KEY: MOD_RES
<222> LOCATION: (5)..(5)
<223> OTHER INFORMATION: Cys(phalloidin)

<400> SEQUENCE: 203

Glu Gly Thr Lys Cys Gly
```

<210> SEQ ID NO 204
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 204

Ala Ala Glu Gln Asn Pro Ile Tyr Trp Ala Arg Tyr Ala Asp Trp Leu
1               5                   10                  15
Phe Thr Thr Pro Leu Leu Leu Leu Asp Leu Ala Leu Leu Val Asp Ala
            20                  25                  30
Asp Glu Gly Thr Lys Cys Gly
        35

<210> SEQ ID NO 205
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Ala Cys Glu Gln Asn Pro Ile Tyr Trp Ala Arg Tyr Ala Asp Trp Leu
1               5                   10                  15
Phe Thr Thr Pro Leu Leu Leu Leu Asp Leu Ala Leu Leu Val Asp Ala
            20                  25                  30
Asp Glu Gly Thr Gly
        35

<210> SEQ ID NO 206
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Cys(phalloidin)

<400> SEQUENCE: 206

Ala Ala Glu Gln Asn Pro Ile Tyr Trp Ala Arg Tyr Ala Asp Trp Leu
1               5                   10                  15
Phe Thr Thr Pro Leu Leu Leu Leu Asp Leu Ala Leu Leu Val Asp Ala
            20                  25                  30
Asp Glu Gly Thr Cys Gly
        35

<210> SEQ ID NO 207
<211> LENGTH: 39
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 207

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 208
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 208

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr Lys Cys Gly
        35

<210> SEQ ID NO 209
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Ala Ala Glu Gln Asn Pro Ile Tyr Trp Ala Arg Tyr Ala Asp Trp Leu
1               5                   10                  15

Phe Thr Asp Leu Pro Leu Leu Leu Asp Leu Leu Ala Leu Leu Val
            20                  25                  30

Asp Ala Asp Glu Gly Thr
        35

<210> SEQ ID NO 210
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 210

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
            35

<210> SEQ ID NO 211
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gly Gly Glu Gln Asn Pro Ile Tyr Trp Ala Gln Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
            35

<210> SEQ ID NO 212
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gly Gly Glu Gln Asn Pro Ile Tyr Trp Ala Gln Asp Tyr Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
            35

<210> SEQ ID NO 213
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
            35

<210> SEQ ID NO 214
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 214

Ala Ala Glu Gln Asn Pro Ile Tyr Trp Ala Arg Tyr Ala Glu Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 215
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Ala Ala Glu Gln Asn Pro Ile Tyr Trp Ala Arg Tyr Ala Glu Trp Leu
1               5                   10                  15

Phe Thr Thr Pro Leu Leu Leu Leu Glu Leu Ala Leu Leu Val Asp Ala
            20                  25                  30

Asp Glu Gly Thr Cys Gly
        35

<210> SEQ ID NO 216
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
            20                  25                  30

Asp Glu Gly Thr Cys Gly
        35

<210> SEQ ID NO 217
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr Cys Gly
        35

<210> SEQ ID NO 218
<211> LENGTH: 38
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 218

Ala Ala Glu Gln Asn Pro Ile Tyr Trp Ala Arg Tyr Ala Glu Trp Leu
1               5                   10                  15

Phe Thr Thr Pro Leu Leu Leu Leu Glu Leu Ala Leu Leu Val Asp Ala
            20                  25                  30

Asp Glu Gly Thr Cys Gly
        35

<210> SEQ ID NO 219
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (37)..(37)
<223> OTHER INFORMATION: Lys(rhodamine)
<220> FEATURE:
<221> NAME/KEY: MOD_RES
<222> LOCATION: (38)..(38)
<223> OTHER INFORMATION: Cys(phalloidin)

<400> SEQUENCE: 219

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr Lys Cys Gly
        35

<210> SEQ ID NO 220
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
            20                  25                  30

Asp Glu Gly Thr Gly
        35

<210> SEQ ID NO 221
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30

Asp Glu Gly Thr Gly
        35

<210> SEQ ID NO 222
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Ala Ala Glu Gln Asn Pro Ile Tyr Trp Ala Arg Tyr Ala Asp Trp Leu
1               5                   10                  15

Phe Thr Thr Ala Leu Leu Leu Leu Asp Leu Ala Leu Leu Val Asp Ala
            20                  25                  30

Asp Glu Gly Thr
        35

<210> SEQ ID NO 223
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 224
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 225
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Glu Gln Asn Pro Ile Tyr Trp Ala Arg Tyr Ala Asp Leu Leu Phe
1               5                   10                  15

Pro Thr Thr Leu Ala Trp
            20

<210> SEQ ID NO 226
<211> LENGTH: 35
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 226

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Thr
        35

<210> SEQ ID NO 227
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 228
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 229
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 230
<211> LENGTH: 36
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 230

Ala Lys Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Cys Thr
            35

<210> SEQ ID NO 231
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 231
cctcttacct cagttaca                                                       18

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 232
cctcttacct cagttaca                                                       18

<210> SEQ ID NO 233
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 233
cctcttacct cagttaca                                                       18

<210> SEQ ID NO 234
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid
```

-continued

<400> SEQUENCE: 234
cctcttacct cagttaca                                                         18

<210> SEQ ID NO 235
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 235
cctctgacct catttaca                                                         18

<210> SEQ ID NO 236
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 236
cctcttacct cagttaca                                                         18

<210> SEQ ID NO 237
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 237
cctctgacct catttaca                                                         18

<210> SEQ ID NO 238
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Peptide nucleic acid

<400> SEQUENCE: 238
cctcttacct cagttaca                                                         18

<210> SEQ ID NO 239
<211> LENGTH: 38
<212> TYPE: PRT
<213> ORGANISM: Unknown
<220> FEATURE:

<223> OTHER INFORMATION: Description of Unknown: pH-sensitive membrane
      polypeptide

<400> SEQUENCE: 239

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Cys Gly
            35

<210> SEQ ID NO 240
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Ala Glu Asp Gln Asn Pro Tyr Trp Ala Arg Tyr Asp Trp Leu Phe Thr
1               5                   10                  15

Thr Pro Leu Leu Leu Leu Asp Leu Ala Leu Leu Val Asp Cys Gly
                20                  25                  30

<210> SEQ ID NO 241
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu Cys Gly
                20                  25                  30

<210> SEQ ID NO 242
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
                20                  25                  30

Glu Gly Cys Thr
        35

<210> SEQ ID NO 243
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Thr
        35

<210> SEQ ID NO 244
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 245
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp Gly
            20                  25                  30

<210> SEQ ID NO 246
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Ala Glu Asp Gln Asn Asp Pro Tyr Trp Ala Arg Tyr Ala Asp Trp Leu
1               5                   10                  15

Phe Thr Thr Pro Leu Leu Leu Leu Asp Leu Ala Leu Leu Val Gly
            20                  25                  30

<210> SEQ ID NO 247
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

```
<210> SEQ ID NO 248
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248
```

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Thr

```
<210> SEQ ID NO 249
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249
```

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

```
<210> SEQ ID NO 250
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250
```

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Cys Thr
        35

```
<210> SEQ ID NO 251
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251
```

Ala Glu Asp Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Cys
            20                  25                  30

Gly Thr

<210> SEQ ID NO 252
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Ala Glu Asp Gln Asn Asp Pro Ile Tyr Trp Ala Arg Tyr Ala Asp Trp
1               5                   10                  15

Leu Phe Thr Thr Pro Leu Leu Leu Glu Leu Ala Leu Leu Val Glu
                20                  25                  30

Cys Gly Thr
        35

<210> SEQ ID NO 253
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ala Cys Glu Glu Gln Asn Pro Trp Ala Arg Tyr Leu Glu Trp Leu Phe
1               5                   10                  15

Pro Thr Glu Thr Leu Leu Leu Glu Leu
                20                  25

<210> SEQ ID NO 254
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
                20                  25                  30

Glu Gly Thr
        35

<210> SEQ ID NO 255
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Ala Lys Glu Asp Gln Asn Pro Tyr Trp Ala Arg Tyr Ala Asp Trp Leu
1               5                   10                  15

Phe Thr Thr Pro Leu Leu Leu Asp Leu Ala Leu Leu Val Asp Gly
                20                  25                  30

<210> SEQ ID NO 256
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 256

Ala Lys Glu Asp Gln Asn Asp Pro Tyr Trp Ala Arg Tyr Ala Asp Trp
1               5                   10                  15

Leu Phe Thr Thr Pro Leu Leu Leu Leu Asp Leu Ala Leu Leu Val Gly
                20                  25                  30

<210> SEQ ID NO 257
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
                20                  25                  30

Glu Gly Cys
        35

<210> SEQ ID NO 258
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp Cys
                20                  25                  30

<210> SEQ ID NO 259
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu Cys
                20                  25                  30

<210> SEQ ID NO 260
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Ala Cys Glu Gln Asn Pro Ile Tyr Trp Ala Arg Tyr Ala Asp Trp Leu
```

```
                1               5                  10                  15
Phe Thr Thr Pro Leu Leu Leu Leu Asp Leu Ala Leu Leu Val Asp Ala
                20                  25                  30
Asp Glu Gly Thr
        35

<210> SEQ ID NO 261
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Ala Cys Glu Asp Gln Asn Pro Tyr Trp Ala Arg Tyr Ala Asp Trp Leu
1               5                  10                  15
Phe Thr Thr Pro Leu Leu Leu Leu Asp Leu Ala Leu Leu Val Asp Gly
                20                  25                  30

<210> SEQ ID NO 262
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Ala Cys Glu Asp Gln Asn Pro Tyr Trp Arg Ala Tyr Ala Asp Leu Phe
1               5                  10                  15
Thr Pro Leu Thr Leu Leu Asp Leu Leu Ala Leu Trp Asp Gly
                20                  25                  30

<210> SEQ ID NO 263
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ala Cys Asp Asp Gln Asn Pro Trp Arg Ala Tyr Leu Asp Leu Leu Phe
1               5                  10                  15
Pro Thr Asp Thr Leu Leu Leu Asp Leu Leu Trp
                20                  25

<210> SEQ ID NO 264
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ala Cys Glu Glu Gln Asn Pro Trp Arg Ala Tyr Leu Glu Leu Leu Phe
1               5                  10                  15
Pro Thr Glu Thr Leu Leu Leu Glu Leu Leu Trp
                20                  25

<210> SEQ ID NO 265
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25

<210> SEQ ID NO 266
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Cys Asp Asn Asn Asn Pro Trp Arg Ala Tyr Leu Asp Leu Leu Phe Pro
1               5                   10                  15

Thr Asp Thr Leu Leu Leu Asp Trp
            20

<210> SEQ ID NO 267
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ala Cys Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 268
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Cys Glu Glu Gln Gln Pro Trp Ala Gln Tyr Leu Glu Leu Leu Phe Pro
1               5                   10                  15

Thr Glu Thr Leu Leu Leu Glu Trp
            20

<210> SEQ ID NO 269
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Cys Glu Glu Gln Gln Pro Trp Arg Ala Tyr Leu Glu Leu Leu Phe Pro
1               5                   10                  15
```

Thr Glu Thr Leu Leu Leu Glu Trp
            20

<210> SEQ ID NO 270
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 271
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ala Cys Glu Glu Gln Asn Pro Trp Ala Arg Tyr Ala Glu Trp Leu Phe
1               5                   10                  15

Pro Thr Thr Leu Leu Leu Leu Glu
            20

<210> SEQ ID NO 272
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ala Cys Glu Asp Gln Asn Pro Trp Ala Arg Tyr Ala Asp Leu Leu Phe
1               5                   10                  15

Pro Thr Thr Leu Ala Trp
            20

<210> SEQ ID NO 273
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ala Cys Glu Glu Gln Asn Pro Trp Ala Arg Tyr Ala Glu Leu Leu Phe
1               5                   10                  15

Pro Thr Thr Leu Ala Trp
            20

<210> SEQ ID NO 274
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Thr Glu Asp Ala Asp Val Leu Leu Ala Leu Asp Leu Leu Leu Pro
1               5                   10                  15

Thr Thr Phe Leu Trp Asp Ala Tyr Arg Ala Trp Tyr Pro Asn Gln Glu
            20                  25                  30

Cys Ala

<210> SEQ ID NO 275
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Cys Asp Asp Asp Asp Asn Pro Asn Tyr Trp Ala Arg Tyr Ala Asn
1               5                   10                  15

Trp Leu Phe Thr Thr Pro Leu Leu Leu Asn Gly Ala Leu Leu Val
            20                  25                  30

Glu Ala Glu Glu Thr
        35

<210> SEQ ID NO 276
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Cys Asp Asp Asp Asp Asn Pro Asn Tyr Trp Ala Arg Tyr Ala Pro
1               5                   10                  15

Trp Leu Phe Thr Thr Pro Leu Leu Leu Pro Gly Ala Leu Leu Val
            20                  25                  30

Glu Ala Glu Glu Thr
        35

<210> SEQ ID NO 277
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Cys Thr
        35

<210> SEQ ID NO 278
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 279
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30

Asp Glu Gly Thr
        35

<210> SEQ ID NO 280
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Thr
        35

<210> SEQ ID NO 281
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Thr
        35

<210> SEQ ID NO 282
<211> LENGTH: 37
<212> TYPE: PRT
<213> ORGANISM: Artificial Sequence
<220> FEATURE:
<223> OTHER INFORMATION: Description of Artificial Sequence: Synthetic

```
                              polypeptide

<400> SEQUENCE: 282

Cys Asp Asp Asp Glu Asp Asn Pro Ile Tyr Trp Ala Arg Tyr Ala His
1               5                   10                  15

Trp Leu Phe Thr Thr Pro Leu Leu Leu His Gly Ala Leu Leu Val
            20                  25                  30

Asp Ala Asp Glu Thr
        35

<210> SEQ ID NO 283
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Gly Thr
        35

<210> SEQ ID NO 284
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Gly Thr
        35

<210> SEQ ID NO 285
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Gly Thr
        35

<210> SEQ ID NO 286
<211> LENGTH: 32
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 286

Ala Lys Glu Asp Gln Asn Asp Pro Tyr Trp Ala Arg Tyr Ala Asp Trp
1               5                   10                  15

Leu Phe Thr Thr Pro Leu Leu Leu Asp Leu Ala Leu Leu Val Gly
            20                  25                  30

<210> SEQ ID NO 287
<211> LENGTH: 31
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 287

Ala Glu Asp Gln Asn Pro Tyr Trp Ala Arg Tyr Ala Asp Trp Leu Phe
1               5                   10                  15

Thr Thr Pro Leu Leu Leu Glu Leu Ala Leu Leu Val Cys Gly
            20                  25                  30

<210> SEQ ID NO 288
<211> LENGTH: 28
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 288

Ala Lys Asp Asp Gln Asn Pro Trp Arg Ala Tyr Leu Asp Leu Leu Phe
1               5                   10                  15

Pro Thr Asp Thr Leu Leu Leu Asp Leu Leu Trp Cys
            20                  25

<210> SEQ ID NO 289
<211> LENGTH: 27
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 289

Ala Cys Glu Glu Gln Asn Pro Trp Arg Ala Tyr Leu Glu Leu Leu Phe
1               5                   10                  15

Pro Thr Glu Thr Leu Leu Leu Glu Leu Leu Trp
            20                  25

<210> SEQ ID NO 290
<211> LENGTH: 25
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 290

Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25

```
<210> SEQ ID NO 291
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Cys Asp Asn Asn Asn Pro Trp Arg Ala Tyr Leu Asp Leu Leu Phe Pro
1               5                   10                  15

Thr Asp Thr Leu Leu Leu Asp Trp
            20

<210> SEQ ID NO 292
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Cys Glu Glu Gln Gln Pro Trp Ala Gln Tyr Leu Glu Leu Leu Phe Pro
1               5                   10                  15

Thr Glu Thr Leu Leu Leu Glu Trp
            20

<210> SEQ ID NO 293
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Cys Glu Glu Gln Gln Pro Trp Arg Ala Tyr Leu Glu Leu Leu Phe Pro
1               5                   10                  15

Thr Glu Thr Leu Leu Leu Glu Trp
            20

<210> SEQ ID NO 294
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Cys Asp Asp Asp Asp Asn Pro Asn Tyr Trp Ala Arg Tyr Ala Asn
1               5                   10                  15

Trp Leu Phe Thr Thr Pro Leu Leu Leu Asn Gly Ala Leu Leu Val
            20                  25                  30

Glu Ala Glu Glu Thr
        35

<210> SEQ ID NO 295
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 295

Cys Asp Asp Asp Asp Asn Pro Asn Tyr Trp Ala Arg Tyr Ala Pro
1               5                   10                  15

Trp Leu Phe Thr Thr Pro Leu Leu Leu Pro Gly Ala Leu Leu Val
            20                  25                  30

Glu Ala Glu Glu
        35

<210> SEQ ID NO 296
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 297
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 298
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Ala Glu Gln Asn Pro Ile Tyr Trp Ala Arg Tyr Ala Asp Leu Leu Phe
1               5                   10                  15

Pro Thr Thr Leu Ala Trp
            20

<210> SEQ ID NO 299
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Lys Glu Asp Gln Asn Pro Trp Ala Arg Tyr Ala Asp Leu Leu Phe Pro
1               5                   10                  15

Thr Thr Leu Trp
        20

<210> SEQ ID NO 300
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ala Cys Glu Glu Gln Asn Pro Gln Ala Glu Tyr Ala Glu Trp Leu Phe
1               5                   10                  15

Pro Thr Thr Leu Leu Leu Leu Glu
            20

<210> SEQ ID NO 301
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Ala Ala Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 302
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ala Lys Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 303
<211> LENGTH: 38
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 303

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly Gly
        35

<210> SEQ ID NO 304
<211> LENGTH: 38
<212> TYPE: PRT
<213> ORGANISM: Artificial Sequence
<220> FEATURE:
<223> OTHER INFORMATION: Description of Artificial Sequence: Synthetic

```
        polypeptide
<220> FEATURE:
<221> NAME/KEY: MOD_RES
<222> LOCATION: (1)..(1)
<223> OTHER INFORMATION: Ala or Asp
<220> FEATURE:
<221> NAME/KEY: MOD_RES
<222> LOCATION: (2)..(2)
<223> OTHER INFORMATION: Ala, Asp or Cys
<220> FEATURE:
<221> NAME/KEY: MOD_RES
<222> LOCATION: (4)..(4)
<223> OTHER INFORMATION: Gln or Asp
<220> FEATURE:
<221> NAME/KEY: MOD_RES
<222> LOCATION: (11)..(11)
<223> OTHER INFORMATION: Arg or Gln
<220> FEATURE:
<221> NAME/KEY: MOD_RES
<222> LOCATION: (12)..(12)
<223> OTHER INFORMATION: Tyr or Asp
<220> FEATURE:
<221> NAME/KEY: MOD_RES
<222> LOCATION: (13)..(13)
<223> OTHER INFORMATION: Ala, Asp or Tyr
<220> FEATURE:
<221> NAME/KEY: MOD_RES
<222> LOCATION: (14)..(14)
<223> OTHER INFORMATION: Asp, Asn, Glu, His, Lys, Ala or Trp
<220> FEATURE:
<221> NAME/KEY: MOD_RES
<222> LOCATION: (15)..(15)
<223> OTHER INFORMATION: Trp or Asp
<220> FEATURE:
<221> NAME/KEY: MOD_RES
<222> LOCATION: (19)..(19)
<223> OTHER INFORMATION: Thr or Asp
<220> FEATURE:
<221> NAME/KEY: MOD_RES
<222> LOCATION: (20)..(20)
<223> OTHER INFORMATION: Pro, Gly or Ala
<220> FEATURE:
<221> NAME/KEY: MOD_RES
<222> LOCATION: (24)..(24)
<223> OTHER INFORMATION: Leu or Asp
<220> FEATURE:
<221> NAME/KEY: MOD_RES
<222> LOCATION: (25)..(25)
<223> OTHER INFORMATION: Asp, Leu, Asn, Glu, His, Lys or Ala
<220> FEATURE:
<221> NAME/KEY: MOD_RES
<222> LOCATION: (26)..(26)
<223> OTHER INFORMATION: Leu, Asp or Gly
<220> FEATURE:
<221> NAME/KEY: MOD_RES
<222> LOCATION: (31)..(31)
<223> OTHER INFORMATION: Asp or Asn
<220> FEATURE:
<221> NAME/KEY: MOD_RES
<222> LOCATION: (33)..(33)
<223> OTHER INFORMATION: Asp or Asn
<220> FEATURE:
<221> NAME/KEY: MOD_RES
<222> LOCATION: (34)..(34)
<223> OTHER INFORMATION: Glu or Gln
<220> FEATURE:
<221> NAME/KEY: MOD_RES
<222> LOCATION: (35)..(35)
<223> OTHER INFORMATION: Gly or Cys
<220> FEATURE:
<221> NAME/KEY: MOD_RES
<222> LOCATION: (37)..(37)
<223> OTHER INFORMATION: Gly or Cys

<400> SEQUENCE: 304

Xaa Xaa Glu Xaa Asn Pro Ile Tyr Trp Ala Xaa Xaa Xaa Xaa Xaa Leu
1               5                  10                  15
```

```
Phe Thr Xaa Xaa Leu Leu Leu Xaa Xaa Xaa Ala Leu Leu Val Xaa Ala
            20                  25                  30

Xaa Xaa Xaa Thr Xaa Gly
        35
```

<210> SEQ ID NO 305
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (21)..(21)
<223> OTHER INFORMATION: May or may not be present
<220> FEATURE:
<221> NAME/KEY: MOD_RES
<222> LOCATION: (29)..(29)
<223> OTHER INFORMATION: May or may not be present
<220> FEATURE:
<221> NAME/KEY: MOD_RES
<222> LOCATION: (40)..(40)
<223> OTHER INFORMATION: May or may not be present

<400> SEQUENCE: 305

```
Asp Ala Ala Glu Gln Asn Pro Ile Tyr Trp Ala Arg Tyr Ala Asp Trp
1               5                   10                  15

Leu Phe Thr Thr Leu Pro Leu Leu Leu Asp Leu Leu Ala Leu Leu
            20                  25                  30

Val Asp Ala Asp Glu Gly Thr Lys Gly Gly
        35                  40
```

<210> SEQ ID NO 306
<211> LENGTH: 38
<212> TYPE: PRT
<213> ORGANISM: Unknown
<220> FEATURE:
<223> OTHER INFORMATION: Description of Unknown: Wild-type pH-sensitive
      membrane polypeptide

<400> SEQUENCE: 306

```
Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly Gly
        35
```

<210> SEQ ID NO 307
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gly, Asp or Ala
<220> FEATURE:
<221> NAME/KEY: MOD_RES
<222> LOCATION: (2)..(2)
<223> OTHER INFORMATION: Gly, Asp or Cys
<220> FEATURE:

```
<221> NAME/KEY: MOD_RES
<222> LOCATION: (4)..(4)
<223> OTHER INFORMATION: Gln or Asp
<220> FEATURE:
<221> NAME/KEY: MOD_RES
<222> LOCATION: (11)..(11)
<223> OTHER INFORMATION: Arg or Gln
<220> FEATURE:
<221> NAME/KEY: MOD_RES
<222> LOCATION: (12)..(12)
<223> OTHER INFORMATION: Tyr or Asp
<220> FEATURE:
<221> NAME/KEY: MOD_RES
<222> LOCATION: (13)..(13)
<223> OTHER INFORMATION: Ala, Asp or Tyr
<220> FEATURE:
<221> NAME/KEY: MOD_RES
<222> LOCATION: (14)..(14)
<223> OTHER INFORMATION: Asp, Asn, Glu, His, Lys, Ala or Trp
<220> FEATURE:
<221> NAME/KEY: MOD_RES
<222> LOCATION: (15)..(15)
<223> OTHER INFORMATION: Trp or Asp
<220> FEATURE:
<221> NAME/KEY: MOD_RES
<222> LOCATION: (19)..(19)
<223> OTHER INFORMATION: Thr or Asp
<220> FEATURE:
<221> NAME/KEY: MOD_RES
<222> LOCATION: (20)..(20)
<223> OTHER INFORMATION: Pro, Gly or Ala
<220> FEATURE:
<221> NAME/KEY: MOD_RES
<222> LOCATION: (24)..(24)
<223> OTHER INFORMATION: Leu or Asp
<220> FEATURE:
<221> NAME/KEY: MOD_RES
<222> LOCATION: (25)..(25)
<223> OTHER INFORMATION: Asp, Leu, Asn, Glu, His, Lys or Ala
<220> FEATURE:
<221> NAME/KEY: MOD_RES
<222> LOCATION: (26)..(26)
<223> OTHER INFORMATION: Leu, Asp or Gly
<220> FEATURE:
<221> NAME/KEY: MOD_RES
<222> LOCATION: (31)..(31)
<223> OTHER INFORMATION: Asp or Asn
<220> FEATURE:
<221> NAME/KEY: MOD_RES
<222> LOCATION: (33)..(33)
<223> OTHER INFORMATION: Asp or Asn
<220> FEATURE:
<221> NAME/KEY: MOD_RES
<222> LOCATION: (34)..(34)
<223> OTHER INFORMATION: Glu or Gln
<220> FEATURE:
<221> NAME/KEY: MOD_RES
<222> LOCATION: (35)..(35)
<223> OTHER INFORMATION: Gly or Cys

<400> SEQUENCE: 307

Xaa Xaa Glu Xaa Asn Pro Ile Tyr Trp Ala Xaa Xaa Xaa Xaa Xaa Leu
1               5                   10                  15

Phe Thr Xaa Xaa Leu Leu Leu Xaa Xaa Xaa Ala Leu Leu Val Xaa Ala
            20                  25                  30

Xaa Xaa Xaa Thr Gly Gly
        35

<210> SEQ ID NO 308
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (7)..(7)
<223> OTHER INFORMATION: May or may not be present
<220> FEATURE:
<221> NAME/KEY: MOD_RES
<222> LOCATION: (22)..(22)
<223> OTHER INFORMATION: May or may not be present
<220> FEATURE:
<221> NAME/KEY: MOD_RES
<222> LOCATION: (30)..(30)
<223> OTHER INFORMATION: May or may not be present
<220> FEATURE:
<221> NAME/KEY: MOD_RES
<222> LOCATION: (40)..(40)
<223> OTHER INFORMATION: May or may not be present
<220> FEATURE:
<221> NAME/KEY: MOD_RES
<222> LOCATION: (42)..(42)
<223> OTHER INFORMATION: Lys, Cys or absent

<400> SEQUENCE: 308

Asp Gly Gly Glu Gln Asn Asp Pro Ile Tyr Trp Ala Arg Tyr Ala Asp
1               5                   10                  15

Trp Leu Phe Thr Thr Leu Pro Leu Leu Leu Asp Leu Leu Ala Leu
            20                  25                  30

Leu Val Asp Ala Asp Glu Gly Cys Thr Xaa Gly Gly
        35                  40

<210> SEQ ID NO 309
<211> LENGTH: 38
<212> TYPE: PRT
<213> ORGANISM: Artificial Sequence
<220> FEATURE:
<223> OTHER INFORMATION: Synthetic polypeptide,which is modified at the
      CYS, residue 37 of the peptide, with a S-S-linker attqached to
      the nitrogen of amino-phalloidin

<400> SEQUENCE: 309

Ala Ala Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 310
<211> LENGTH: 31
<212> TYPE: PRT
<213> ORGANISM: Artificial Sequence
<220> FEATURE:
<223> OTHER INFORMATION: modification of Cys residue 30 with a S-S
      linker attached to 2-amino phalloidin, Lys residue  29 modified
      with an alkyl linker attached to rhodamine, and Alanine residue 1
      modified with a COCH3 group.

<400> SEQUENCE: 310

Ala Glu Asp Gln Asn Pro Tyr Trp Ala Arg Tyr Asp Trp Leu Phe Thr
1               5                   10                  15

Thr Pro Leu Leu Leu Leu Asp Leu Ala Leu Leu Val Asp Cys Gly
            20                  25                  30

<210> SEQ ID NO 311
<211> LENGTH: 34
```

```
<212> TYPE: PRT
<213> ORGANISM: Artificial Sequence
<220> FEATURE:
<223> OTHER INFORMATION: synthetic peptide

<400> SEQUENCE: 311

Gly Leu Ala Gly Leu Ala Gly Leu Leu Gly Leu Glu Gly Leu Leu Gly
1               5                   10                  15

Leu Pro Leu Gly Leu Leu Glu Gly Leu Trp Leu Gly Leu Glu Leu Glu
            20                  25                  30

Gly Asn
```

COMPOUNDS, COMPOSITIONS, AND METHODS FOR TREATMENT OF DISEASES INVOLVING ACIDIC OR HYPOXIC DISEASED TISSUES

FIELD OF THE INVENTION

The present invention relates to therapeutic compounds and pharmaceutical compositions for treatment of diseases involving acidic or hypoxic diseased tissues, including cancer, cardiovascular diseases such as stroke and myocardial infarction, and long-term neurodegenerative diseases, as well as to methods for their use and manufacture.

BACKGROUND OF THE INVENTION

Hypoxia and acidosis are physiological markers of many disease processes, including cancer. In cancer, hypoxia is one mechanism responsible for development of an acid environment within solid tumors. As a result, hydrogen ions must be removed from the cell (e.g., by a proton pump) to maintain a normal pH within the cell. As a consequence of this export of hydrogen ions, cancer cells have an increased pH gradient across the cell membrane lipid bilayer and a lower pH in the extracellular milieu when compared to normal cells.

Cancer is a group of diseases characterized by aberrant control of cell growth. The annual incidence of cancer is estimated to be in excess of 1.6 million in the United States alone. While surgery, radiation, chemotherapy, and hormones are used to treat cancer, it remains the second leading cause of death in the U.S. It is estimated that about 600,000 Americans will die from cancer each year.

Treatment of cancer in humans by systemic administration of pharmaceutical agents often functions by slowing or terminating the uncontrolled replication that is a characteristic of cancer cells. One class of such agents is DNA repair inhibitors. Such slowing or termination, however, affects not only the replication of cancer cells but also the replication of non-cancerous cells, which leads to the well-known undesirable side effects of such cancer treatment. It would be highly desirable to selectively deliver such agents to the target cancer cells and minimize or avoid the side effects caused by systemic administration.

The PARP enzyme family, including poly(ADP-ribose) polymerase (PARP-1) and the related enzymes PARP-2 and PARP-3 (collectively "PARP"), are important elements in the repair of DNA single-strand breaks, particularly by the base excision repair pathway. If single-strand breaks are not repaired prior to DNA replication, then double strand breaks may form. Cells with increasing numbers of double strand breaks become more dependent on other repair pathways, such as homologous recombination, and (if single strand breaks continue unrepaired) the cells die.

Inhibitors of PARP have been developed and continue to be developed as anti-cancer agents. Because these inhibitors prevent the repair of DNA single-strand breaks, they have a variety of roles in treatment of cancer. (See, e.g., Nicola J. Curtin and Ricky A. Sharma—"PARP Inhibitors for Cancer Treatment", Cancer Drug Discovery and Development, vol 83, Humana Press 2015.)

PARP inhibitors can be used for treatment of forms of cancer that are more dependent on PARP than normal cells (so-called "PARP-sensitive" cancers). For example, patients with homologous recombination deficiency (HRD), such as that involving the BRCA1 and BRCA2 genes, are beneficially treated with a PARP inhibitor, either as monotherapy or in combination with other agents. Since DNA repair and survival of PARP inhibited cells are heavily dependent on HR, patients carrying BRCA related mutations (who exhibit HRD) are well suited to treatment with PARP inhibitors.

Although PARP inhibitors are useful in the treatment of cancer, the compounds also exhibit side effects. PARP side effects, which include serious hematologic and gastrointestinal adverse reactions and potentially fatal acute myeloid leukemia, are highly undesirable.

Other DNA repair inhibiting cancer therapeutics would be expected to similarly exhibit unwanted side effects when administered systemically. Such other DNA repair inhibiting cancer therapeutics include those targeting the protein kinase ataxia-telangiectasia mutated (ATM), the ATM-Rad3-related protein kinase (ATR), and the nuclear serine/threonine protein kinase DNA-PK. Cancer therapy would benefit significantly if compounds acting by these mechanisms could be delivered selectively to cancer calls and thus avoid undesired effects on normal cells.

Moreover, PARP inhibitors have potential for utility in treatment of other diseases besides cancer, including cardiovascular and inflammatory diseases, through possible roles for PARP in functions other than DNA repair, such as involvement in regulating the mitochondria-to-nucleus translocation of apoptosis-inducing-factor (AIF) or involvement in regulating the expression of proteins implicated in inflammation. (See, e.g., Pacher and Szabo—"Role of Poly (ADP-ribose) polymerase 1 (PARP-1) in Cardiovascular Diseases: The Therapeutic Potential of PARP Inhibitors, Cardiovasc Drug Rev. 2007; 25(3): 235-260). Preferential delivery of PARP inhibitors to these diseased tissues would likewise be beneficial.

SUMMARY

The present disclosure provides, inter alia, a compound of Formula (I):

$$R8\text{-}Q\text{-}R7 \qquad (I)$$

or a pharmaceutically acceptable salt thereof, wherein constituent variables are defined herein.

Broadly speaking, the invention provides (1) compounds comprising a therapeutic molecule (e.g., $R^7$) and a pH-sensitive (or pH-dependent) peptide (e.g., $R^8$) linked together, such as by a disulfide-containing linker or other linker which would be cleaved in the intracellular environment, (2) pharmaceutical compositions comprising these compounds and a pharmaceutically-acceptable carrier, (3) methods of using these compounds and compositions in the treatment of diseases and conditions in humans and other mammals involving acidic and/or hypoxic cells, and (4) methods of making the compounds and compositions, and intermediates useful in said methods.

The present disclosure further provides a pharmaceutical composition comprising a compound of the disclosure, or a pharmaceutically acceptable salt thereof, and at least one pharmaceutically acceptable carrier or excipient.

The present disclosure also provides methods of treating diseases or conditions involving acidic or hypoxic diseased tissues by administering to a human or other mammal in need of such treatment a therapeutically effective amount of a compound of the disclosure. The disclosure also provides methods of reducing bone marrow toxicity associated with administration of an ionizing radiation or cytotoxic agent, which comprises administering to a human or other mammal a therapeutically-effective amount of a compound of the disclosure in combination with the ionizing radiation or cytotoxic agent.

The present disclosure also provides uses of the compounds described herein in the manufacture of a medicament for use in therapy. The present disclosure also provides the compounds described herein for use in therapy.

The present disclosure also provides methods for synthesizing the compounds of the disclosure and intermediates useful in these methods.

DETAILED DESCRIPTION

Figure 1:
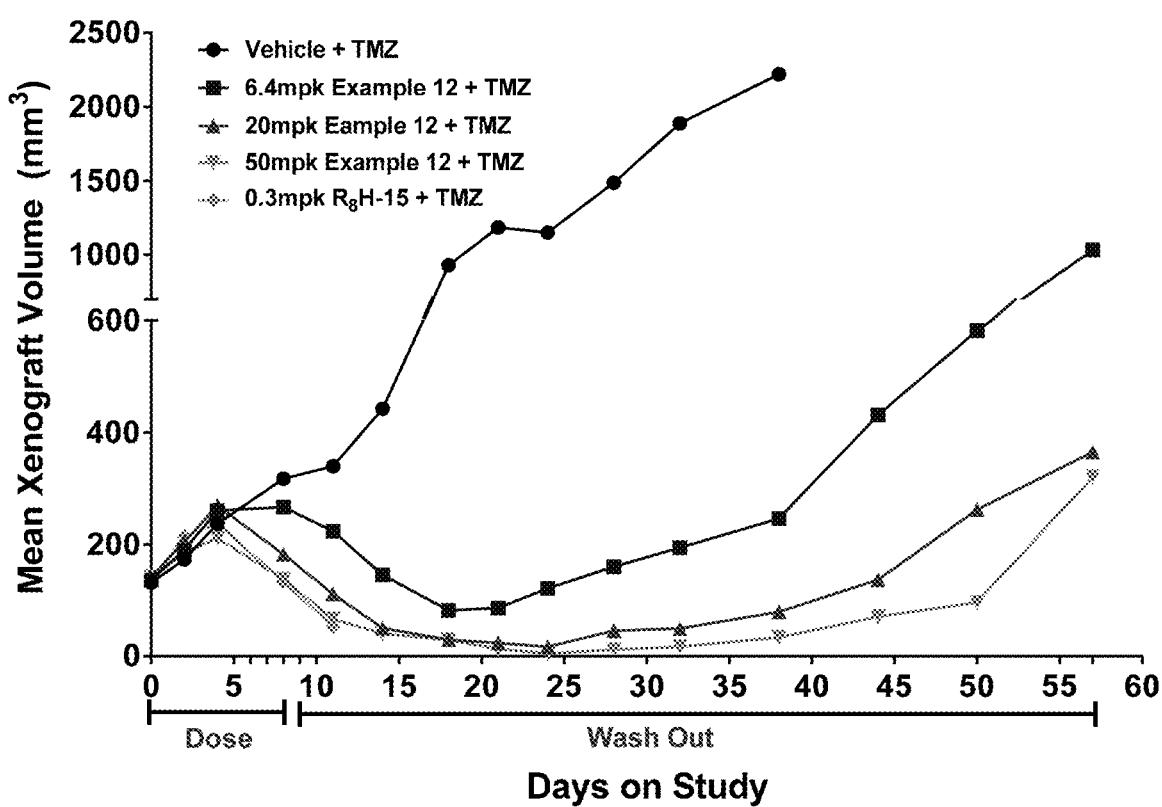
FIG. 1 shows the tumor growth delay of $R^8H$-15 and Example 12 in $BRCA^{-/-}$ Mice.

Provided herein is a compound of Formula (I):

R8-Q-R7    (I)

or a pharmaceutically acceptable salt thereof, wherein:
$R^7$ is a peptide;
$R^8$ is selected from the group consisting of:

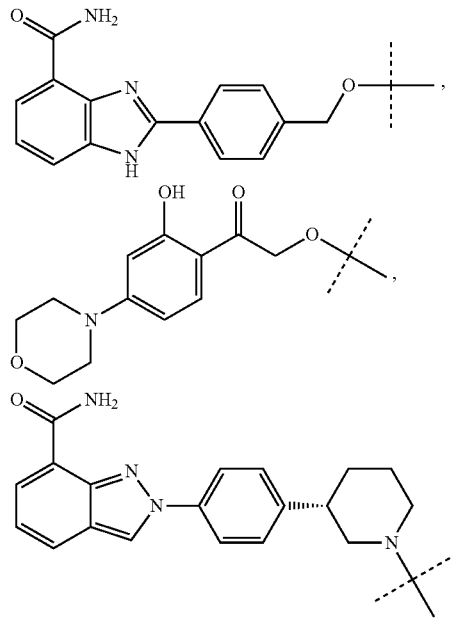

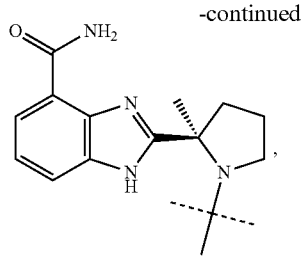

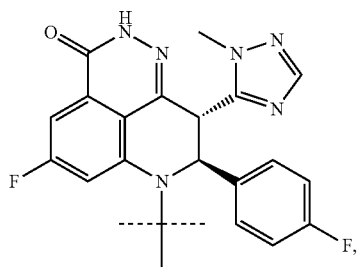

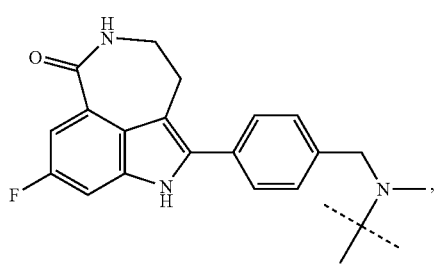

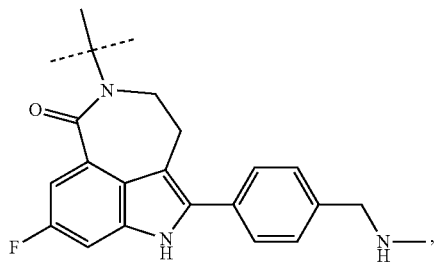

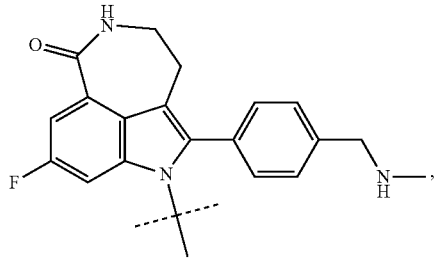

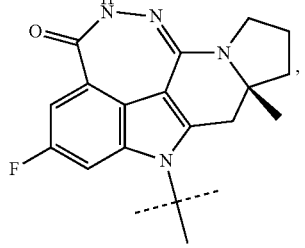

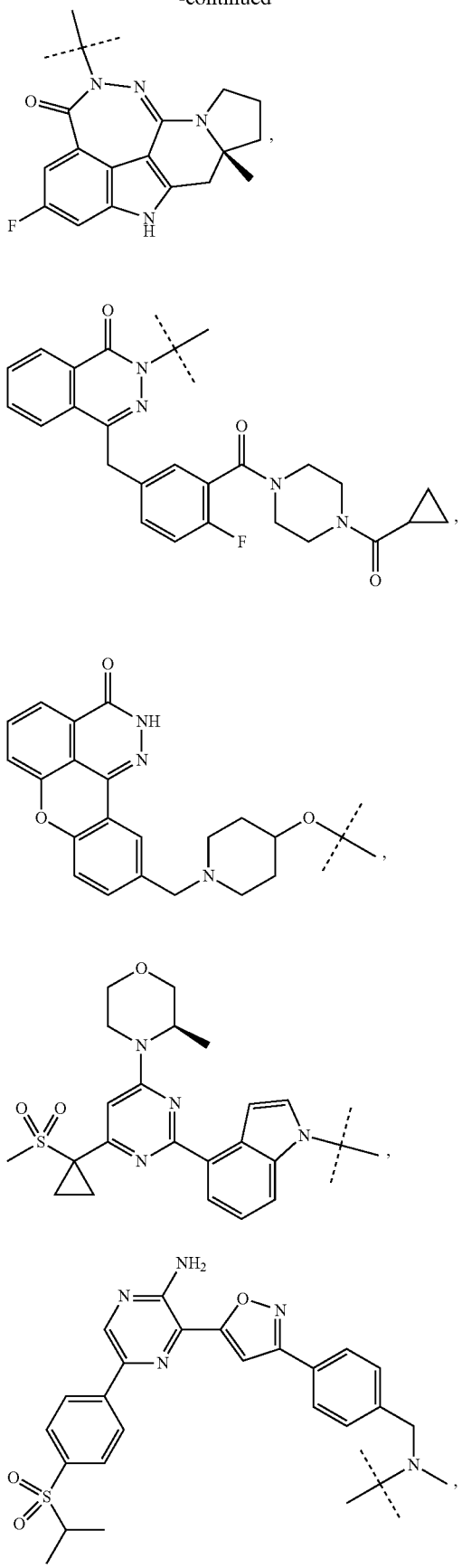
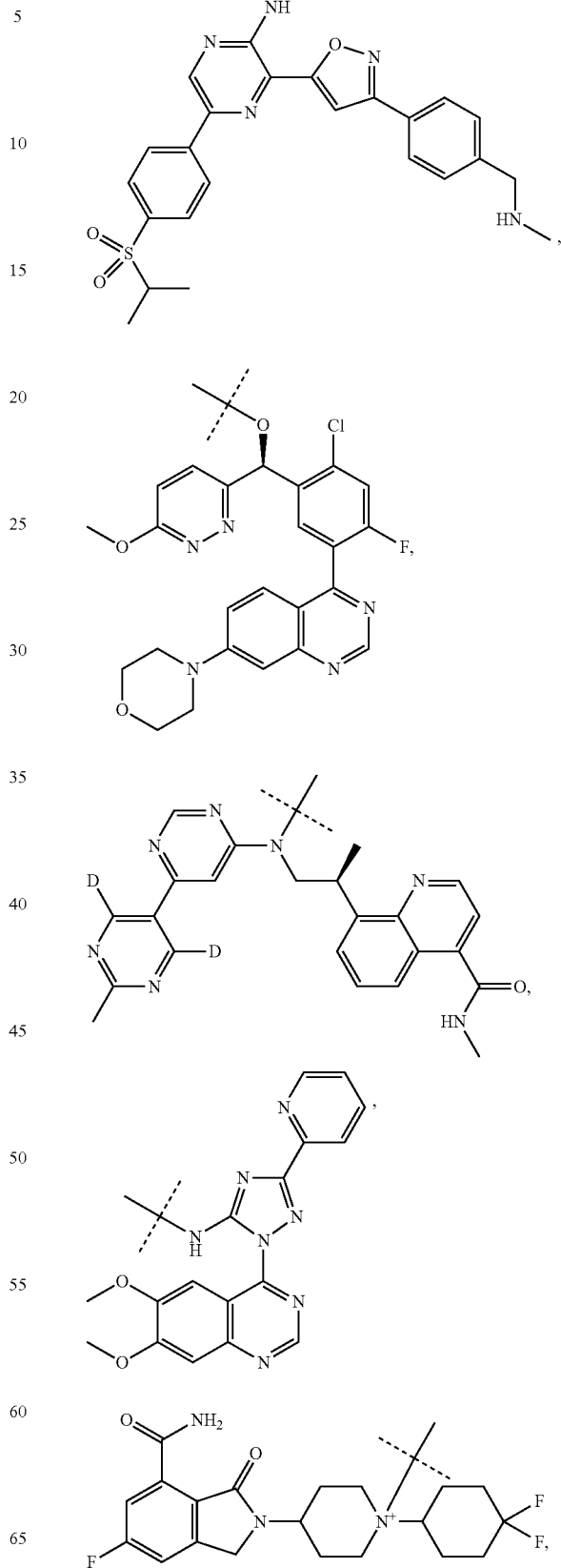

-continued
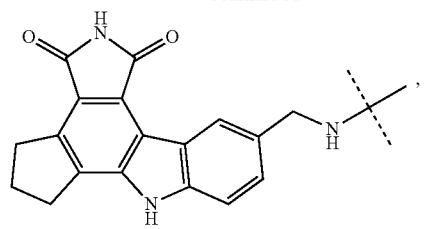
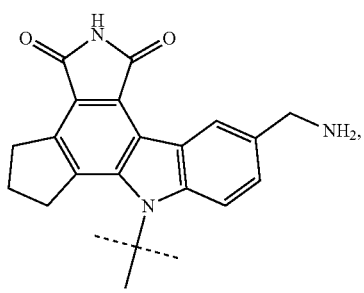
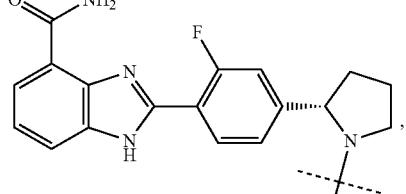
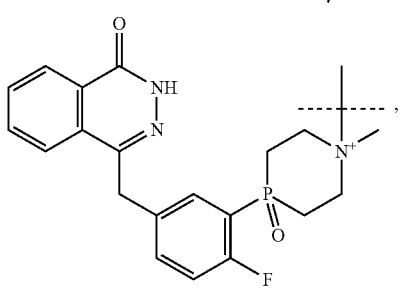
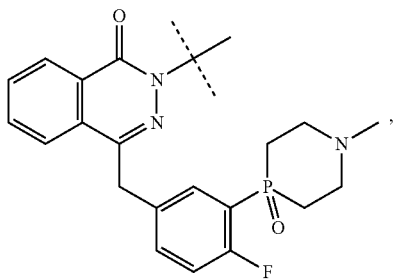
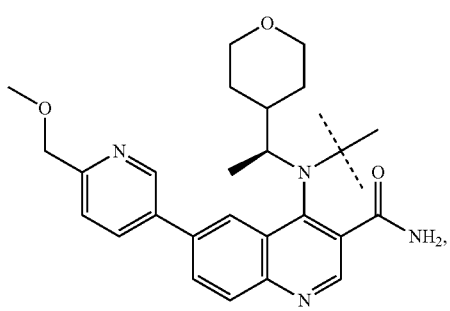
-continued
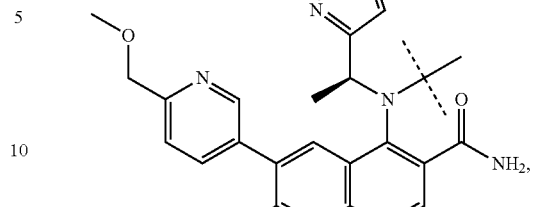
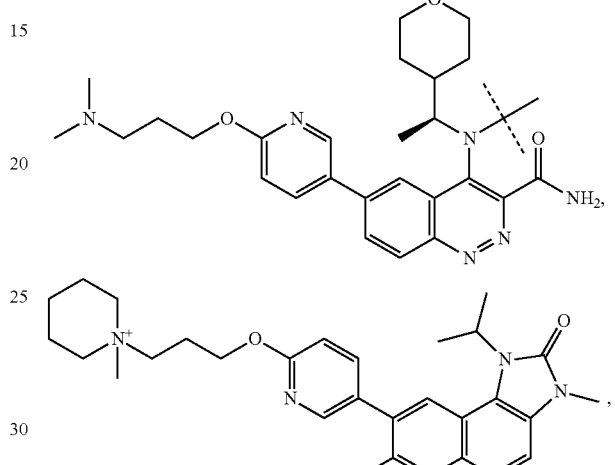

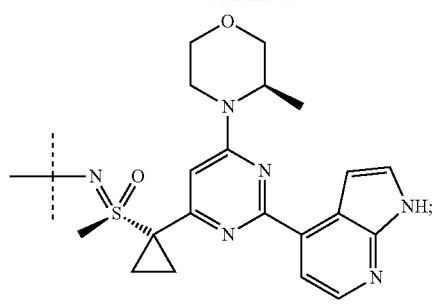
Q is selected from the group consisting of
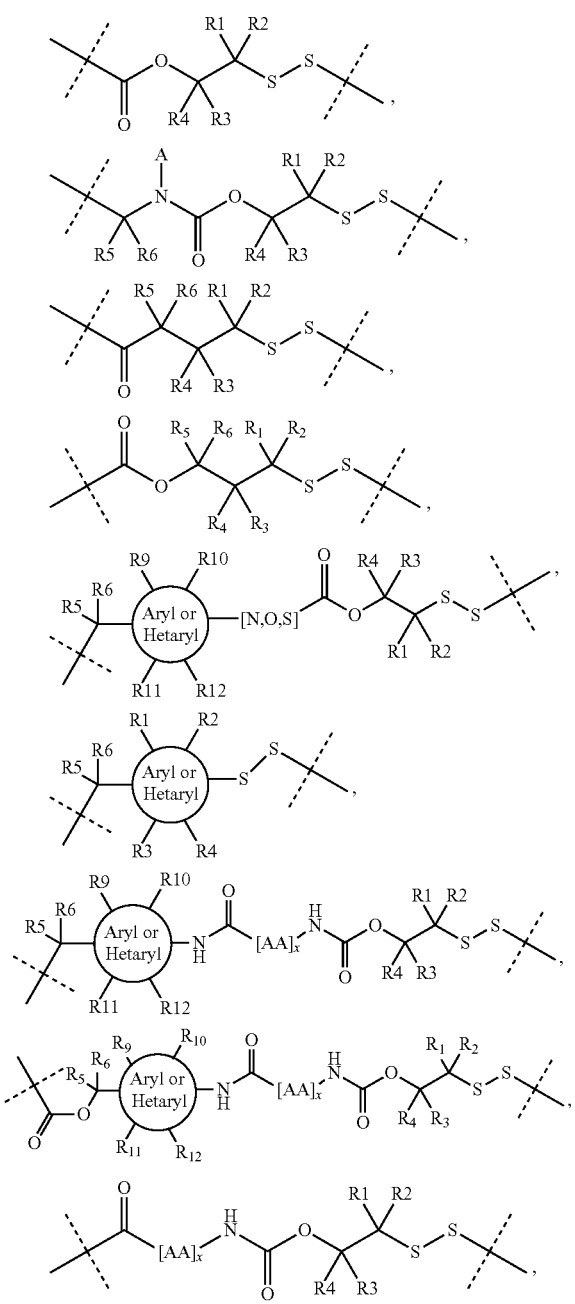
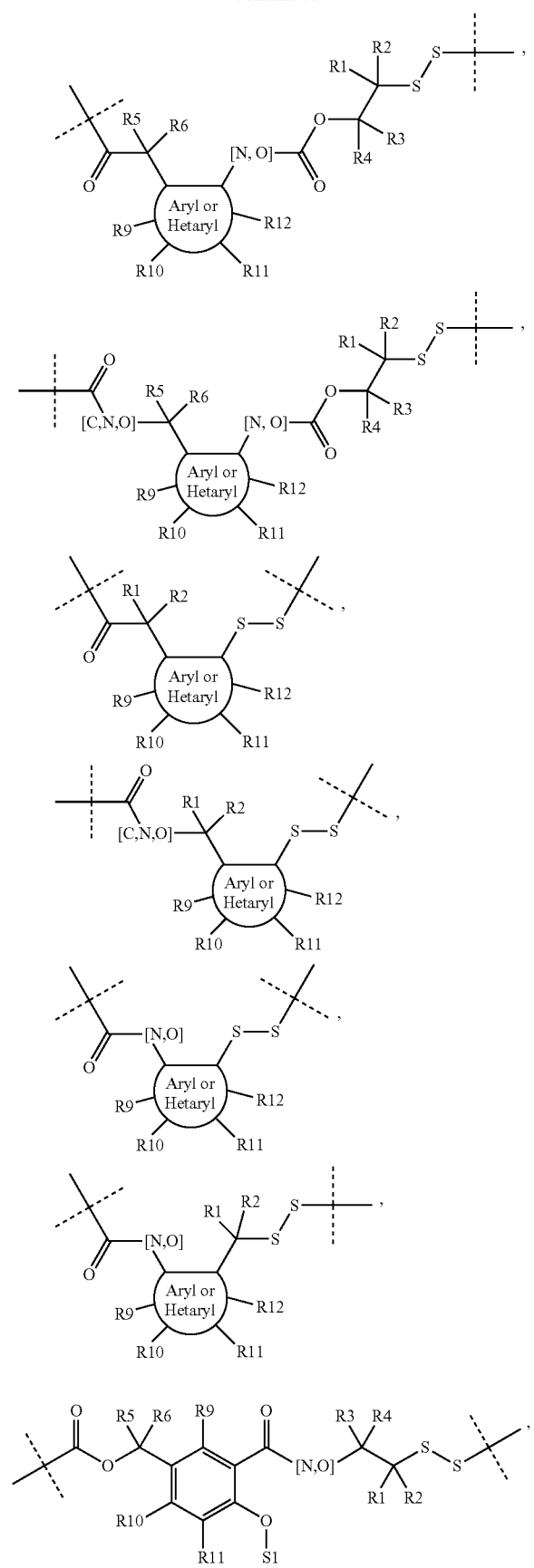

-continued

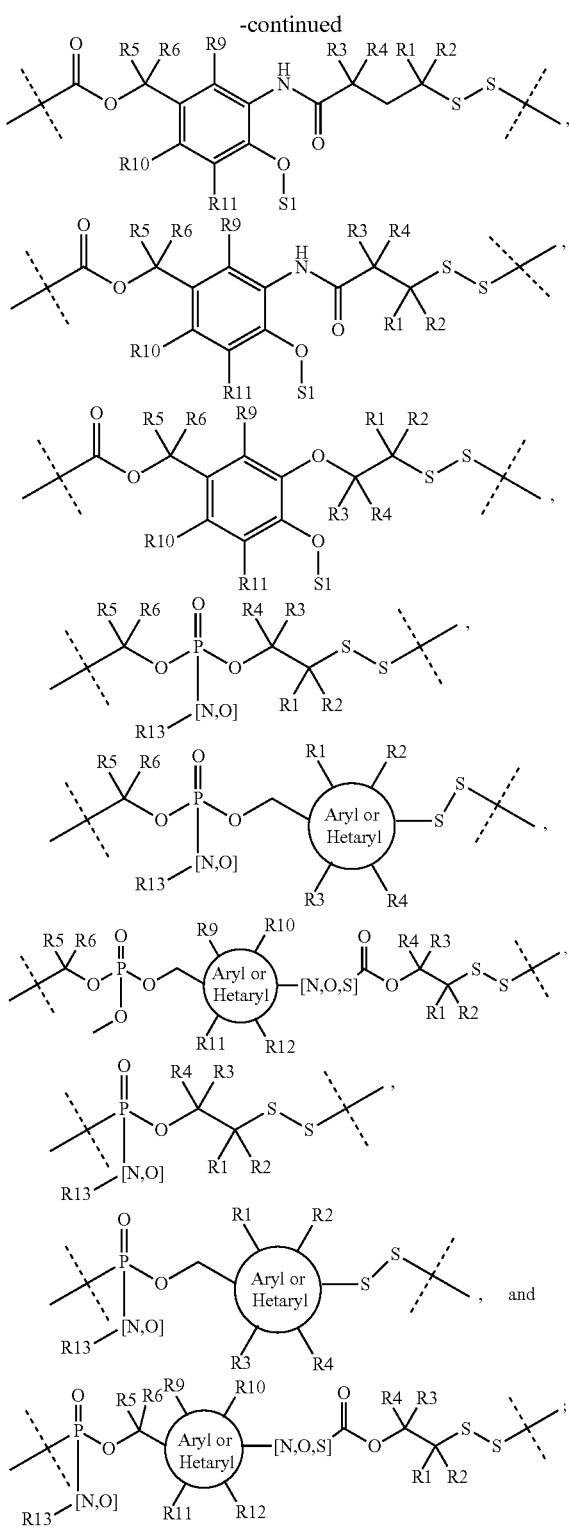

$R^1$, $R^2$, $R^3$, $R^4$, $R^5$, $R^6$, $R^9$, $R^{10}$, $R^{11}$, and $R^{12}$ are each independently selected from H, $C_{1-4}$ alkyl, $C_{1-4}$ alkenyl, $C_{6-10}$ aryl, 5-10 membered heteroaryl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, wherein said $C_{1-4}$ alkyl, $C_{1-4}$ alkenyl, $C_{6-10}$ aryl, and 5-10 membered heteroaryl are each optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^1$ and $R^2$ together with the carbon atom to which they are attached form a $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^1$ and $R^3$ together with the carbon atom to which they are attached form a $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^3$ and $R^4$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

or $R^5$ and $R^6$ together with the carbon atom to which they are attached form an $C_{3-7}$ cycloalkyl group optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$;

$R^{13}$ is H or $C_{1-6}$ alkyl;

A is H or $C_{1-4}$ alkyl;

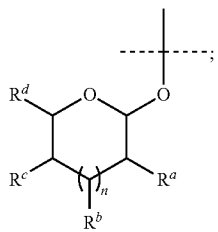

is $C_{6-10}$ aryl or 5-10 membered heteroaryl; wherein the 5-10 membered heteroaryl has at least one ring-forming carbon atom and 1, 2, 3, or 4 ring-forming heteroatoms independently selected from N, O, and S;

[N, O, S] is NH, O, or S;

[N, O] is NH or O;

[C, N, O] is $CR^XR^Y$, NH, or O;

each $R^X$ and $R^Y$ are independently selected from H and $C_{1-4}$ alkyl;

[AA]x is a peptide that may be cleaved by enzymatic action;

S1 is each $R^a$, $R^b$, $R^c$, and $R^d$ are independently selected from H, $C_{1-4}$ alkyl, $OR^{a2}$, $CO_2R^{a2}$, and $OC(=O)R^{a2}$, wherein said $C_{1-4}$ alkyl is optionally substituted with $OR^{a2}$, $CO_2R^{a2}$, and $OC(=O)R^{a2}$;

$R^{a1}$, $R^{b1}$, $R^{c1}$, and $R^{d1}$ are each independently selected from H, $C_{1-6}$ alkyl, $C_{2-6}$ alkenyl, $C_{2-6}$ alkynyl, $C_{1-6}$ haloalkyl, OH, CN, $NO_2$, and $CO_2CH_3$; wherein said $C_{1-6}$ alkyl and $C_{2-6}$ alkenyl are each optionally substituted with OH, CN, $NO_2$, or $CO_2CH_3$;

$R^{a2}$ is H or $C_{1-4}$ alkyl; and n is 0 or 1.

In some embodiments, the lefthand side of Q attaches to $R^8$ and the righthand side of Q attaches to $R^7$.

In some embodiments, a sulfur atom of the disulfide moiety of Q is part of a cysteine residue of $R^7$.

Suitable peptides for use as $R^7$ are described, for example, in U.S. Pat. Nos. 8,076,451 and 9,289,508 (which are incorporated herein by reference in their entirety), although other peptides capable of such selective insertion could be used. Other suitable peptides are described, for example, in Weerakkody, et al., PNAS 110 (15), 5834-5839 (Apr. 9, 2013), which is also incorporated herein by reference in its entirety. Without being bound by theory, it is believed that the $R^7$ peptide reversibly folds and inserts across cell membranes in response to pH changes. The $R^7$ peptide can target acidic tissue and selectively translocate polar, cell-impermeable molecules across cell membranes in response to low extracellular pH. In some embodiments, $R^7$ is a peptide capable of selectively delivering $R_8Q$-across a cell membrane having an acidic or hypoxic mantle having a pH less than about 6.0. In some embodiments, $R^7$ is a peptide capable of selectively delivering $R_8Q$-across a cell membrane having an acidic or hypoxic mantle having a pH less than about 6.5. In some embodiments, $R^7$ is a peptide capable of selectively delivering $R_8Q$-across a cell membrane having an acidic or hypoxic mantle having a pH less than about 5.5. In some embodiments, $R^7$ is a peptide capable of selectively delivering $R_8Q$-across a cell membrane having an acidic or hypoxic mantle having a pH between about 5.0 and about 6.0.

In some embodiments, $R^7$ is attached to Q through a cysteine residue of $R^7$. In some embodiments, the sulfur atom of the cysteine residue can form part of the disulfide bond of the disulfide bond-containing linker.

In some embodiments, $R^7$ is a peptide comprising at least one of the following sequences:

```
                                    (SEQ ID NO. 1; Pv1)
ADDQNPWRAYLDLLFPTDTLLLDLLWCG, (SEQ ID NO. 2; Pv2)
AEQNPIYWARYADWLFTTPLLLLDLALLVDADECG,
and (SEQ ID NO. 3; Pv3)
ADDQNPWRAYLDLLFPTDTLLLDLLWDADECG;

(SEQ ID NO. 4; Pv4)
Ac-AAEQNPIYWARYADWLFTTPLLLLDLALLVDADEGTKCG;
and (SEQ ID No. 5; Pv5)
AAEQNPIYWARYADWLFTTPLLLLDLALLVDADEGTC;
``` wherein $R^7$ is attached to Q through a cysteine residue of $R^7$.

In some embodiments, $R^7$ is a peptide comprising at least one of the following sequences:

```
                                    (SEQ ID NO. 1; Pv1)
ADDQNPWRAYLDLLFPTDTLLLDLLWCG, (SEQ ID NO. 2; Pv2)
AEQNPIYWARYADWLFTTPLLLLDLALLVDADECG,
and (SEQ ID NO. 3; Pv3)
ADDQNPWRAYLDLLFPTDTLLLDLLWDADECG,
``` wherein $R^7$ is attached to Q through a cysteine residue of $R^7$.

In some embodiments, $R^7$ is a peptide comprising the sequence

```
                                    (SEQ ID NO. 1; Pv1)
ADDQNPWRAYLDLLFPTDTLLLDLLWCG.
```

In some embodiments, $R^7$ is a peptide comprising the sequence

```
                                    (SEQ ID NO. 2; Pv2)
AEQNPIYWARYADWLFTTPLLLLDLALLVDADECG.
```

In some embodiments, $R^7$ is a peptide comprising the sequence

```
                                    (SEQ ID NO. 3; Pv3)
ADDQNPWRAYLDLLFPTDTLLLDLLWDADECG.
```

In some embodiments, $R^7$ is a peptide comprising the sequence

```
                                    (SEQ ID NO. 4; Pv4)
Ac-AAEQNPIYWARYADWLFTTPLLLLDLALLVDADEGTKCG.
```

In some embodiments, $R^7$ is a peptide comprising the sequence

```
                                    (SEQ ID NO. 5; Pv5)
AAEQNPIYWARYADWLFTTPLLLLDLALLVDADEGTC.
```

In some embodiments, $R^7$ is a peptide consisting of the sequence

```
                                    (SEQ ID NO. 1; Pv1)
ADDQNPWRAYLDLLFPTDTLLLDLLWCG.
```

In some embodiments, $R^7$ is a peptide consisting of the sequence

```
                                    (SEQ ID NO. 2; Pv2)
AEQNPIYWARYADWLFTTPLLLLDLALLVDADECG.
```

In some embodiments, $R^7$ is a peptide consisting of the sequence

```
                                    (SEQ ID NO. 3; Pv3)
ADDQNPWRAYLDLLFPTDTLLLDLLWDADECG.
```

In some embodiments, R⁷ is a peptide consisting of the sequence Ac—

AAEQNPIYWARYADWLFTTPLLLLDLALLVDADEGTKCG. (SEQ ID NO. 4; Pv4)

In some embodiments, R⁷ is a peptide consisting of the sequence

AAEQNPIYWARYADWLFTTPLLLLDLALLVDADEGTC. (SEQ ID NO. 5; Pv5)

In some embodiments, R⁷ is a peptide comprising at least one sequence selected from SEQ ID NO: 6 to SEQ ID NO: 311 as shown in Table 1.

In some embodiments, R⁷ is a peptide consisting of a sequence selected from SEQ ID NO: 6 to SEQ ID NO: 311 as shown in Table 1.

TABLE 1

Additional R⁷ Sequences

| SEQ ID NO. | Sequence |
|---|---|
| 6 | AAEQNPIYWWARYADWLFTTPLLLLDLALLVDADEGTCG |
| 7 | AEQNPIYWARYADWLFTTPLLLLDLALLVDADEGT |
| 8 | GGEQNPIYWARYADWLFTTPLLLLDLALLVDADEGT |
| 9 | AEQNPIYWARYADWLFTTPLLLLDLALLVDADEGT |
| 10 | AAEQNPIYWARYADWLFTTPLLLLDLALLVDADEGTCG |
| 11 | GGEQNPIYWARYADWLFTTPLLLLDLALLVDADEGTCG |
| 12 | ACEQNPIYWARYADWLFTTPLLLLDLALLVDADEGTG |
| 13 | ACEQNPIYWARYADWLFTTPLLLLDLALLVDADEGT |
| 14 | AKEQNPIYWARYADWLFTTPLLLLDLALLVDADEGT |
| 15 | AAEQNPIYWARYADWLFTTPLLLLDLALLVDADEGTKCG |
| 16 | AKEQNPIYWARYADWLFTTPLLLLDLALLVDADECT |
| 17 | ACEQNPIYWARYANWLFTTPLLLLNLALLVDADEGTG |
| 18 | ACEQNPIYWARYAKWLFTTPLLLLKLALLVDADEGTG |
| 19 | GGEQNPIYWARYADWLFTTPLLLLDLALLVNANQGT |
| 20 | AAEQNPIYWARYADWLFTTPLLLLALALLVDADEGT |
| 21 | AAEQNPIYWARYAAWLFTTPLLLLDLALLVDADEGT |
| 22 | AAEQNPIYWARYADWLFTTALLLLDLALLVDADEGT |
| 23 | AAEQNPIYWARYADWLFTTPLLLLELALLVDADEGT |
| 24 | AAEQNPIYWARYAEWLFTTPLLLLDLALLVDADEGT |
| 25 | AAEQNPIIYWARYADWLFTDLPLLLLDLLALLVDADEGT |
| 26 | GEQNPIYWAQYADWLFTTPLLLLDLALLVDADEGTCG |
| 27 | GGEQNPIYWARYADWLFTTPLLLDLLALLVDADEGTCG |
| 28 | GGEQNPIYWARYADWLFTTPLLLLDALLVDADEGTCG |
| 29 | GGEQNPIYWARYDAWLFTTPLLLLDLALLVDADEGTCG |
| 30 | GGEQNPIYWARYAWDLFTTPLLLLDLALLVDADEGTCG |

TABLE 1-continued

Additional R⁷ Sequences

| SEQ ID NO. | Sequence |
|---|---|
| 31 | AAEQNPIYWARYADWLFTTGLLLLDLALLVDADEGT |
| 32 | DDDEDNPIYWARYADWLFTTPLLLLHGALLVDADECT |
| 33 | DDDEDNPIYWARYAHWLFTTPLLLLHGALLVDADEGCT |
| 34 | DDDEDNPIYWARYAHWLFTTPLLLLHGALLVNADECT |
| 35 | DDDEDNPIYWARYAHWLFTTPLLLLHGALLVNANECT |
| 36 | AEQNPIYWARYADFLFTTPLLLLDLALLVDADET |
| 37 | AEQNPIYFARYADWLFTTPLLLLDLALLVDADEGT |
| 38 | AEQNPIYFARYADFLFTTPLLLLDLALLWDADET |
| 39 | AKEDQNPYWARYADWLFTTPLLLLDLALLVDG |
| 40 | ACEDQNPYWARYADWLFTTPLLLLDLALLVDG |
| 41 | AEDQNPYWARYADWLFTTPLLLLDLALLVDCG |
| 42 | AEDQNPYWARYADWLFTTPLLLLELALLVECG |
| 43 | AKEDQNPYWRAYADLFTPLTLLDLLALWDG |
| 44 | ACEDQNPYWRAYADLFTPLTLLDLLALWDG |
| 45 | ACDDQNPWRAYLDLLFPTDTLLLDLLW |
| 46 | TEDADVLLALDLLLLPTTFLWD |
| 47 | AEQNPIYWARYADWLFTTPL |
| 48 | AEQNPIYWARYADWLFTTPCL |
| 49 | ACEQNPIYWARYADWLFTTPL |
| 50 | AEQNPIYFARYADWLFTTPL |
| 51 | KEDQNPWARYADLLFPTTLAW |
| 52 | ACEDQNPWARYADLLFPTTLAW |
| 53 | ACEDQNPWARYADWLFPTTLLLLD |
| 54 | ACEEQNPWARYAELLFPTTLAW |
| 55 | ACEEQNPWARYAEWLFPTTLLLLE |
| 56 | ACEEQNPWARYLEWLFPTETLLLEL |
| 57 | GGEQNPIYWARYADWLFTTPLLLLLDLALLV DADEGT |
| 58 | ACEQNPIYWARYADWLFTTPLLLLLDLALLV |
| 59 | WARYADWLFTTPLLLLDLALLV DADEGTCG |
| 60 | WARYADWLFTTPLLLLDLALLV DADEGCT |
| 61 | GGEQNPIY WARYADWLFTTPLLLLDLALLV DADEGTCG |
| 62 | ACEQNPIY WARYADWLFTTPLLLLDLALLV DADEGT |
| 63 | AKEQNPIY WARYADWLFTTPLLLLDLALLV DADEGT |
| 64 | AKEQNPIY WARYADWLFTTPLLLLDLALLV DADECT |
| 65 | AAEQNPIY WARYADWLFTTALLLLDLALLV DADEGT |
| 66 | ACAEQNPIY WARYADWLFTTGLLLLDLALLV DADEGT |
| 67 | AEQNPIY WARYADFLFTTALLLLDLALLV DADE_T |

TABLE 1-continued

Additional R⁷ Sequences

| SEQ ID NO. | Sequence |
|---|---|
| 68 | AEQNPIY FARYADWLFTTPLLLLDLALLV DADEGT |
| 69 | AEQNPIY FARYADFLFTTPLLLLDLALLV DADE_T |
| 70 | AKEDQNP_Y WARYADWLFTTPLLLLDLALLV DG_— |
| 71 | ACEDQNP_Y WARYADWLFTTPLLLLDLALLV DG_— |
| 72 | AEDQNP_Y WARYADWLFTTPLLLLDLALLV DG_— |
| 73 | AEDQNP_Y WARYADWLFTTPLLLLELALLV ECG_— |
| 74 | AKEDQNP_Y WRAYAD_LFT_PLTLLDLLALW DG_— |
| 75 | ACEDQNP_Y WRAYAD_LFT_PLTLLDLLALW DG_— |
| 76 | AKEDQNDP_Y WARYADWLFTTPLLLLDLALLV G_— |
| 77 | TEDADVLLALDLLLLPTTFLWDAYRAWYPNQECA |
| 78 | GGEQNPIY WARYADWLFTTPLLLLLDLALLV DADEGT |
| 79 | AEQNPIY WARYADWLFTTPL |
| 80 | AEQNPIY WARYADWLFTTPCL |
| 81 | ACEQNPIY WARYADWLFTTPL |
| 82 | ACEQNPIY FARYADWLFTTPL |
| 83 | ACDDQNP WRAYLDLLFPTDTLLLDLLW |
| 84 | ACEEQNP WRAYLELLFPTETLLLELLW |
| 85 | ACDDQNP WARYLDWLFPTDTLLLDL |
| 86 | CDNNNP WRAYLDLLFPTDTLLLDW |
| 87 | ACEEQNP WARYLEWLFPTETLLLEL |
| 88 | ACEDQNP WARYADWLFPTTLLLLD |
| 89 | ACEEQNP WARYAEWLFPTTLLLLE |
| 90 | ACEDQNP WARYADLLFPTTLAW |
| 91 | ACEDQNP WARYAELLFPTTLW |
| 92 | KEDQNP WARYADLLFPTTLW |
| 93 | DDDEDNP IYWARYAHWLFTTPLLLLHGALLVDADECT |
| 94 | DDDEDNPIYWARYAHWLFTTPLLLLDGALLVDADECT |
| 95 | DDDEDNPIYWARYAHWLFTTPLLLLHGALLVNADECT |
| 96 | DDDEDNPIYWARYAHWLFTTPLLLLHGALLVNANECT |
| 97 | DDDEDNPIYWARYADWLFTTPLLLLHGALLVDADECT |
| 98 | ACEQNPIYWARYADWLFTTPLLLLDLALLVDADEGIG |
| 99 | ACEQNPIYWARYADWLFTTPLLLLDLALLVDADET |
| 100 | ACEQNPIYWARYADWLFTTPLLLLDLALLVDADEGT |
| 101 | GGEQNPIYWARYADWLFTTPLLLDLLALLVDADEGTCG |
| 102 | GGEQNPIYWARYADWLFTTPLLLLDALLVDADEGTCG |
| 103 | GGEQNPIYWARYAWDLFTTPLLLLDLALLVDADEGTCG |
| 104 | AAEQNPIYWARYAEWLFTTPLLLLDLALLVDADEGTCG |
| 105 | AAEQNPIYWARYAEWLFTTPLLLLELALLVDADEGTCG |
| 106 | GGEQNPIYWARYDAWLFTTPLLLLDLALLVDADEGTCG |
| 107 | GGEQNPIYWAQYDAWLFTTPLLLLDLALLVDADEGTCG |
| 108 | GGEQNPIYWAQDYAWLFTTPLLLLDLALLVDADEGTCG |
| 109 | AAEQNPIYWARYAAWLFTTPLLLLDLALLVDADEGTCG |
| 110 | ACEQNPIYWARYANWLFTTPLLLLNLALLVDADEGTG |
| 111 | DDDEDNPIYWARYAHWLFTTPLLLLHGALLVNANECT |
| 112 | DDDEDNPIYWARYAHWLFTTPLLLLHGALLVNADECT |
| 113 | DDDEDNPIYWARYADWLFTTPLLLLLHGALLVDADECT |
| 114 | DDDEDNPIYWARYAHWLFTTPLLLLHGALLVDADECT |
| 115 | DDDEDNPIYWARYAHWLFTTPLLLLLDGALLVDADECT |
| 116 | GGEQNPIYWARYADWLFTTPLLLLDLALLVNANQGT |
| 117 | AAEQNPIYWARYADWLFTTPLLLLELALLVDADEGTCG |
| 118 | AAEQNPIYWARYAEWLFTTPLLLLELALLVDADEGTCG |
| 119 | AAEQNPIYWARYADWLFTTPLLLLELALLVDADEGTKCG |
| 120 | GGEQNPIYWAQYADWLFTTPLLLLDLALLVDADEGTCG |
| 121 | GGEQNPIYWAQYDAWLFTTPLLLLDLALLVDADEGTCG |
| 122 | GGEQNPIYWAQDYAWLFTTPLLLLDLALLVDADEGTCG |
| 123 | GGEQNPIYWARYADWLFTTPLLLDALLVNANQGT |
| 124 | DDDEDNPIYWARYAHWLFTTPLLLLHGALLVNADECT |
| 125 | DDDEDNPIYWARYAHWLFTTPLLLLHGALLVNANECT |
| 126 | ACEQNPIYWARYAKWLFTTPLLLLKLALLVDADEGTG |
| 127 | GGEQNPIYWAQDYAWLFTTPLLLLLDLALLVDADEGTCG |
| 128 | GGEQNPIYWAQYDAWLFTTPLLLLDLALLVDADEGTCG |
| 129 | GGEQNPIYWAQYDAWLFTTPLLLLDLALLVDADEGTCG |
| 130 | AAEQNPIYWARYAAWLFTTPLLLLDLALLVDADEGTCG |
| 131 | AAEQNPIYWARYADWLFTDLPLLLLDLLALLVDADEGT |
| 132 | GGEQNPIYWARYADWLFTTPLLLLLLDALLVDADEGTCG |
| 133 | GGEQNPIYWARYADWLFTTPLLLLDLLALLVDADEGTCG |
| 134 | AAEQNPIYWARYADWLFTTGLLLLDLALLVDADEGT |
| 135 | AEQNPIYWARYAAWLFTTPLLLLDLALLVDADEGTCG |
| 136 | GGEQNPIYWAQYDAWLFTTPLLLLDLALLVDADEGTCG |
| 137 | GGEQNPIYWAQDYAWLFTTPLLLLLDLALLDADEGTCG |
| 138 | GGEQNPIYWARYDAWLFTTPLLLLLDLALLVDADEGTCG |
| 139 | AAEQNPIYWARYADWLFTTPLLLLALALLVDADEGTCG |
| 140 | AAEQNPIYWARYADWLFTTPLLLLDLALLVDADEGTKCG.........EGTK(rhodamine)C(phalloidin)G |
| 141 | AAEQNPIYWARYADWLFTTPLLLLELALLDADEGTKCG |

TABLE 1-continued

Additional R⁷ Sequences

| SEQ ID NO. | Sequence |
|---|---|
| 142 | AAEQNPIYWARYADWLFTTPLLLLDLALLVDADEGTCG |
| 143 | AAEQNPIYWARYADWLFTTPLLLLDLALLVDADEGTC(phalloidin)G |
| 144 | GGEQNPIYWARYADWLFTTPLLLLDLALLVDADEGTCG |
| 145 | ACEQNPIYWARYADWLFTTPLLLLDLALLVDADET |
| 146 | ACEQNPIYWARYADWLFTTPLLLLDLALLVDADEGTG |
| 147 | ACEQNPIYWARYADWLFTTPLLLLDLALLVDADEGT |
| 148 | GGEQNPIYWARYADWLFTTPLLLLDLALLVNANQGT |
| 149 | DDDEDNPIYWARYAHWLFTTPLLLLHGALLVNADECT |
| 150 | DDDEDNPIYWARYAHWLFTTPLLLLHGALLVNANECT |
| 151 | GGEQNPIYWARYADWLFTTPLLLLDLALLVDADEGTCG |
| 152 | AAEQNPIYWARYADWLFTTPLLLLDLALLVDADEGTC(phalloidin)G |
| 153 | AAEQNPIYWARYADWLFTTPLLLLELALLVDADEGTKCG |
| 154 | AAEQNPIYWARYADWLFTTPLLLLDLALLVDADEGTKCG |
| 155 | DDDEDNPIYWARYAHWLFTTPLLLLBGALLVDADECT |
| 156 | DDDEDNPIYWARYAHWLFTTPLLLLDGALLVDADECT |
| 157 | DDDEDNPIYWARYAHWLFTTPLLLLBGALLVNADECT |
| 158 | DDDEDNPIYWARYAHWLFTTPLLLLBGALLVNANECT |
| 159 | DDDEDNPIYWARYADWLFTTPLLLLIBGALLVDADECT |
| 160 | DDDEDNPIYWARYADWTFTTPLLLLHGALLVDADECT |
| 161 | DDDEDNPIYWARYAHWLFTTPLLLLDGALLVDADECT |
| 162 | DDDEDNPIYWARYAHWLFTTPLLLLHGALLVDADECT |
| 163 | DDDEDNPIYWARYAHWLFTTPLLLLHGALLVNADECT |
| 164 | DDDEDNPIYWARYHWLFTTPLLLLHGALLVNANECT |
| 165 | DDDEDNPIYWARYAHWLFTTPLLLLHGALLVNANECT |
| 166 | DDDEDNPIYWARYAHWLFTTPLLLLHGALLVNADECT |
| 167 | DDDEDNPIYWARYADWLFTTPLLLLDGALLVDADECT |
| 168 | DDDEDNPIYWARYAHWLFTTPLLLLHGALLVDADECT |
| 169 | DDDEDNPIYWARYAHWLFTTPLLLLDGALLVDADECT |
| 170 | GGEQNPIYWARYADWLFTTPLLLLDLALLVNANQGT |
| 171 | DDDEDNPIYWARYAHWLFTTPLLLLHGALLVNADECT |
| 172 | DDDEDNPIYWARYAHWLFTTPLLLLHGALLVDADECT |
| 173 | DDDEDNPIYWARYAHWLFTTPLLLLHGALLVDADECT |
| 174 | DDDEDNPIYWARYAHMLFTTPLLLLDGALLVDADECT |
| 175 | DDDEDNPIYWARYAHWLFTTPLLLLHGALLVNANECT |
| 176 | DDDEDNPIYWARYAHWLFTTPLLLLDGALLVDADECT |
| 177 | DDDEDNPIYWARYADWLFTTPLLLLHGALLVDADECT |
| 178 | DDDEDNPIYWARYAHWLFTTPLLLLHGALLVDADECT |
| 179 | DDDEDNPIYWARYAHWLFTTPLLLLHGALLVNADECT |
| 180 | DDDEDNPIYWARYAHWLFTTPLLLLHGALLVNANECT |
| 181 | AAEQNPIYWARYADWLFTTGLLLLDLALLVDADEGT |
| 182 | GGEQNPIYWARYAWDLFTTPLLLLDLALLVDADEGTCG |
| 183 | GGEQNPIYWARYDAWLFTTPLLLLDLALLVDADEGTCG |
| 184 | GGEQNPIYWAQYDAWLFTTPLLLLDLALLVDADEGTCG |
| 185 | GGEQNPIYWAQDYAWLFTTPLLLLDLALLVDADEGTCG |
| 186 | AAEQNPIYWARYAAWLFTTPLLLLDLALLVDADEGTCG |
| 187 | GGEQNPIYWARYADWLFTTPLLLLDALLVDADEGTCG |
| 188 | GGEQNPIYWARYADWLFTTPLLLDLLALLVDADEGTCG |
| 189 | GGEQNPIYWARYADWLFTTPLLLDLLALLVDADEGTCG |
| 190 | GGEQNPIYWARYADWLFTTPLLLLLDALLVDADEGTCG |
| 191 | GGEQNPIYWAQYADWLFTTPLLLLDLALLVDADEGTCG |
| 192 | GGEQNPIYWAQDYAWLFTTPLLLLDLALLVDADEGTCG |
| 193 | GGEQNPIYWAQDYAWLFTTPLLLLDLALLVDADEGTCG |
| 194 | GGEQNPIYWAQYDAWLFTTPLLLLDLALLVDADEGTCG |
| 195 | GGEQNPIYWAQDYAWLFTTPLLLLDLALLVDADEGTCG |
| 196 | GGEQNPIYWAQYDAWLFTTPLLLLDLALLVDADEGTCG |
| 197 | AAEQNPIYWARYAAWLFTTPLLLLLDLALLVDADEGTCG |
| 198 | GGEQNPIYWAQDYAWLFTTPLLLLDLALLVDADEGTCG |
| 199 | GGEQNPIYWAQYDAWLFTTPLLLLDLALLVDADEGTCG |
| 200 | GGEQNPIYWAQYADWLFTTPLLLLDLALLVDADEGTCG |
| 201 | AAEQNPIYWARYAAWLFTTPLLLLDLALLVDADEGTCG |
| 202 | AAEQNPIYWARYADWLFTTPLLLLELALLVDADEGTKCG |
| 203 | ..............EGTK(rhidamine)C(phalloidin)G |
| 204 | AAEQNPIYWARYADWLFTTPLLLLDLALLVDADEGTKCG |
| 205 | ACEQNPIYWARYADWLFTTPLLLLDLALLVDADEGTG |
| 206 | AAEQNPIYWARYADWLFTTPLLLLDLALLVDADEGTC(phalloidin)G |
| 207 | AAEQNPIYWARYADWLFTTPLLLLDLALLVDADEGTKCG |
| 208 | AAEQNPIYWARYADWLFTTPLLLLELALLVDADEGTKCG |
| 209 | AAEQNPIYWARYADWLFTDLPLLLLDLLALLVDADEGT |
| 210 | AAEQNPIYWARYAAWLFTTPLLLLDLALLVDADEGTCG |
| 211 | GGEQNPIYWAQYDAWLFTTPLLLLDLALLVDADEGTCG |
| 212 | GGEQNPIYWAQDYAWLFTTPLLLLDLALLVDADEGTCG |
| 213 | GGEQNPIYWARYDAWLFTTPLLLLDLALLVDADEGTCG |

TABLE 1-continued

Additional R⁷ Sequences

| SEQ ID NO. | Sequence |
|---|---|
| 214 | AAEQNPIYWARYAEWLFTTPLLLLDLALLVDADEGTCG |
| 215 | AAEQNPIYWARYAEWLFTTPLLLLELALLVDADEGTCG |
| 216 | AAEQNPIYWARYADWLFTTPLLLLALALLVDADEGTCG |
| 217 | AAEQNPIYWARYADWLFTTPLLLLELALLVDADEGTCG |
| 218 | AAEQNPIYWARYAEWLFTTPLLLLELALLVDADEGTCG |
| 219 | AAEQNPIYWARYADWLFTTPLLLLELALLVDADEGTKCG |
| 220 | ACEQNPIYWARYAKWLFTTPLLLLKLALLVDADEGTG |
| 221 | ACEQNPIYWARYANWLFTTPLLLLNLALLVDADEGTG |
| 222 | AAEQNPIYWARYADWLFTTALLLLDLALLVDADEGT |
| 223 | AEQNPIYFARYADLLFPTTLAW |
| 224 | AEQNPIYWARYADLLFPTTLAF |
| 225 | AEQNPIYWARYADLLFPTTLAW |
| 226 | ACEQNPIYWARYADWLFTTPLLLLDLALLVDADET |
| 227 | GGEQNPIYWARYADWLFTTPLLLLDLALLVDADEGT |
| 228 | AAEQNPIYWARYADWLFTTPLLLLDLALLVDADEGTCG |
| 229 | AAEQNPIYWARYADWLFTTPLLLLDLALLVDADEGTKCG |
| 230 | AKEQNPIYWARYADWLFTTPLLLLDLALLVDADECT |
| 231 | CCTCTTACCTCAGTTACA |
| 232 | D-Arg8 D-Arg8-CCTCTTACCTCAGTTACA |
| 233 | D-Lys4 D-Lys4-CCTCTTACCTCAGTTACA |
| 234 | S-S-CCTCTTACCTCAGTTACA |
| 235 | S-S-CCTCTGACCTCATTTACA |
| 236 | D-Arg8-Deca D-Arg8-Deca-CCTCTTACCTCAGTTACA |
| 237 | D-Arg8-Deca-mismatch D-Arg8-Deca-CCTCTGACCTCATTTACA |
| 238 | S-S-CCTCTTACCTCAGTTACA |
| 239 | AAEQNPIYWARYADWLFTTPLLLLDLALLVDADEGTCG |
| 240 | AEDQNPYWARYDWLFTTPLLLLDLALLVDCG |
| 241 | AEDQNPYWARYADWLFTTPLLLLELALLVECG |
| 242 | AEQNPIYWARYADWLFTTPLLLLDLALLVDADEGCT |
| 243 | ACEQNPIYWARYADWLFTTPLLLLDLALLVDADET |
| 244 | AE-QN-PI YWARYADWLFTTPLLLLDLALLV DADEGT-COOH |
| 245 | AEDQN-P-YWARYADWLFTTPLLLLDLALLV D---G--COOH |
| 246 | AEDQNDP-YWARYADWLFTTPLLLLDLALLV----G--COOH |
| 247 | AEQNPI YWARYADFLFTTPLLLLDLALLV DADET-COOH |
| 248 | AEQNPI YFARYADWLFTTPLLLLDLALLV DADET-COOH |
| 249 | AEQNPI YFARYADFLFTTPLLLLDLALLW DADET-COOH |
| 250 | AE-QN-PI YWARYADWLFTTPLLLLDLALLV DADEGCT-COOH |
| 251 | AEDQN-PI YWARYADWLFTTPLLLLDLALLV DC--G-T-COOH |
| 252 | AEDQNDPI YWARYADWLFTTPLLLLELALLV EC--G-T-COOH |
| 253 | Chelate-ACEEQNPWARYLEWLFPTETLLLEL |
| 254 | AEQNPIY WARYADWLFTTPLLLLDLALLV DADEGT-COOH |
| 255 | AKEDQNPY WARYADWLFTTPLLLLDLALLV DG-COOH |
| 256 | AKEDQNDPY WARYADWLFTTPLLLLDLALLV G-COOH |
| 257 | AEQNPI YWARYADWLFTTPLLLLDLALLV DADEGC-Biotin-T-COOH |
| 258 | AEDQNP YWARYADWLFTTPLLLLDLALLV DC-Biotin-G-COOH |
| 259 | AEDQNP YWARYADWLFTTPLLLLELALLV EC-Biotin-G-COOH |
| 260 | ACEQNPIY WARYADWLFTTPLLLLDLALLV DADEGT |
| 261 | ACEDQNPY WARYADWLFTTPLLLLLDLALLV DG |
| 262 | ACEDQNPY WRAYADLFTPLTLLDLLALW DG |
| 263 | ACDDQNP WRAYLDLLFPTDTLLLDLLW |
| 264 | WRAYLELLFPTETLLLELLW |
| 265 | WARYLDWLFPTDTLLLDL |
| 266 | WRAYLDLLFPTDTLLLDW |
| 267 | WARYLEWLFPTETLLLEL |
| 268 | WAQYLELLFPTETLLLEW |
| 269 | WRAYLELLFPTETLLLEW |
| 270 | WARYADWLFPTTLLLLD |
| 271 | WARYAEWLFPTTLLLLE |
| 272 | ACEDQNP WARYADLLFPTTLAW |
| 273 | ACEEQNP WARYAELLFPTTLAW |
| 274 | Ac-TEDAD VLLALDLLLLPTTFLWDAYRAW YPNQECA-Am |
| 275 | CDDDDDNPNY WARYANWLFTTPLLLLNGALLV EAEET |
| 276 | CDDDDDNPNY WARYAPWLFTTPLLLLPGALLV EAEET |
| 277 | Ac-AEQNPIYWARYADWLFTTPLLLLDLALLVDADEGCT |
| 278 | Ac-AKEQNPIYWARYADWLFTTPLLLLDLALLVDADEGTG |
| 279 | ACEQNPIYWARYANWLFTTPLLLLNLALLVDADEGT |
| 280 | Ac-AAEQNPIYWARYADWLFTTPLLLLELALLVDADEGTKCG |
| 281 | DDDEDNPIYWARYADWLFTTPLLLLHGALLVDADET |
| 282 | CDDDEDNPIYWARYAHWLFTTPLLLLHGALLVDADET |

TABLE 1-continued

Additional R⁷ Sequences

| SEQ ID NO. | Sequence |
|---|---|
| 283 | DDDEDNPIYWARYAHWLFTTPLLLLHGALLVDADEGT |
| 284 | DDDEDNPIYWARYAHWLFTTPLLLLHGALLVNADEGT |
| 285 | DDDEDNPIYWARYAHWLFTTPLLLLHGALLVNANEGT |
| 286 | AKEDQNDPYWARYADWLFTTPLLLLDLALLVG |
| 287 | AEDQNPYWARYADWLFTTPLLLLELALLVCG |
| 288 | AKDDQNPWRAYLDLLFPTDTLLLDLLWC |
| 289 | ACEEQNPWRAYLELLFPTETLLLELLW |
| 290 | ACDDQNPWARYLDWLFPTDTLLLDL |
| 291 | CDNNNPWRAYLDLLFPTDTLLLDW |
| 292 | CEEQQPWAQYLELLFPTETLLLEW |
| 293 | EEQQPWRAYLELLFPTETLLLEW |
| 294 | CDDDDDNPNYWARYANWLFTTPLLLLNGALLVEAEET |
| 295 | CDDDDDNPNYWARYAPWLFTTPLLLLPGALLVEAEE |
| 296 | AEQNPIYFARYADLLFPTTLAW |
| 297 | AEQNPIYWARYADLLFPTTLAF |
| 298 | AEQNPIYWARYADLLFPTTLAW |
| 299 | KEDQNPWARYADLLFPTTLW |
| 300 | ACEEQNPQAEYAEWLFPTTLLLLE |
| 301 | AAEEQNPWARYLEWLFPTETLLLEL |
| 302 | AKEEQNPWARYLEWLFPTETLLLEL |
| 303 | AAEQNPIYWARYADWLFTTPLLLLDLALLVDADEGTGG |
| 304 | XXEXNPIYWAXXXXXLFTXXLLLXXXALLVXAXXXTXG |
| 305 | DAAEQNPIYWARYADWLFTTLPLLLLDLLALLVDADEGTKGG |
| 306 | GGEQNPIYWARYADWLFTTPLLLLDLALLVDADEGTGG |
| 307 | XXEXNPIYWAXXXXXLFTXXLLLXXXALLVXAXXXTGG |
| 308 | DGGEQNDPIYWARYADWLFTTLPLLLLDLLALL VDADEGCTXGG |
| 309 | AAEQNPIYWARYADWLFTTPLLLLDLALLVDADEGTCG |
| 310 | AEDQNPYWARYDWLFTTPLLLLDLALLVDCG |
| 311 | GLAGLAGLLGLEGLLGLPLGLLEGLWLGLELEGN |

In some embodiments, $R^7$ is a peptide having 10 to 50 amino acids. In some embodiments, $R^7$ is a peptide having 20 to 40 amino acids. In some embodiments, $R^7$ is a peptide having 20 to 40 amino acids. In some embodiments, $R^7$ is a peptide having 10 to 20 amino acids. In some embodiments, $R^7$ is a peptide having 20 to 30 amino acids. In some embodiments, $R^7$ is a peptide having 30 to 40 amino acids.

Suitable therapeutic molecules (e.g., $R^8$) for use in the invention include those which have undesirable side effects when delivered systemically because of their possible deleterious effect on normal tissue. Example therapeutic molecules are DNA repair inhibiting compounds such as inhibitors of PARP, ATR, DNK-PK, and ATM. Such DNA repair inhibiting compound are useful for treatment of cancer and other diseases in which inhibition of DNA repair would be desirable.

Three PARP inhibitors (olaparib, rucaparib, and niraparib) are currently commercially available and others are in development, such as AG-014699 (Agouron/Pfizer), KU-0059436 (KuDOS/AstraZeneca), INO-1001 (Inotek/Genentech), NT-125 (now E-7449; Eisai; 3H-Pyridazino[3,4,5-de]quinazolin-3-one, 8-[(1,3-dihydro-2H-isoindol-2-yl)methyl]-1,2-dihydro-), 2×-121 (2× Oncology; 3H-pyridazino[3,4,5-de]quinazolin-3-one, 8-[(1,3-dihydro-2H-isoindol-2-yl)methyl]-1,2-dihydro-), and ABT-888 (Abbvie). PARP inhibitors are disclosed in (for example) U.S. Pat. Nos. 6,100,283; 6,310,082; 6,495,541; 6,548,494; 6,696,437; 7,151,102; 7,196,085; 7,449,464; 7,692,006; 7,781,596; 8,067,613; 8,071,623; and 8,697,736, which patents are incorporated herein by reference in their entirety.

In some embodiments, $R^1$ and $R^2$ are each independently selected from H and methyl, and $R^3$, $R^4$, $R^5$, and $R^6$ are each hydrogen.

In some embodiments, $R^1$ and $R^2$ are each independently selected from H and methyl.

In some embodiments, $R^1$ and $R^2$ are each H.

In some embodiments, $R^3$ and $R^4$ are each H.

In some embodiments, $R^5$ and $R^6$ are each H.

In some embodiments, $R^9$, $R^{10}$, $R^{11}$, and $R^{12}$ are each independently selected from H and methyl.

In some embodiments, the enzyme capable of cleaving [AA]x is Cathepsin B, matrix-metalloproteinases (MMP), DPPIV, glycoprotein, peptidase, or caspase. In some embodiments, [AA]x is a peptide having two to twelve (x is 2 to 12) amino acid (AA) residues. In some embodiments, [AA]x is a peptide having two to ten (x is 2 to 10) amino acid (AA) residues. In some embodiments, [AA]x is a peptide having two to five (x is 2 to 5) amino acid (AA) residues. In some embodiments, [AA]x is a peptide having six to nine (x is 6 to 9) amino acid (AA) residues. In some embodiments, [AA]x is a peptide having three to eight (x is 3 to 8) amino acid (AA) residues.

Peptide linkers (e.g., [AA]x) that are capable of being cleaved by proteins are described in Yang, Y., Acta Pharmaceutica Sinica B 2011, 1(3), 143-159; Choi, K., Theranostics 2012, 2, 156-178; and Anderson, C., Ind. Eng. Chem. Res. 2017, 56, 4761-5777.

Peptide linkers (e.g., [AA]x) that are capable of being cleaved by DPPIV are described in Diez-Torrubia, A., J. Med. Chem. 2010, 53, 559-572; Garcia-Aparicio, C., J. Med. Chem. 2006, 49, 5339-5351; Diez-Torrubia, A., ChemMedChem 2012, 7, 618-628; Dahan, A., Mol. Pharmaceutics 2014, 11, 4385-4394; Wickstrom, M., Oncotarget 2017, 8, 66641-66655; and Simplicio, A. L., Molecules, 2008, 13, 519-547.

Peptide linkers (e.g., [AA]x) that are capable of bring cleaved by cathepsin B are described in Caculitan, N., Cancer Res. 2017, 77(24), 7027-7037; Zhong, Y-J, International Journal of Oncology 2013, 42, 373-383; and Fan, P., Drug Metabolism and Disposition 2016, 44, 1253-1261.

Peptide linkers (e.g., [AA]x) that are capable of bring cleaved by MMP (e.g., MMP-9) are described in Kalafatovic, D., Biomaterials 98 (2016), 192-202; Kim, H S, Gene Therapy 2013, 20, 378-385; and Yao, W., Trends in Pharmacological Sciences 2018, 39, 766-781.

In some embodiments, [AA]x is -Pro_Gly-; -Val_Cit-, -Gly_Pro_Leu_Gly_Leu_Ala_Gly_Asp_Asp-, -Gly_Pro_GLeu_Gly_Val_Arg_Gly, or -Ser_Ser_Lys_Leu_Gly-.

In some embodiments, S1 is a group having the following structure:

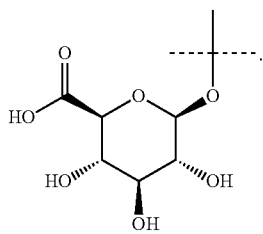

In some embodiments, S1 is a group having the following structure:

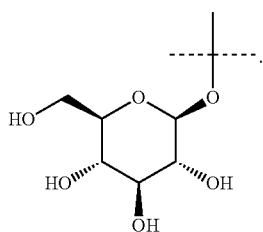

The S1 group can be a carbohydrate that can be cleaved by glucuronidase. Such carbohydrate groups are used in the art as glucuronide prodrugs, and are described in Grinda, M. Med. Chem. Commun. 2012, 3, 68-70; Herceg, V., Biorganic Chemistry 2018, 78, 372-380; Adiyala P., Bioorganic Chemistry 2018, 76, 288-293; and Kolakowski, R., Angew. Chem. Int. Ed. 2016, 55, 7948-7951.

Also provided herein is a compound of formula (I)

R8-Q-R7     (I)

and the pharmaceutically acceptable salts thereof, wherein $R^8$ is a member selected from the group consisting of:

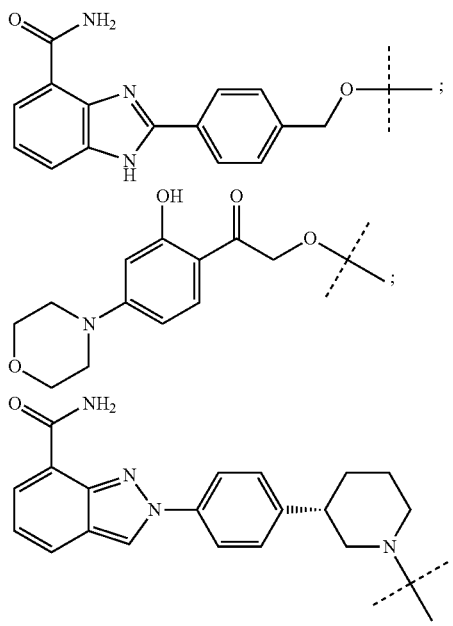

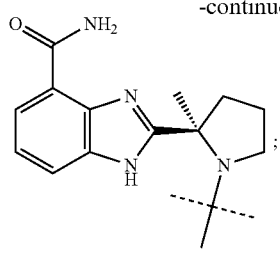

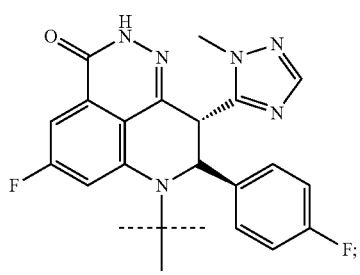

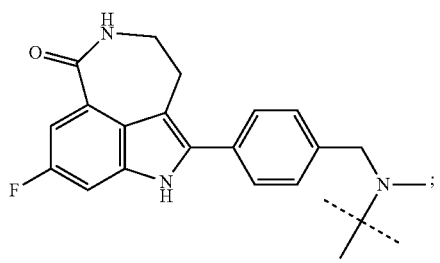

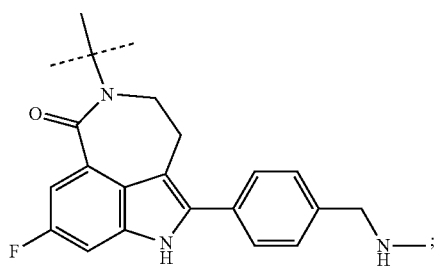

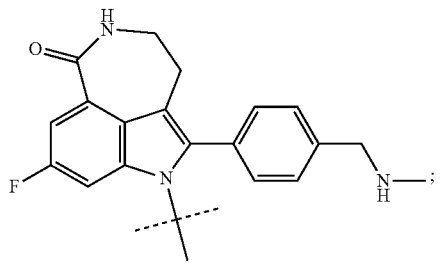

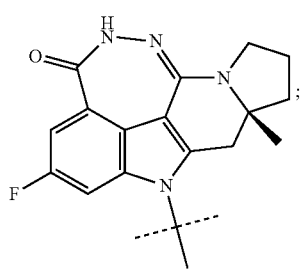

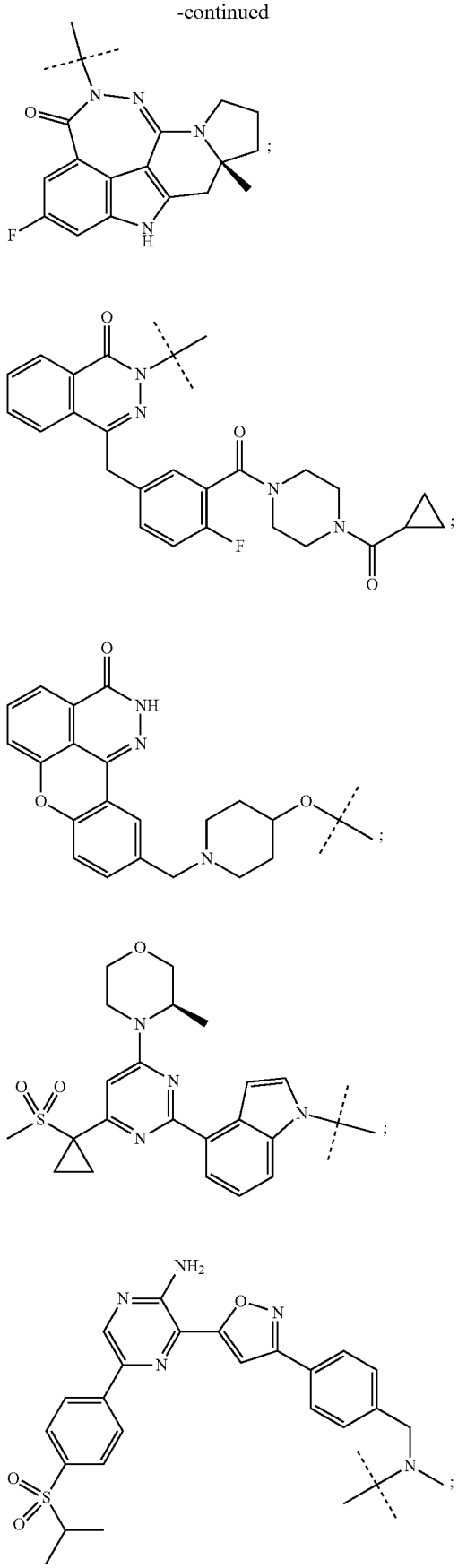
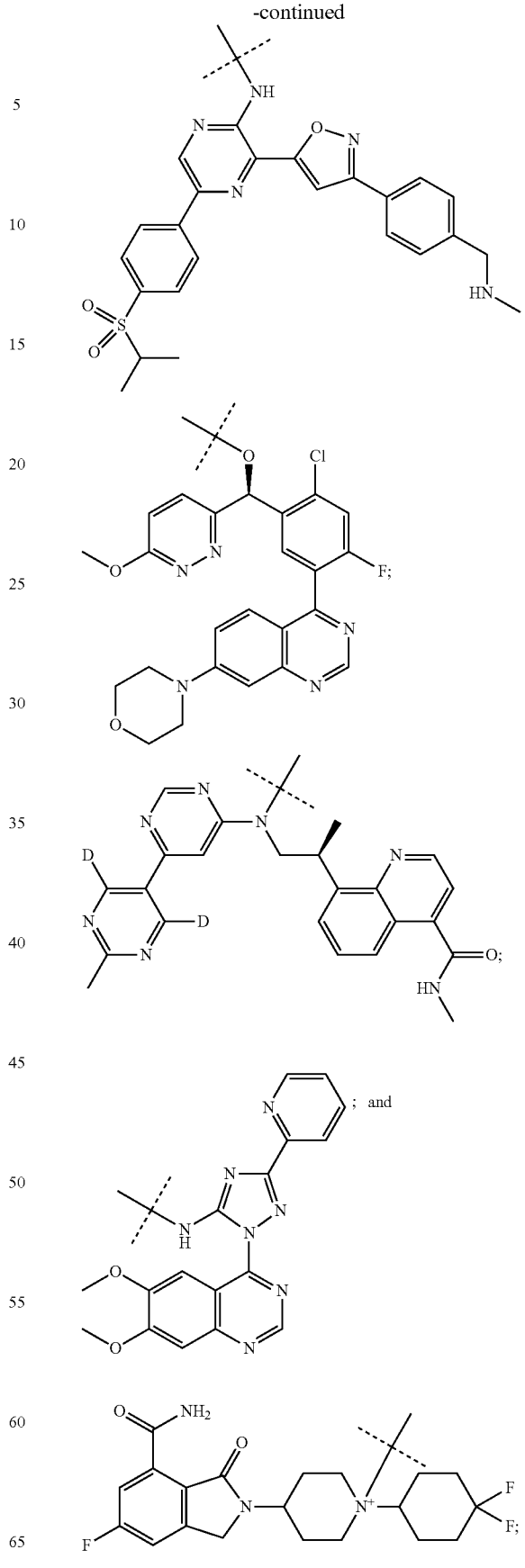

Q is a member selected from the group consisting of

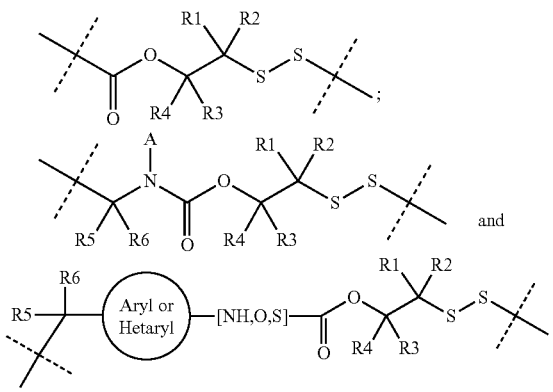

wherein $R^1$, $R^2$, $R^3$, $R^4$, $R^5$, and $R^6$ are independently selected from H, optionally substituted $C_1$-$C_4$ alkyl, optionally substituted $C_1$-$C_4$ alkenyl, optionally substituted $C_1$-$C_4$ alkoxy, amino optionally substituted with one or two $C_1$-$C_4$ alkyl substituents, halo, nitro or hydroxyl, and wherein [NH,O,S} means a linking NH, O, or S moiety, and $R^7$ is a peptide capable of selectively delivering $R^8Q$ across a cell membrane having an acidic or hypoxic mantle in a pH dependent fashion.

In some embodiments, $R^7$ is a member selected from the group consisting of

```
                                    (SEQ ID NO. 1; Pv1)
ADDQNPWRAYLDLLFPTDTLLLDLLWCG, (SEQ ID NO. 2; Pv2)
AEQNPIYWARYADWLFTTPLLLLDLALLVDADECG,
and (SEQ ID NO. 3; Pv3)
ADDQNPWRAYLDLLFPTDTLLLDLLWDADECG,
``` wherein $R^7$ and Q are attached through a cysteine residue.

In some embodiments, $R^1$ and $R^2$ are each independently selected from H and methyl and $R^3$, $R^4$, $R^5$, and $R^6$ are each hydrogen.

In some embodiments, $R^7$ is ADDQNPWRAYLDLL-FPTDTLLLDLLWCG (SEQ ID NO. 1; Pv1).

In some embodiments, $R^7$ is AEQNPIYWARY-ADWLFTTPLLLLDLALLVDADECG (SEQ ID NO. 2; Pv2).

In some embodiments, $R^7$ is ADDQNPWRAYLDLL-FPTDTLLLDLLWDADECG (SEQ ID NO. 3; Pv3).

In some embodiments, the compound of formula (I) is selected from:

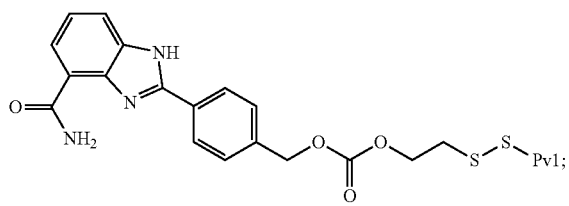

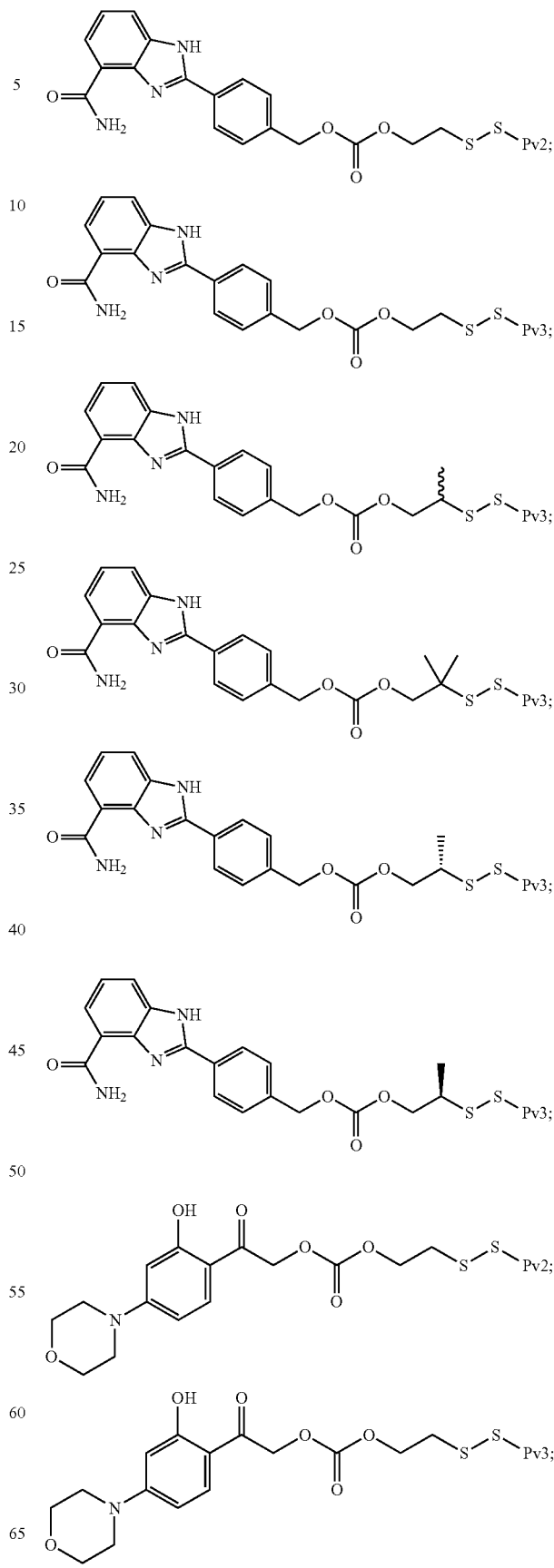

-continued

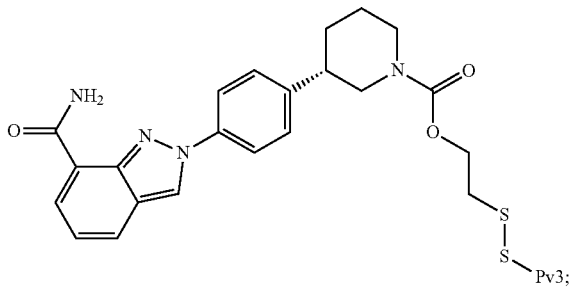

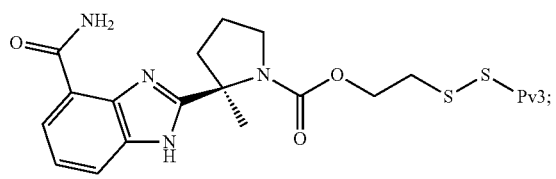

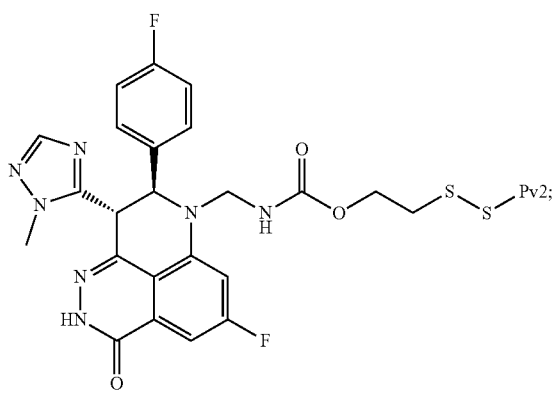

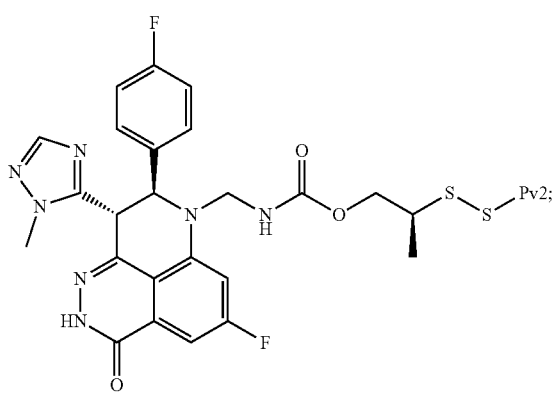

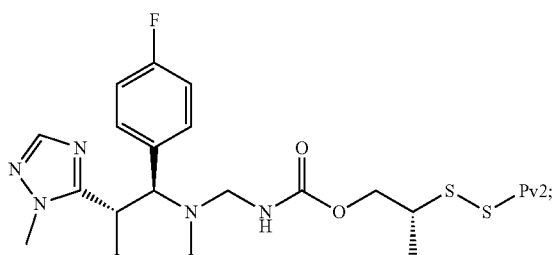

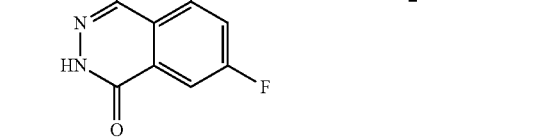

-continued

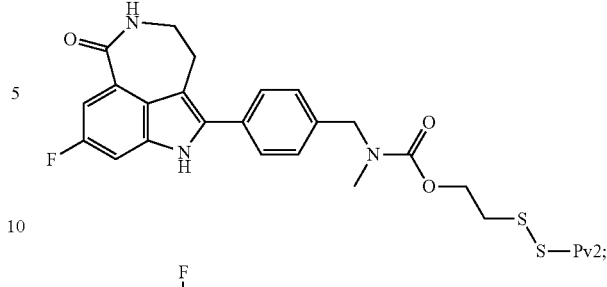

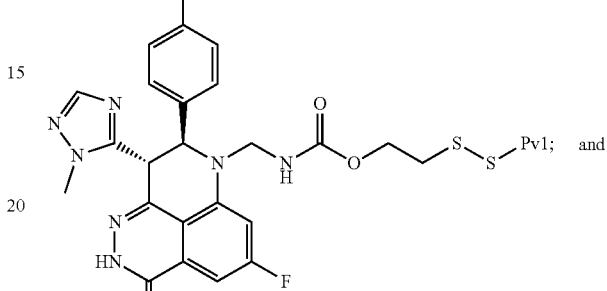

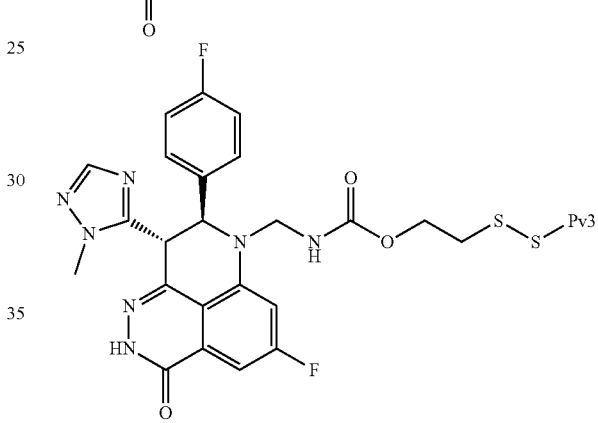

The molecules of the invention can be tagged, for example, with a probe such as a fluorophore, radioisotope, and the like. In some embodiments, the probe is a fluorescent probe, such as LICOR. A fluorescent probe can include any moiety that can re-emit light upon light excitation (e.g., a fluorophore).

The Amino acids are represented by the IUPAC abbreviations, as follows: Alanine (Ala; A), Arginine (Arg; R), Asparagine (Asn; N), Aspartic acid (Asp; D), Cysteine (Cys; C), Glutamine (Gln; Q), Glutamic acid (Glu; E), Glycine (Gly; G), Histidine (His; H), Isoleucine (Ile; I), Leucine (Leu; L), Lysine (Lys; K), Methionine (Met; M), Phenylalanine (Phe; F), Proline (Pro; P), Serine (Ser; S), Threonine (Thr; T), Tryptophan (Trp; W), Tyrosine (Tyr; Y), Valine (Val; V). The term "Pv1" means ADDQNPWRAYLDLL-FPTDTLLLDLLWCG, which is the peptide of SEQ ID No. 1. The term "Pv2" means AEQNPIYWARY-ADWLFTTPLLLLDLALLVDADECG, which is the peptide of SEQ ID No. 2. The term "Pv3" means ADDQNP-WRAYLDLLFPTDTLLLDLLWDADECG, which is the peptide of SEQ ID No. 3. The term "Pv4" means Ac-AAEQNPIYWARYADWLFTTPLLLLDLALLVDADE-GTKCG, which is the peptide of SEQ ID NO. 4. The term "Pv5" means AAEQNPIYWARYADWLFTTPLLLLD-LALLVDADEGTC, which is the peptide of SEQ ID NO. 5. In the compounds of the invention, the peptides $R^7$ are attached to the disulfide linker by the cysteine moiety.

The term "acidic and/or hypoxic mantle" refers to the environment of the cell in the diseased tissue in question having a pH lower than 7.0 and preferably lower than 6.5. An acidic or hypoxic mantle more preferably has a pH of about 5.5 and most preferably has a pH of about 5.0. The compounds of formula (I) insert across a cell membrane having an acidic and/or hypoxic mantle in a pH dependent fashion to insert $R^8Q$ into the cell, whereupon the disulfide linker is cleaved to deliver free $R^8H$. Since the compounds of formula (I) are pH-dependent, they preferentially insert across a cell membrane only in the presence of an acidic or hypoxic mantle surrounding the cell and not across the cell membrane of "normal" cells, which do not have an acidic or hypoxic mantle.

The terms "pH-sensitive" or "pH-dependent" as used herein to refer to the peptide $R_7$ or to the mode of insertion of the peptide $R^7$ or of the compounds of the invention across a cell membrane, means that the peptide has a higher affinity to a cell membrane lipid bilayer having an acidic or hypoxic mantle than a membrane lipid bilayer at neutral pH. Thus, the compounds of the invention preferentially insert through the cell membrane to insert $R^8Q$ to the interior of the cell (and thus deliver $R^8H$ as described above) when the cell membrane lipid bilayer has an acidic or hypoxic mantle (a "diseased" cell) but does not insert through a cell membrane when the mantle (the environment of the cell membrane lipid bilayer) is not acidic or hypoxic (a "normal" cell). It is believed that this preferential insertion is achieved as a result of the peptide $R^7$ forming a helical configuration, which facilitates membrane insertion.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "amino" refers to a group of formula —NH$_2$.

The term "carbonyl", employed alone or in combination with other terms, refers to a —C(=O)— group, which also may be written as C(O).

The term "cyano" or "nitrile" refers to a group of formula —CN, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring.

A five-membered heteroaryl ring is a heteroaryl group having five ring atoms wherein one or more (e.g., 1, 2 or 3) ring atoms are independently selected from N, O and S.

A six-membered heteroaryl ring is a heteroaryl group having six ring atoms wherein one or more (e.g., 1, 2 or 3) ring atoms are independently selected from N, O and S.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2pyrrolidinyl; morpholinul; azetidinyl; and piperazinyl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in Remington's Pharmaceutical Sciences, 17$^{th}$ Ed., (Mack Publishing Company, Easton, 1985), p. 1418, Berge et al., J. Pharm. Sci., 1977, 66(1), 1-19 and in Stahl et al., Handbook of Pharmaceutical Salts: Properties, Selection, and Use, (Wiley, 2002). In some embodiments, the compounds described herein include the N-oxide forms.

As understood in the art, the symbol

is used in structural formulas to indicate the bond that is the point of attachment of the moiety containing it to the adjacent portion of the compound. According to a similar convention, pendant carbon atoms and their attached hydrogen atoms may not be explicitly expressed. Thus, the symbol ╱ represents a methyl group, the symbol

represents an ethyl group, the symbol

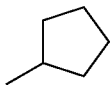

represents a cyclopentyl group, and so on. The orientation of a substituent group in a molecule or moiety is represented by the convention that the symbol ╱ represents a bond in which the group is projecting out of the plane of the page toward the reader, while the symbol ⁓ represents a bond in which the group is projecting behind the plane of the page away from the reader, and the symbol ⁓ represents a bond in which the group has indeterminate orientation (i.e., the compound is diasteriomeric).

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to 6, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{3-n}$-cycloalkyl", wherein n is an integer 4 to 7, either alone or in combination with another radical denotes a cyclic, saturated, unbranched hydrocarbon radical with 3 to n C atoms. For example, the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In some embodiments, alkyl groups or carbon chains, one or more carbon atoms can be optionally replaced by heteroatoms: O, S or N. It shall be understood that if N is not represented as substituted then it is NH, and that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

In some embodiments, the term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

In some embodiments, the term "heteroaryl" (sometimes abbreviated "hetaryl") means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

As used in Q, the definition of "aryl and hetaryl" are as described above. They are preferably phenyl or imidazoyl such as the following moieties that in conjunction with [NH,O,S] chemically undergo immolation to release $R_8H$ as described below.

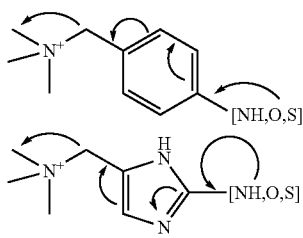

In some embodiments, the term "heterocyclyl" means a stable non-aromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. The term "heterocyclyl" or is intended to include all the possible isomeric forms.

The term "halogen" and the corresponding term "halo" as used in the present specification shall be understood to mean bromine, chlorine, fluorine or iodine, or the corresponding bromo, chloro, fluoro, or iodo. The definitions "halogenated", "partially or fully halogenated"; partially or fully fluorinated; "substituted by one or more halogen atoms", includes for example, mono, di or tri halo derivatives on one or more carbon atoms. For alkyl, non-limiting examples would be —$CH_2CHF_2$, —$CF_3$, etc.

Each alkyl, cycloalkyl, heterocycle, aryl or heteroaryl, or the analogs thereof, described herein shall be understood to be optionally partially or fully halogenated.

As used herein, "nitrogen" or "N" and "sulfur" or "S" includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—$R_a$ may be represented as phenyl-S(O)$_m$— when $R_a$ is phenyl and where m is 0, 1 or 2.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In the peptides $R_7$, the amino acids may be all of L configuration, all of D configuration, or a mixture of D and L configuration.

Compounds of the invention also include their isotopically-labelled forms. An isotopically-labelled form of a compound of the present invention is identical to said active agent but for the fact that one or more atoms of said compound have been replaced by an atom or atoms having an atomic mass or mass number different from the atomic mass or mass number of said atom which is usually found in nature. Examples of isotopes which are readily available commercially and which can be incorporated into a compound of the present invention in accordance with well established procedures, include isotopes of hydrogen, carbon, nitrogen, oxygen, phosphorous, fluorine and chlorine, e.g., $^2$H (deuterium or "D"), $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. A compound of the present invention, a prodrug thereof, or a pharmaceutically acceptable salt of either which contains one or more of the above-mentioned isotopes and/or other isotopes of other atoms is contemplated to be within the scope of the present invention.

The invention includes pharmaceutically acceptable derivatives of compounds of formula (I). The term "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methyl sulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (See, e.g., Pharmaceutical Salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention are prodrugs of the compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect. By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

The terms "a," "an," and "the" are intended to include plural alternatives, e.g., at least one, unless otherwise specified. For instance, the disclosure of "a therapeutic agent" or "a compound" is meant to encompass one, or mixtures or combinations of more than one, therapeutic agent or compound, respectively.

While compositions and methods are described in terms of "comprising" various components or steps, the compositions and methods can also "consist essentially of" or "consist of" the various components or steps. For example, a pharmaceutical composition described herein can comprise; alternatively, can consist essentially of; or alternatively, can consist of; (i) a therapeutically effective amount of a compound, or a pharmaceutically acceptable salt thereof, and (ii) a pharmaceutically acceptable diluent, excipient, or carrier.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in the schemes below.

As shown in Scheme 1, Intermediate II, which is flanked by orthogonal leaving groups, can be reacted with a nucleophilic R$^8$H compound to give intermediate III. Intermediate III is then reacted with a thiol containing peptide (HS—R$^7$) that participates in a disulfide exchange reaction to give the final compound. Suitable leaving groups are described below.

Scheme 1: Synthesis of Carbonate and Carbamate Linked Compounds

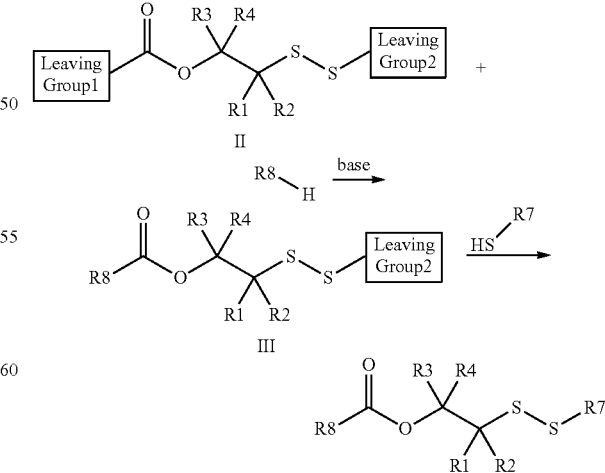

The synthesis of aminal linked compounds is shown in Scheme 2. A nucleophilic R$_8$H compound is reacted with a bromoacetic acid derivative to provide intermediate IV. This ester containing intermediate is hydrolyzed under basic conditions to give intermediate acid V. The resulting acid is transformed to the acyl azide intermediate and then subjected to Curtius rearrangement conditions. The corresponding transient isocyanate is trapped with hydroxy containing intermediate I to give intermediate VII. Intermediate VII is then reacted with a thiol containing peptide (HS—R⁷) that participates in a disulfide exchange reaction to give the final compound.

Scheme 2: Synthesis of Aminal Linked Compounds

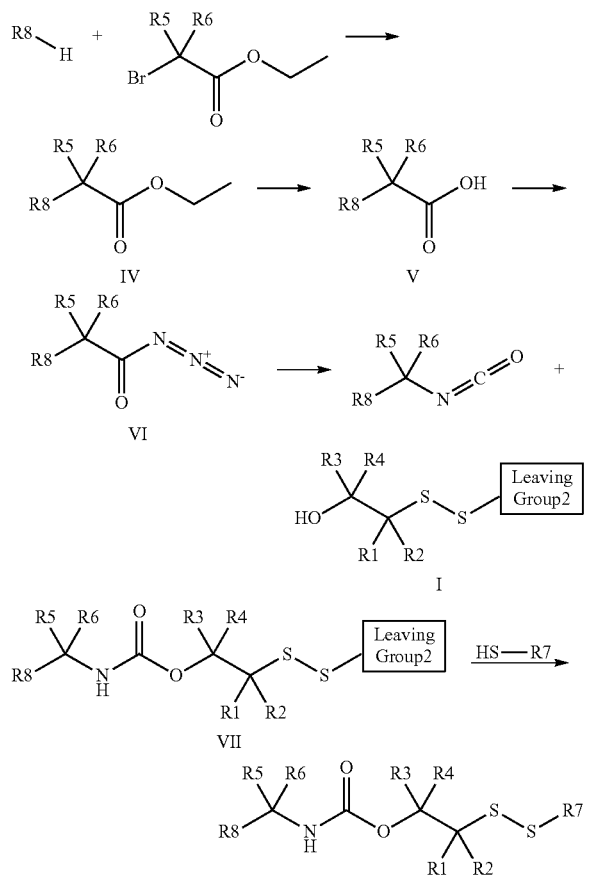

An alternative synthesis of aminal linked conjugates is shown in Scheme 3. Nucleophilic $R^8$—H, which can include a protecting group (PG), is reacted with AcO-hemi-aminal carbamate VIII with a pre-installed linked Leaving Group 2 to give Intermediate IX. This compound is treated with conditions to remove the protecting group and the resulting compound VII is reacted with $R^7$—SH to give the desired conjugate.

Scheme 3: Synthesis 2 of Aminal Linked Conjugates

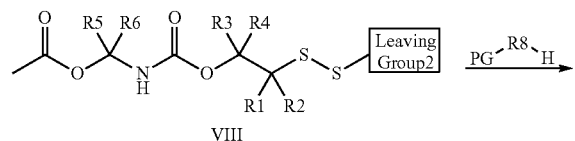

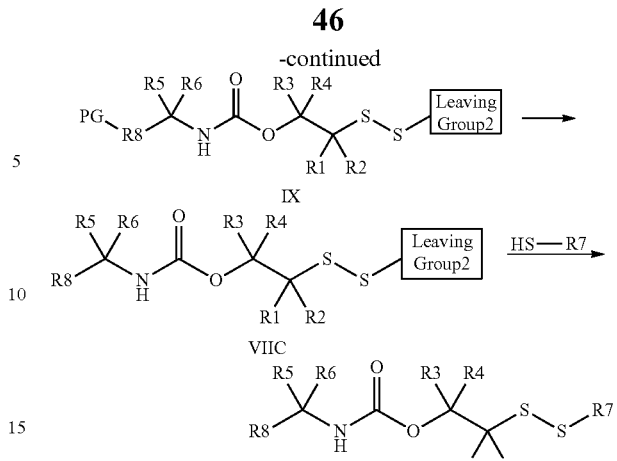

A further alternative synthesis of aminal linked conjugates is shown in Scheme 4. Primary carbamate X with a pre-installed linked Leaving Group 2 is reacted with a carbonyl compound and p-toluene sulfinate sodium salt to give sulfonyl carbamate XI. This is further treated with nucleophilic $R^8$—H with a protecting group (PG) to give IX. This compound is treated as previously described to give the desired conjugate.

Scheme 4: Synthesis 3 of Aminal Linked Conjugates

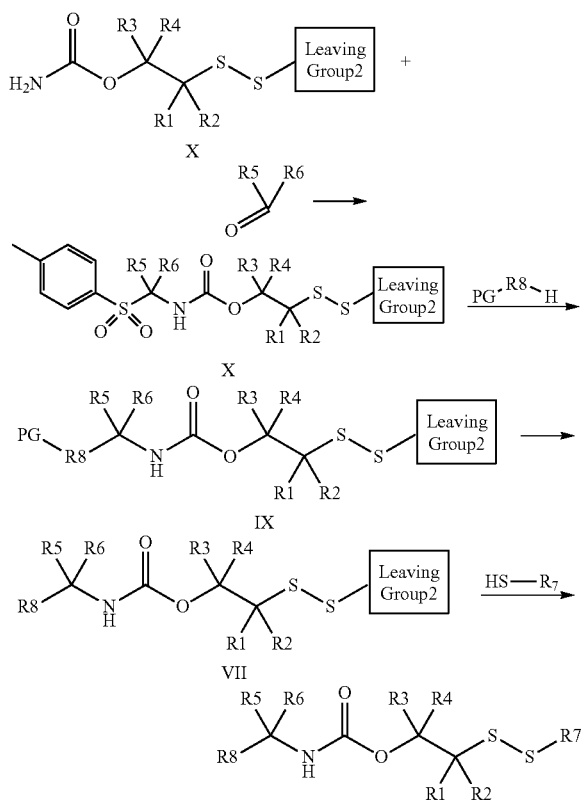

An exemplary synthesis of thiopropionate linked conjugates is shown in Scheme 5. Propionate disulfide XII with previously installed Leaving Groups 1 and 2 is reacted selectively with nucleophilic $R^8$—H to give XII. This compound is further reacted with $R^7$—SH to provide the desired conjugate.

Scheme 5: Synthesis 1 of Thiopropionate Linked Conugates

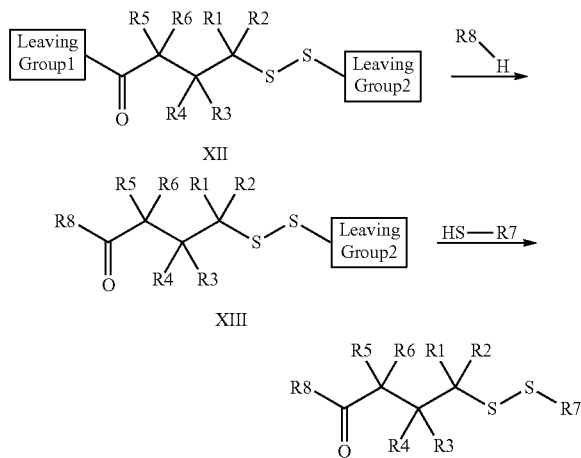

An alternative synthesis of thiopropionate linked conjugates is shown in Scheme 6. Thionoester XIV is reacted with nucleophilic $R^8$—H to give propionate thiol XV. This compound engages in a disulfide exchange reaction to provide XIII. This compound is treated with $R^7$—SH to provide the desired conjugate.

Scheme 6: Synthesis 2 of Thio Propionate Linked Conjugates

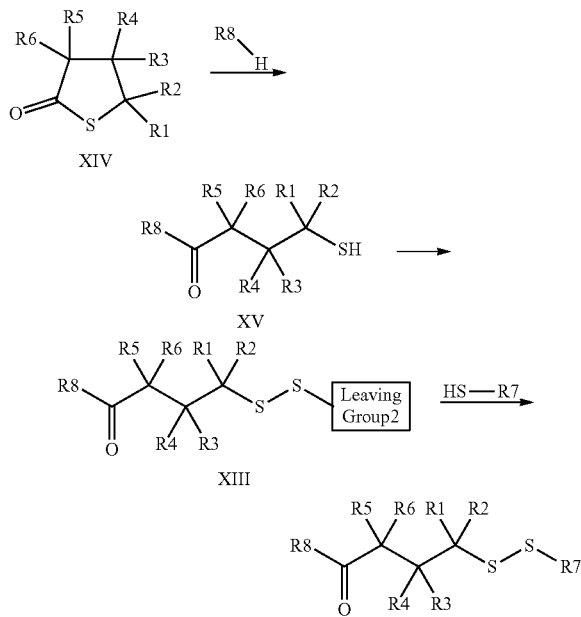

Scheme 7: Synthesis 1 of Para Benzoic-Linked Conjugates

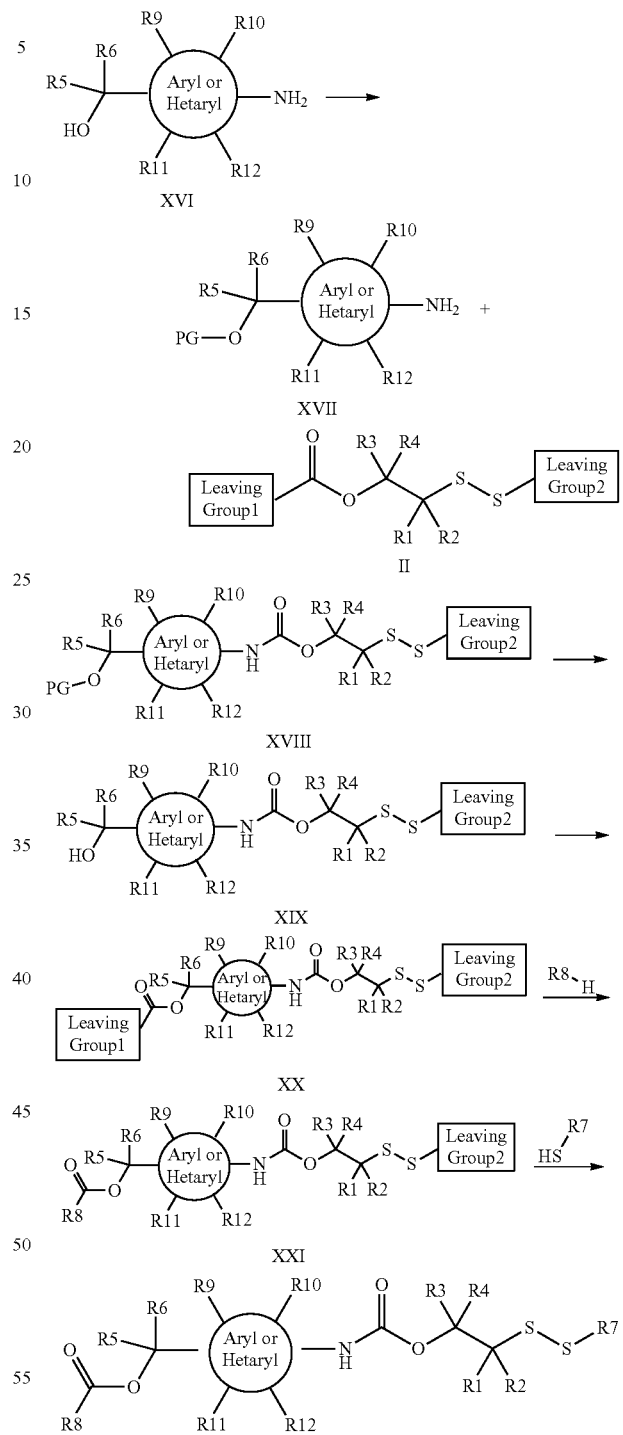

The synthesis of para benzoic-linked conjugates is depicted in Scheme 7. Para amino benzoic alcohol XVI is selectively protected at the oxygen to give XVII. This is then reacted at the aniline position with II to provide aryl carbamate XVIII. The protecting group is removed giving free OH XIX which is treated with an activating agent to provide XX which contains orthogonal leaving groups. Reaction of XX with $R^8$—H to give XXI followed by $R^7$—SH give provides the desired conjugate.

An alternative synthesis of para benzoic-linked conjugates is shown in Scheme 8. 4-Mercapto benzoic alcohol XXII is reacted in a disulfide exchange reaction to give 4-mercapto benzoic alcohol disulfide XXI containing Leaving Group 2. The remaining benzyl alcohol is treated to provide activated compound XXIV. This is further reacted selectively with nucleophilic $R^8$—H and resulting XXV with $R^7$—SH to give the desired conjugate.

Scheme 8: Synthesis 2 of Para Benzoic-Linked Conjugates

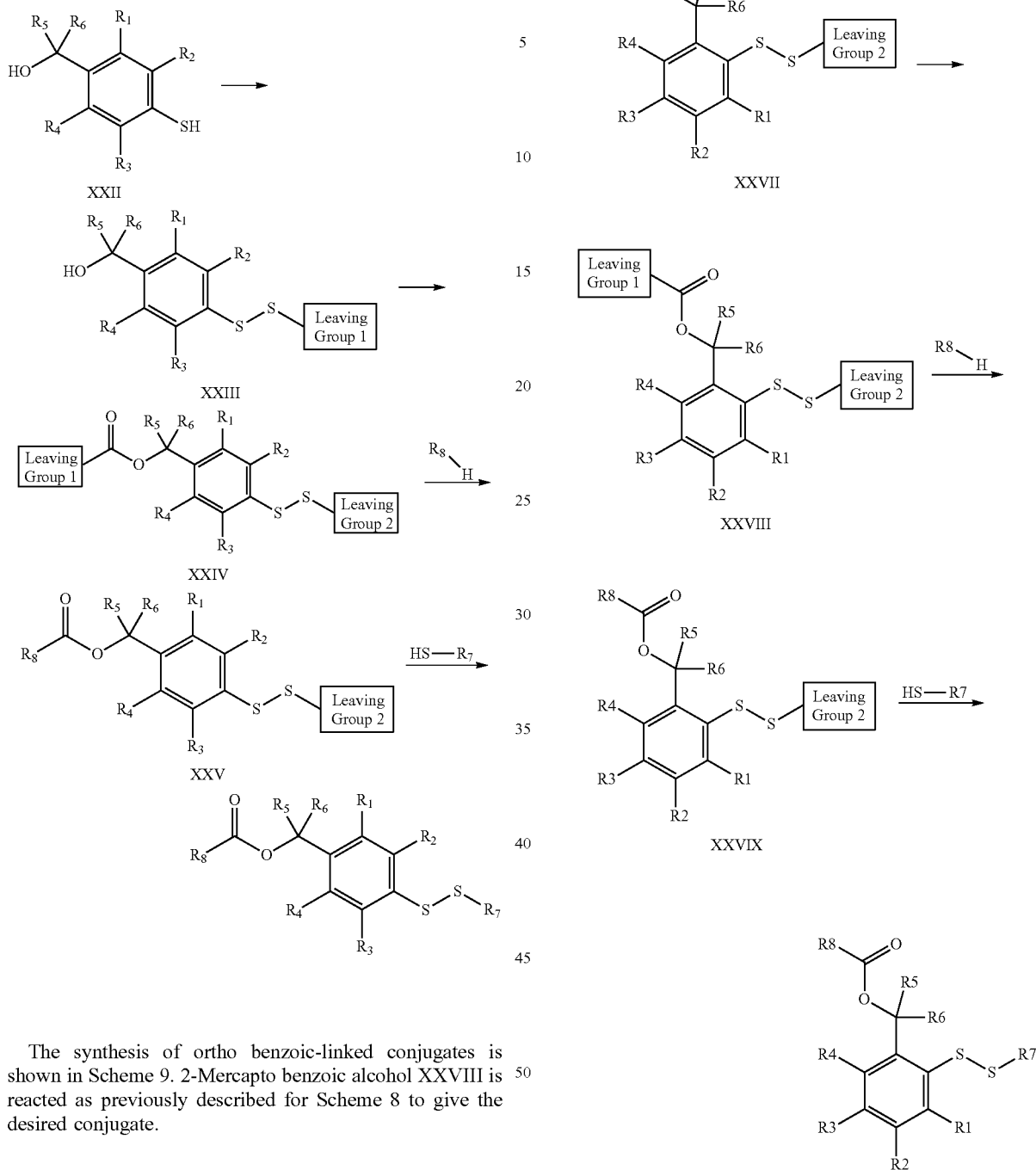

The synthesis of ortho benzoic-linked conjugates is shown in Scheme 9. 2-Mercapto benzoic alcohol XXVIII is reacted as previously described for Scheme 8 to give the desired conjugate.

Scheme 9: Synthesis of Ortho Benzoic-Linked Conjugates

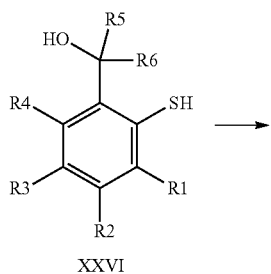

The synthesis of amino acid benzoic carbamate-linked conjugates is shown in Scheme 10. Para amino benzoic/ heterobenzoic alcohol XVI can be selectively coupled to N-protected amino acid or peptide XXX to give XXXI. The protecting group can be removed to provide XXXII which is then reacted with II to give carbamate XXXIII with Leaving Group 2 installed. The alcohol can be selectively reacted to give carbonate XXXIV which has Leaving Group 1 present. Leaving Group 1 can be subsequently displaced with $R^8$—H to give XXXV which is reacted with $R^7$—SH to provide the desired amino acid benzoic carbamate-linked conjugate.

Scheme 10: Synthesis of Amino Acid Benzoic Carbamate-Linked Conjugates
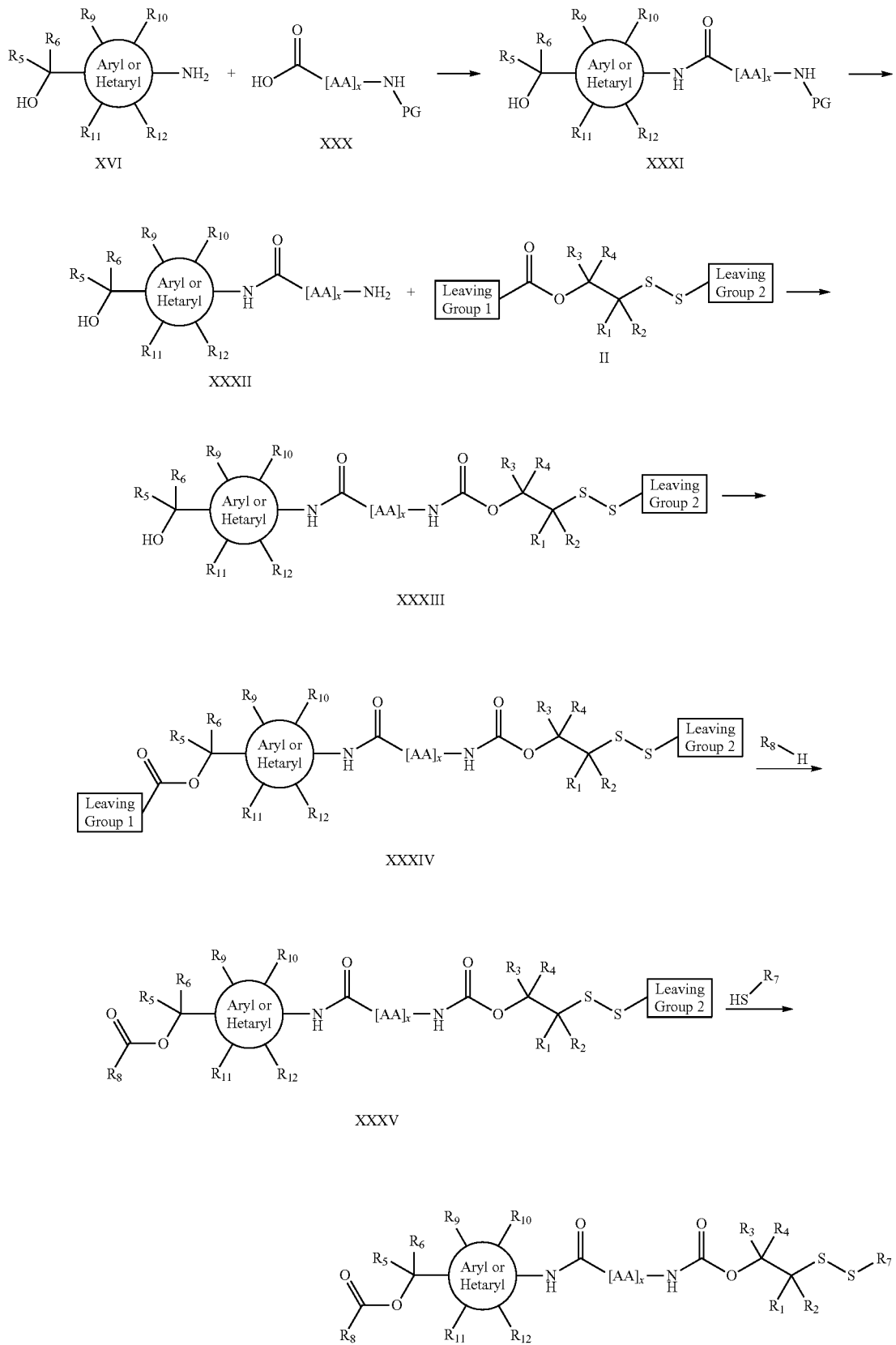

The synthesis of amino acid-linked conjugates is shown in Scheme 11. N-Protected amino acid or peptide XXX can be coupled to $R^8$—H to give XXXVI. The protecting group can be removed to give XXXVII which can be subsequently reacted with II, displacing Leaving Group 1 to give XXXVIII. This intermediate can then be treated with $R^7$—SH to provide the conjugate.

Scheme 11: Synthesis of Amino Acid-linked Conjugates

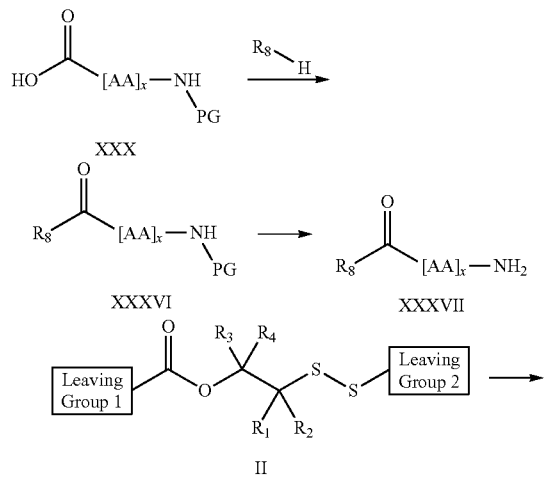

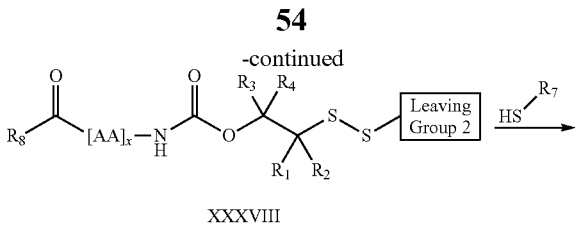

-continued

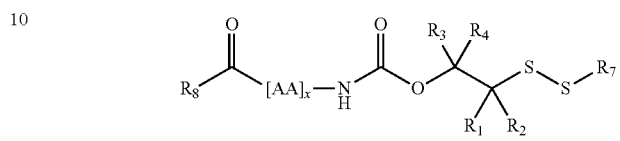

The synthesis of benzoic alcohol-linked, glucuronide conjugates is shown in Scheme 12. 2-Nitro phenol XXXIX can be coupled with protected glucuronide XL to give XLI. This intermediate can be reduced selectively at the carbonyl to give alcohol XLII and then the nitro group can be reduced to provide aniline XLIII. This intermediate can be further coupled with propionic acid derivative XLIV to give amide XLV which contains Leaving Group 2. XLV can then be reacted at the alcohol to install Leaving Group 2, giving XLVI. Leaving Group 1 can be selectively displaced with $R^8$—H to give XLVII. The protecting groups on the glucuronide can be removed and XLVIII can be reacted with $R^7$—SH to give the conjugate.

Scheme 12: Synthesis of Benzoic Alcohol-Linked, Glucoronide Conjugates

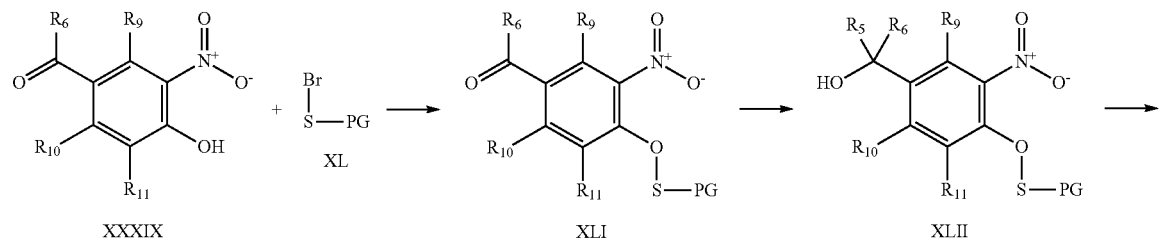

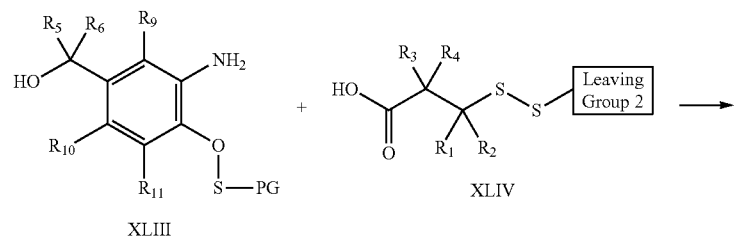

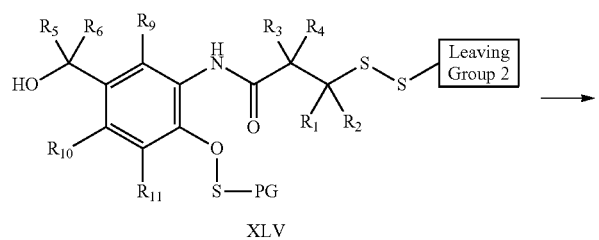

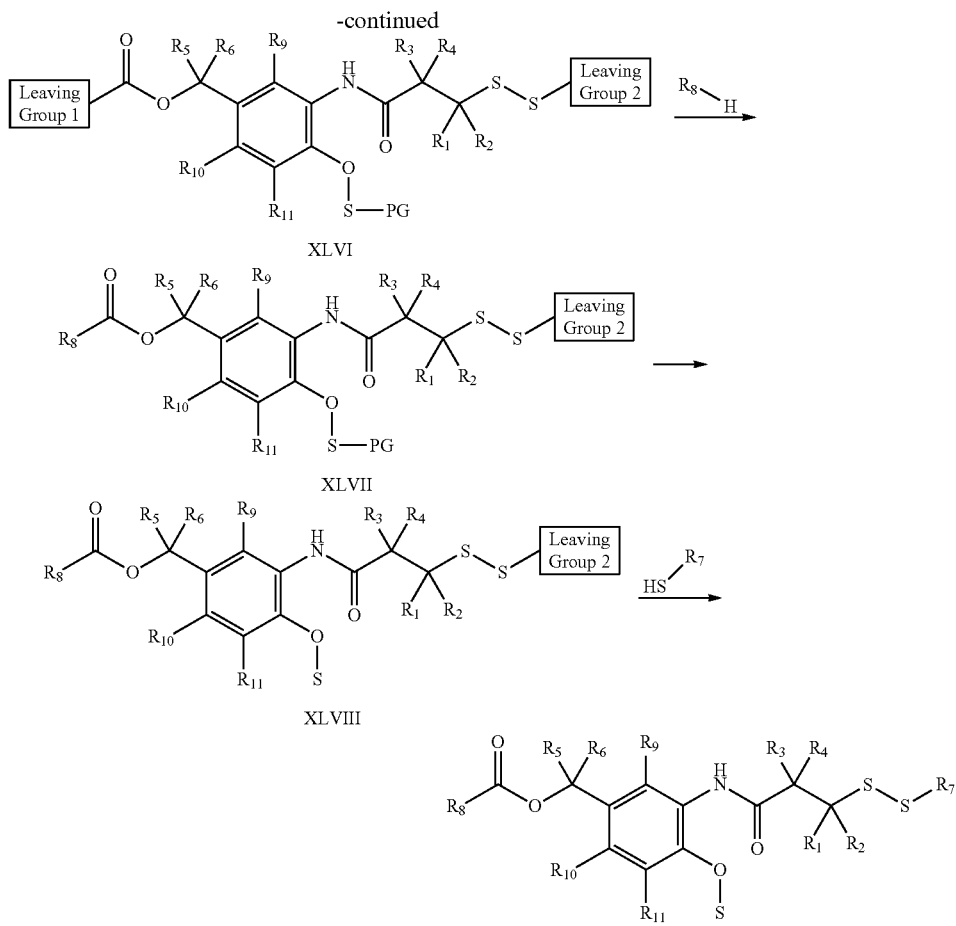

XLVI

XLVII

XLVIII

Cleavage of the final compound to release $R^8H$ can be achieved by treating the compound with an excess of glutathione (GSH) in a buffer with incubation at 37° C. Reversed phase HPLC analysis at a desired time course is used to follow the course of the cleavage.

Scheme 13: Cleavage of Peptide Conjugates

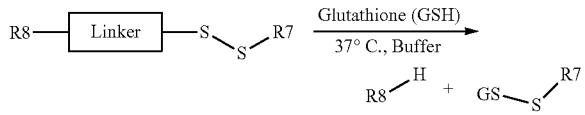

The peptides $R^7$ may be prepared using the solid-phase synthetic method first described by Merrifield in J.A.C.S., Vol. 85, pgs. 2149-2154 (1963), although other art-known methods may also be employed. The Merrifield technique is well understood and is a common method for preparation of peptides. Useful techniques for solid-phase peptide synthesis are described in several books such as the text "Principles of Peptide Synthesis" by Bodanszky, Springer Verlag 1984. This method of synthesis involves the stepwise addition of protected amino acids to a growing peptide chain which was bound by covalent bonds to a solid resin particle. By this procedure, reagents and by-products are removed by filtration, thus eliminating the necessity of purifying intermediates. The general concept of this method depends on attachment of the first amino acid of the chain to a solid polymer by a covalent bond, followed by the addition of the succeeding protected amino acids, one at a time, in a stepwise manner until the desired sequence is assembled. Finally, the protected peptide is removed from the solid resin support and the protecting groups are cleaved off.

The amino acids may be attached to any suitable polymer. The polymer must be insoluble in the solvents used, must have a stable physical form permitting ready filtration, and must contain a functional group to which the first protected amino acid can be firmly linked by a covalent bond. Various polymers are suitable for this purpose, such as cellulose, polyvinyl alcohol, polymethylmethacrylate, and polystyrene.

Methods of Use

Another aspect of the present invention is the use of the compounds of formula (I) in the treatment of diseases involving acidic or hypoxic diseased tissue, such as cancer, stroke, myocardial infarction, or long-term neurodegenerative disease. In some embodiments, the cancer is PARP-sensitive. In some embodiments, the cancer is associated with abnormal expression or activity of ATM. In some embodiments, the cancer is associated with abnormal expression or activity of ATM. In some embodiments, the cancer is associated with abnormal expression or activity of DNA-PK. In some embodiments, the cancer is a BRCA-mutated breast cancer. In some embodiments, the cancer is germline BRCA-mutated ovarian cancer.

3. In these methods of treatment, a therapeutically-effective amount of a compound of formula (I) or a pharmaceutically-acceptable salt thereof may be administered as a single agent or in combination with other forms of therapy, such as ionizing radiation or cytotoxic agents in the case of cancer. In combination therapy, the compound of formula (I) may be administered before, at the same time as, or after the other therapeutic modality, as will be appreciated by those of skill in the art. Either method of treatment (single agent or combination with other forms of therapy) may be administered as a course of treatment involving multiple doses or treatments over a period of time. Also provided herein is a method of reducing bone marrow toxicity associated with administration of an ionizing radiation or cytotoxic agent, which comprises administering to a human or other mammal a therapeutically-effective amount of a compound of the disclosure, or a pharmaceutically acceptable salt thereof, in combination with the ionizing radiation or cytotoxic agent. The reduction in bone marrow toxicity can be relative to bone marrow toxicity observed when the ionizing radiation or cytotoxic agent is administered together with $R^8H$ instead of the compound of the invention having the same $R^8$ (e.g., where the $R^8H$ compound corresponds to the protonated $R^8$ moiety of the $R^8$-Q-$R^7$ compound of the invention). In some embodiments, toxicity can be measured by PARylation in bone marrow tissue. In some embodiments, toxicity can be measured according to total nucleated bone marrow cells. In some embodiments, the cytotoxic agent can be any of those listed herein. In some embodiments, the cytoxic agent is temozolomide (TMZ).

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CIVIL), DLBCL, mantle cell lymphoma, Non-Hodgkin lymphoma (including relapsed or refractory NHL and recurrent follicular), Hodgkin lymphoma or multiple myeloma) and combinations of said cancers.

In certain embodiments, a compound of formula (I) or a pharmaceutically-acceptable salt thereof may be used in combination with a chemotherapeutic agent, a targeted cancer therapy, an immunotherapy or radiation therapy. The agents can be combined with the present compounds in a single dosage form, or the agents can be administered simultaneously or sequentially as separate dosage forms. In some embodiments, the chemotherapeutic agent, targeted cancer therapy, immunotherapy or radiation therapy is less toxic to the patient, such as by showing reduced bone marrow toxicity, when administered together with a compound of formula (I), or a pharmaceutically acceptable salt thereof, as compared with when administered in combination with the corresponding free DNA repair inhibiting compound (e.g., $R^8$—H) such as an inhibitor of PARP, ATR, DNK-PK, or ATM as described herein.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents that can be administered in combination with the compounds of the invention include, for example, navelbene, CPT-11, anastrazole, letrozole, capecitabine, reloxafine, cyclophosphamide, ifosamide, and droloxafine.

Also suitable are cytotoxic agents such as, for example, epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-α, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines that can be administered in combination with the compounds of the invention include, for example, dendritic cells, synthetic peptides, DNA vaccines and recombinant viruses.

Other suitable agents for use in combination with the compounds of the present invention include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compounds of the present invention may be combined with or administered in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with the compounds of the invention. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with compounds of the invention. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present invention include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with compounds of the invention. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds of the present invention.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

The phrase "therapeutically effective amount" of a compound (therapeutic agent, active ingredient, drug, etc.) refers to an amount of the compound to be administered to a subject in need of therapy or treatment which alleviates a symptom, ameliorates a condition, or slows the onset of disease conditions, according to clinically acceptable standards for the disorder or condition to be treated. For instance, a therapeutically effective amount can be an amount which has been demonstrated to have a desired therapeutic effect in an in vitro assay, an in vivo animal assay, or a clinical trial. The therapeutically effective amount can vary based on the particular dosage form, method of administration, treatment protocol, specific disease or condition to be treated, the benefit/risk ratio, etc., among numerous other factors.

Said therapeutically effective amount can be obtained from a clinical trial, an animal model, or an in vitro cell culture assay. It is known in the art that the effective amount suitable for human use can be calculated from the effective amount determined from an animal model or an in vitro cell culture assay. For instance, as reported by Reagan-Shaw et al., FASEB J. 2008: 22(3) 659-61, "μg/ml" (effective amount based on in vitro cell culture assays)="mg/kg body weight/day" (effective amount for a mouse). Furthermore, the effective amount for a human can be calculated from the effective amount for a mouse based on the fact that the metabolism rate of mice is 6 times faster than that of humans.

As an example of treatment using a compound of formula (I) as monotherapy, a therapeutically-effective dosage of a compound of formula (I) wherein $R^8H$ is a PARP inhibitor may be administered to a patient suffering from a PARP dependent cancer, such as a female suffering from BRCA-mutated breast cancer, germ line BRCA-mutated ovarian cancer, or fallopian tube cancer or to a patient suffering from primary peritoneal cancer, squamous cell lung cancer, or non-small cell lung cancer, or to a patient suffering from stroke, myocardial infarction, or long-term neurodegenerative disease. As another example, a therapeutically-effective dosage of a compound of formula (I) wherein $R^8H$ is a DNA repair inhibitor targeting the protein kinase ataxia-telangiectasia mutated (ATM), the ATM-Rad3-related protein kinase (ATR), or the nuclear serine/threonine protein kinase DNA-PK could be administered to a patient suffering from a cancer in which inhibition of one or more of the above proteins would be therapeutically useful.

As an example of treatment using a compound of formula (I) in combination with a cytotoxic agent, a therapeutically-effective amount of a compound of formula (I) may be administered to a patient suffering from cancer as part of a treatment regimen also involving a therapeutically-effective amount of ionizing radiation or a cytotoxic agent. In the context of this treatment regimen, the term "therapeutically-effective" amount should be understood to mean effective in the combination therapy. It will be understood by those of skill in the cancer-treatment field how to adjust the dosages to achieve the optimum therapeutic outcome.

Similarly, the appropriate dosages of the compounds of the invention for treatment of non-cancerous diseases or conditions (such as cardiovascular diseases) may readily be determined by those of skill in the medical arts.

The term "treating" as used herein includes the administration of a compound or composition which reduces the frequency of, delays the onset of, or reduces the progression of symptoms of a disease involving acidic or hypoxic diseased tissue, such as cancer, stroke, myocardial infarction, or long-term neurodegenerative disease, in a subject relative to a subject not receiving the compound or composition. This can include reversing, reducing, or arresting the symptoms, clinical signs, or underlying pathology of a condition in a manner to improve or stabilize a subject's condition (e.g., regression of tumor growth, for cancer or decreasing or ameliorating myocardial ischemia reperfusion injury in myocardial infarction, stroke, or the like cardiovascular disease). The terms "inhibiting" or "reducing" are used for cancer in reference to methods to inhibit or to reduce tumor growth (e.g., decrease the size of a tumor) in a population as compared to an untreated control population.

All publications (including patents) mentioned herein are incorporated herein by reference for the purpose of describing and disclosing, for example, the constructs and methodologies that are described in the publications, which might be used in connection with the disclosure herein described. The publications discussed throughout the text are provided solely for their disclosure prior to the filing date of the present application.

Disclosed herein are several types of ranges. When a range of any type is disclosed or claimed, the intent is to disclose or claim individually each possible number that such a range could reasonably encompass, including end points of the range as well as any sub-ranges and combinations of sub-ranges encompassed therein. When a range of therapeutically effective amounts of an active ingredient is disclosed or claimed, for instance, the intent is to disclose or claim individually every possible number that such a range could encompass, consistent with the disclosure herein. For example, by a disclosure that the therapeutically effective amount of a compound can be in a range from about 1 mg/kg to about 50 mg/kg (of body weight of the subject), the intent is to recite that the therapeutically effective amount can be equal to about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, about 49 mg/kg, or about 50 mg/kg. Additionally, the therapeutically effective amount can be within any sub-range included within about 1 mg/kg to about 50 mg/kg (for example, the amount can be in a range from about 2 mg/kg to about 10 mg/kg), and this also includes any combination of ranges between about 1 mg/kg and about 50 mg/kg (for example, the amount can be in a range from about 1 mg/kg to about 5 mg/kg or from about 20 mg/kg to about 35 mg/kg). Likewise, all other ranges disclosed herein should be interpreted in a manner similar to this example.

Formulation, Dosage Forms and Administration

To prepare the pharmaceutical compositions of the present invention, a compound of Formula (I) or a pharmaceutically-acceptable salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixirs, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. One of skill in the pharmaceutical and medical arts will be able to readily determine a suitable dosage of the pharmaceutical compositions of the invention for the particular disease or condition to be treated.

EXAMPLES

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997. The following definitions describe terms and abbreviations used herein:
- Brine: a saturated NaCl solution in water
- DCM: dichloromethane
- TFA: trifluoroacetic acid
- DIPEA: diisopropylethylamine
- DMA: dimethylacetamide
- DME: dimethoxyethane
- DMF: dimethylformamide
- DMSO: methylsulfoxide
- DTT: dithiothreitol
- MSD: mass spec detector
- $Et_2O$ ethyl ether
- EtOAc: ethyl acetate
- EtOH: ethyl alcohol
- HATU: O-(7-azabenzotriazol-1-yl)-N,N,N',N'-tetramethyluronium hexafluorophosphate
- HOBt: 1-hydroxybenzotriazole
- RP: reverse phase
- HPLC: high performance liquid chromatography
- IPA: isopropanol
- LAH: lithium aluminum hydride
- N-BuLi: n-butyl lithium
- LC-MS: liquid chromatography-mass spectrometry
- LDA: lithium diisoproylethylamide
- Me: methyl
- MeOH: methanol
- MTBE: methyl t-butyl ether
- NMP: N-methylpyrrolidine
- Ph: phenyl
- PNPC: para-nitrophenylchloroformate
- RT or rt: room temperature
- SFC: supercritical fluid chromatography
- TBAI: tetrabutylammonium iodide
- TBME: tort-butylmethyl ether
- tBu: tertiary butyl
- THF: tetrahydrofuran
- TEA: triethylamine
- TMEDA: tetramethylethylenediamine
- GSH: Glutathione
- GS: Glutathione bonded at sulfur
- LiOH: lithium hydroxide
- DPPA: diphenyl phosphoryl azide
- $Sn(Bu)_2(Laurate)_2$: dibutyltin dilaurate
- PBS: phosphate buffered saline
- ACN: acetonitrile
- AcOH: acetic add
- EEDQ: N-ethoxycarbonyl-2-ethoxy-1,2-dihydroquinoline
- DMAP: 4-dimethylaminopyridine
- EDC: 1-ethyl-3-(3-dimethylaminopropyl)carbodiimide HPLC Methods All HPLC methods use reverse phase conditions: $H_2O$/Acetonitrile with TFA modifier (0.05%); Flow rate: 1 mL/min; Wavelength=217 nm. Column conditions are described below:
- A: Sunfire C18 150×4.6 mm
- B: Ace Equivalence 250×4.6 mm
- C: Sunfire C18 150×30 mm $R^8H$ Intermediates The $R^8H$ groups used throughout the Examples were purchased or synthesized as indicated in Table 2.

TABLE 2

| | $R^8H$ Intermediates | | |
|---|---|---|---|
| $R^8$ Code | $R^8H$ Structure | Synthesis Reference or Purchased | Class |
| $R^8H$-1 | | Synthesized- Bioorganic & Medicinal Chemistry Letters 14 (2004) 2433- 2437; J. Med. Chem. 2000, 43, 4084-4097 | PARP |
| $R^8H$-2 | | Synthesized- WO0220500A2 | DNA-PK |
| $R^8H$-3 | | Astatech 42568 | PARP |

TABLE 2-continued

R⁸H Intermediates

| R⁸ Code | R⁸H Structure | Synthesis Reference or Purchased | Class |
|---|---|---|---|
| R⁸H-4 | [structure] | MedKoo 203115 | PARP |
| R⁸H-15 | [structure] | Chemscene CS-0937 | PARP |
| R⁸H-16 | [structure] | Astatech 81136 | PARP |
| R⁸H-17 | [structure] | MentonChem MC7030606 | PARP |
| R⁸H-18 | [structure] | Selleckchem S1060 | PARP |
| R⁸H-19 | [structure] | MedKoo 205150 | PARP |

TABLE 2-continued
R⁸H Intermediates
| R⁸ Code | R⁸H Structure | Synthesis Reference or Purchased | Class |
|---|---|---|---|
| R⁸H-20 | 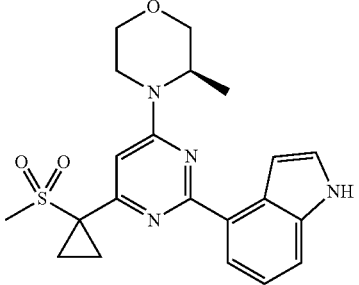 [SMILES: C[C@@H]1COCCN1c1cc(C2(S(C)(=O)=O)CC2)nc(-c2cccc3[nH]ccc23)n1] | Advanced Chemblocks 10278 | ATR |
| R⁸H-21 | 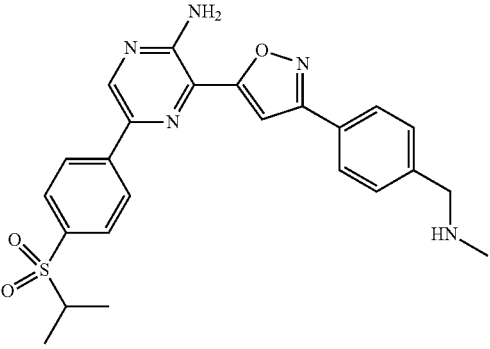 [SMILES: CNCc1ccc(-c2cc(-c3nc(-c4ccc(S(=O)(=O)C(C)C)cc4)cnc3N)on2)cc1] | Astatech 42043 | ATR |
| R⁸H-22 | 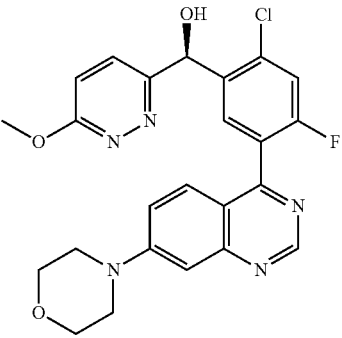 [SMILES: COc1ccc([C@@H](O)c2cc(-c3ncnc4cc(N5CCOCC5)ccc34)c(F)cc2Cl)nn1] | Medchem Express HY-10619B | DNA-PK |
| R⁸H-23 | 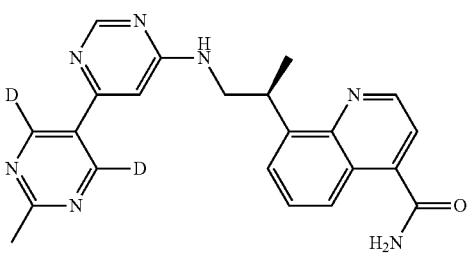 [SMILES: [2H]c1nc(C)nc([2H])c1-c1cc(NC[C@@H](C)c2cccc3c(C(N)=O)ccnc23)ncn1] | Synthesized-WO2013163190A1 | DNA-PK |

TABLE 2-continued
R⁸H Intermediates
| R⁸ Code | R⁸H Structure | Synthesis Reference or Purchased | Class |
|---|---|---|---|
| R⁸H-24 | 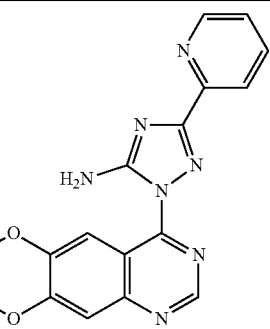 | Astatech 40964 | ATM |
| R⁸H-25 | 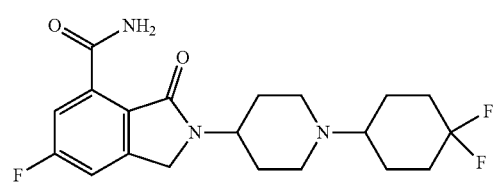 [SMILES: NC(=O)c1cc(F)cc2c1C(=O)N(C1CCN(C3CCC(F)(F)CC3)CC1)C2] | MedKoo 407142 | PARP |
| R⁸H-26 | 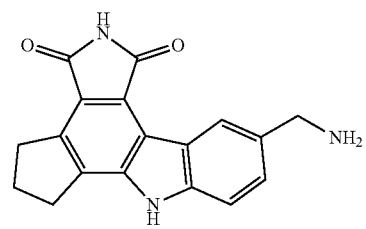 [SMILES: NCc1ccc2[nH]c3c4c(c5c(c3c2c1)C(=O)NC5=O)CCC4] | MedKoo 406357 | PARP |
| R⁸H-27 | 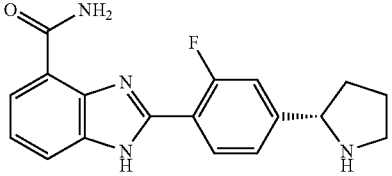 [SMILES: NC(=O)c1cccc2[nH]c(-c3ccc([C@@H]4CCCN4)cc3F)nc12] | MedKoo 406362 | PARP |
| R⁸H-28 | 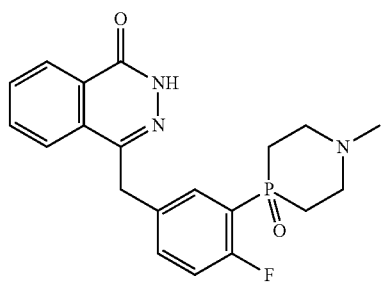 [SMILES: CN1CCP(=O)(c2cc(Cc3n[nH]c(=O)c4ccccc34)ccc2F)CC1] | Synthesized WO2012166983A1 | PARP |
| R⁸H-29 | 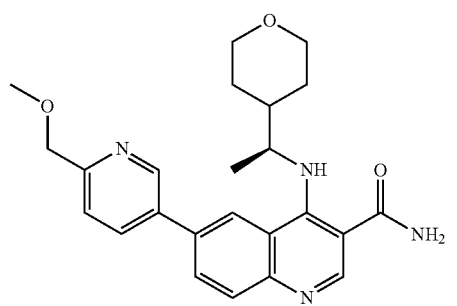 [SMILES: COCc1ccc(-c2ccc3ncc(C(N)=O)c(N[C@@H](C)C4CCOCC4)c3c2)cn1] | Synthesized J. Med. Chem. 2016, 59, 6281-6292 | ATM |

TABLE 2-continued

R⁸H Intermediates

| R⁸ Code | R⁸H Structure | Synthesis Reference or Purchased | Class |
|---|---|---|---|
| R⁸H-30 | | Synthesized J. Med. Chem. 2016, 59, 6281-6292 | ATM |
| R⁸H-31 | | ACS Med. Chem. Lett. 2018, 9, 809-814 | ATM |
| R⁸H-32 | | J. Med. Chem. 2018, 61, 3823-3841. | ATM |
| R⁸H-33 | | Synthesized ACS Med. Chem. Lett. 2015, 6, 42-46 | ATR |
| R⁸H-34 | | Synthesized ACS Med. Chem. Lett. 2015, 6, 37-41 | ATR |

TABLE 2-continued

R⁸H Intermediates

| R⁸ Code | R⁸H Structure | Synthesis Reference or Purchased | Class |
|---|---|---|---|
| R⁸H-35 | | Oncotarget, 6, 42, 44289-44305 | ATR |
| R⁸H-36 | | Oncotarget, 6, 42, 44289-44305 | ATR |

Linkers

Linkers used herein were either purchased or synthesized as shown below in Table 3:

TABLE 3

| Linker Code | Linker Structure | Synthetic Reference or Purchased |
|---|---|---|
| L1 | | Alfa Aesar A15890 |
| L2 | | Enamine EN300-9515 |
| L4 | | Synthesized-WO2013055987A1 |
| L5 | | Synthesized-WO2013055987A1 |
| L3 | | Enamine EN300-220914 |
| L6 | | Synthesized-ACS Med. Chem. Lett. 2016, 7, 988-993 |

TABLE 3-continued
Commerically Available Linkers
| Linker Code | Linker Structure | Synthetic Reference or Purchased |
|---|---|---|
| L7 | 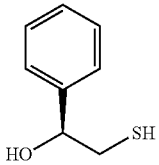 | Synthesized Synlett, 2005, 20 3063 |
| L8 | 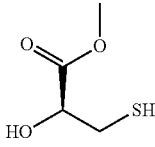 | Synthesized Synlett, 2005, 20 3063 |
| L9 | 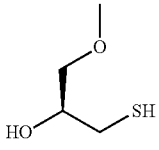 | Synthesized Synlett, 2005, 20 3063 |
| L10 | 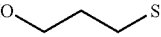 | TCI M1206 |
| L11 | 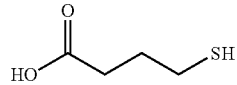 | Aurum GN23710 |
| Linker XVI-1 | 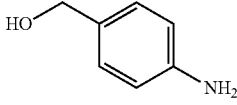 | Combiblocks OR-0735 |
| Linker XXII-1 | 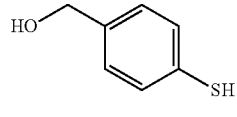 | Combiblocks OR-5865 |
| Linker XXVI-1 | 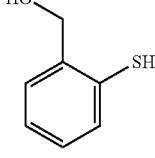 | Oakwood 001239 |
| Linker XXXI-1 | 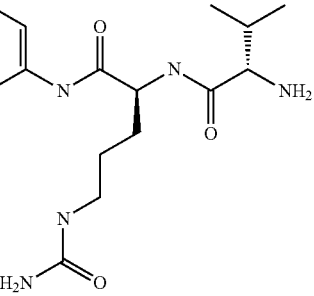 | Aurum DS18383 |

Linker L4: (2R)-2-sulfanylpropan-1-ol

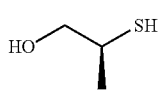

Step 1: Methyl (2R)-2-acetylsulfanylpropanoate

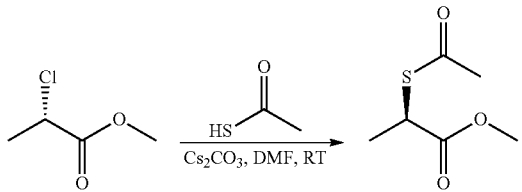

Thioacetic acid (2.24 g, 29.4 mmol) and cesium carbonate (7.98 g, 24.5 mmol) were taken up in 40 mL of dry DMF. The mixture was stirred at RT for 30 min before the methyl (2S)-2-chloropropanoate (3.00 g, 24.5 mmol) was added. The mixture was then stirred for an additional 3 h. Diethyl ether (150 mL) and water (150 mL) were added and the layers separated. The aqueous layer was washed with additional ether and the combined organics dried over $Na_2SO_4$. The organic layer was concentrated and the residue purified by column chromatography ($SiO_2$, 0-10% EtOAc/Hexanes) to give 3.50 g, 88% of methyl (2R)-2-acetylsulfanylpropanoate.

Step 2: (2R)-2-sulfanylpropan-1-ol

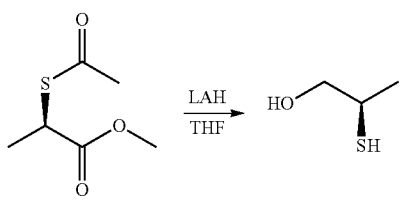

A solution of methyl (2R)-2-acetylsulfanylpropanoate (3.50 g, 21.6 mmol) in THF (30 mL) was added dropwise to a suspension of LAH (4.10 g, 108 mmol) in THF (60 mL) at 0° C. After addition was complete, the mixture was stirred at RT for 3 h. The reaction was cooled to 0° C., then quenched by adding 2N HCl (~75 mL) dropwise. After complete addition, the mixture was stirred at RT for 1 h. The mixture was extracted with $CH_2Cl_2$ (5×100 mL) and dried with $Na_2SO_4$. The crude (2R)-2-sulfanylpropan-1-ol, 1.60 g, 81% was carried on without further purification.

Linker XXII-2: (3-methyl-4-sulfanyl-phenyl)methanol

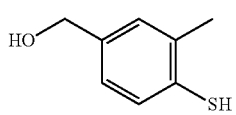

Step 1: 4-((3-((2-ethylhexyl)oxy)-3-oxopropyl)thio)-3-methylbenzoate

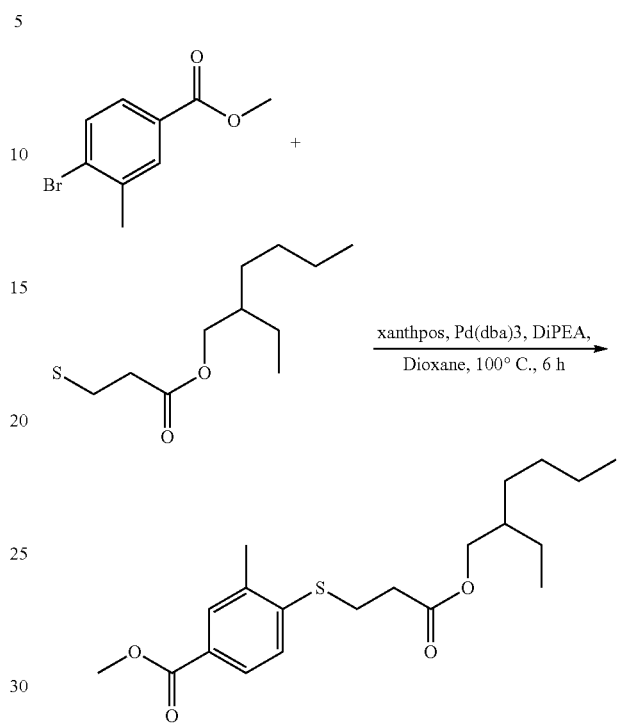

To a stirred solution of methyl 4-bromo-3-methylbenzoate (0.20 g, 0.88 mmol) and 2-ethylhexyl 3-mercaptopropanoate (0.21 g, 0.96 mmol) in 1,4-dioxane (2 mL), DIPEA (0.32 mL, 1.80 mmol), Xanthphos (0.005 g, 0.009 mmol) were added. The reaction mixture was purged with argon for 5 min. $Pd(dba)_3$ (0.008 g, 0.009 mmol) was added and the reaction mixture was heated at 100° C. for 6 h. After completion of the reaction, the reaction mixture was quenched with water (10 mL), and extracted into ethyl acetate (20 mL). The organic layer was washed with sodium chloride solution (20 mL) and dried over $Na_2SO_4$ to afford the crude product. The crude product was purified by flash chromatography ($SiO_2$, 0-5% ethyl acetate/hexane) to afford 4-((3-((2-ethylhexyl)oxy)-3-oxopropyl)thio)-3-methylbenzoate as a yellow color liquid (0.2 g, 62% yield). MS m/z 367.1 [M+H]$^+$.

Step 2: Ethyl 4-mercapto-3-methylbenzoate

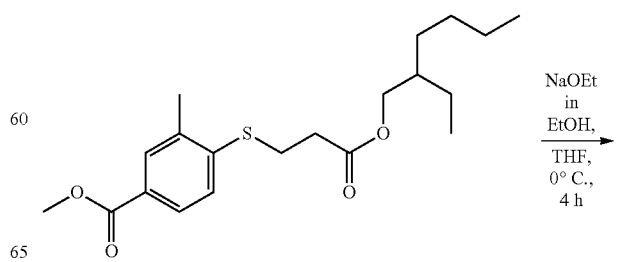

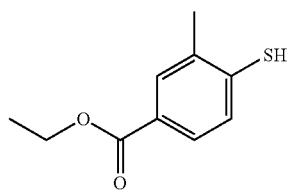

A stirred solution of methyl 4-((3-((2-ethylhexyl)oxy)-3-oxopropyl)thio)-3-methylbenzoate (0.20 g, 0.54 mmol) in THF (5 mL) was cooled to 0° C. Sodium ethoxide (35 wt. %, 2 mL) was added and the mixture was stirred for 4 h at room temperature. After completion of the reaction, the reaction mixture was acidified with 2N HCl (10 mL) and concentrated. The resulting residue was extracted into ethyl acetate (20 mL). The organic layer was washed with water (20 mL), saturated sodium chloride solution (20 mL) and dried over $Na_2SO_4$ to afford ethyl 4-mercapto-3-methylbenzoate as a colorless liquid (80 mg, 80% yield). MS m/z 197.1 $[M+H]^+$.

Step 3: (3-methyl-4-sulfanyl-phenyl)methanol

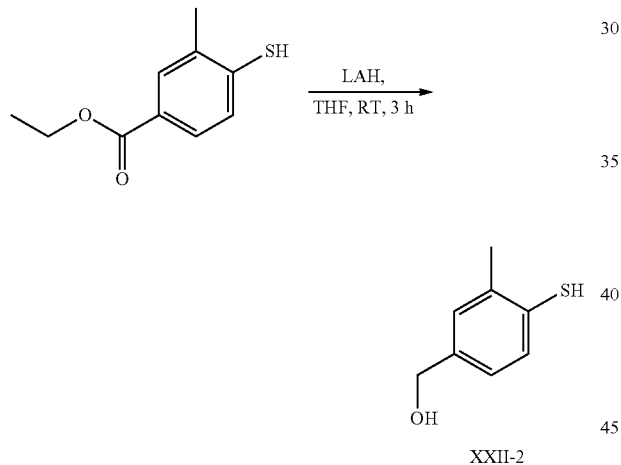

To a stirred solution of ethyl 4-mercapto-3-methylbenzoate (0.60 g, 3.07 mmol) in THF (20 mL) maintained at 0° C. was slowly added a 1M solution of LAH in THF (7.80 mL, 7.80 mmol). The reaction mixture was stirred at room temperature for 3 h. After completion of the reaction, the reaction mixture was cooled to 0° C. and quenched with water (20 mL). Temperature was maintained below 20° C. during quenching. After completion of quenching, the pH was adjusted to 2-3 with 2N HCl. The resulting residue was extracted into ethyl acetate (20 mL) and the organic layer was washed with sodium chloride solution (20 mL). The organic phase was dried over $Na_2SO_4$ to afford the crude product. The crude product was purified by flash chromatography ($SiO_2$, 0-20% ethyl acetate/hexane) to afford (3-methyl-4-sulfanyl-phenyl)methanol as a colorless liquid (0.45 g, 90% yield). MS m/z 153.0 $[M-H]^-$.

XXII-3 and XXII-4, as shown in Table 4 below, were synthesized in an analogous manner to Linker XXII-2.

TABLE 4

Additional Linkers

| Linker Code | Linker Structure | m/z found [M − H] |
|---|---|---|
| XXII-3 | | 153.1 |
| XXII-4 | | 167.0 |

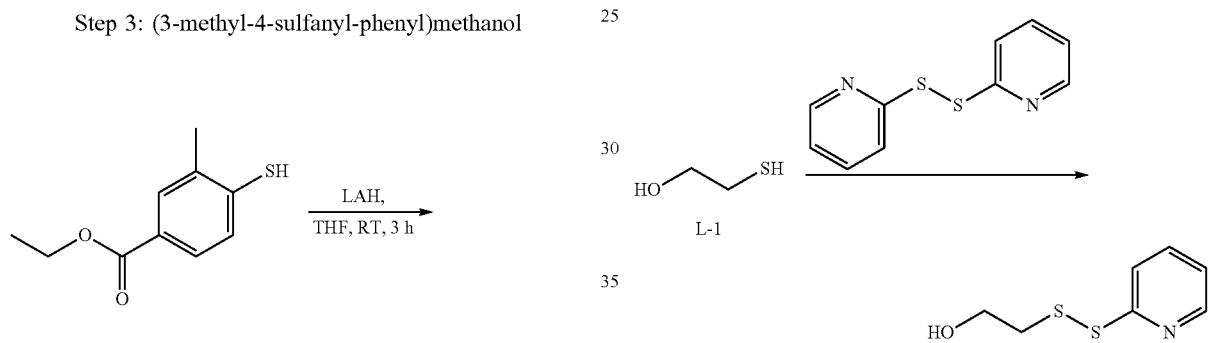

Intermediates

Intermediate I-1: 2-(2-pyridyldisulfanyl)ethanol

To 2-(2-pyridyldisulfanyl)pyridine (4.693 g, 21.3 mmol) in 40 ml of degassed ($N_2$) MeOH was added 2-sulfanylethanol (0.498 mL, 7.10 mmol) in a drop-wise fashion. The mixture was stirred for 2-20 h under $N_2$. The mixture was concentrated to dryness and directly purified ($SiO_2$, 0-5% EtOAc/$CH_2Cl_2$) to give 3 fractions; (F1 mix SM A and product; F2 product; F3 2-thiopyridine/product mix). The impure material was purified again ($SiO_2$, 0-50% EtOAc/Hexanes) to give 1.17 g, 88% yield of 2-(2-pyridyldisulfanyl)ethanol. MS m/z found 188.4 $[M+H]^+$ The following Intermediates shown in Table 5 were prepared analogously to Intermediate I-1.

TABLE 5

Intermediates

| Intermediate | $R^1$, $R^2$ | $R^3$, $R^4$ | n | $R^5$, $R^6$ | X | MH+ |
|---|---|---|---|---|---|---|
| I-2 | Me-H (rac) | H, H | 0 | — | H | 202.1 |
| I-7 | H, H | H, Ph | 0 | — | H | 264.1 |

TABLE 5-continued

Intermediates

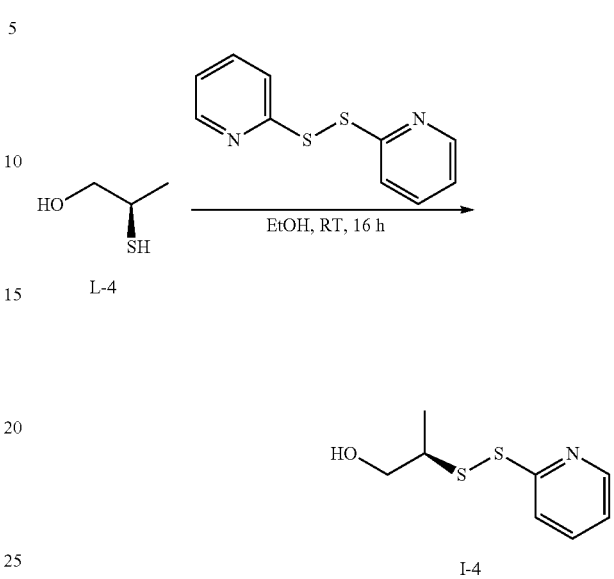

| Intermediate | R¹, R² | R³, R⁴ | n | R⁵, R⁶ | X | MH+ |
|---|---|---|---|---|---|---|
| I-8 | H, H | H, CO₂Me | 0 | — | H | 246.1 |
| I-9 | H, H | H, CH₂OMe | 0 | — | H | 232.0 |
| I-10 | H, H | H, H | 1 | H, H | H | 367.0 |

Intermediate I-3: 2-methyl-2-[(5-nitro-2-pyridyl)disulfanyl]propan-1-ol

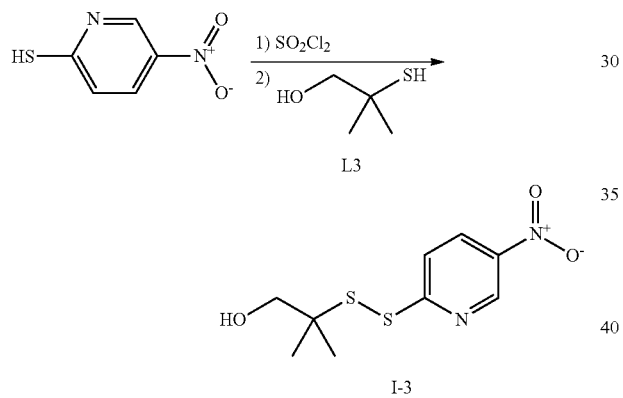

SO₂Cl₂ (0.382 mL, 4.71 mmol) was added drop-wise to a stirred suspension of 5-nitropyridine-2-thiol (668 mg, 4.28 mmol) in dry DCM (15 mL) at 4° C. under an N₂ atmosphere. The reaction mixture turned from a yellow suspension to a yellow solution and was allowed to warm to room temperature with stirring for 2 hours, after which time the mixture was concentrated to provide a yellow solid. The solid was re-dissolved in DCM (15 mL) and treated drop-wise with a solution of 2-methyl-2-sulfanyl-propan-1-ol (454 mg, 4.28 mmol) in dry DCM (10 mL) at 4° C. under an N₂ atmosphere. The reaction mixture was allowed to warm to room temperature and stirred for 20 hours. The reaction was monitored by LC/MS for the desired product mass. To the mixture was added 50 mL of H₂O and the diluted mixture was treated with ammonium hydroxide solution. The reaction mixture was diluted with 50 mL of EtOAc, partitioned, and separated. The organic phase was dried with MgSO₄, filtered, and concentrated to give the crude product. The crude mixture was purified (SiO₂, 0-50% EtOAc/hexanes) to give 721 mg, 65% yield of 2-methyl-2-[(5-nitro-2-pyridyl)disulfanyl]propan-1-ol. MS m/z found 261.7 [M+H]⁺.

Intermediate I-4: (2R)-2-(2-pyridyldisulfanyl)propan-1-ol

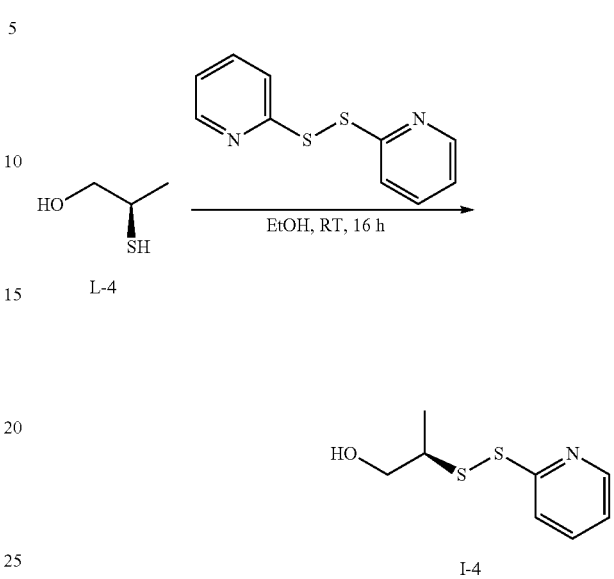

To 2-(2-pyridyldisulfanyl)pyridine (5.00 g, 22.7 mmol) in 40 ml of MeOH degassed with N₂ was added (2R)-2-sulfanylpropan-1-ol (0.75 g, 8.14 mmol) in a drop-wise fashion. The mixture was stirred for 2 h under N₂. The mixture was concentrated to dryness and directly loaded onto a SiO₂ flash column and eluted with 0-50% EtOAc/Hexanes to give 1.17 g, 71% of (2R)-2-(2-pyridyldisulfanyl)propan-1-ol. MS m/z found 202.1 [M+H]⁺

Intermediate I-5

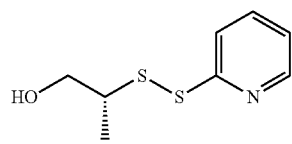

Intermediate I-5 was prepared in an analogous fashion to Intermediate I-4 from L-5.

Intermediate I-6

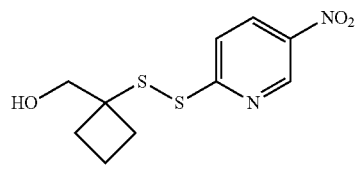 [SMILES: O=[N+]([O-])c1ccc(SSC2(CO)CCC2)nc1]

Intermediate I-6 was prepared analogously to Intermediate I-3 from Linker L-6.

Synthesis of Intermediates XII

TABLE 6
Intermediates XII

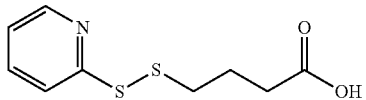 [SMILES: O=C(O)CCCSSc1ccccn1]

| Int. | R¹, R² | R³, R⁴ | R⁵, R⁶ | X | MH+ |
|---|---|---|---|---|---|
| XII-1 | H, H | H, H | H, H | H | 230.0 |

Synthesis of Intermediate XII-1:
4-(2-pyridyldisulfanyl)butanoic acid

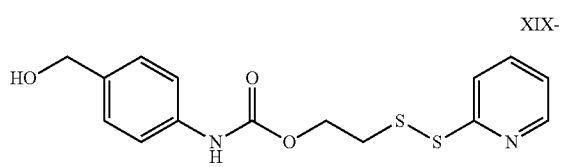

To 2-(2-pyridyldisulfanyl)pyridine (1120 mg, 5.08 mmol) in 20 ml of degassed (N₂) MeOH was added 4-sulfanylbutanoic acid (500 mg, 4.16 mmol) in a drop-wise fashion. The mixture was stirred for 16 h under N₂. The mixture was concentrated to dryness and purified by reverse-phase chromatography (Sunfire C18, 30×150 mm, 5-95% CH₃CN/ H₂O, 0.05% TFA) to give 187 mg, 19.6% of 4-(2pyridyldisulfanyl)butanoic acid. MS m/z found 230.0 [M+H]⁺.

Intermediate XIX-1: 2-(2-pyridyldisulfanyl)ethyl N-[4-(hydroxymethyl) phenyl]carbamate

XIX-1

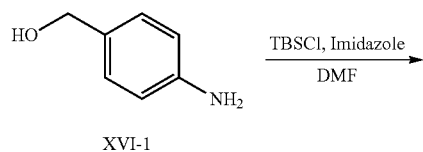

Step 1: Synthesis of 4-[[tert-butyl(dimethyl)silyl]oxymethyl]aniline

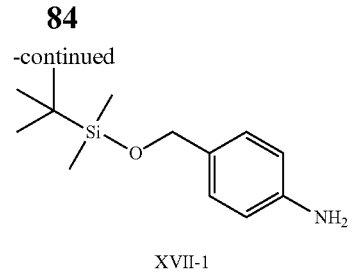

XVII-1

A solution of (4-aminophenyl)methanol (5.00 g, 40.6 mmol) in anhydrous DMF (10 mL) was added dropwise within 30 min to a stirred solution of tert-butyl-chlorodimethyl-silane (7.34 g, 48.7 mmol) and imidazole (7.90 mL, 81.2 mmol) in anhydrous DMF (40 mL). After stirring at room temperature for 16 h, the reaction mixture was poured into water (400 mL) and extracted with CH₂Cl₂ (3×100 mL). The combined organic layers were washed with water (2×100 mL) and dried over MgSO4. After removing the volatiles in vacuo, the residue was purified by column chromatography (SiO2, 0-25% EtOAc/hexanes) affording 4-[[tert-butyl(dimethyl)silyl]oxymethyl]aniline (7.91 mg, 33.3 mmol, yield: 82.1%).

Step 2: Synthesis of 2-(2-pyridyldisulfanyl)ethylN-[4-[[tert-butyl(dimethyl)silyl]oxymethyl]phenyl] carbamate

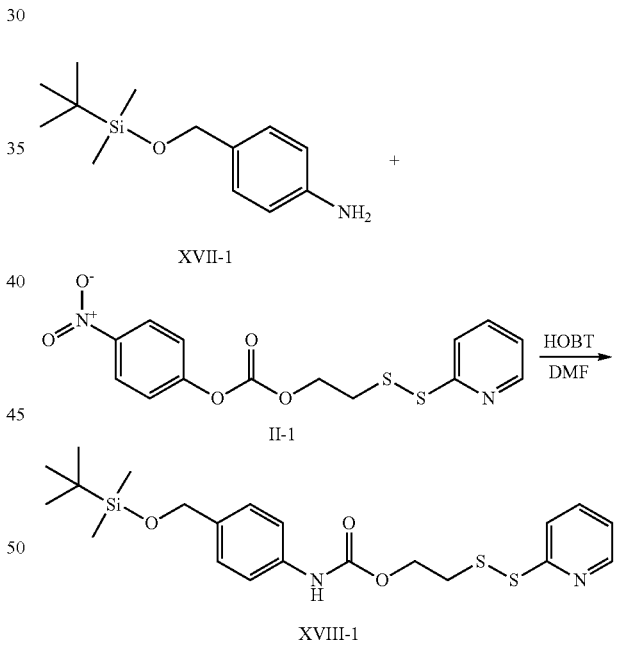

To (4-nitrophenyl) 2-(2-pyridyldisulfanyl)ethyl carbonate (200 mg, 0.57 mmol) in 2 mL of DMF was added 4-[[tertbutyl(dimethyl)silyl]oxymethyl]aniline (202 mg, 0.85 mmol), 1-hydroxybenzotriazole hydrate (104 mg, 0.68 mmol) and 200 mg of activated 4 A Mol sieves. The mixture was stirred for 18 h. The solids were filtered off and the celite plug rinsed with 2 mL of DMF. The filtrate was concentrated to dryness and the residue purified by column chromatography (SiO2, 0-50% EtoAc/hexanes) to afford 2-(2-pyridyldisulfanyl)ethyl N-[4-[[tert-butyl(dimethyl)silyl] oxymethyl]phenyl]carbamate (244 mg, 0.54 mmol, yield: 95.4%).

Step 3: 2-(2-pyridyldisulfanyl)ethyl N-[4-(hydroxymethyl) phenyl]carbamate

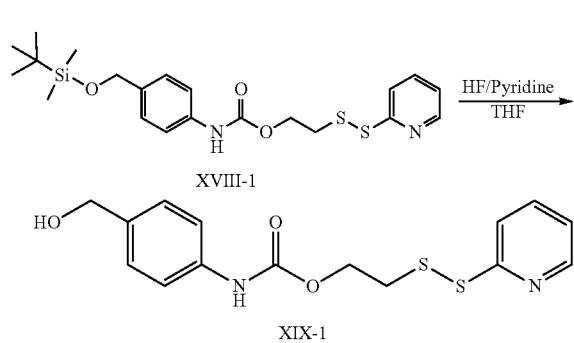

2-(2-Pyridyldisulfanyl)ethyl N-[4-[[tert-butyl(dimethyl) silyl]oxymethyl]phenyl]-carbamate (194 mg, 0.430 mmol) was dissolved in 2 mL of THF and cooled to 0° C. under $N_2$. HF-pyridine (780 µL, 8.89 mmol) was added and the solution continued to stir at 0° C. for 1 h. Water (3 mL) was added, and the reaction was neutralized with sat. $NaHCO_3$ and extracted with $CH_2Cl_2$ (3×50 mL). The organic layer was concentrated and purified by column chromatography ($SiO_2$, 0-75% EtOAc/hexane) to give 2-(2-pyridyldisulfanyl)ethylN-[4-(hydroxymethyl) phenyl]carbamate (99.1 mg, 0.29 mmol, yield: 68.4%).

Intermediate XXIII-1: [4-(2-pyridyldisulfanyl)phenyl]methanol

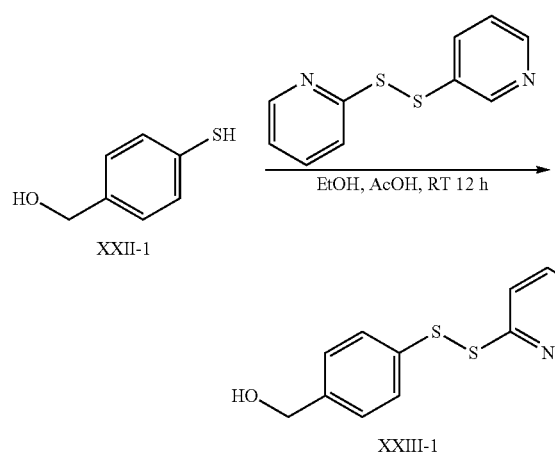

A stirred solution of 1,2-di(pyridin-2-yl)disulfane (2.68 g, 12.1 mmol) in a mixture of AcOH:ethanol (5 mL, 1:10) solvent was degassed under $N_2$. This was followed by addition of 4-mercaptophenyl)methanol (0.74 g, 5.2 mmol) in a mixture of AcOH/ethanol (5 mL) solvent drop-wise over 20 min and stirred for 12 h under $N_2$ atmosphere at room temperature. The reaction was concentrated under reduced pressure to afford the crude product which is purified by column chromatography ($SiO_2$, 60-70% EtOAc/hexanes) to afford [4-(2-pyridyldisulfanyl)phenyl]methanol as a colourless liquid (800 mg, 61% yield).

Intermediate XXIII-2: [3-methyl-4-(2-pyridyldisulfanyl)phenyl]methanol

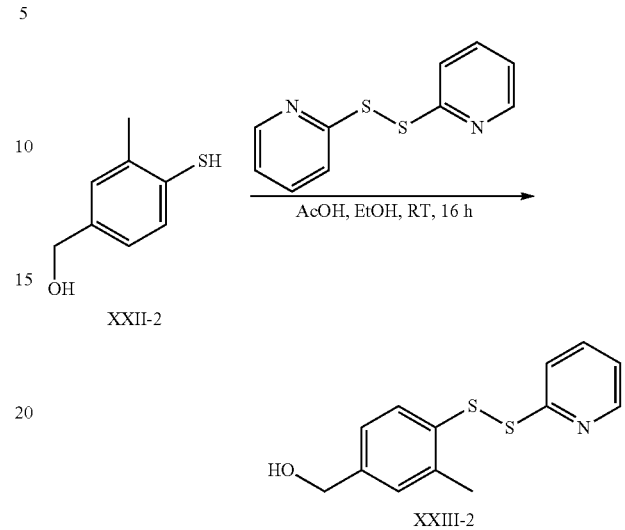

A stirred solution of 1,2-di(pyridin-2-yl)disulfane (1.10 g, 4.90 mmol) dissolved in acetic acid/ethanol (1:10, 37 mL) was purged with $N_2$ for 5 min. To this, a solution of 4-mercapto-3-methylphenyl)methanol (0.51 g, 3.30 mmol) in acetic acid/ethanol (1:10, 18 mL) was added drop-wise over a period of 20 min. The resulting reaction mixture was stirred for 16 h at room temperature. After completion of the reaction, the mixture was concentrated under reduced pressure to afford the crude product. The crude product was purified by flash chromatography ($SiO_2$, 0-70% EtOAc/hexane gradient) to afford [3-methyl-4-(2-pyridyl disulfanyl)phenyl]methanol as a colorless liquid (0.69 g, 80% yield). MS m/z found 264.0 [M+H]⁻.

Intermediates XXIII-3 and XXIII-4

Intermediates XXIII-3 and XXIII-4 as shown in Table 7 were prepared analogously to XXIII-2.

TABLE 7

Intermediates XXIII

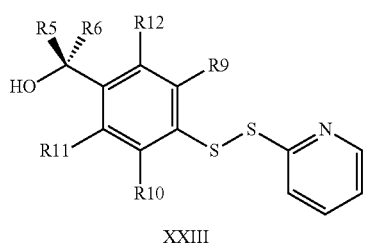

XXIII

| Intermediate | $R^5, R^6$ | $R^9, R^{10}, R^{11}, R^{12}$ | MH+ |
|---|---|---|---|
| XXIII-3 | H, H | H, H, H, Me | 264.2 |
| XXIII-4 | H, H | Me, Me, H, H | 278.0 |

Intermediates XXXIII from Intermediates XXXII

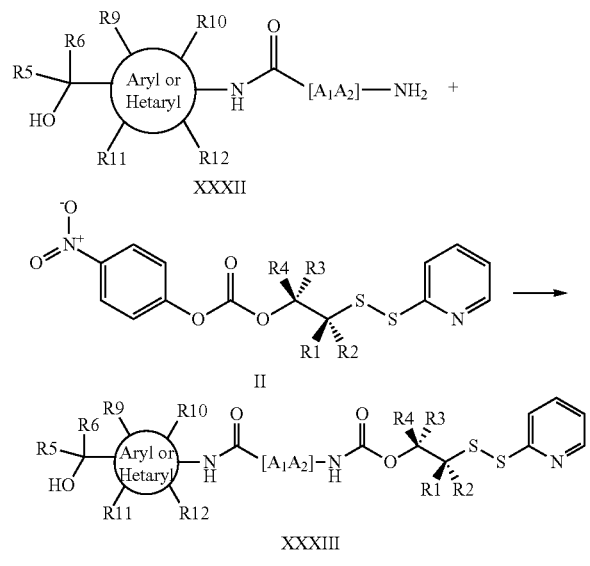

TABLE 8

| Intermediates XXXIII | | | | |
|---|---|---|---|---|
| Int. | $R_1, R_2, R_3, R_4$ | $R_5, R_6$ | $R_9, R_{10}, R_{11}, R_{12}$ | $A_1, A_2$ | MH+ |
| XXXIII-1 | H, H, H, H | H, H | H, H, H, H | Cit, Val | 593.2 |

Synthesis of Intermediate XXXIII-1: 2-(2-pyridyldisulfanyl)ethyl N-[(1S)-1-[[(1S)-1-[[4-(hydroxymethyl)phenyl]carbamoyl]-4-ureido-butyl]carbamoyl]-2-methyl-propyl]carbamate To (2S)-2-[[(2S)-2-amino-3-methyl-butanoyl]amino]-N-[4-(hydroxymethyl)phenyl]-5-ureido-pentanamide (100 mg, 0.264 mmol) in 2 mL of dry DMF under $N_2$ is added N,N-Diisopropylethylamine (0.122 mL, 0.659 mmol) and (4-nitrophenyl) 2-(2-pyridyldisulfanyl)ethyl carbonate (92.9 mg, 0.264 mmol). The mixture is stirred for 16 h under $N_2$. The mixture is concentrated to a solid. The crude residue is purified on an $SiO_2$ column (12 g, 0-10% MeOH/$CH_2Cl_2$) to give 2-(2-pyridyldisulfanyl)ethyl N-[(1S)-1-[[(1S)-1-[[4-(hydroxymethyl)phenyl]carbamoyl]-4-ureido-butyl]carbamoyl]-2-methyl-propyl]carbamate (149 mg, 0.251 mmol, yield: 95.4%). MS m/z found 593.2 [M+H]+.

Synthesis of XLI-1: Methyl (2S,3S,4S,5R,6S)-3,4,5-triacetoxy-6-(4-formyl-2-nitro-phenoxy)tetrahydropyran-2-carboxylate

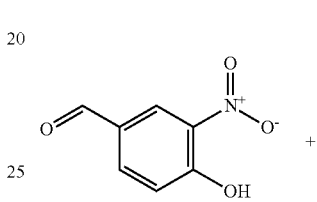

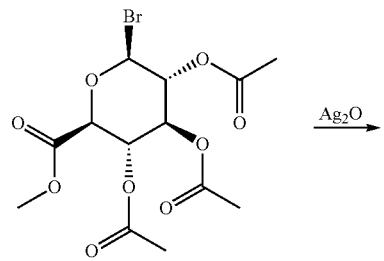

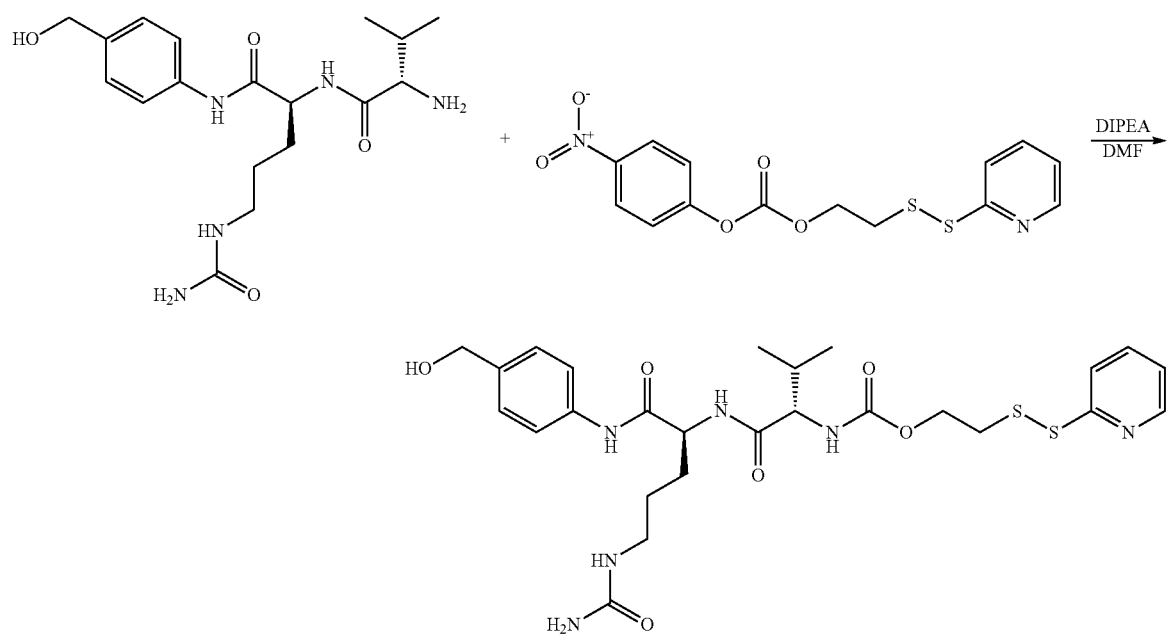

-continued

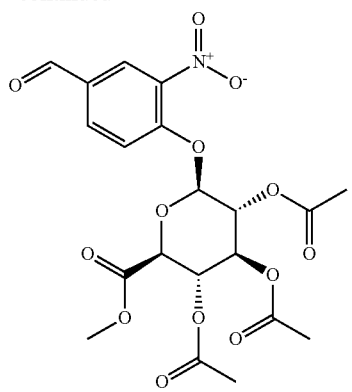

The title compound was prepared as outlined in US 2017/0145044 A1.

Synthesis of XLII-1: Methyl (2S,3S,4S,5R,6S)-3,4,5-triacetoxy-6-[4-(hydroxymethyl)-2-nitro-phenoxy]tetrahydropyran-2-carboxylate

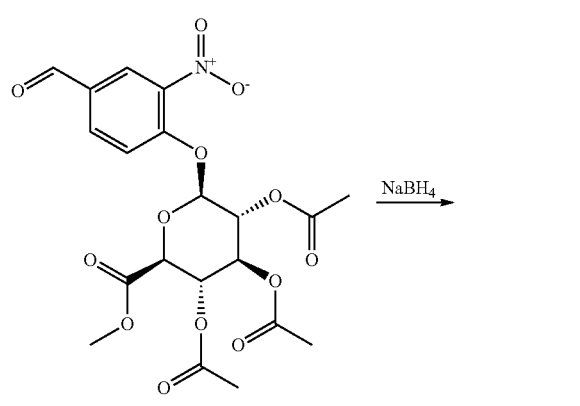

The title compound was prepared as outlined in WO 2011/066418 A1.

Synthesis of XLIII-1: Methyl (2S,3S,4S,5R,6S)-3,4,5-triacetoxy-6-[2-amino-4-(hydroxymethyl)phenoxy]tetrahydropyran-2-carboxylate

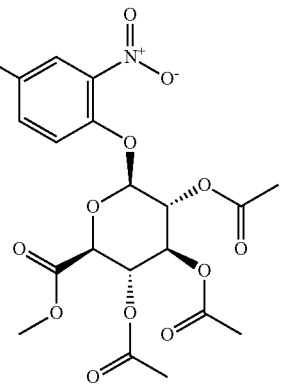

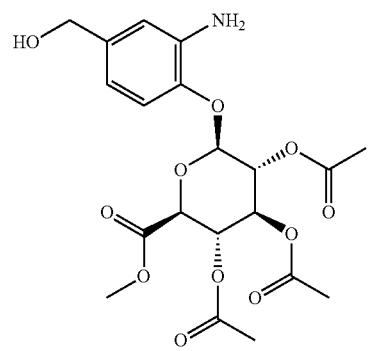

Methyl (2S, 3S, 4S, 5R)-3,4,5-triacetoxy-6-[4-(hydroxymethyl)-2-nitro-phenoxy]tetrahydropyran-2-carboxylate (361 mg, 0.74 mmol) was dissolved in MeOH and to it was added Pd/C (50.0 mg, 0.47 mmol) followed by NaBH$_4$ (84.4 mg, 2.23 mmol). The reaction mixture was stirred at RT for 15 min. LC-MS indicated the desired product had formed. The reaction mixture was filtered through celite and then quenched with sat. NH$_4$Cl. The product was extracted with DCM, EtOAc and the organic layers combined. They were washed with brine and concentrated. The crude product was partitioned in half and one portion was purified by RP HPLC (20-95% ACN/H$_2$O) to give methyl (2S,3S,4S,5R,6S)-3,4,5-triacetoxy-6-[2-amino-4-(hydroxymethyl)phenoxy]tetrahydropyran-2-carboxylate (180 mg, 0.40 mmol, 53.1% yield). MS m/z found 456.2 [M+H]$^+$.

Synthesis of XLV-1: Methyl (2S,3S,4S,5R,6S)-3,4,5-triacetoxy-6-[3-R10-2-R11-4-(hydroxymethyl)-6-[3-(2-pyridyldisulfanyl)propanoylamino]phenoxy]tetrahydropyran-2-carboxylate

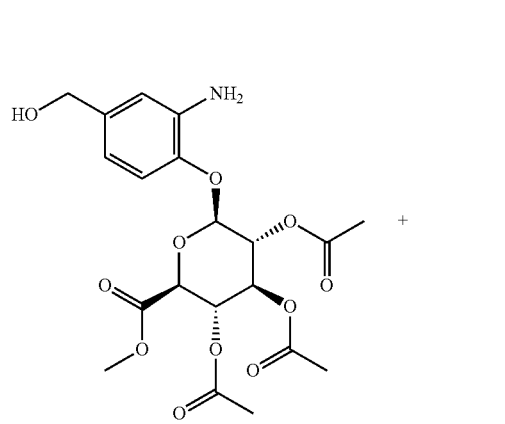

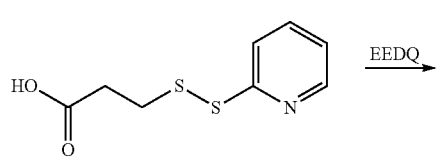

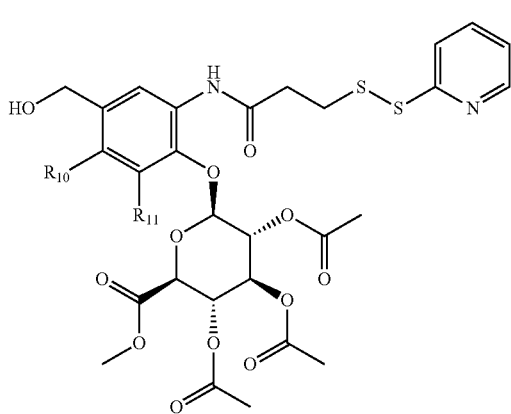

EEDQ (130 mg, 0.527 mmol) was added to 3-(2-pyridyldisulfanyl)propanoic acid (56.7 mg, 0.263 mmol) dissolved in DCM and was stirred for 20 min under N₂. The methyl (2S,3S,4S,5R)-3,4,5-triacetoxy-6-[2-amino-4-(hydroxymethyl)phenoxy]tetrahydropyran-2-carboxylate (120 mg, 0.263 mmol) was dissolved in DCM and added to the mixture and stirred overnight. LC-MS indicated the desired product had been formed. The reaction mixture was concentrated and purified by reverse phase chromatography (20-95% ACN/H₂O) to give 63 mg of methyl (2S,3S,4S,5R)-3,4,5-triacetoxy-6-[4-(hydroxymethyl)-2-[3-(2-pyridyldisulfanyl)propanoylamino]phenoxy]tetrahydropyran-2-carboxylate (63.0 mg, 0.0965 mmol, yield: 36.6%). MS m/z found 653.2 [M+H]⁺.

Intermediate II-1: (4-nitrophenyl) 2-(2-pyridyldisulfanyl)ethyl carbonate

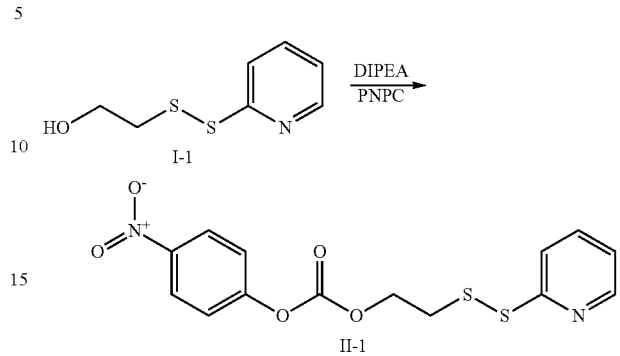

To 2-(2-pyridyldisulfanyl)ethanol (517 mg, 2.76 mmol) in 20 ml CH₂Cl₂ under N₂ at 4° C. was added N,N-Diisopropylethylamine (1.02 mL, 5.52 mmol) and (4-nitrophenyl) carbonochloridate (834 mg, 4.14 mmol). The mixture was stirred for 16 h under N₂. The mixture was dissolved into 40 mL of EtOAc and quenched with 20 mL of sat. NH₄Cl. The mixture was washed with 2×20 mL H2O and 1×20 mL sat. brine. The crude mixture was purified via SiO₂ column, eluting from 0-50% EtOAc/hexanes to give (4-nitrophenyl) 2-(2-pyridyldisulfanyl)ethyl carbonate (482 mg, 50% yield).

Intermediates II-2, II-3, and II-5

Intermediates II-2, II-3, and II-5 were prepared analogously to Intermediate II-1 using the appropriate intermediates I-2, I-3, and I-5, as shown below:

TABLE 9

Additional Intermediates

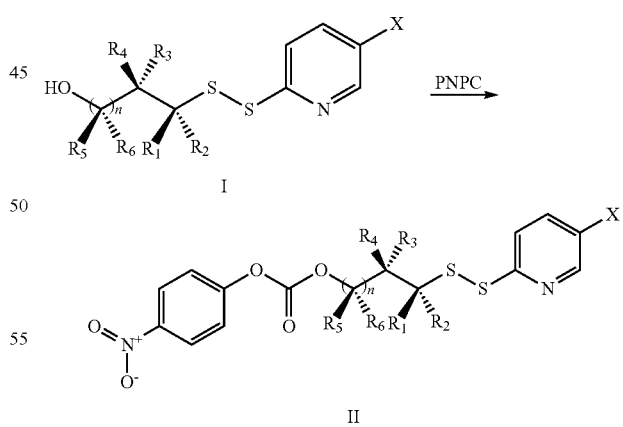

| Intermediate | R¹, R² | R³, R⁴ | n | R⁵, R⁶ | X | MH+ |
|---|---|---|---|---|---|---|
| II-2 | Me-H (rac) | H, H | 0 | — | H | 367.1 |
| II-5 | H, Me | H, H | 0 | — | H | 367.1 |
| II-3 | Me, Me | H, H | 0 | — | NO₂ | |

Intermediate II-4: (4-nitrophenyl) [(2R)-2-(2-pyridyldisulfanyl)propyl]carbonate

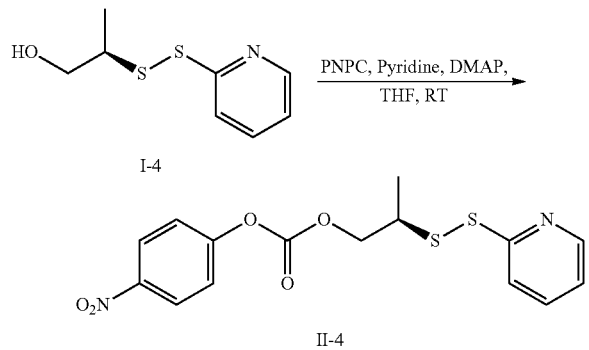

To (2R)-2-(2-pyridyldisulfanyl)propan-1-ol (0.39 g, 1.94 mmol) in THF under $N_2$ was added pyridine (0.16 mL, 1.94 mmol) and the (4-nitrophenyl) carbonochloridate (0.59 g, 2.91 mmol). The mixture was stirred for 16 h under $N_2$. The mixture was diluted with EtOAc and quenched with 20 mL of sat. $NH_4Cl$. The mixture was washed with water and brine and the organic layer concentrated. The crude mixture was purified by column chromatography ($SiO_2$, 0-50% EtOAc/Hexanes) to afford 0.59 g, 83% of (4-nitrophenyl) [(2R)-2-(2-pyridyldisulfanyl)propyl]carbonate. MS m/z found 367.1 $[M+H]^+$.

Intermediates II-6 Through II-9

Intermediates II-6, II-7, II-8, and II-9 were prepared analogously to Intermediate II-4, as shown below in Table 10:

TABLE 10

Additional Intermediates

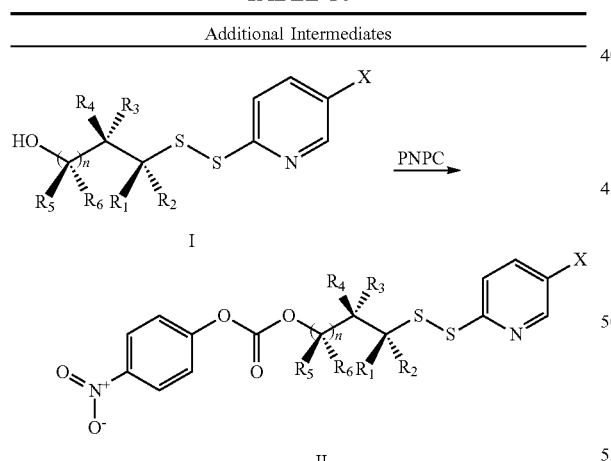

TABLE 10-continued

| Intermediate | $R^1, R^2$ | $R^3, R^4$ | n | $R^5, R^6$ | X | MH+ |
|---|---|---|---|---|---|---|
| II-6 | —$CH_2CH_2CH_2$— ($R^1$ and $R^2$ form a cyclobutyl) | H, H | 0 | — | $NO_2$ | 438.0 |
| II-7 | H, H | H, Ph | 0 | — | H | 429.1 |
| II-8 | H, H | H, $CO_2Me$ | 0 | — | H | 411.0 |
| II-9 | H, H | H, $CH_2OMe$ | 0 | — | H | 397.1 |
| II-10 | H, H | H, H | 1 | H, H | H | 495.1 |

Synthesis of Intermediate XXVII-1

Intermediate XXVII-1 is prepared analogously to Intermediates XXII.

TABLE 11

Intermediates XXVII

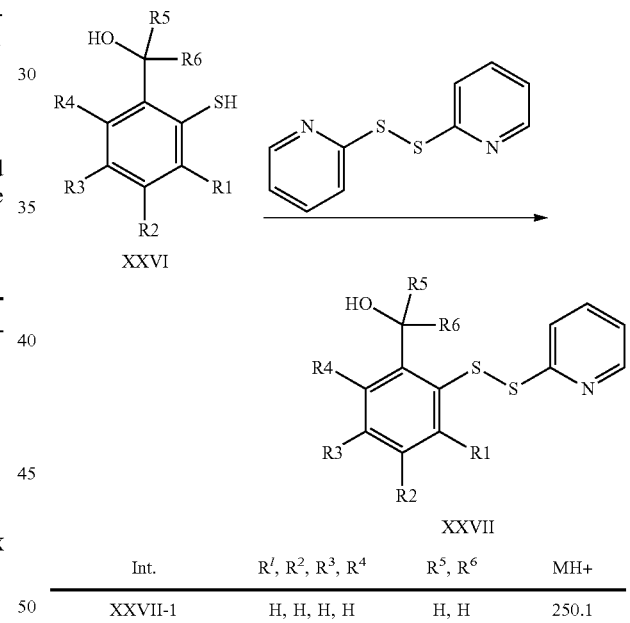

| Int. | $R^1, R^2, R^3, R^4$ | $R^5, R^6$ | MH+ |
|---|---|---|---|
| XXVII-1 | H, H, H, H | H, H | 250.1 |

Intermediate XX-1: (4-nitrophenyl) [4-[2-(2-pyridyldisulfanyl)ethoxycarbonyl amino]phenyl] methyl carbonate

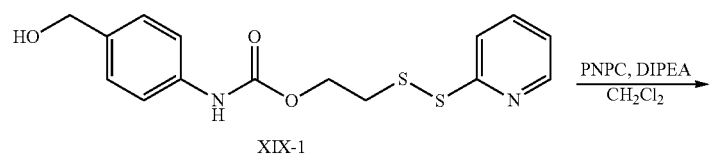

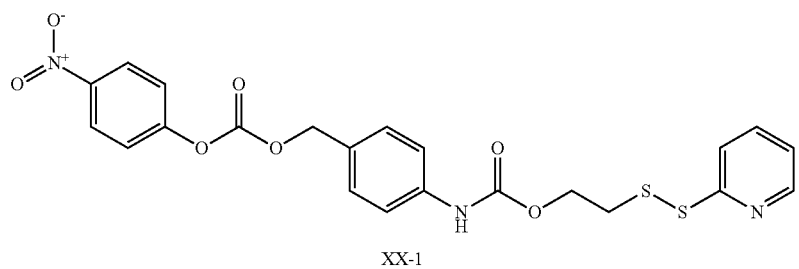

XX-1

To 2-(2-pyridyldisulfanyl)ethyl N-[4-(hydroxymethyl)phenyl]carbamate (136 mg, 0.41 mmol) in 5 ml CH$_2$Cl$_2$ under N$_2$ was added DIPEA (0.15 mL, 0.81 mmol) and (4-nitrophenyl) carbonochloridate (122 mg, 0.61 mmol). The mixture was stirred for 16 h under N$_2$. The mixture was dissolved into 20 mL of EtOAc and quenched with 20 mL of sat. NH$_4$C$_1$. The mixture was washed with 2×20 mL H$_2$O and 1×20 mL sat. brine. The crude mixture was purified via column chromatography (SiO$_2$, 0-25% EtOAc/hexanes) to afford (4-nitrophenyl) [4-[2-(2-pyridyldisulfanyl)ethoxycarbonylamino]phenyl]methyl carbonate (44.2 mg, 0.09 mmol, yield: 21.8%).

Intermediate XXIV-1: (4-nitrophenyl) [4-(2-pyridyldisulfanyl)phenyl]methyl carbonate

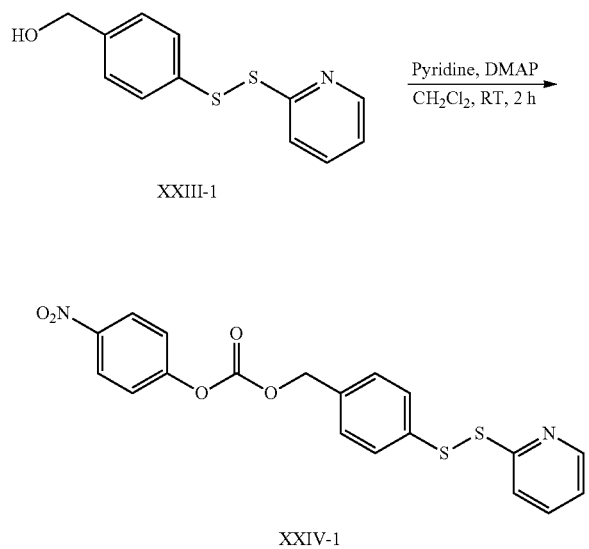

To a stirred solution of (4-(pyridin-2-yldisulfanyl)phenyl)methanol (0.40 g, 1.60 mmol) in CH$_2$Cl$_2$ (10 mL) were added 4-nitrophenyl chloroformate (0.65 g, 3.2 mmol), pyridine (0.25 mL, 3.20 mmol), catalytic amount of DMAP (0.005 g) at 0° C. The mixture was allowed to stir for 2 h at room temperature. The reaction mixture was quenched with 1.5 N HCl solution. The organic layer was separated and washed with brine, dried over anhydrous Na$_2$SO$_4$ and concentrated. The crude product was purified by column chromatography (SiO$_2$, 20-30% of EtOAc/hexanes) to afford (4-nitrophenyl) [4-(2-pyridyldisulfanyl)phenyl]methyl carbonate as a colourless liquid (600 mg, 91% yield); MS m/z 415.0 [M+H]$^+$ Intermediate XXIV-2: [3-methyl-4-(2-pyridyldisulfanyl)phenyl]methyl (4-nitrophenyl) carbonate

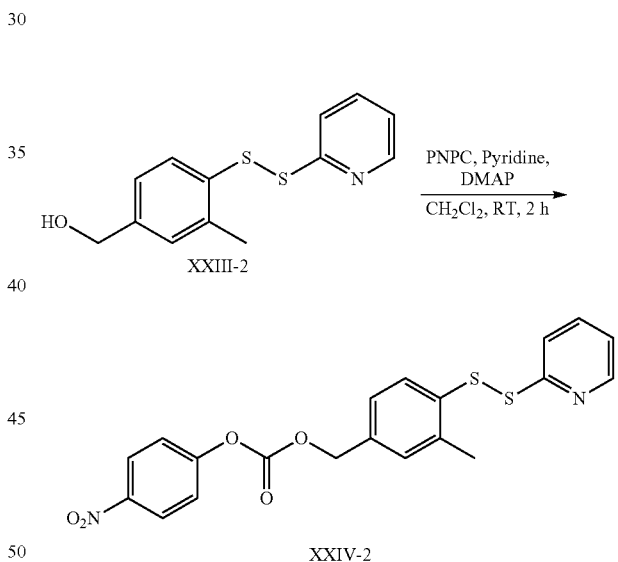

To a stirred solution of (3-methyl-4-(pyridin-2-yldisulfaneyl)phenyl)methanol (0.69 g, 2.60 mmol) dissolved in CH$_2$Cl$_2$ (10 mL) was added 4-nitrophenyl chloroformate (1.05 g, 5.2 mmol), pyridine (0.43 mL, 5.2 mmol), and a catalytic amount of DMAP (0.005 g) at 0° C. The mixture was allowed to stir for 2 h at room temperature. After completion of the reaction, the reaction mixture was quenched with 1.5 N HCl. The organic layer was separated, washed with sodium chloride solution (10 mL), dried over anhydrous Na$_2$SO$_4$ and concentrated. The crude product was purified by flash column chromatography (SiO$_2$, 20-30% EtOAc/hexanes) to afford [3-methyl-4-(2-pyridyldisulfanyl)phenyl]methyl (4-nitrophenyl) carbonate (700 mg, 62% yield). MS m/z 429.0 [M+H]$^+$.

The following intermediate were prepared analogously to Intermediates XXIV-1 and XXIV-2 as shown below in Table 12:

TABLE 12

Additional Intermediates

XXIII

XXIV

| Intermediate | $R^5, R^6$ | $R^9, R^{10}, R^{11}, R^{12}$ | X | MH+ |
|---|---|---|---|---|
| XXIV-3 | H, H | H, H, Me, H | H | 429.0 |
| XXIV-4 | H, H | Me, Me, H, H | H | 443.0 |

Intermediates XXVIII

TABLE 13

Intermediates XXVIII

XXVII

XXVIII

| Int. | $R^1, R^2, R^3, R^4$ | $R_5, R_6$ | MH+ |
|---|---|---|---|
| XXVIII-1 | H, H, H, H | H, H | 415.0 |

Intermediate XXVIII-1 was prepared analogously to Intermediates XXIV.

Intermediates XXXIV

TABLE 14

Intermediates XXXIV

XXXIII

XXXIV

| Int. | $R^1, R^2, R^3, R^4$ | $R^5, R^6$ | $R^9, R^{10}, R^{11}, R^{12}$ | $A_1, A_2$ | MH+ |
|---|---|---|---|---|---|
| XXXIV-1 | H, H, H, H | H, H | H, H, H, H | Cit, Val | 758.2 |

Synthesis of XXXIV-1: [4-[[(2S)-2-[[(2S)-3-methyl-2-[2-(2-pyridyldisulfanyl)-ethoxycarbonylamino]butanoyl]amino]-5-ureido-pentanoyl]amino]phenyl]methyl (4-nitrophenyl) carbonate

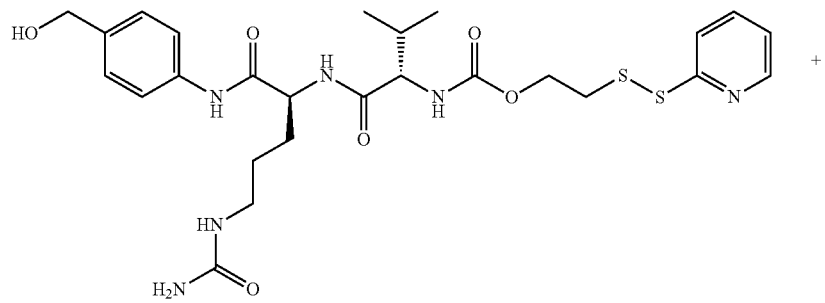

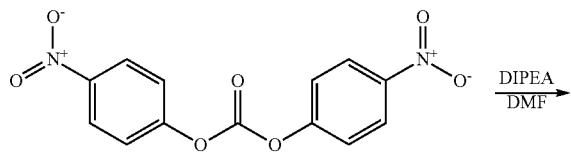

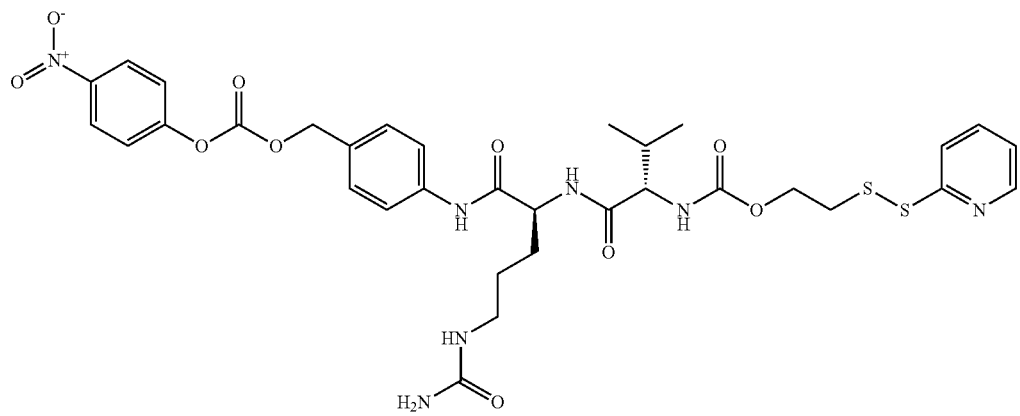

2-(2-pyridyldisulfanyl)ethyl N-[(1S)-1-[[(1S)-1-[[4-(hydroxymethyl)phenyl]carbamoyl]-4-ureido-butyl]carbamoyl]-2-methyl-propyl]carbamate (149 mg, 0.251 mmol) was dissolved into 2 mL of dry DMF and cooled to 4° C. To this is added bis(4-nitrophenyl) carbonate (153 mg, 0.503 mmol) and N,N-Diisopropylethylamine (0.0928 mL, 0.503 mmol). The mixture was allowed to warm to RT over 2 h. The progress of the reaction was monitored by LC-MS. The mixture was concentrated and purified (25 g SiO$_2$, 0-10% MeOH/CH2Cl2) to give [4-[[(2S)-2-[[(2S)-3-methyl-2-[2-(2-pyridyldisulfanyl)ethoxycarbonylamino]butanoyl]amino]-5-ureido-pentanoyl]amino]phenyl]methyl (4-nitrophenyl) carbonate (139 mg, yield: 73.1%). MS m/z found 758.2 [M+H]$^+$.

101

Synthesis of XLVI-1: Methyl (2S,3S,4S,5R,6S)-3,4,5-triacetoxy-6-[2-R11-4-[(4-nitrophenoxy)carbonyloxymethyl]-6-[3-(2-pyridyldisulfanyl)propanoylamino]-phenoxy]tetrahydropyran-2-carboxylate

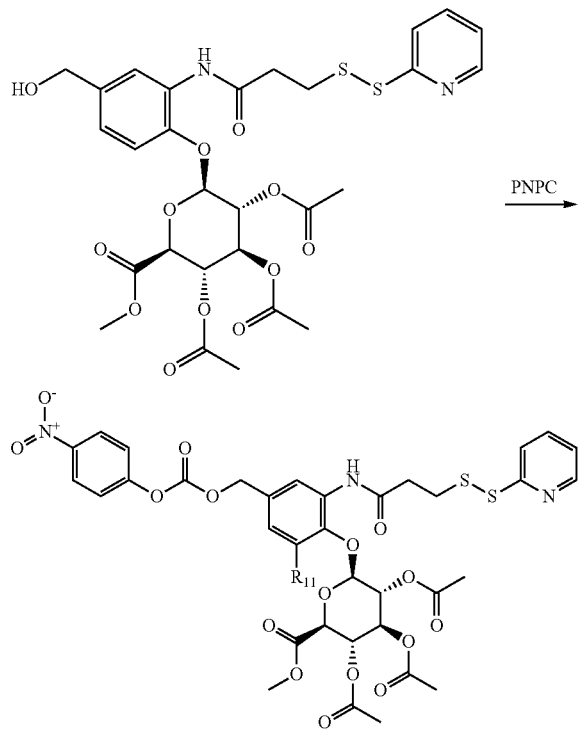

Methyl (2S,3S,4S,5R)-3,4,5-triacetoxy-6-[4-(hydroxymethyl)-2-[3-(2-pyridyldisulfanyl)propanoylamino]phenoxy]tetrahydropyran-2-carboxylate (102 mg, 0.15 mmol) was dissolved in THF and to it was added pyridine (0.02 mL, 0.19 mmol) followed by (4-nitrophenyl) carbonochloridate (63.0 mg, 0.313 mmol). The reaction mixture was stirred under $N_2$ overnight. LC-MS indicated a complete reaction. The mixture was diluted with 100 mL EtOAc and quenched with 50 mL of sat. $NH_4Cl$. The mixture was washed with 50 mL sat. brine. The organic layer was dried with $NaSO_4$ and concentrated. The crude mixture was purified by column chromatography (50-100% EtOAc/Hexanes) to give (58.0 mg, 0.07 mmol, 45.4%). MS m/z found 818.2 $[M+H]^+$.

Intermediate III-1: [4-(4-carbamoyl-1H-benzimidazol-2-yl)phenyl]methyl 2-(2-pyridyldisulfanyl)ethyl carbonate

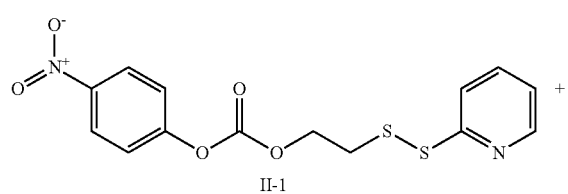

102

-continued

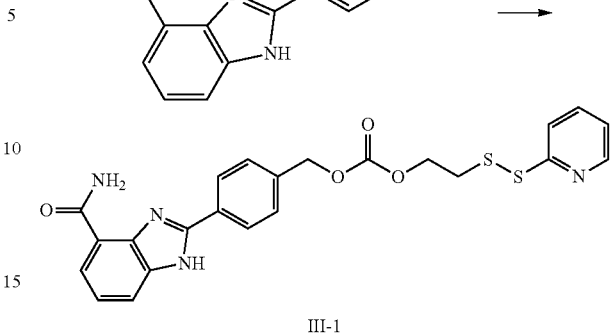

To 2-[4-(hydroxymethyl)phenyl]-1~{H}-benzimidazole-4-carboxamide (150 mg, 0.561 mmol) in 4 mL of dry DMF under $N_2$ was added N,N-diisopropylethylamine (0.207 mL, 1.12 mmol), DMAP (68.6 mg, 0.561 mmol), and (4-nitrophenyl) 2-(2-pyridyldisulfanyl)ethyl carbonate (241 mg, 0.684 mmol). The mixture was stirred for 16 h., and then diluted with 50 ml of EtOAc and successively washed with 1×20 mL of sat. $NH_4Cl$, 3×30 mL of sat. $NaHCO_3$, 3×30 mL of $H_2O$, and 1×20 mL of sat. brine. The organic phase was dried with $MgSO_4$, filtered, and concentrated. The crude residue was purified ($SiO_2$, 50-100% EtOAc/hexanes) to give 260 mg, 97% yield of [4-(4-carbamoyl-1H-benzimidazol-2-yl)phenyl]methyl2-(2-pyridyldisulfanyl)ethyl carbonate.

Intermediate III-4: [(2R)-2-(2-pyridyldisulfanyl)propyl] N-[[4-(6-fluoro-3,10-diazatricyclo[6.4.1.04,13]trideca-1,4,6,8(13)-tetraen-2-yl)phenyl]methyl]-N-methyl-carbamate

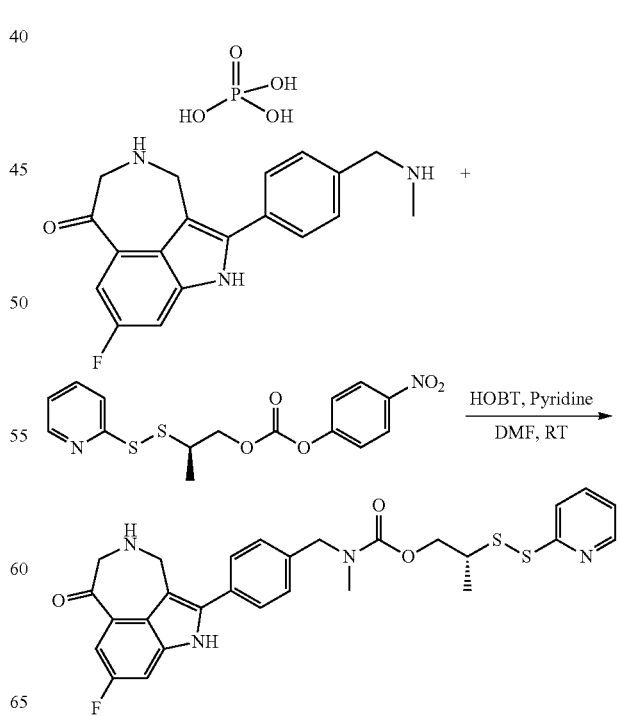

To a mixture of HOBt (48.0 mg, 0.31 mmol), pyridine (0.11 mL, 1.31 mmol), finely ground molecular sieve 4 Å (250 mg), and the 6-fluoro-2-[4-(methylaminomethyl)phenyl]-3,10-diazatricyclo[6.4.1.04,13]trideca-1,4,6,8(13)-tetraen-9-one phosphate (110 mg, 0.26 mmol) in 5 mL of anhydrous DMF was added the (4-nitrophenyl) [(2R)-2-(2-pyridyldisulfanyl)propyl]carbonate [Intermediate II-4] (105 mg, 0.29 mmol). After stirring for 16 h at room temperature, the molecular sieves were filtered off and the solvent removed in vacuo. The residue was then adsorbed onto $SiO_2$ and purified by column chromatography ($SiO_2$, 0-10% MeOH/$CH_2Cl_2$) to afford [(2R)-2-(2-pyridyldisulfanyl)propyl] N-[[4-(6-fluoro-3,10-diazatricyclo[6.4.1.04,13]trideca-1,4,6,8(13)-tetraen-2-yl)phenyl]methyl]-N-methyl-carbamate (115 mg, 80% yield) MS m/z 551.1 $(M+H)^+$.

Intermediates III-2, III-3, and III-5 Through III-15

The following intermediates were prepared analogously to Intermediates III-1 and III-4 as shown below in Table 15.

TABLE 15

Additional Intermediates

| Inter-mediate | $R^8H$ | $R^1, R^2$ | $R^3, R^4$ | n | $R^5, R^6$ | X | MH+ |
|---|---|---|---|---|---|---|---|
| III-2 | $R^8H$-1 | Me-H (rac) | H, H | — | — | H | 495.1 |
| III-3 | $R^8H$-1 | Me, Me | H, H | — | — | $NO_2$ | |
| III-5 | $R^8H$-1 | Me, H | H, H | — | — | H | 496.1 |
| III-6 | $R^8H$-2 | H, H | H, H | — | — | H | 451.1 |
| III-7 | $R^8H$-3 | H, H | H, H | — | — | H | 534.2 |
| III-8 | $R^8H$-4 | H, H | H, H | — | — | H | 458.1 |
| III-9 | $R^8H$-16 | H, H | H, H | — | — | H | 536.4 |
| III-10 | $R^8H$-16 | H, Me | H, H | — | — | H | 551.1 |
| III-11 | $R^8H$-16 | Me, H | H, H | — | — | H | 551.1 |
| III-12 | $R^8H$-16 | —$CH_2CH_2CH_2$— | H, H | — | — | $NO_2$ | 622.2 |
| III-13 | $R^8H$-16 | H, H | Ph, H | — | — | H | 613.2 |
| III-14 | $R^8H$-16 | H, H | $CO_2Me$• H | — | — | H | 595.2 |
| III-15 | $R^8H$-16 | H, H | $CH_2OMe$ | — | — | H | 581.2 |
| III-16 | $R_8H$-3 | H, Me | H, H | 0 | — | H | 548.1 |
| III-17 | $R_8H$-3 | Me, H | H, H | 0 | — | H | 548.1 |
| III-18 | $R_8H$-4 | H, Me | H, H | 0 | — | H | 472.1 |
| III-19 | $R_8H$-4 | Me, H | H, H | 0 | — | H | 472.1 |
| III-20 | $R_8H$16 | H, H | H, H | 1 | H, H | H | 495.2 |

Ester Linked Intermediates XIII

TABLE 16

Intermediates XIII

| Int. | $R^8$ | $R^1, R^2$ | $R^3, R^4$ | $R^5, R^6$ | X | MH+ |
|---|---|---|---|---|---|---|
| XIII-1 | $R^8H$-1 | H, H | H, H | H, H | H | 479.0 |

Synthesis of XIII-1: [4-(4-carbamoyl-1H-benzimidazol-2-yl)phenyl]methyl 4-(2-pyridyldisulfanyl)butanoate

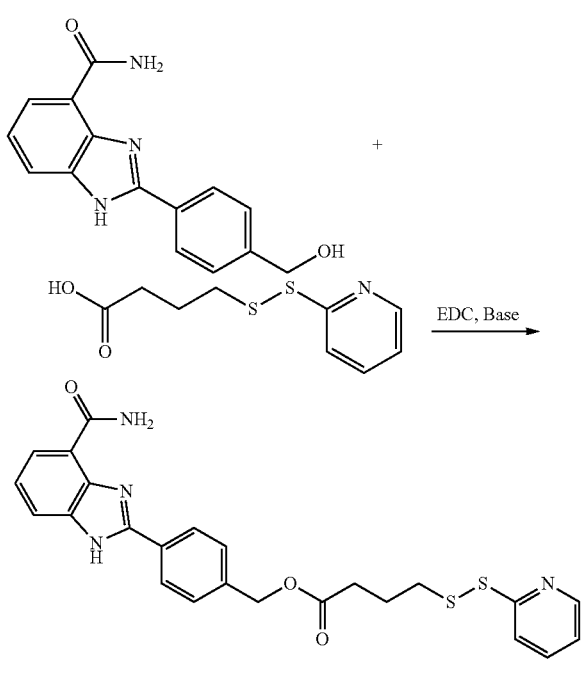

To a mixture of 4-(2-pyridyldisulfanyl)butanoic acid TFA salt (81.2 mg, 0.236 mmol), EDC HCl (47.8 mg, 0.250 mmol), and DIEA (0.0986 mL, 0.576 mmol) in 2 mL of DMF was added 2-[4-(hydroxymethyl)phenyl]-1H-benzimidazole-4-carboxamide (51.3 mg, 0.192 mmol). The mixture was stirred overnight and monitored by LC-MS. The mixture was concentrated and purified with $SiO_2$ chromatography (0-10% MeOH/CH2Cl2) to give (83.1 mg, 0.17 mmol, yield: 90.4%) MS m/z found 479.0 $[M+H]^+$.

Intermediate VII-1: 2-(2-pyridyldisulfanyl)ethyl N-[[(11S,12R)-7-fluoro-11-(4-fluorophenyl)-12-(2-methyl-1,2,4-triazol-3-yl)-4-oxo-2,3,10-triazatricyclo[7.3.1.05,13]trideca-1,5,7,9(13)-tetraen-10-yl]methyl]carbamate

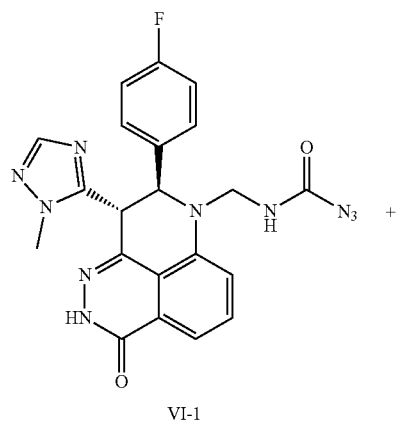

VI-1

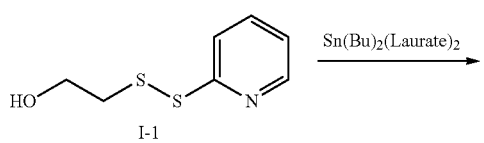

I-1

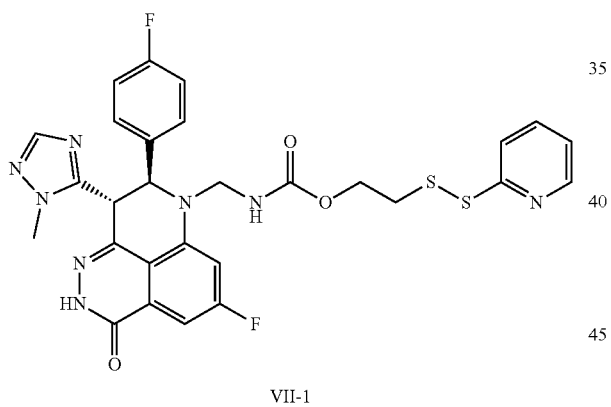

VII-1

The 2-[(11S,12R)-7-fluoro-11-(4-fluorophenyl)-12-(2-methyl-1,2,4-triazol-3-yl)-4-oxo-2,3,10-triazatricyclo[7.3.1.05,13]trideca-1,5,7,9(13)-tetraen-10-yl]acetyl azide, V-1, (170 mg, 0.367 mmol) was dissolved in dry DMF (2 mL) and 2-(2-pyridyldisulfanyl)ethanol (137 mg, 0.734 mmol) is added. The reaction was heated to 65° C. for 2 h. Catalytic dibutyltin dilaurate (40 uL) was added and the reaction mixture stirred overnight at 65° C. The mixture was concentrated and purified by column chromatography (0-10% MeOH/DCM) to give 3 peaks. NMR indicated peak 2 was the desired product. MALDI showed 3 masses of 624 (desired product), 646 (product+23) and 380 (BMN). Yield: 80 mg of Intermediate VII-1: 2-(2-pyridyldisulfanyl)ethyl N-[[(11S,12R)-7-fluoro-11-(4-fluorophenyl)-12-(2-methyl-1,2,4-triazol-3-yl)-4-oxo-2,3,10-triazatricyclo[7.3.1.05,13]trideca-1,5,7,9(13)-tetraen-10-yl]methyl]carbamate.

Intermediates VII-2 Through VII-5

Intermediates VII-2, VII-3 and VII-4 were prepared using $R_8H$-15 and intermediates II-4, II-5 and II-6, respectively. Intermediate VII-5 was prepared using $R_8H$-17 and intermediate II-1 as shown in Table 17.

TABLE 17

Additional Intermediates

VII

| Int. | $R^8H$ | $R^1, R^2$ | $R^3, R^4$ | $R^5, R^6$ | X | MH+ |
|---|---|---|---|---|---|---|
| VII-2 | $R^8H$-15 | H, Me | H, H | H, H | H | 637.2 |
| VII-3 | $R^8H$-15 | Me, H | H, H | H, H | H | 637.2 |
| VII-4 | $R^8H$-15 | —CH$_2$CH$_2$CH$_2$— (R1 and R2 form a cyclopropyl) | H, H | H, H | NO$_2$ | 708.2 |
| VII-5 | $R^8H$-17 | H, H | H, H | H, H | H | 541.1 |

Intermediate VII-6: 2-(2-pyridyldisulfanyl)ethyl N-[[6-fluoro-2-[4-(methylaminomethyl)phenyl]-9-oxo-3,10-diazatricyclo[6.4.1.04,13]trideca-1,4,6,8(13)-tetraen-3-yl]methyl]carbamate

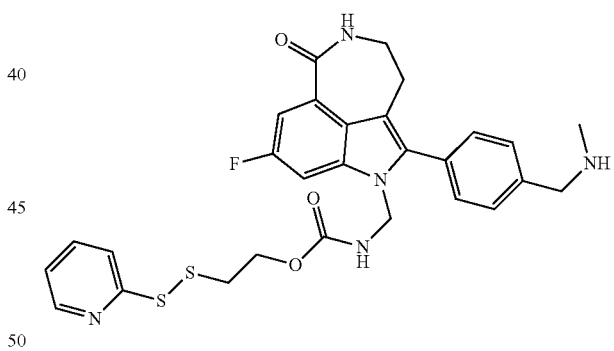

Step 1: (((2-(pyridin-2-yldisulfanyl)ethoxy)carbonyl)amino)methyl acetate

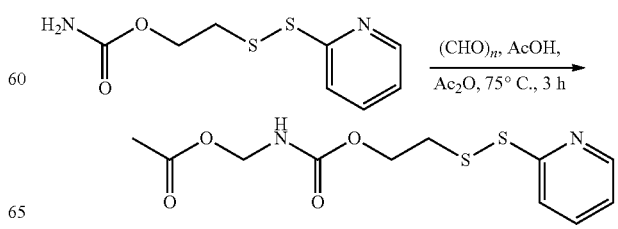

To a stirred solution of 2-(pyridin-2-yldisulfanyl)ethyl carbamate (0.10 g, 0.43 mmol) in acetic acid (0.59 mL) was added paraformaldehyde (0.01 g, 0.47 mmol) and acetic anhydride (1.78 mL). The mixture was heated at 75° C. for 3 h. After completion of reaction, the reaction was quenched with water (20 mL) and extracted with ethyl acetate (20 mL×2). The combined organic layer was washed with water (20 mL) and brine solution (20 mL). The organic phase was dried over anhydrous Na$_2$SO$_4$ and concentrated. The crude product was purified by column chromatography (SiO$_2$, 40-50% of ethyl acetate/hexanes) to afford (((2-(pyridin-2-yldisulfanyl)ethoxy)carbonyl)amino)methyl acetate as a yellow liquid (120 mg, 70%). MS m/z 303.3 (M+H)$^+$ Step 2: (9H-fluoren-9-yl)methyl(4-(8-fluoro-1-oxo-6-((((2-(pyridin-2yldisulfanyl)ethoxy)carbonyl)amino)methyl)-2,3,4,6-tetrahydro-1H-azepino[5,4,3-cd]indol-5-yl)benzyl)(methyl)carbamate

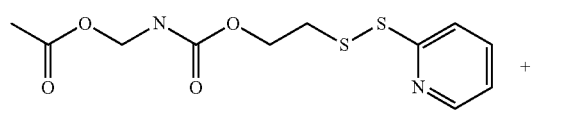

+

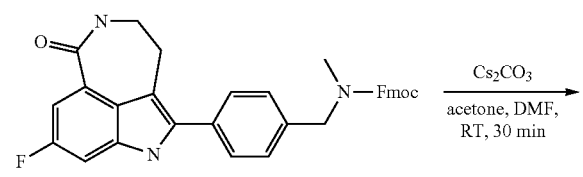

Cs$_2$CO$_3$
acetone, DMF,
RT, 30 min

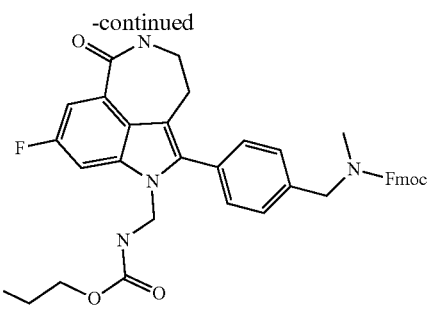

-continued

To a stirred solution of (9H-fluoren-9-yl)methyl (4-(8-fluoro-1-oxo-2,3,4,6-tetrahydro-1H-azepino[5,4,3-cd]indol-5-yl)benzyl)(methyl)carbamate (0.05 g, 0.09 mmol) in acetone (1.0 mL) was added cesium carbonate (0.06 g, 0.18 mmol) and stirred for 5 min at room temperature under N$_2$ atmosphere. Then (((2-(pyridin-2-yldisulfanyl)ethoxy)carbonyl)amino)methyl acetate (0.03 g, 0.09 mmol) and DMF (0.1 mL) were added and further stirred for 30 min at room temperature. The reaction was quenched with water (25 mL) and then extracted with 10% of MeOH/CH$_2$Cl$_2$ mixture (50 mL×2). The combined organic layer was dried over anhydrous sodium sulphate and concentrated under reduced pressure to afford the crude product which was purified by flash column chromatography using 60-70% of EtOAc/hexanes mixture to afford (9H-fluoren-9-yl)methyl(4-(8-fluoro-1-oxo-6-((((2-(pyridin-2yldisulfanyl)ethoxy)carbonyl) amino)methyl)-2,3,4,6-tetrahydro-1H-azepino[5,4,3-cd]indol-5-yl)benzyl)(methyl)carbamate (12 mg, 17% yield); MS m/z 788.8 (M+H)$^+$.

Step 3: 2-(2-pyridyldisulfanyl)ethyl N-[[6-fluoro-2-[4-(methylaminomethyl)phenyl]-9-oxo-3,10-diazatricyclo[6.4.1.04,13]trideca-1,4,6,8(13)-tetraen-3-yl]methyl]carbamate

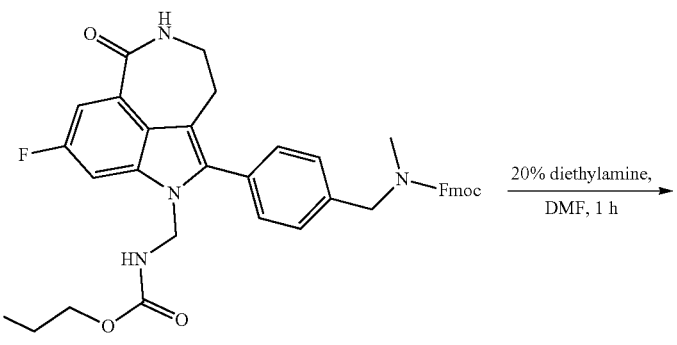

20% diethylamine,
DMF, 1 h

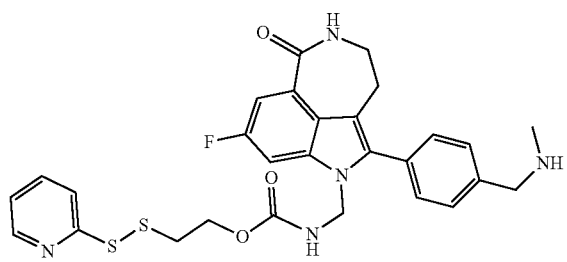

(9H-fluoren-9-yl)methyl(4-(8-fluoro-1-oxo-6-((((2-(pyridin-2yldisulfanyl)ethoxy)carbonyl) amino)methyl)-2,3,4,6-tetrahydro-1H-azepino[5,4,3-cd]indol-5-yl)benzyl)(methyl)carbamate (0.15 g, 0.19 mmol) was stirred with 20% of diethylamine in DMF (1.4 mL) for 1 h under $N_2$ at room temperature. The reaction mixture was concentrated to dryness and purified by prep-HPLC [Column: Inertsil ODS 3V (250 mm×20 mm X 5 mic); Mobile phase-A-0.1% ammonia in $H_2O$: Mobile phase-B-ACN] to afford 2-(2-pyridyldisulfanyl)ethyl N-[[6-fluoro-2-[4-(methylaminomethyl)phenyl]-9-oxo-3,10-diazatricyclo[6.4.1.04,13]trideca-1,4,6,8(13)-tetraen-3-yl]methyl]carbamate as a colorless solid (30 mg, 28% yield). MS m/z 566.4 (M+H)+.

Intermediate VII-7: 2-(2-pyridyldisulfanyl)ethyl N-[1-[6-fluoro-2-[4-(methylaminomethyl)phenyl]-9-oxo-3,10-diazatricyclo[6.4.1.04,13]trideca-1,4,6,8(13)-tetraen-3-yl]-3-methyl-butyl]carbamate

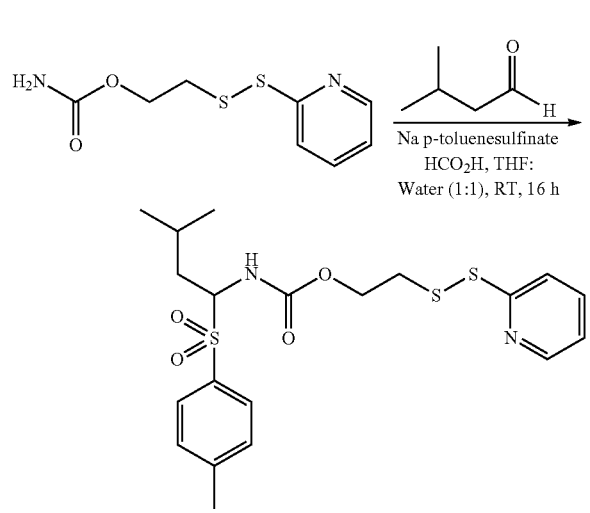

Step 1: 2-(pyridin-2-yldisulfanyl) ethyl(3-methyl-1-(phenylsulfonyl)butyl)carbamate

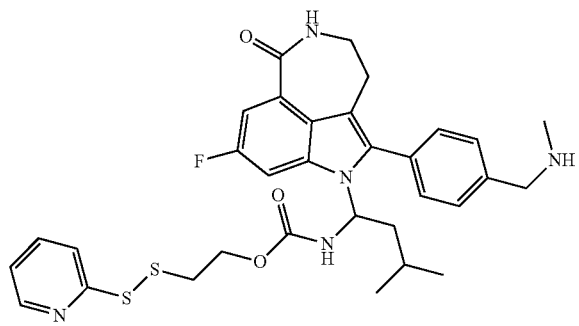 [SMILES: CNCc1ccc(-c2c3c4c(cc(F)cc4n2C(CC(C)C)NC(=O)OCCSSc2ccccn2)C(=O)NCC3)cc1]

To a stirred solution of 2-(pyridin-2-yldisulfanyl)ethyl carbamate (2.50 g, 0.01 mol) in THF:water (19 mL, 1:1) were added sodium p-toluenesulfinate (1.93 g, 0.01 mol), 3-methylbutanal (1.26 mL, 0.01 mol) and then formic acid (2.5 mL). The mixture was stirred for 16 h at room temperature under $N_2$. The reaction mixture was concentrated to dryness and then purified by flash column chromatography (SiO$_2$, 40-70% EtOAc/hexanes) to afford 2-(pyridin-2-yldisulfanyl) ethyl(3-methyl-1-(phenylsulfonyl)butyl)carbamate (1.7 g, 41% yield). MS m/z 455.1 [M+H]+.

Step 2: (9H-fluoren-9-yl)methyl (4-(8-fluoro-6-(3-methyl-1-(((2-(pyridin-2-yldisulfanyl) ethoxy) carbonyl)amino)butyl)-1-oxo-2,3,4,6-tetrahydro-1H-azepino[5,4,3-cd]indol-5-yl)benzyl)(methyl) carbamate

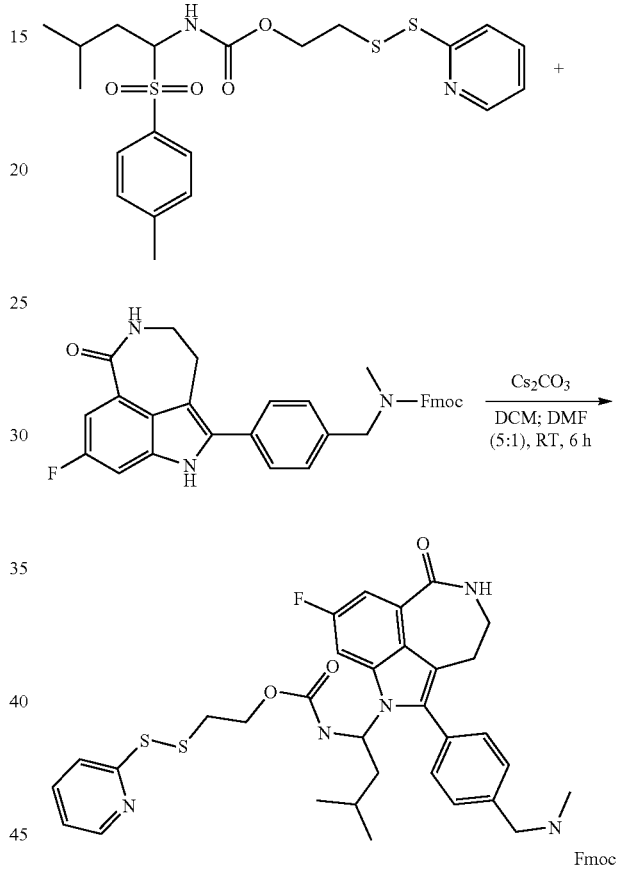

To a stirred suspension of (9H-fluoren-9-yl)methyl(4-(8-fluoro-1-oxo-2,3,4,6-tetrahydro-1H-azepino[5,4,3-cd]indol-5yl)benzyl)(methyl)carbamate (0.5 g, 0.92 mmol) and cesium carbonate (0.89 g, 2.74 mmol) in CH$_2$Cl$_2$:DMF (5:1, 12 mL) was added 2-(pyridin-2-yldisulfanyl) ethyl(3-methyl-1-(phenylsulfonyl)butyl)carbamate (0.80 g, 1.83 mmol) portion wise over 4 h. The mixture was stirred an additional 2 h under $N_2$ at room temperature. The reaction was monitored by TLC. The reaction mixture was diluted with water (25 mL) and DCM (100 mL). The organic layer was separated, washed with water, brine. The organic phase was dried over anhydrous Na$_2$SO$_4$ and concentrated. The crude product was purified by flash column chromatography (SiO$_2$, 90-100% EtOAc/hexanes) to afford (9H-fluoren-9-yl)methyl (4-(8-fluoro-6-(3-methyl-1-(((2-(pyridin-2-yldisulfanyl) ethoxy) carbonyl)amino)butyl)-1-oxo-2,3,4,6-tetrahydro-1H-azepino[5,4,3-cd]indol-5-yl)benzyl)(methyl) carbamate (0.35 g, 45% yield). MS m/z 844.1 [M+H]+.

Step 3: 2-(2-pyridyldisulfanyl)ethyl N-[1-[6-fluoro-2-[4-(methylaminomethyl)phenyl]-9-oxo-3,10-diaza-tricyclo[6.4.1.04,13]trideca-1,4,6,8(13)-tetraen-3-yl]-3-methyl-butyl]carbamate

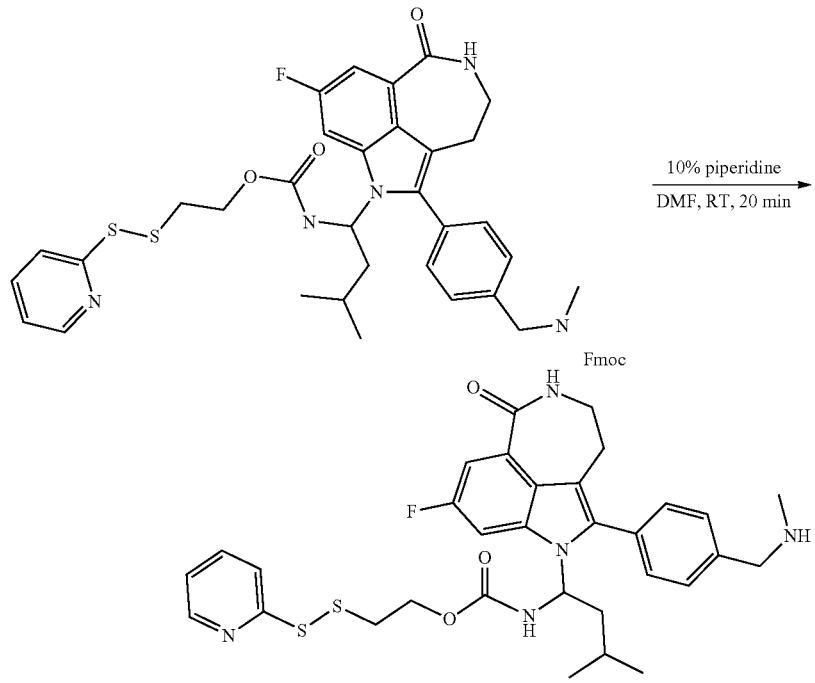

(9H-fluoren-9-yl)methyl (4-(8-fluoro-6-(3-methyl-1-(((2-(pyridin-2-yldisulfanyl) ethoxy) carbonyl)amino)butyl)-1-oxo-2,3,4,6-tetrahydro-1H-azepino[5,4,3-cd]indol-5-yl) benzyl)(methyl) carbamate (0.30 g, 0.355 mmol) was stirred with 10% piperidine in DMF (1.4 mL) for 20 min at room temperature under $N_2$. The reaction mixture was concentrated to dryness and then triturated with diethyl ether to obtain a colorless solid. The resultant solid was further purified by prep HPLC [Column: Inertsil ODS 3V (250 mm×20 mm X 5 mic), Mobile phase-A-0.1% ammonia in $H_2O$: Mobile phase-B-ACN] to afford 2-(2-pyridyldisulfa- nyl)ethyl N-[1-[6-fluoro-2-[4-(methylaminomethyl)phenyl]-9-oxo-3,10-diazatricyclo[6.4.1.04,13]trideca-1,4,6,8 (13)-tetraen-3-yl]-3-methyl-butyl]carbamate (0.07 g, 30% yield). MS m/z 622.0 [M+H]$^+$.

Intermediate XXI-1: [4-[2-(2-pyridyldisulfanyl) ethoxycarbonylamino]phenyl]methyl N-[[4-(6-fluoro-9-oxo-3,10-diazatricyclo[6.4.1.04,13]trideca-1,4(13),5,7-tetraen-2-yl)phenyl]methyl]-N-methyl-carbamate

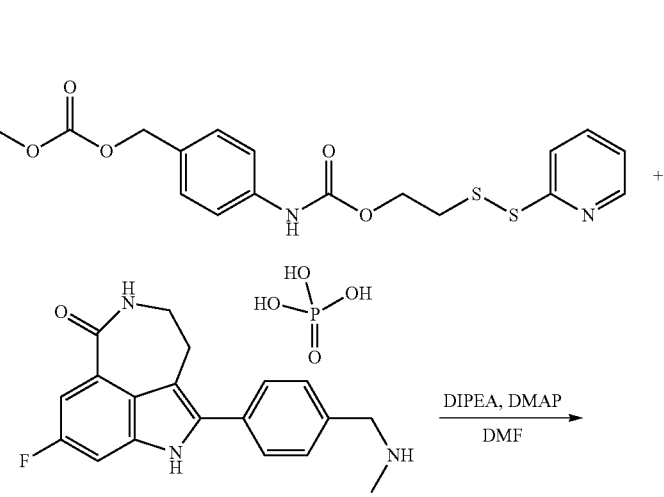

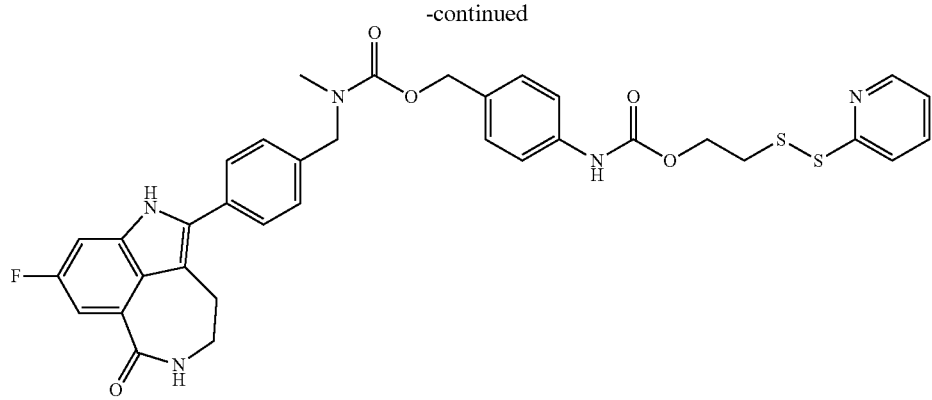

To 2-[4-(methylaminomethyl)phenyl]-3,10-diazatricyclo[6.4.1.04,13]trideca-1,4(13),5,7-tetraen-9-one; phosphoric acid (36.0 mg, 0.09 mmol) in 2 mL of dry DMF under N₂ was added DIPEA (0.03 mL, 0.18 mmol), DMAP (10.9 mg, 0.09 mmol) and (4-nitrophenyl) [4-[2-(2-pyridyldisulfanyl) ethoxycarbonyl amino]phenyl]methyl carbonate (44.8 mg, 0.09 mmol). The mixture was stirred for 16 h. The mixture was diluted with 20 ml of EtOAc, washed with 1×20 mL of sat. NH₄Cl, 2×20 mL of sat. NaHCO₃, 3×30 mL of H₂O and 1×20 mL of sat. brine. The mixture was dried with MgSO₄, filtered and concentrated. The crude residue was purified by column chromatography (SiO₂, 0-5% MeOH/CH₂Cl₂) to give [4-[2-(2-pyridyldisulfanyl) ethoxycarbonylamino]phenyl]methyl N-[[4-(6-fluoro-9-oxo-3,10-diazatricyclo[6.4.1.04,13]trideca-1,4(13),5,7-tetraen-2-yl)phenyl]methyl]-N-methyl-carbamate (44.2 mg, 0.06 mmol, yield: 75.4%).

Intermediate XXV-1: [4-(2-pyridyldisulfanyl)phenyl]methyl N-[[4-(6-fluoro-9-oxo-3,10-diazatricyclo[6.4.1.04,13]trideca-1,4,6,8(13)-tetraen-2-yl)phenyl]methyl]-N-methyl-carbamate

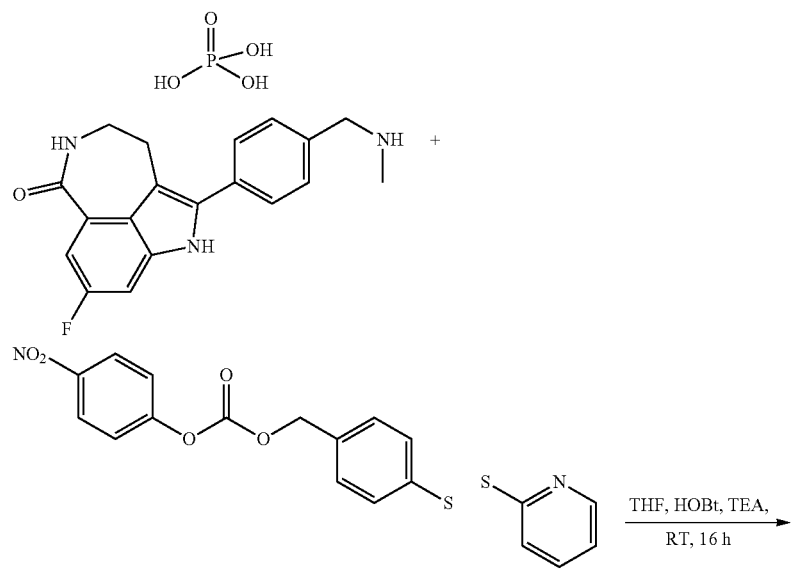

XXIV-1

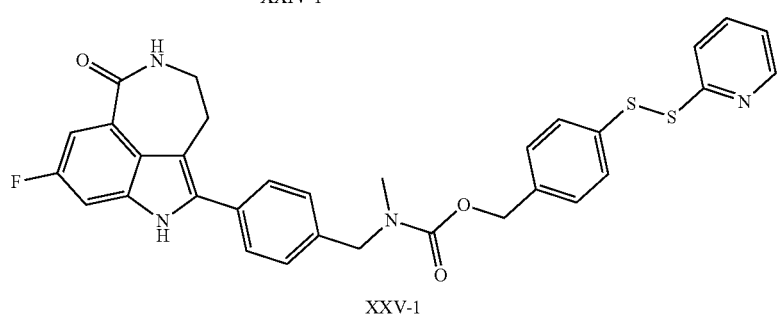

XXV-1

To a stirred solution of 2-[4-(methylaminomethyl)phenyl]-3,10-diazatricyclo[6.4.1.0⁴,¹³]trideca-1,4(13),5,7-tetraen-9-one; phosphoric acid (1.00 g, 3.09 mmol) in THF (20 mL) under $N_2$ was added TEA (1.40 mL, 3.04 mmol), HOBt (0.21 g, 1.50 mmol) and 4-nitrophenyl (4-(pyridin-2-yldisulfaneyl)benzyl) carbonate (1.40 g, 3.40 mmol). The mixture was stirred under $N_2$ for 16 h at room temperature. The reaction mixture was concentrated and the crude purified by flash chromatography ($SiO_2$, 0-5% $MeOH/CH_2Cl_2$ to afford [4-(2-pyridyldisulfanyl)phenyl]methyl N-[[4-(6-fluoro-9-oxo-3,10-diazatricyclo[6.4.1.0⁴,¹³]trideca-1,4,6,8(13)-tetraen-2-yl)phenyl]methyl]-N-methyl-carbamate as a colourless solid (1.13 g, 59% yield). MS m/z 599.0 (M+H)⁺.

Intermediates XXV-2 Through XXV-5

Intermediates XXV-2 through XXV-5 were prepared analogously to Intermediate XXV-1 using the appropriate $R_8$—H compound and intermediates XXIV-2 through XXIV-5 as shown below in Table 18.

TABLE 18

Additional Intermediates

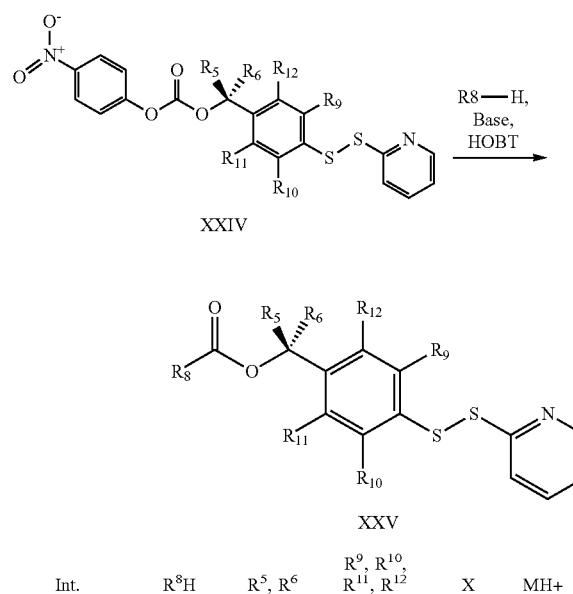

| Int. | $R^8$H | $R^5$, $R^6$ | $R^9$, $R^{10}$, $R^{11}$, $R^{12}$ | X | MH+ |
|---|---|---|---|---|---|

TABLE 18-continued

| XXV-2 | R⁸H-16 | H, H | Me, H, H, H | H | 613.2 |
| XXV-3 | R⁸H-16 | H, H | H, H, Me, H | H | 613.0 |
| XXV-4 | R⁸H-16 | H, H | Me, Me, H, H | H | 627.0 |
| XXV-5 | R₈H-3 | H, H | H, H, H, H | H | 596.2 |
| XXV-6 | R₈H-4 | H, H | H, H, H, H | H | 520.2 |
| XXV-7 | R₈H-21 | H, H | H, H, H, H | H | 739.2 |

Synthesis of Intermediates XXVIX from XXVII

TABLE 19

Intermediates XXVIX

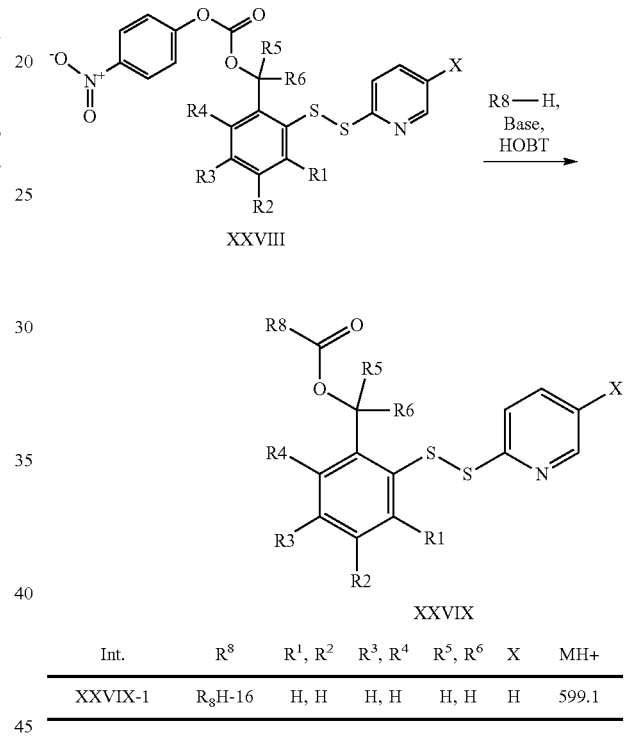

| Int. | $R^8$ | $R^1$, $R^2$ | $R^3$, $R^4$ | $R^5$, $R^6$ | X | MH+ |
|---|---|---|---|---|---|---|
| XXVIX-1 | R₈H-16 | H, H | H, H | H, H | H | 599.1 |

Intermediate XXVIX-1 was prepared from Intermediate XXVIII-1 analogously to Intermediate XXV-1.

Intermediates XXXV from XXXIV

TABLE 20

Intermediates XXXV

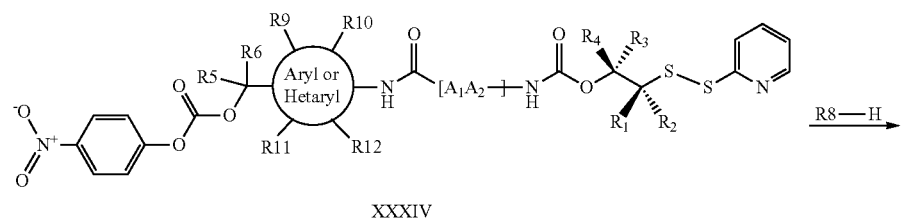

XXXIV

TABLE 20-continued

[Structure XXXV shown]

XXXV

| Int. | R[8] | R[1], R[2], R[3], R[4] | R[5], R[6] | R[9], R[10], R[11], R[12] | A[1], A[2] | MH+ |
|---|---|---|---|---|---|---|
| XXXV-1 | R[8]H-16 | H, H, H, H | H, H | H, H, H, H | Cit, Val | 942.4 |

Intermediate XXXV-1 was prepared from Intermediate XXXIV-1 analogously to Intermediate XXV-1.

Intermediates XXXVII from XXX

TABLE 21

Intermediates XXXVII

[Reaction scheme shown]

XXX → XXXVI → XXXVII

| Int. | R[8] | R[1], R[2], R[3], R[4] | A[1], A[2] | X | MH+ |
|---|---|---|---|---|---|
| XXXVII-1 | R[8]H-16 | H, H, H, H | Pro, Gly | H | 478.2 |

Synthesis of XXXVII-1: (2S)-1-(2-aminoacetyl)-N-[[4-(6-fluoro-9-oxo-3,10-diazatricyclo[6.4.1.04,13]trideca-1,4,6,8(13)-tetraen-2-yl)phenyl]methyl]-N-methyl-pyrrolidine-2-carboxamide

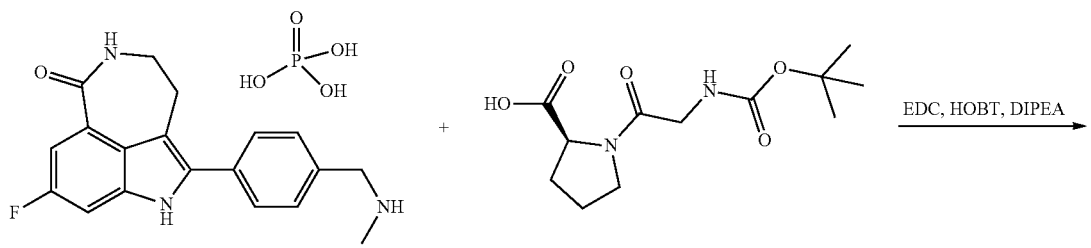

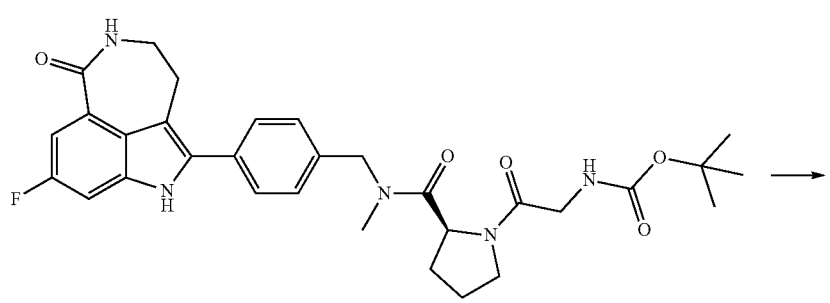

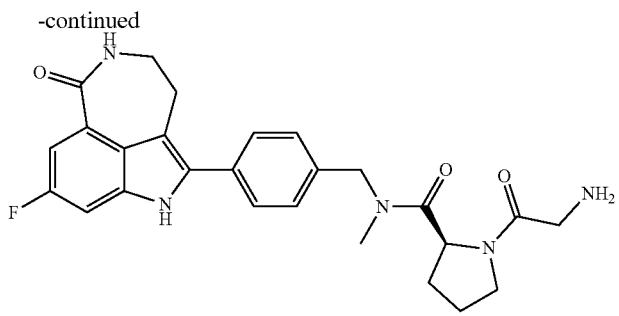

Step 1. Synthesis of tert-butyl-N-[2-[(2S)-2-[[4-(6-fluoro-9-oxo-3,10-diazatricyclo[6.4.1.04,13]trideca-1,4,6,8(13)-tetraen-2-yl)phenyl]methyl-methyl-carbamoyl]pyrrolidin-1-yl]-2-oxo-ethyl]carbamate 1-[2-(tert-Butoxycarbonylamino)acetyl]pyrrolidine-2-carboxylic acid (0.16 g, 0.59 mmol) was dissolved in DMF and to it was added 1-hydroxybenzotriazole hydrate (80.0%, 114 mg, 0.59 mmol) and EDC HCl (114 mg, 0.59 mmol). The solution was stirred at RT for 15 min before the 6-fluoro-2-[4-(methylaminomethyl)phenyl]-3,10-diazatricyclo[6.4.1.04,13]trideca-1,4,6,8(13)-tetraen-9-one; phosphoric acid (200 mg, 0.475 mmol) and N,N-diisopropylethylamine (0.44 mL, 2.37 mmol) were added. The solution was then heated to 65° C. overnight. LC-MS indicated a complete reaction. The reaction mixture was diluted with EtOAc, washed with sat. NH4Cl, water, and brine. The crude [1-[2-(tert-butoxycarbonylamino)acetyl]pyrrolidin-2-yl] N-[[4-(6-fluoro-9-oxo-3,10-diazatricyclo[6.4.1.04,13]trideca-1,4,6,8(13)-tetraen-2-yl)phenyl]methyl]-N-methyl-carbamate (141 mg, 0.24 mmol, yield: 50.0%) was carried on as is. MS m/z 478.2 (M+H minus BOC)+.

Step 2. Synthesis of (2S)-1-(2-aminoacetyl)-N-[[4-(6-fluoro-9-oxo-3,10-diazatricyclo[6.4.1.04,13]trideca-1,4,6,8(13)-tetraen-2-yl)phenyl]methyl]-N-methyl-pyrrolidine-2-carboxamide The tert-Butyl-N-[2-[2-[[4-(6-fluoro-9-oxo-3,10-diazatricyclo[6.4.1.04,13]trideca-1,4,6,8(13)-tetraen-2-yl)phenyl]methyl-methyl-carbamoyl]pyrrolidin-1-yl]-2-oxo-ethyl]carbamate (141 mg, 0.24 mmol) was dissolved in DCM and 1 mL HCl (4.00 M, 0.12 mL, 0.48 mmol) in dioxane was added. The reaction mixture was stirred at RT overnight. LC-MS indicated a complete reaction. The reaction mixture was concentrated and purified by reverse phase chromatography (20-85% ACN/H2O). to give 68 mg of 1-(2-aminoacetyl)-N-[[4-(6-fluoro-9-oxo-3,10-diazatricyclo[6.4.1.04,13]trideca-1,4,6,8(13)-tetraen-2-yl)phenyl]methyl]-N-methyl-pyrrolidine-2-carboxamide (68.0 mg, 0.142 mmol, yield: 58.3%). MS m/z 478.2 (M+H)+.

Intermediates XXXVIII

TABLE 22

Intermediates XXXVIII

| Int. | R8 | R1, R2, R3, R4 | A1, A2 | X | MH+ |
|---|---|---|---|---|---|
| XXXVIII-1 | R8H-16 | H, H, H, H | Pro, Gly | H | 691.2 |

Synthesis of XXXVIII-1: 2-(2-pyridyldisulfanyl) ethyl N-[2-[(2S)-2-[[4-(6-fluoro-9-oxo-3,10-diazatricyclo[6.4.1.04,13]trideca-1,4,6,8(13)-tetraen-2-yl)phenyl]methyl-methyl-carbamoyl]pyrrolidin-1-yl]-2-oxo-ethyl]carbamate

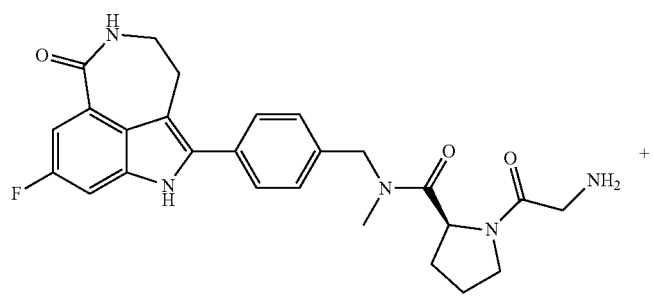

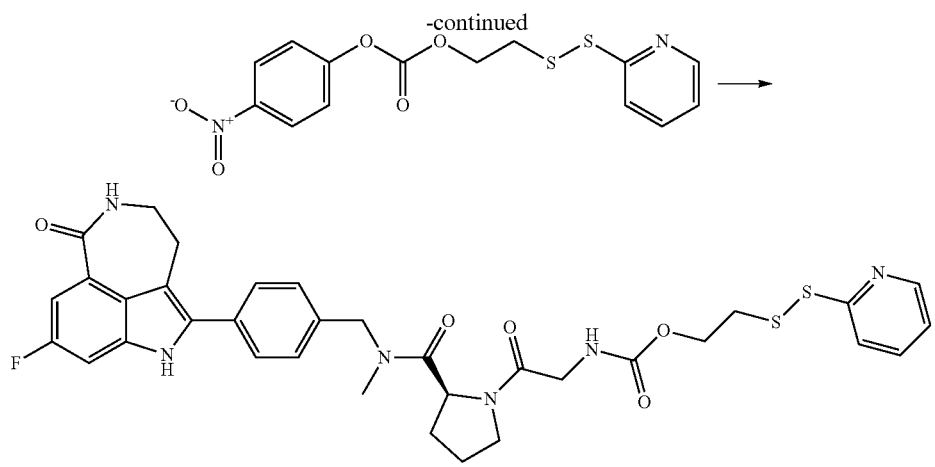

To 1-(2-aminoacetyl)-N-[[4-(6-fluoro-9-oxo-3,10-diazatricyclo[6.4.1.04,13]trideca-1,4,6,8(13)-tetraen-2-yl)phenyl]methyl]-N-methyl-pyrrolidine-2-carboxamide (68.0 mg, 0.142 mmol) in 2 mL of dry DMF was added DMAP (17.4 mg, 0.142 mmol), (4-nitrophenyl) 2-(2-pyridyldisulfanyl)ethyl carbonate (50.2 mg, 0.142 mmol) and N,N-diisopropylethylamine (27.6 mg, 0.214 mmol). The mixture stirred for 16 h and then diluted with 50 ml of EtOAc, washed with 1×20 mL of sat. NH$_4$Cl, 3×30 mL of H$_2$O and 1×20 mL of sat. brine. The mixture was dried with MgSO$_4$, filtered and concentrated. The crude residue was purified on an SiO$_2$ column (0-3% MeOH/DCM) to give 30 mg of 2-(2-pyridyldisulfanyl)ethyl N-[2-[2-[[4-(6-fluoro-9-oxo-3,10-diazatricyclo[6.4.1.04,13]trideca-1,4,6,8(13)-tetraen-2-yl)phenyl]methyl-methyl-carbamoyl]pyrrolidin-1-yl]-2-oxo-ethyl]carbamate (30.0 mg, 0.0434 mmol, yield: 30.5%). MS m/z 691.2 (M+H)$^+$.

Intermediates XLVIII from XLVI

TABLE 23

Intermediates XLVIII

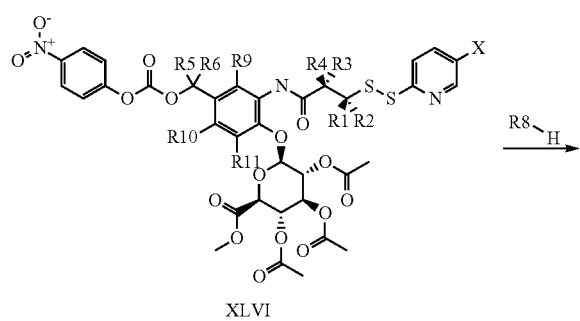

XLVI

TABLE 23-continued

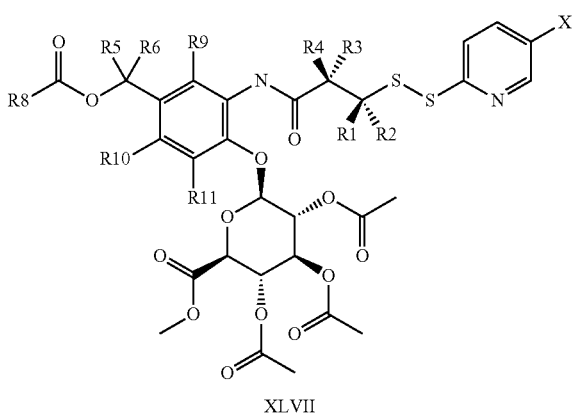

XLVII

| Int. | R8 | R$_1$, R$_2$, R$_3$, R$_4$, | R$_5$, R$_6$ | R$_9$, R$_{10}$, R$_{11}$, R$_{12}$ | X | MH+ |
|---|---|---|---|---|---|---|
| XLVII-1 | R$_8$H-16 | H, H, H, H | H | H, H, H, H | H | 1002.1 |

Synthesis of XLVII-1: Methyl (2S,3S,4S,5R,6S)-3,4,5-triacetoxy-6-[3-R10-2-R11-4-[[[4-(6-fluoro-9-oxo-3,10-diazatricyclo[6.4.1.04,13]trideca-1,4,6,8(13)-tetraen-2-yl)phenyl]methyl-methyl-carbamoyl]oxymethyl]-6-[3-(2-pyridyldisulfanyl)propanoylamino]phenoxy]tetrahydropyran-2-carboxylate

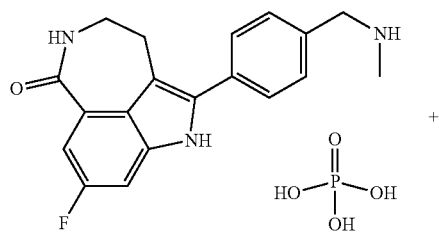

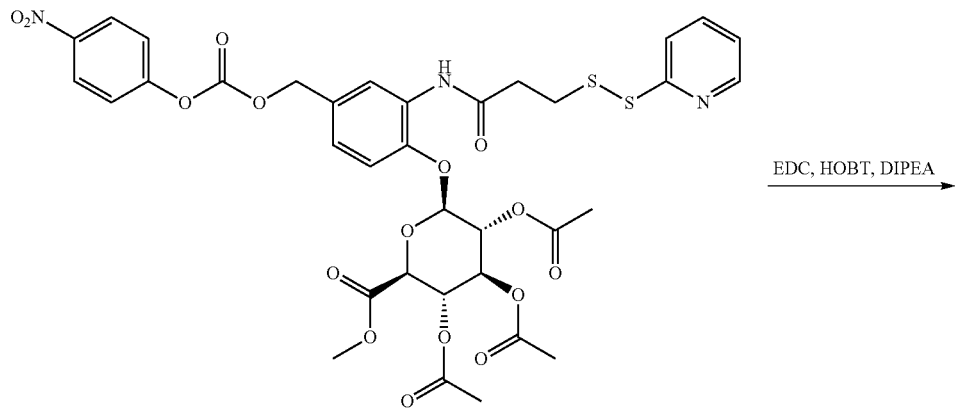

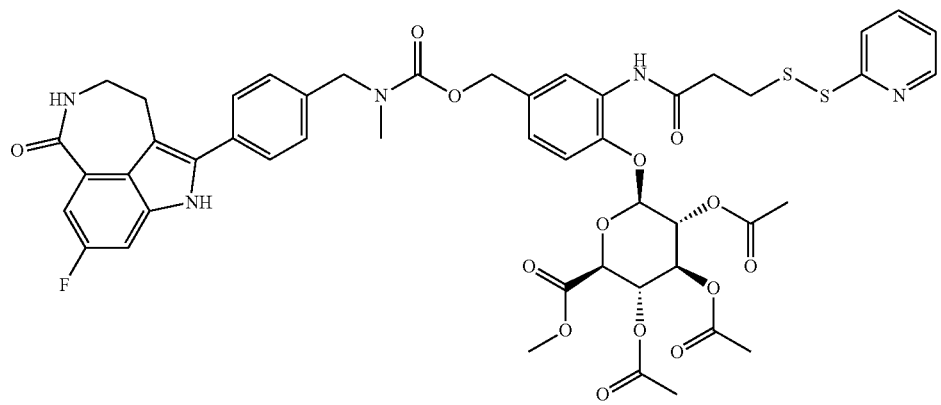

To a mixture of 1-hydroxybenzotriazole hydrate (13.0 mg, 0.0851 mmol), finely ground molecular sieve 4 Å (100 mg), and 6-fluoro-2-[4-(methylaminomethyl)phenyl]-3,10-diazatricyclo[6.4.1.04,13]trideca-1,4,6,8(13)-tetraen-9-one; phosphoric acid (35.9 mg, 0.0851 mmol) in 2 mL of anhydrous DMF was added methyl (2S,3S,4S,5R)-3,4,5-triacetoxy-6-[4-[(4-nitrophenoxy)carbonyloxymethyl]-2-[3-(2-pyridyldisulfanyl)propanoylamino]phenoxy]tetrahydropyran-2-carboxylate (58.0 mg, 0.0709 mmol). After stirring for 16 h at room temperature, the molecular sieve was filtered off and the solvent was removed in vacuo. The reaction mixture was diluted with EtOAc, washed with sat. NH$_4$Cl, water and brine. The organic layer was dried with NaSO$_4$ and concentrated. The crude residue was purified by column chromatography (0-3% MeOH/DCM) to give 35 mg of methyl (2S,3S,4S,5R)-3,4,5-triacetoxy-6-[4-[[[4-(6-fluoro-9-oxo-3,10-diazatricyclo[6.4.1.04,13]trideca-1,4,6,8(13)-tetraen-2-yl)phenyl]methyl-methyl-carbamoyl]oxymethyl]-2-[3-(2-pyridyldisulfanyl)propanoylamino]phenoxy]tetrahydropyran-2-carboxylate (43.0 mg, 0.0429 mmol, yield: 60.5%) with a slight unknown impurity. MS m/z 1002.1 (M+H)$^+$.

Conjugated Compounds

Example 3

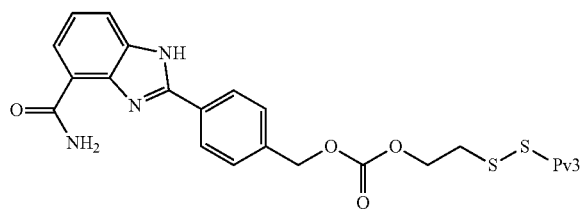

One 8 mL vial containing PBS and one 8 mL vial containing DMF were degassed with bubbling $N_2$ for 1 h. In a separate vial was placed Peptide Variant 3 ("Pv3," 50.0 mg, 1.31e-5 mol). The degassed 1.0 mL of PBS and a 3.0 mL portion of DMF were added to [4-(4-carbamoyl-1H-benzimidazol-2-yl)phenyl]methyl 2-(2-pyridyldisulfanyl)ethyl carbonate (18.9 mg, 3.92e-5 mol). To the mixture was added $CH_3CO_2H$ (0.05 mL 0.000873 mol). The mixture was placed under $N_2$ and stirred for at RT for 16 h. The mixture was monitored for progress with RP HPLC until complete consumption of the starting peptide and remaining pyridyl disulfide (Ace Equivalence 250×4.6 mm, 50% isocratic, 25 min run). The crude reaction mixture was purified by preparative RP HPLC (Sunfire 30×150 mm; $CH_3CN/H_2O$ (0.1% TFA) gradient, 16 min run) to give 28.6 mg, 54% yield of Example 3.

Example 18

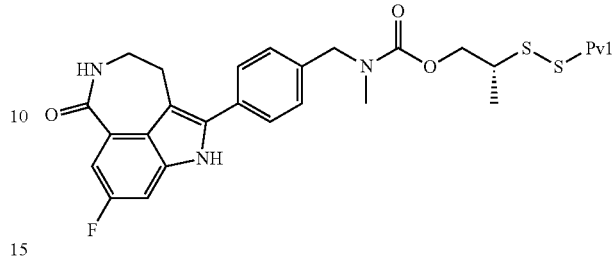

Two separate 8 mL vials containing PBS and DMF, respectively, were degassed with bubbling $N_2$ for 1 h. In a separate vial was placed Pv1 (50.0 mg, 0.02 mmol). To this vial was added [(2R)-2-(2-pyridyldisulfanyl)propyl] N-[[4-(6-fluoro-3,10-diazatricyclo[6.4.1.04,13]trideca-1,4,6,8 (13)-tetraen-2-yl)phenyl]methyl]-N-methyl-carbamate [Intermediate III-4] (16.2 mg, 0.03 mmol), 1.33 mL of PBS and 4 mL of DMF followed by acetic acid (4.2 μL, 0.08 mmol). The mixture was placed under $N_2$ and stirred at RT overnight. The mixture was purified by prep HPLC (40-72% $CH_3CN/H_2O$, 15 min) to give 29.0 mg, 0.008 mmol, 53% of example 18.

The following compounds were prepared analogously to Example 18 using the appropriate Intermediates and peptides.

TABLE 24

Example Compounds

| Example | Structure | MS<br>A: Maldi-TOF<br>B: m/z = 3 | Column<br>% ACN/$H_2O$<br>Run Time<br>RT |
|---|---|---|---|
| 1 | 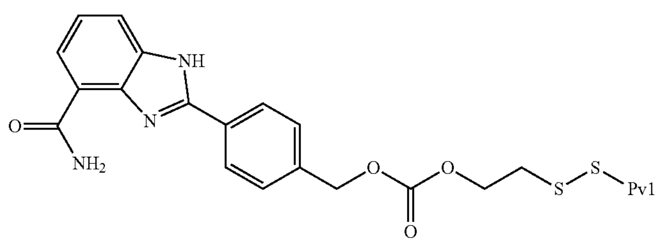 | A: 3649.5 | A<br>25-75%<br>10 min<br>6.9 min |
| 2 | 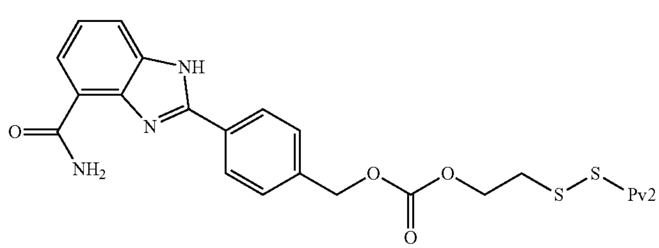 | A: 4381.8 | A<br>25-75%<br>10 min<br>7.7 min |

TABLE 24-continued

Example Compounds

| Example | Structure | MS<br>A: Maldi-TOF<br>B: m/z = 3 | Column<br>% ACN/H$_2$O<br>Run Time<br>RT |
|---|---|---|---|
| 3 | 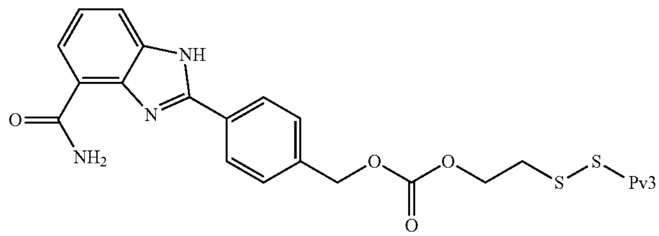 | A: 4081.8 | B<br>20-80%<br>15 min<br>15.6 min |
| 4 | 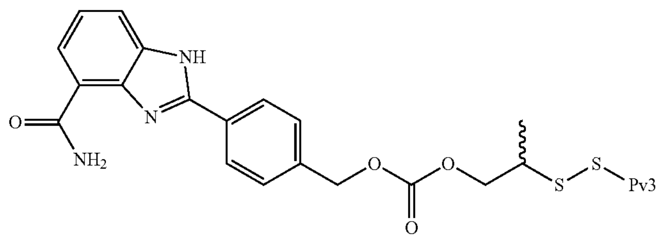 | A: 4094.2 | Diastereomer1<br>A<br>45-55%<br>10 min<br>6.3 min<br><br>Diastereomer2<br>A<br>45-55%<br>10 min<br>6.6 min |
| 5 | 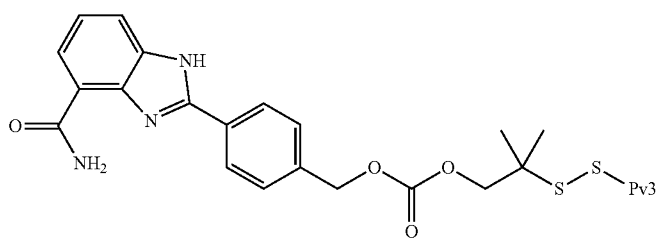 | A: 4107.7 | A<br>30-50%<br>10 min<br>6.6 min |
| 6 | 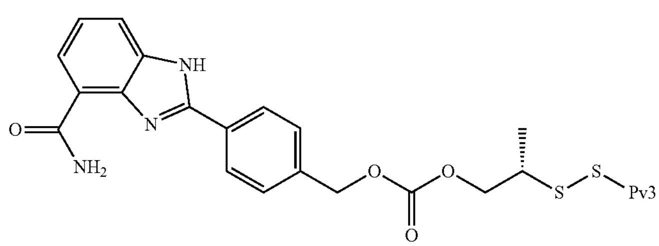 | A: 4095.0 | A<br>45-55%<br>10 min<br>6.3 min |
| 7 | 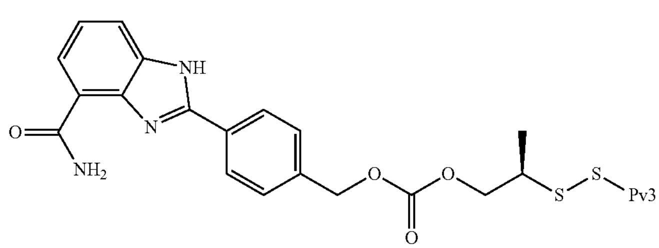 | A: 4094.7 | A<br>45-55%<br>10 min<br>6.6 min |

TABLE 24-continued
Example Compounds
| Example | Structure | MS<br>A: Maldi-TOF<br>B: m/z = 3 | Column<br>% ACN/H₂O<br>Run Time<br>RT |
|---|---|---|---|
| 8 | 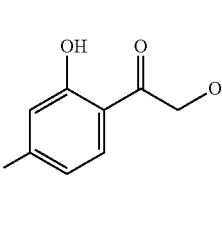 | A: 4350.8 | A<br>50% iso<br>10 min<br>5.5 min |
| 9 | 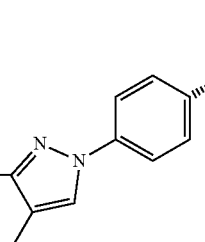 | A: 4049.6 | A<br>25-75%<br>10 min<br>8.5 min |
| 10 | 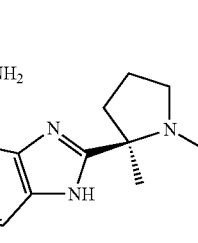 | A: 4133.0 | A<br>50% iso<br>10 min<br>6.5 min |
| 11 | 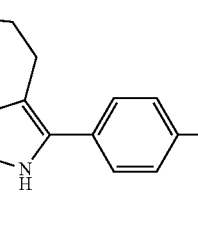 | A: 4055.3 | A<br>25-75%<br>10 min<br>6.7 min |
| 15 | 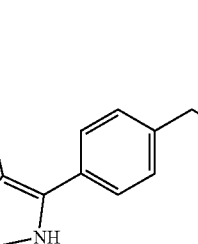 | A: 4436.2 | A<br>10-95%<br>10 min<br>9.1 min |
| 18 | 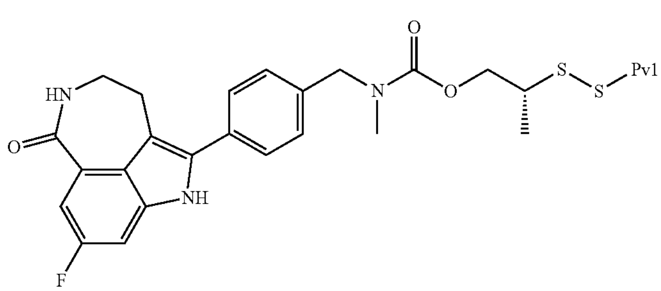 | A: 3718.3 | C<br>40-80%<br>15 min<br>7.4 min |

TABLE 24-continued

Example Compounds

| Example | Structure | MS<br>A: Maldi-TOF<br>B: m/z = 3 | Column<br>% ACN/H$_2$O<br>Run Time<br>RT |
|---|---|---|---|
| 19 | 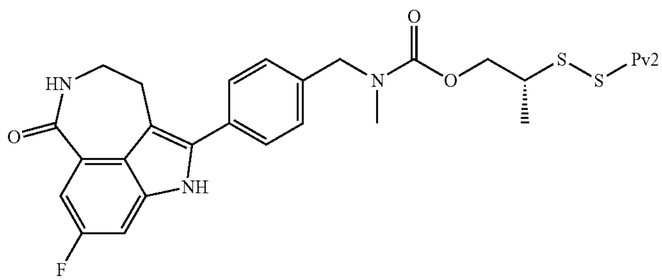 | A: 4450.3 | C<br>45-71%<br>11 min<br>7.9 min |
| 20 | 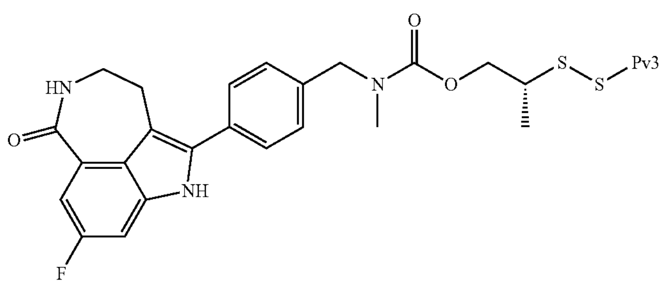 | A: 4147.2 | C<br>40-80%<br>15 min<br>6.9 min |
| 21 | 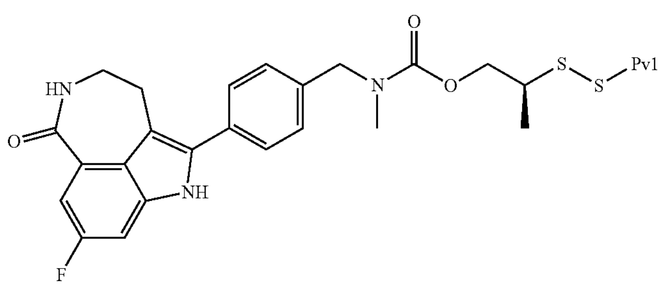 | A: 3718.6 | C<br>30-45%<br>15 min<br>6.0 min |
| 22 | 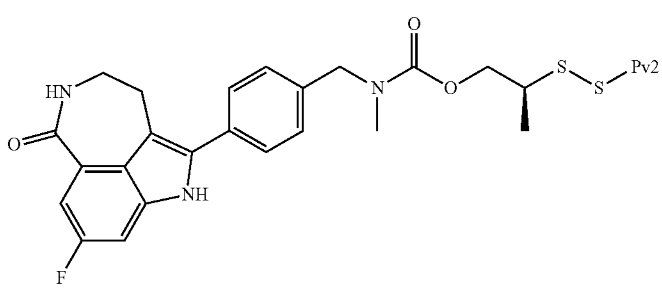 | A: 4449.8 | C<br>45-71%<br>11 min<br>8.3 min |
| 23 | 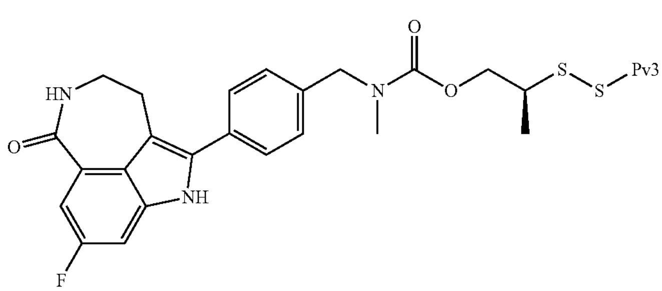 | A: 4148.9 | C<br>40-72%<br>12 min<br>7.0 |

TABLE 24-continued

Example Compounds

| Example | Structure | MS<br>A: Maldi-TOF<br>B: m/z = 3 | Column<br>% ACN/H$_2$O<br>Run Time<br>RT |
|---|---|---|---|
| 24 | 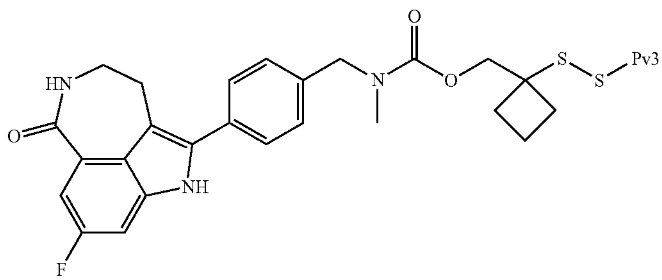 | A: 4477.3 | C<br>30-50%<br>13 min<br>6.3 min |
| 25 | 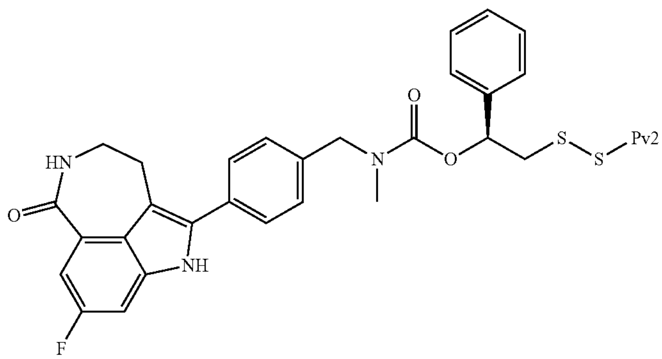 | A: 4511.8 | C<br>30-50%<br>11 min<br>7.5 min |
| 26 | 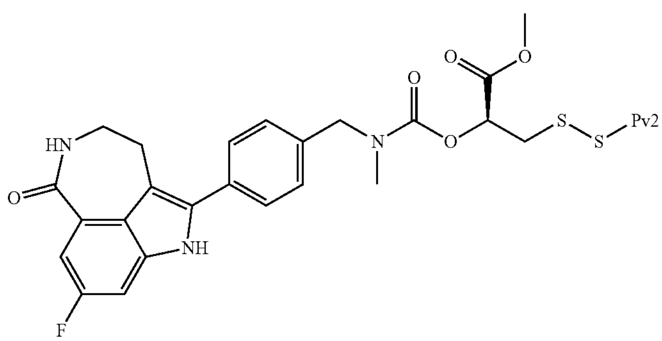 | A: 4493.8 | C<br>48-64%<br>11 min<br>8.0 min |
| 27 | 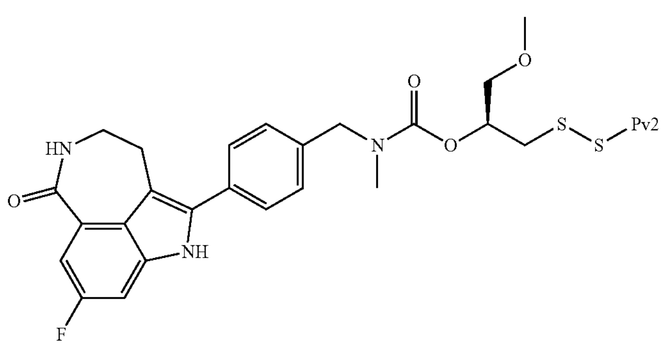 | A: 4478.6 | C<br>52-60%<br>11 min<br>8.5 min |

TABLE 24-continued

Example Compounds

| Example | Structure | MS<br>A: Maldi-TOF<br>B: m/z = 3 | Column<br>% ACN/H₂O<br>Run Time<br>RT |
|---|---|---|---|
| 44 | 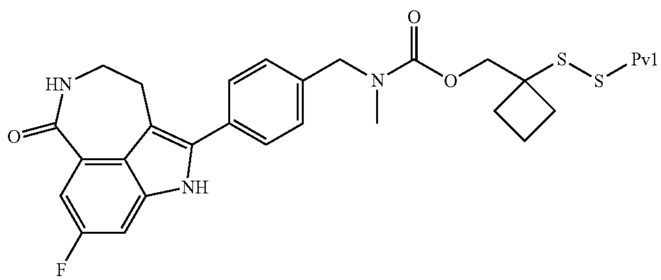 | A: 3744.3 | C<br>50-85%<br>13 min<br>4.4 min |
| 45 | 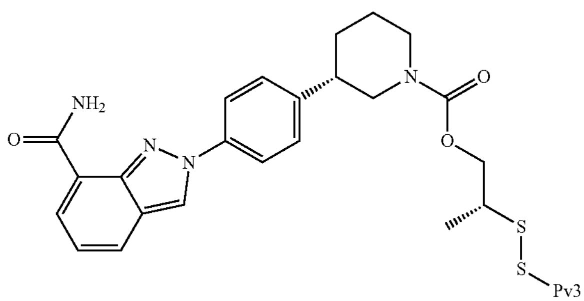 | A: 4145.3 | C<br>25-95%<br>15 min<br>8.5 min |
| 46 | 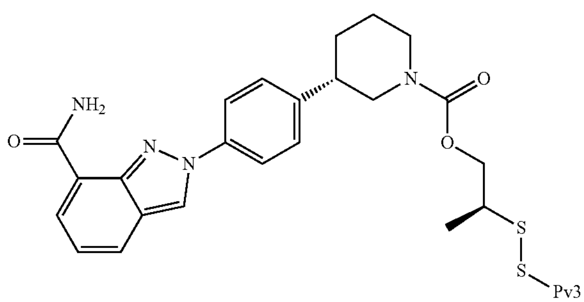 | A: 4146.0 | C<br>25-95%<br>15 min<br>8.5 min |
| 47 | 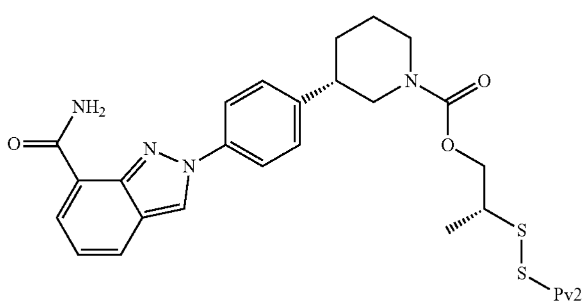 | A: 4446.5 | C<br>35-95%<br>12 min<br>7.3 min |
| 48 | 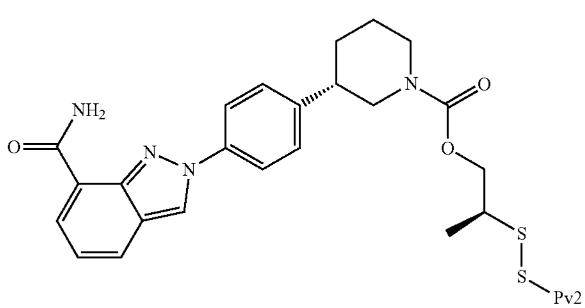 | A: 4446.5 | C<br>35-95%<br>12 min<br>7.3 min |

TABLE 24-continued

Example Compounds

| Example | Structure | MS<br>A: Maldi-TOF<br>B: m/z = 3 | Column<br>% ACN/H₂O<br>Run Time<br>RT |
|---|---|---|---|
| 49 | 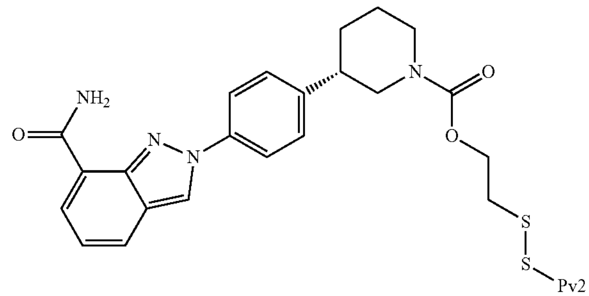 | A: 4434.2 | C<br>35-91%<br>11 min<br>7.2 min |
| 51 | 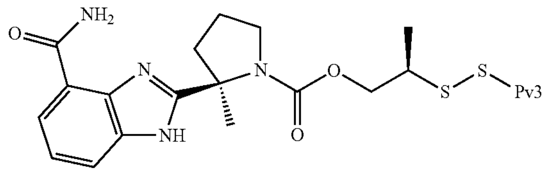 | A: 4069.7 | C<br>20-65%<br>10 min<br>8.2 min |
| 52 | 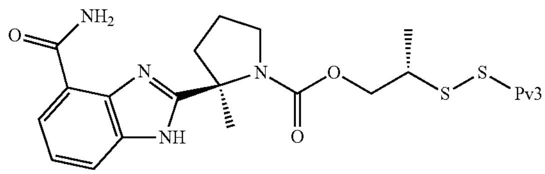 | A: 4070.3 | C<br>20-65%<br>10 min<br>8.2 min |
| 53 | 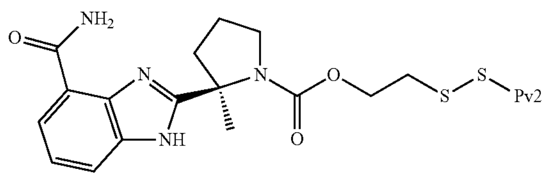 | A: 4357.6 | C<br>35-91%<br>12 min<br>7.3 min |
| 54 | 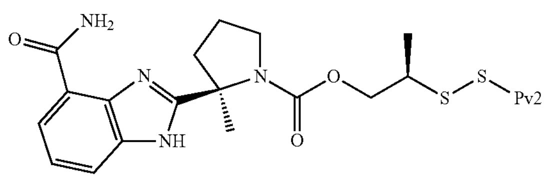 | A: 4370.6 | C<br>35-70%<br>11 min<br>7.4 min |
| 55 | 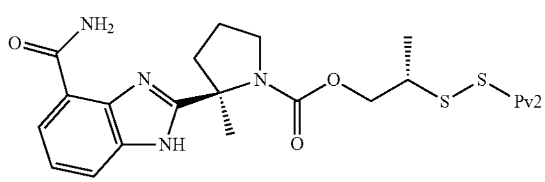 | A: 4369.9 | C<br>35-70%<br>11 min<br>7.4 min |
| 57 | 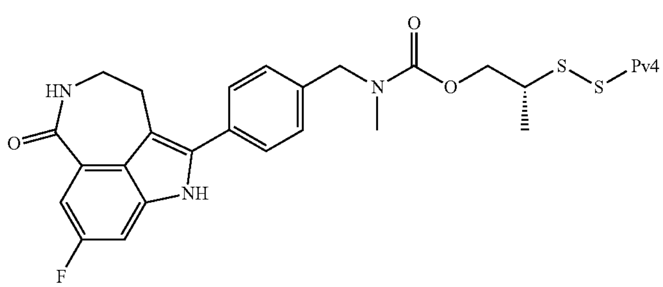 | B: 1617.1 | C<br>25-75%<br>15 min<br>11.5 min |

TABLE 24-continued

Example Compounds

| Example | Structure | MS<br>A: Maldi-TOF<br>B: m/z = 3 | Column<br>% ACN/H$_2$O<br>Run Time<br>RT |
|---|---|---|---|
| 58 | 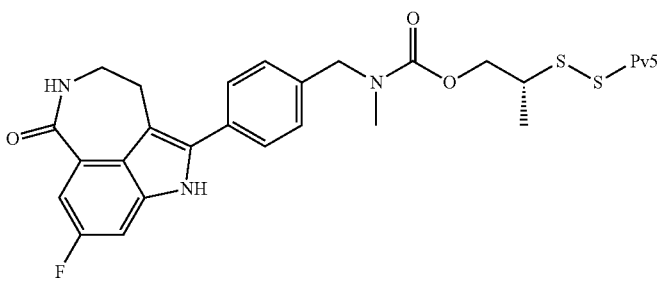 | B: 1542.1 | C<br>25-75%<br>15 min<br>11.7 min |
| 61 | 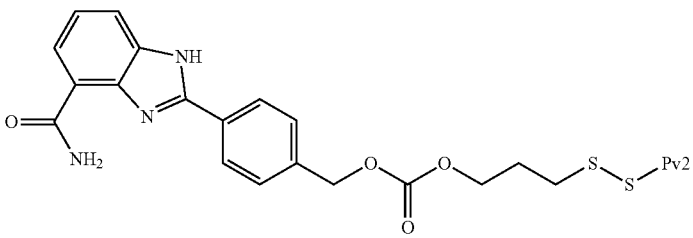 | B: 1465.5 | C<br>40-64%<br>10 min<br>6.3 min |

The following compounds were prepared analogously to Example 18 from the appropriate VII Intermediates and peptides.

TABLE 25

Example Compounds

| Example | Structure | MS<br>A: Maldi-TOF<br>B: m/z = 3 | Column<br>% ACN/H$_2$O<br>Run Time<br>RT |
|---|---|---|---|
| 12 | 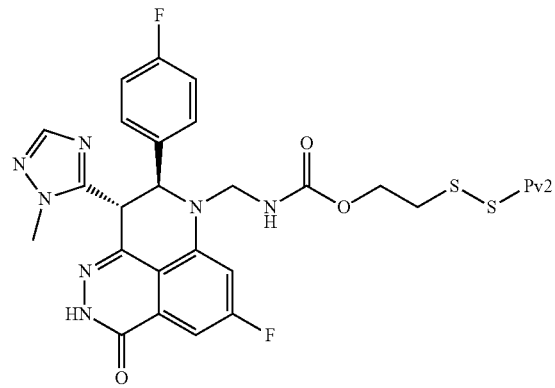 | A: 4522.3 | A<br>40-80%<br>8.2 min |

TABLE 25-continued

Example Compounds

| Example | Structure | MS<br>A: Maldi-TOF<br>B: m/z = 3 | Column<br>% ACN/H₂O<br>Run Time<br>RT |
|---|---|---|---|
| 13 | 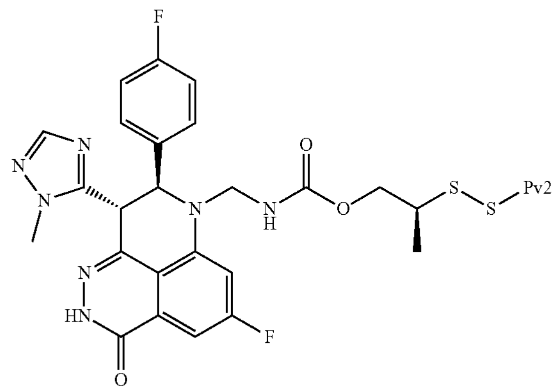 | A: 4536.5 | A<br>40-80%<br>10 min<br>8.4 min |
| 14 | 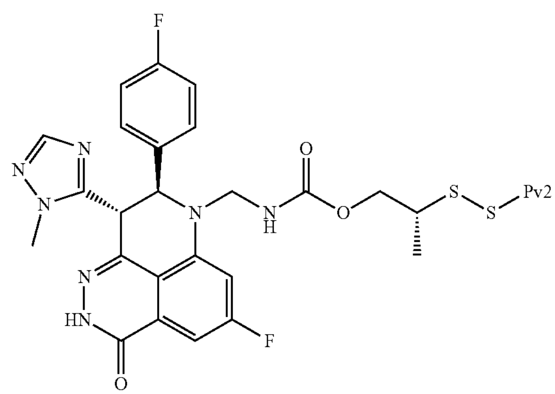 | A: 4535.7 | A<br>40-80%<br>10 min<br>8.4 min |
| 16 | 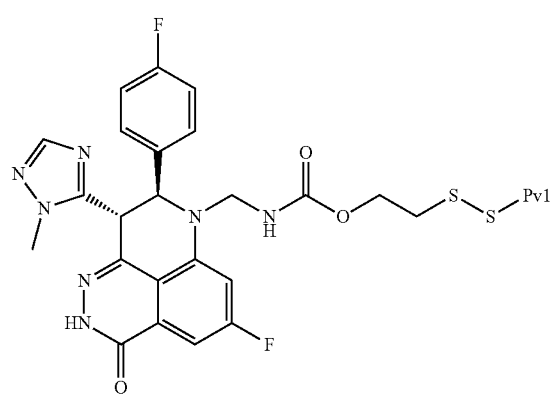 | A: 3790.0 | A<br>40-80%<br>10 min<br>7.1 min |

TABLE 25-continued

Example Compounds

| Example | Structure | MS A: Maldi-TOF B: m/z = 3 | Column % ACN/H$_2$O Run Time RT |
|---|---|---|---|
| 17 | 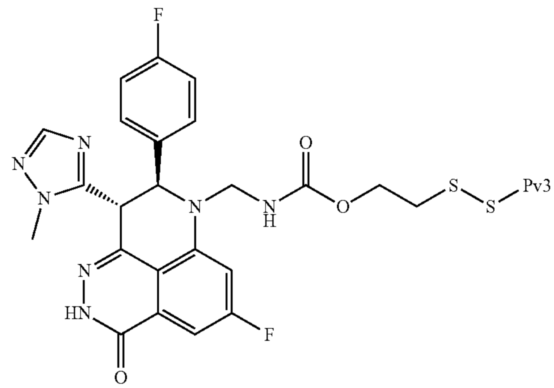 | A: 4220.1 | A 40-80% 10 min 6.7 min |
| 33 | 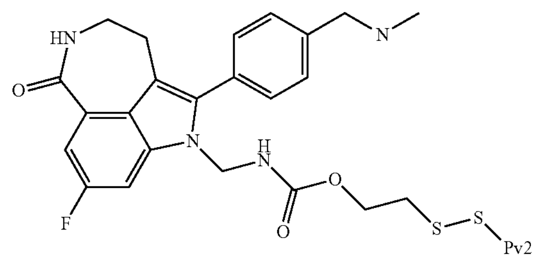 | A: 4462.8 | C 40-58% 9 min 6.8 min |
| 34 | 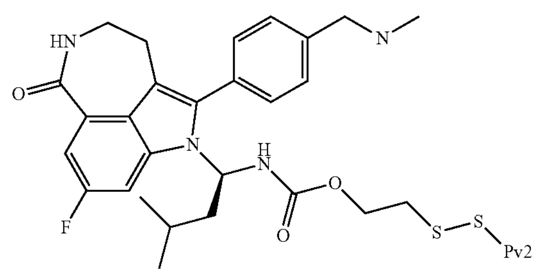 | A: 4520.7 | Diastereomer1 C 40-67% 12 min 9.8 min |
| 35 | 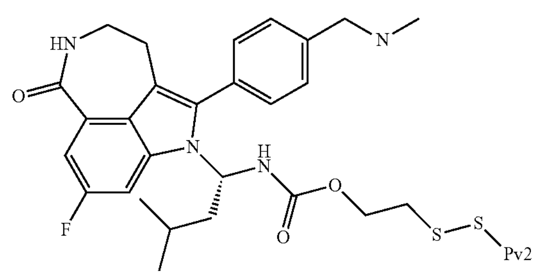 | A: 4521.4 | Diastereomer2 C 40-57% 12 min 10.2 min |
| 38 | 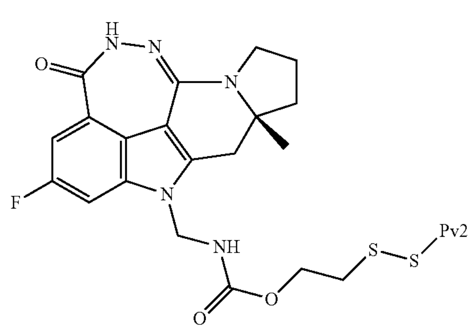 | A: 4440.5 | C 40-60% 12 min 8.5 min |

TABLE 25-continued

Example Compounds

| Example | Structure | MS<br>A: Maldi-TOF<br>B: m/z = 3 | Column<br>% ACN/H$_2$O<br>Run Time<br>RT |
|---|---|---|---|
| 39 | 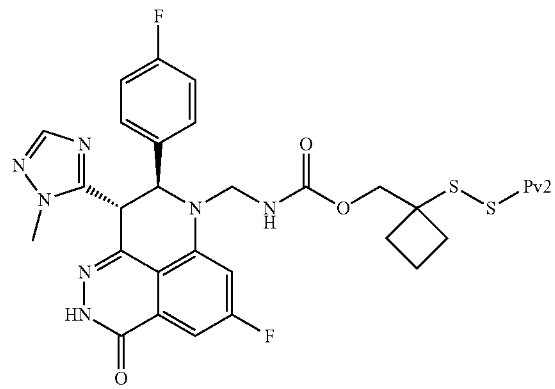 | A: 4559.6 | C<br>50-80%<br>15 min<br>6.5 min |
| 40 | 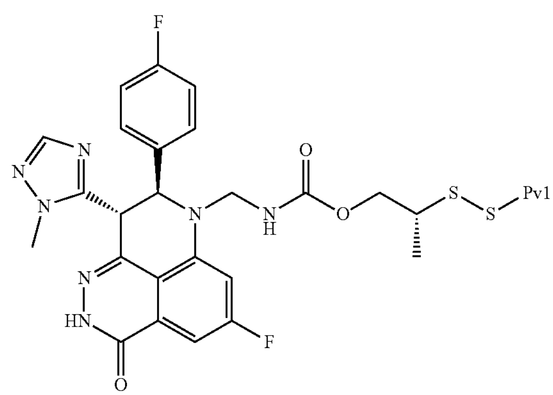 | A: 3804.0 | C<br>40-62%<br>12 min<br>8.6 min |
| 41 | 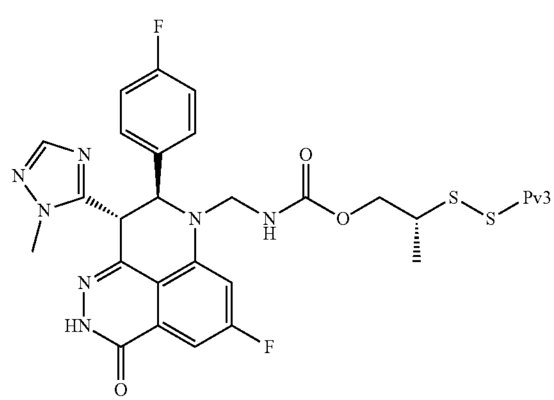 | A: 4234.7 | C<br>40-70%<br>11 min<br>6.5 min |

TABLE 25-continued

Example Compounds

| Example | Structure | MS<br>A: Maldi-TOF<br>B: m/z = 3 | Column<br>% ACN/H$_2$O<br>Run Time<br>RT |
|---|---|---|---|
| 42 | 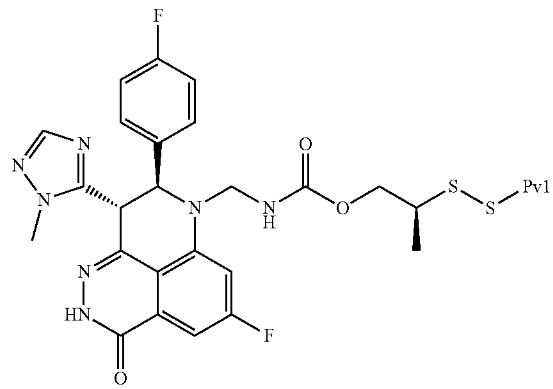 | A: 3805.3 | C<br>40-62%<br>12 min<br>8.5 min |

Synthesis of the Final Compounds from Intermediates XII

The following compound was synthesized from Intermediate XII-1.

TABLE 26

Additional Examples

| Example | Structure | MS<br>A: Maldi-TOF<br>B: m/z = 3 | Column<br>% ACN/H$_2$O<br>Run Time<br>RT |
|---|---|---|---|
| 60 | 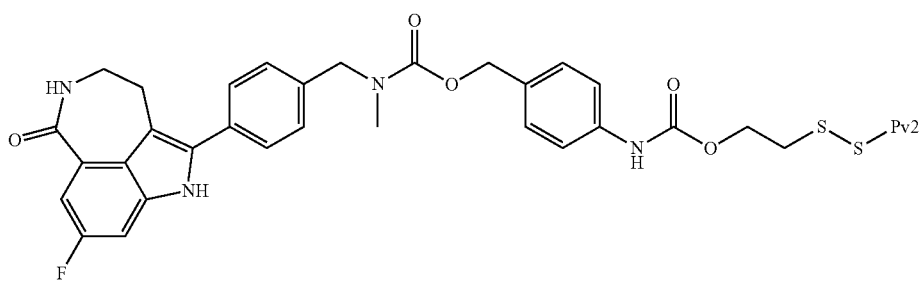 | B: 1460.8 | C<br>20-65%<br>2 min<br>11.1 min |

Example 32

Example 32 was synthesized from Intermediate XXI and peptide Pv2. The MS (Maldi-TOF) found was 4582.9. The compound was purified using 30-50% acetonitrile in water, Conditions 3, eluting at 11 and 8.3 min.

Synthesis of Compounds from Intermediates XXV

The following compounds were synthesized analogously to Example 18 from Intermediates XXV.

TABLE 27

Example Compounds

| Example | Structure | MS<br>A: Maldi-TOF<br>B: m/z = 3 | Column<br>% ACN/H$_2$O<br>RT |
|---|---|---|---|
| 28 | 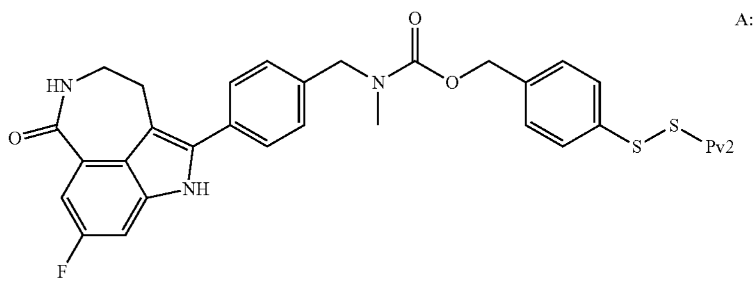 | A: 4497.8 | C<br>50-80%<br>15 min<br>6.5 min |
| 29 | 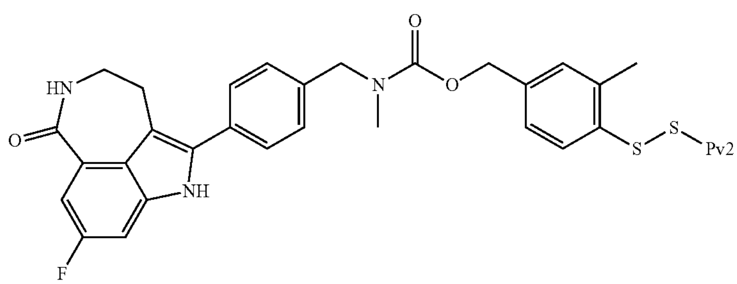 | A: 4510.9 | C<br>50-100%<br>20 min<br>7.4 min |
| 30 | 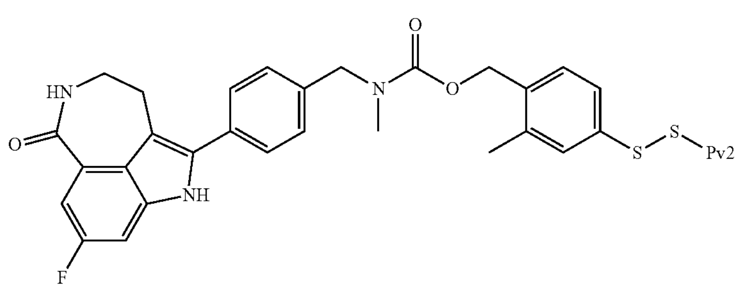 | A: 4510.3 | C<br>50-100%<br>20 min<br>7.3 min |
| 31 | 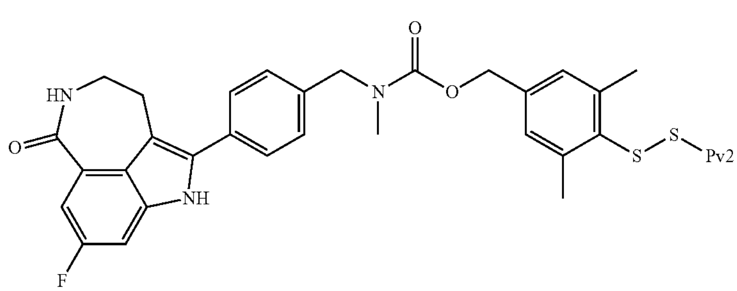 | A: 4526.2 | C<br>50-100%<br>20 min<br>7.0 min |

TABLE 27-continued

Example Compounds

| Example | Structure | MS<br>A: Maldi-TOF<br>B: m/z = 3 | Column<br>% ACN/H₂O<br>RT |
|---|---|---|---|
| 36 | 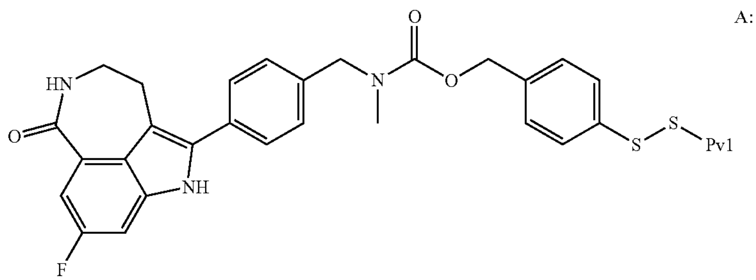 | A: 3767.3 | C<br>40-90%<br>15 min<br>7.0 |
| 37 | 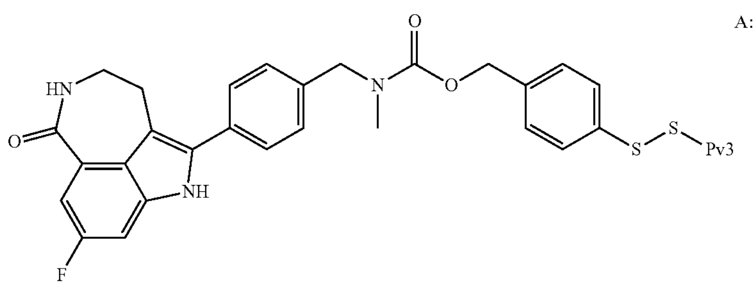 | A: 4196.8 | C<br>40-90%<br>15 min<br>6.4 min |
| 50 | 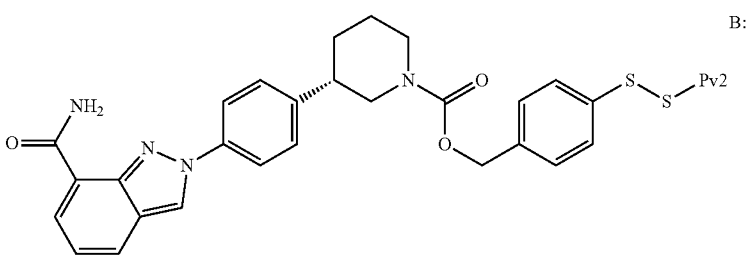 | B: 1397.6 | C<br>20-95%<br>16 min<br>9.5 min |
| 56 | 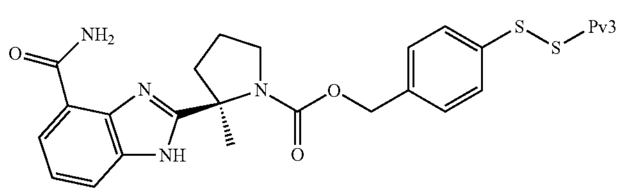 | B: 1373.5 | C<br>35-60%<br>15 min<br>9.3 min |

Synthesis of the Final Compounds from Intermediates XXV

The following compound was synthesized analogously to Example 18 from Intermediate XXV.

TABLE 28

Example Compounds

| Example | Structure | MS<br>A: Maldi-TOF<br>B: m/z = 3 | Column<br>% ACN/H$_2$O<br>RT |
|---|---|---|---|
| 59 | 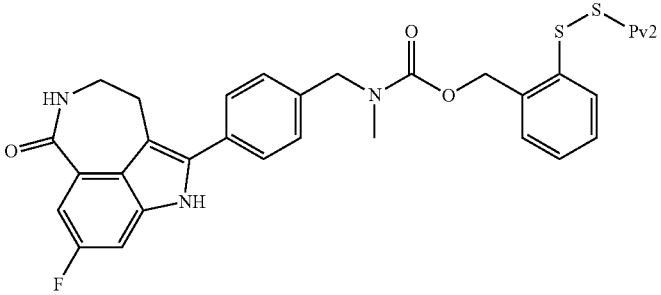 | B: 1499.8 | C<br>50-92%<br>16 min<br>6.1 min |

Synthesis of the Final Compounds from Intermediates XXXV

The following compound was synthesized analogously to Example 18 from Intermediate XXXV-1.

TABLE 29

Example Compounds

| Example | Structure | MS<br>A: Maldi-TOF<br>B: m/z = 3 | Column<br>% ACN/H$_2$O<br>RT |
|---|---|---|---|
| 62 | 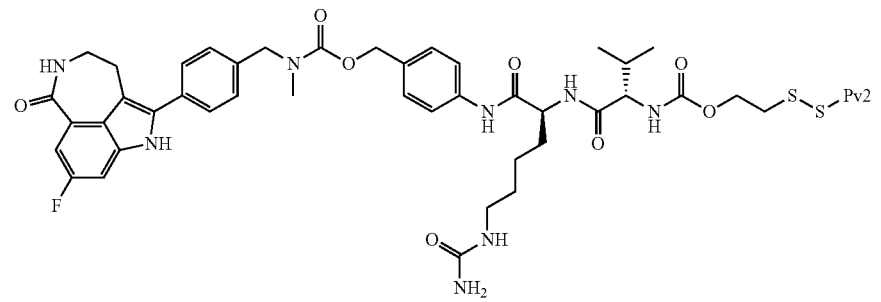 | 1614.4 | C<br>40-68%<br>10 min<br>8.4 min |

Synthesis of the Final Compounds from Intermediates XXXVIII

The following compound was synthesized analogously to Example 18 from Intermediates XXXVIII-1.

TABLE 30

Example Compounds

| Example | Structure | MS A: Maldi-TOF B: m/z = 3 | Column % ACN/H₂O RT |
|---|---|---|---|
| 64 | 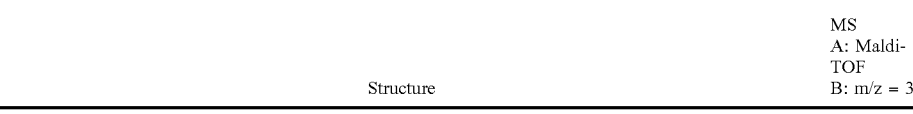 | B: 1531.8 | C 35-75% 10 min 7.6 min |

Example A. Cleavage of Compounds

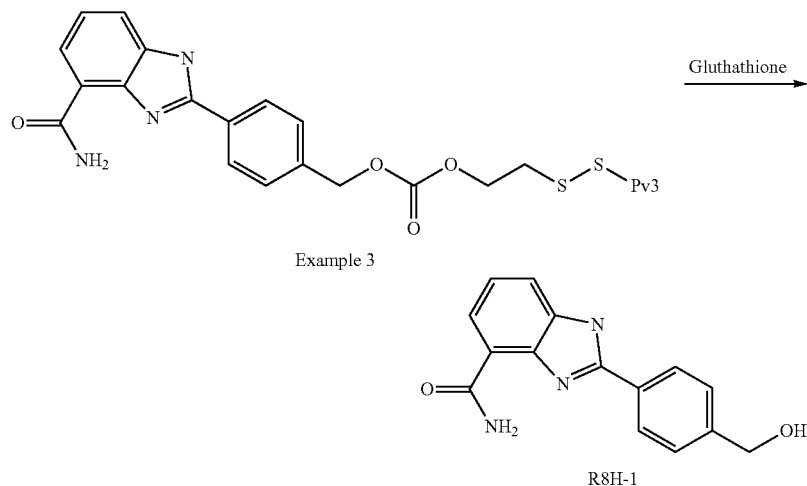

To (2S)-2-amino-5-[[(1R)-2-(carboxymethylamino)-2-oxo-1-(sulfanylmethyl)ethyl] amino]-5-oxo-pentanoic acid (4.90 mg, 0.0159 mmol) was added 2 mL of 1M Tris HCl buffer (pH 7.0) to create an 8 mM solution. An aliquot of 1 mL of this solution was added to Example 3 (0.400 mg, 9.81×10⁻⁵ mmol) to create a 100 μM solution. This mixture was heated at 37° C. with time points taken at 15 minute intervals to measure for conjugate integrity. A steady loss of conjugate is observed with commensurate appearance of 2-[4-(hydroxymethyl)phenyl]-1~{H}-benzimidazole-4-carboxamide. The cleavage was complete by the 60 min time point as observed/confirmed by MSD. HPLC conditions: ES Industries Sonoma 4.6×50 mm; 5-100% CH₃CN/H₂O (0.1% TFA); 5.5 min run Conjugate RT: 3.71 Product RT: 2.24.

Other compounds were similarly cleaved to give the appropriate R₈H molecules.

The crude cleavage solution containing the cleaved compounds of the invention was assayed as described below in Examples B and C to assess the amount of cleaved R⁸H. In addition to the cleaved compounds, assays were also performed on several of the R⁸ starting materials set out in Table 2.

Example B. Enzymatic Assay 1 of Cleaved Compounds (PARP)

Analysis was performed using Trevigen's HT F Homogeneous PARP Inhibition Assay Kit (#4690-096-K) as follows: Purified PARP enzyme was incubated in the presence of a serially diluted PARP inhibitor (e.g., a compound of the Examples cleaved according to Example A) in duplicate and 1 uM NAD for thirty minutes at room temperature in black, round-bottom 96-well plates. An equal volume of cycling mix was added to each well and the reaction was incubated for one hour at room temperature. The reactions were stopped with the addition of Stop Solution and the plates were read on a BioTek Cytation 5 plate reader using the fluorescence (544 nm excitation and 590 nm emission) endpoint. Results were plotted in GraphPad Prism and are given below.

TABLE 31

HT F Homogeneous PARP Inhibition Assay of Cleaved Compounds

| Assayed Compound | $IC_{50}$ Enzymatic Assay 1 (nM) |
|---|---|
| $R^8H$-1 | 96.8 |
| Example 3 (cleaved) | 104 |
| Example 6 (cleaved) | 202 |
| Example 7 (cleaved) | 111 |

Example C. Enzymatic Assay 2 of Cleaved Compounds (PARP)

Analysis was performed using Trevigen's HT Universal Chemiluminescent PARP Assay Kit (#4676-096-K) as follows: Purified PARP enzyme was incubated in the presence of a serially diluted PARP inhibitor (e.g., a compound of the Examples cleaved according to Example A) in duplicate for ten minutes at room temperature in rehydrated 96-well stripwells containing bound histones. An equal volume of 1×PARP cocktail containing activated DNA was added to each well and the reaction was incubated for one hour at room temperature. The wells were washed twice with 1×PBS+0.1% Triton X-100 and twice with PBS. 50 ul/well of diluted streptavidin-HRP was added and the wells were incubated for one hour at room temperature. The wells were washed twice with 1×PBS+0.1% Triton X-100 and washed twice with PBS. The liquid was removed, 100 ul/well 1:1 PeroxyGlow A/PeroxyGlow B was added and the chemiluminescent readings were measured on a BioTek Cytation 5 plate reader using the luminescence fiber endpoint. Results were plotted in GraphPad Prism and are shown below.

TABLE 32

HT Universal Chemiluminescent PARP Assay of Cleaved Compounds

| Assayed Compound | $IC_{50}$ Enzymatic Assay 2 (nM) |
|---|---|
| $R^8H$-1 | 6.4 |
| $R^8H$-3 | 3.9 |
| $R^8H$-4 | 1.3 |
| $R^8H$-15 | 1.0 |
| $R^8H$-16 | 0.8 |
| $R^8H$-17 | 1.0 |
| Example 1 (Cleaved) | 12.1 |
| Example 2 (Cleaved) | 9.52 |
| Example 3 (Cleaved) | 9.15 |
| Example 6 (Cleaved) | 9.29 |
| Example 7 (Cleaved) | 6.45 |
| Example 10 (Cleaved) | 64.9 |
| Example 11 (Cleaved) | 1.08 |
| Example 12 (Cleaved) | 0.47 |
| Example 13 (Cleaved) | 1.0 |
| Example 14 (Cleaved) | 0.5 |
| Example 15 (Cleaved) | 6.47 |
| Example 16 (Cleaved) | 0.61 |
| Example 17 (Cleaved) | 0.41 |
| Example 18 (Cleaved) | 1.1 |

TABLE 32-continued

HT Universal Chemiluminescent PARP Assay of Cleaved Compounds

| Assayed Compound | $IC_{50}$ Enzymatic Assay 2 (nM) |
|---|---|
| Example 19 (Cleaved) | 2.2 |
| Example 20 (Cleaved) | 1.7 |
| Example 21 (Cleaved) | 2.2 |
| Example 22 (Cleaved) | 1.8 |
| Example 23 (Cleaved) | 2.5 |
| Example 24 (Cleaved) | 7.6 |
| Example 25 (Cleaved) | 3.4 |
| Example 26 (Cleaved) | 2.0 |
| Example 27 (Cleaved) | 3.9 |
| Example 28 (Cleaved) | 2.4 |
| Example 29 (Cleaved) | 6.4 |
| Example 30 (Cleaved) | 2.9 |
| Example 31 (Cleaved) | 3.3 |
| Example 32 (Cleaved) | 43.9 |
| Example 33 (Cleaved) | 2.3 |
| Example 34 (Cleaved) | 2.5 |
| Example 35 (Cleaved) | 3.1 |
| Example 36 (Cleaved) | 2.2 |
| Example 37 (Cleaved) | 3.1 |
| Example 38 (Cleaved) | 2.8 |
| Example 39 (Cleaved) | 3.0 |
| Example 40 (Cleaved) | 1.1 |
| Example 41 (Cleaved) | 1.9 |
| Example 42 (Cleaved) | 1.4 |
| Example 43 (Cleaved) | 1.4 |
| Example 44 (Cleaved) | 1.5 |
| Example 45 (Cleaved) | 3.2 |
| Example 46 (Cleaved) | 3.7 |
| Example 47 (Cleaved) | 2.4 |
| Example 48 (Cleaved) | 2.1 |
| Example 49 (Cleaved) | 26 |
| Example 50 (Cleaved) | 2.0 |
| Example 51 (Cleaved) | 0.9 |
| Example 52 (Cleaved) | 1.1 |
| Example 53 (Cleaved) | 1.0 |
| Example 54 (Cleaved) | 0.6 |
| Example 55 (Cleaved) | 0.7 |
| Example 56 (Cleaved) | 0.8 |

Example D. Elisa Parylation Assay

Twelve-well tissue culture plates were seeded with HeLa cells and incubated at 37° C. in 5% $CO_2$ to yield 80% confluent cell monolayers the following day. The monolayers were treated with a three-fold dilution series of either free drug or conjugate at a desired pH for 1 hour at 37° C. The monolayers were aspirated and each well received 150 ul of RIPA lysis buffer supplemented with protease and phosphatase inhibitors. Plates were incubated on ice for 10 minutes and then frozen. Upon thawing, the lysates were supplemented with Mg and incubated with DNAse for 90 minutes at 37° C. The samples were clarified by centrifugation at 12,000×g for 5' at 4° C. and the cleared lysate was transferred to a clean tube and protein determinations were performed using a BCA Protein Assay.

Analysis was performed using Trevigen's HT PARP in vivo Pharmacodynamic Assay II (#4520-096-K) as follows: Duplicate 25 ul sample lysates were loaded on pre-coated/pre-blocked ELISA stripwells and incubated for 16 hours at 4° C. in tandem with serially diluted purified PAR standards. The wells were washed 4× with PBST and incubated with 50 ul/well of PAR polyclonal detecting antibody in antibody diluent for 2 hours at room temperature. The wells were washed 4× with PBST and incubated with 50 ul/well Goat anti-rabbit IgG-HRP conjugate in antibody diluent for 1 hour at room temperature. The wells were washed 4× with PBST, incubated with 100 ul/well of 1:1 PARP PeroxyGlow A and PARP PeroxyGlow B and read in a BioTek Cytation 5 using the luminescence fiber endpoint. Results were plotted as raw luminescence units or as PAR (pg/ml) using values calculated from the standard curve and are presented below.

TABLE 33

Parylation Assay Results

| Example | $IC_{50}$ Elisa PARP Inhibition(nM) pH 5.5 | $IC_{50}$ Elisa PARP Inhibition(nM) pH 6.2 | $IC_{50}$ Elisa PARP Inhibition(nM) pH 7.4 | $IC_{50}$ Elisa PARP Inhibition(nM) pH 8.0 |
|---|---|---|---|---|
| 1 | 115 | | | 587 |
| 2 | 93, 135 | | | 1290, 1400 |
| 3 | 151 | | | 616 |
| 6 | 239 | | | 456 |
| 7 | 282 | | | 542 |
| 10 | 785 | | | 3075 |
| 11 | IC | | | 9102 |
| 12 | 101 | 159 | 186 | 116 |

Cells are treated as previously described at pH 7.4 and incubated for 16 h.

TABLE 34

Parylation Assay Results

| Compound | IC50 Elisa PARP Inhibition(nM) pH 7.4 (BRCA−/−) DLD-1 cells, 16 h | IC50 Elisa PARP Inhibition(nM) pH 7.4 SW620 cells, 16 h |
|---|---|---|
| 18 | 2401 | |
| 19 | 2381 | |
| 20 | 2196 | 2767 |
| 21 | 3545 | |
| 22 | 3877 | |
| 23 | 1425 | |
| 28 | 712 | 2197 |
| 29 | 1314 | |
| 30 | 497 | |
| 31 | 1140 | |
| 32 | 4995 | |
| 34 | 2092 | |
| 35 | 1580 | |
| 36 | 271 | 1174 |
| 37 | 439 | 1386 |
| 40 | 522 | |
| 41 | 459 | |
| 42 | 540 | |
| 43 | 380 | |
| 51 | 4178 | |
| 54 | 1857 | |
| 55 | 2928 | |
| 56 | 103 | |

Example E. Growth Delay Assay

Cells were plated in 96 well black walled-clear bottom plates (Griener), DLD-1 WT cells at 2500 cells per well, DLD-1 BRCA2−/− at 5000 cells per well, in growth media containing 10% FBS. Cells were allowed to adhere at room temperature for 60 minutes before returning to a 37 C, 5% CO2 incubator. After 24 hours, media was removed and replaced with fresh growth media containing various drug concentrations. Each drug concentration was added in triplicate. Non-drug treated controls contained growth media only. Cells were returned to the incubator. Ninety-six hours after addition of drug, cells were fixed with 4% paraformaldehyde for 20 minutes and stained with Hoechst at 1 ug/mL. The plates were imaged on a Cytation 5 auto imager (BioTek) and cells were counted using CellProfiler (http://cellprofiler.org). The percent cell growth delay was calculated and data plotted using GraphPad Prism.

TABLE 35

Growth Delay Assay Summary

| Example | $IC_{50}$ Growth Delay (nM) pH 7.4, BRCA (−/−) DLD-1, 96 h |
|---|---|
| 12 | 162 |
| 13 | 51 |
| 14 | 72 |
| 16 | 84 |
| 17 | 50 |
| 39 | 104 |
| 40 | 64 |
| 41 | 43 |
| 42 | 53 |
| 43 | 46 |

The above results demonstrate that the compounds of the invention are cleaved to release free $R^8H$ when subjected to conditions replicating those within a cell and exhibit inhibition of the biological target, which in this particular assay is PARP. Based on these results one of skill in the art would readily recognize the compounds of the invention to be useful for treatment of diseases involving acidic or hypoxic diseased tissue, and particularly for treating PARP mutated cancers.

Example F. In Vivo Tumor Growth Delay

Study Design ($R^8H$-15, Example 12)

Female Nude mice arrived at the facility at 6 weeks of age and were housed 5 per cage on Alpha-Dri bedding in a disposable IVC caging system (Innovive). After an acclimation period of 5-10 days, DLD-1 BRACA2$^{-/-}$ cells were diluted 1:1 in Phenol Red-free Matrigel and subcutaneously implanted into the left flank of each mouse at a density of $5\times10^6$ cells in 100 μL. Xenograft tumor growth was monitored and caliper measurements were obtained twice weekly. When xenografts reached a minimal volume of 100 mm$^3$, mice were administered an intraperitoneal (IP) dose of vehicle, Example 12 (6.4, 20 or 50 mg/kg), or an oral dose of $R^8H$-15 (0.3 mg/kg) once daily for 8 days. All mice were administered an oral dose of 10 mg/kg temozolomide (TMZ) prepared in 20% glucose immediately after dosing. Caliper measurements were obtained twice weekly to evaluate compound effect on tumor growth. Monitoring of tumor growth continued after the 8-day dosing period for another 7 weeks (wash out period). Mice were euthanized if body weight loss exceeded 20% or if tumor volume increased to 4× the original size. Kaplan-Meier analysis was used to evaluate survival rate based on death or removal from study.

Study Design ($R^8H$-16, Example 18)

Female Nude mice arrived at the facility at 6 weeks of age and were housed 5 per cage on Alpha-Dri bedding in a disposable IVC caging system (Innovive). After an acclimation period of 5-10 days, DLD-1 BRACA2$^{-/-}$ cells were diluted 1:1 in Phenol Red-free Matrigel and subcutaneously implanted into the left flank of each mouse at a density of $5\times10^6$ cells in 100 μL. Xenograft tumor growth was monitored and caliper measurements were obtained twice weekly. When xenografts reached a minimal volume of 100 mm$^3$, mice were administered an intraperitoneal (IP) dose of vehicle, Example 18 (8.8, 17.7 or 44.2 mg/kg), or $R^8H$-16

(1, 2, 5 mg/kg), once daily for 8 days. All mice were administered an oral dose of 10 mg/kg temozolomide (TMZ) prepared in 20% glucose immediately after dosing for 5 days. Caliper measurements were obtained twice weekly to evaluate compound effect on tumor growth. Monitoring of tumor growth continued after the 8-day dosing period for another 8-day (wash out period). Mice were euthanized if body weight loss exceeded 20% or if tumor volume increased to 4× the original size.

DLD-1 BRCA2$^{-/-}$ Cell Preparation for Implantation ($R^8H$-15, Example 12; $R^8H$-16, Example 18

Matrigel was thawed overnight on ice at 4° C. prior to prepare for DLD-1 BRCA2$^{-/-}$ cell implantation and was kept on ice during all preparatory steps. Cells were passaged between one and three days prior to preparation for implantation. Growth medium was replaced every 2-3 days as needed to maintain cell viability. On the day of implantation, cells were trypsinized, washed with complete media and pelleted by centrifugation at 1200 rpm for 5 minutes. The supernatant was decanted and cells were washed three times with sterile PBS and pelleted by centrifugation. During the final centrifugation, viability was determined using trypan blue exclusion. Cells were resuspended in sterile PBS at a concentration of 5×10$^6$ cells/50 µL. Prior to implantation, cells were mixed 1:1 with Matrigel for a final concentration of 5×10$^6$ cells/100 µL. The Matrigel/cell mixture was kept on ice in a conical tube until used for implantation.

DLD-1 BRCA2$^{-/-}$ Cell Implantation ($R^8H$-15, Example 12; $R^8H$-16, Example 18)

Matrigel/DLD-1 BRCA2$^{-/-}$ cells (5×10$^6$ cells/100 µL) kept on ice in a conical tube were drawn into sterile 1 cc syringes fitted with sterile 27-gauge needles. Excess Matrigel/cell mixture was expelled back into the conical tube leaving an injection volume of 100 µL in each syringe. Filled syringes were kept on ice until time of implantation to avoid polymerization of the Matrigel in the syringe. Cells were subcutaneously implanted into the left flank of each mouse and upon the development of palpable xenografts, caliper measurements were obtained twice weekly. Compound evaluation proceeded when xenografts reached a minimal volume of 100 mm$^3$.

Compound Administration ($R^8H$-15, Example 12)

Intraperitoneal doses of 6.4, 20 and 50 mg/kg Example 12 were prepared in 8% PEG400+2% Tween 80 in PBS as described above and were administered once daily for 8 days. Mice were dosed at a volume of 12 mL/kg (300 µL per 25 g mouse). Oral doses of 0.3 mg/kg $R^8H$-15 (BMN673) were prepared in 0.5% methyl cellulose and were administered once daily for 8 days at volume of 10 mL/kg (250 µL per 25 g mouse) for comparison. Immediately after compound administration, all mice were administered an oral dose of 10 mg/kg temozolomide (TMZ) in 20% glucose.

Compound Administration ($R^8H$-16, Example 18)

Example 18 was dissolved in 100% dimethyl sulfoxide (DMSO) to yield a 0.1 mg/µL stock solution. Intraperitoneal (IP) doses of 8.83, 17.66 or 44.15 mg/kg were prepared fresh daily by diluting 14, 29 or 72 µL of the stock, respectively, with 1950 µL of a vehicle comprised of 8% PEG400+2% Tween 80 in PBS. The doses were vortexed to achieve homogenous suspensions and were administered at a concentration of 12 mg/mL (300 µL per 25 g mouse), once daily for 8 days. Each day, 2.5 mg of $R^8H$-16 was suspended in 6 mL of a vehicle comprised of 8% PEG400+2% Tween 80 in PBS. The suspension was sonicated for 10 minutes to result in a homogeneous 5 mg/kg intraperitoneal dose which was further diluted 1 to 5 and 1 to 2.5 with vehicle to result in 1 and 2 mg/kg doses, respectively. All doses were vortexed and administered at a concentration of 12 mL/kg (300 µL per 25 g mouse) once daily for 8 days. Oral doses of 50 mg/kg temozolomide (TMZ) were prepared fresh daily by suspending 70 mg of compound in 14 mL of a 20% glucose vehicle. The final 5 mg/mL doses were sonicated for 15 minutes until homogenous suspensions were achieved. Mice were orally administered TMZ at 10 mL/kg (250 µL per 25 g mouse) once daily for 5 days immediately following administration of Example 18 or $R^8H$-16.

Tumor Growth

Tumor growth was monitored and caliper measurements were obtained twice weekly over a dosing period of 8 days to evaluate compound efficacy against tumor growth rate. Growth measurements continued for another 7 weeks after dosing ceased. Mice were removed from study when tumor volume exceeded 4× its original size.

Statistical Analysis

Analysis of variance (ANOVA) was used to test for significant differences between groups. Post-hoc Bonferroni multiple comparison test analysis was used to determine significant differences among means. All statistical analysis was accomplished using Graph Pad Prism 7.03 software. Kaplan-Meier analysis was used to evaluate survival rate based on death or removal from study when body weight loss exceeded 20% from initial body weight.

FIG. 1 shows the tumor growth delay of $R^8H$-15 and Example 12 in BRCA$^{-/-}$ Mice.

Figure 2:
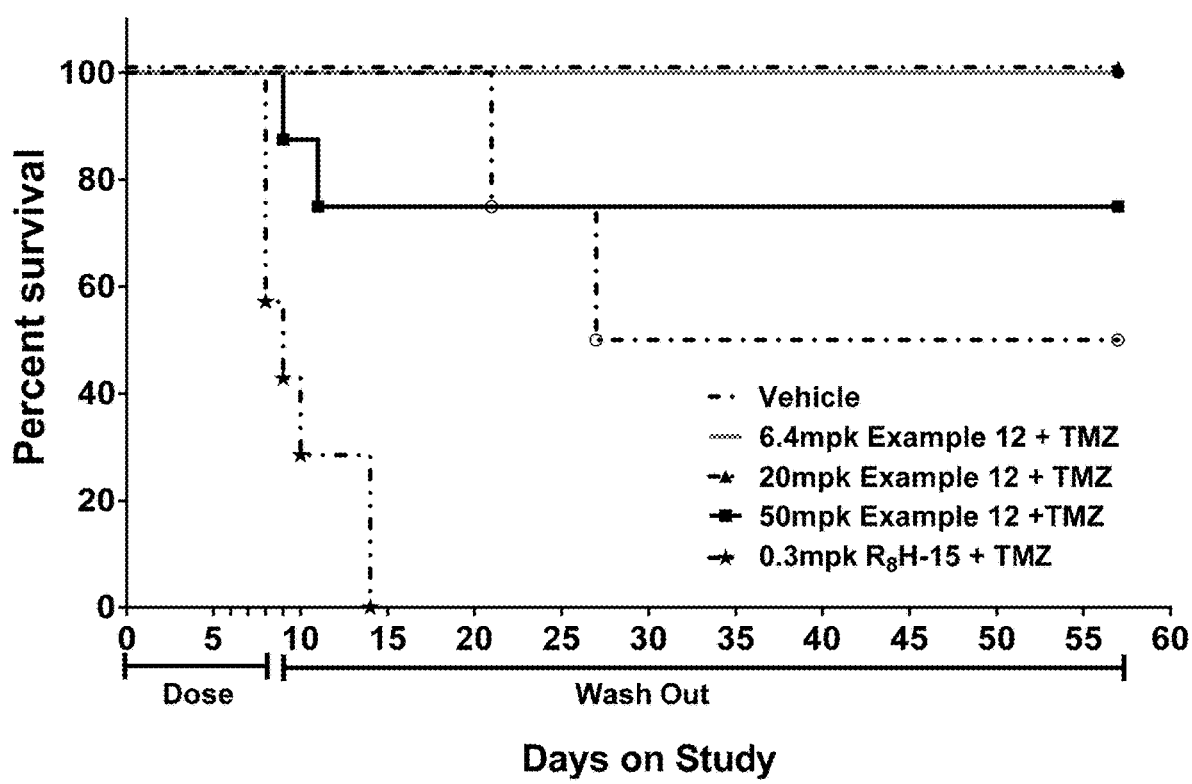
FIG. 2 shows survival of $R^8H$-15 and Example 12 in $BRCA^{-/-}$ Mice.

FIG. 2 shows survival of $R^8H$-15 and Example 12 in BRCA$^{-/-}$ Mice.

Figure 3:
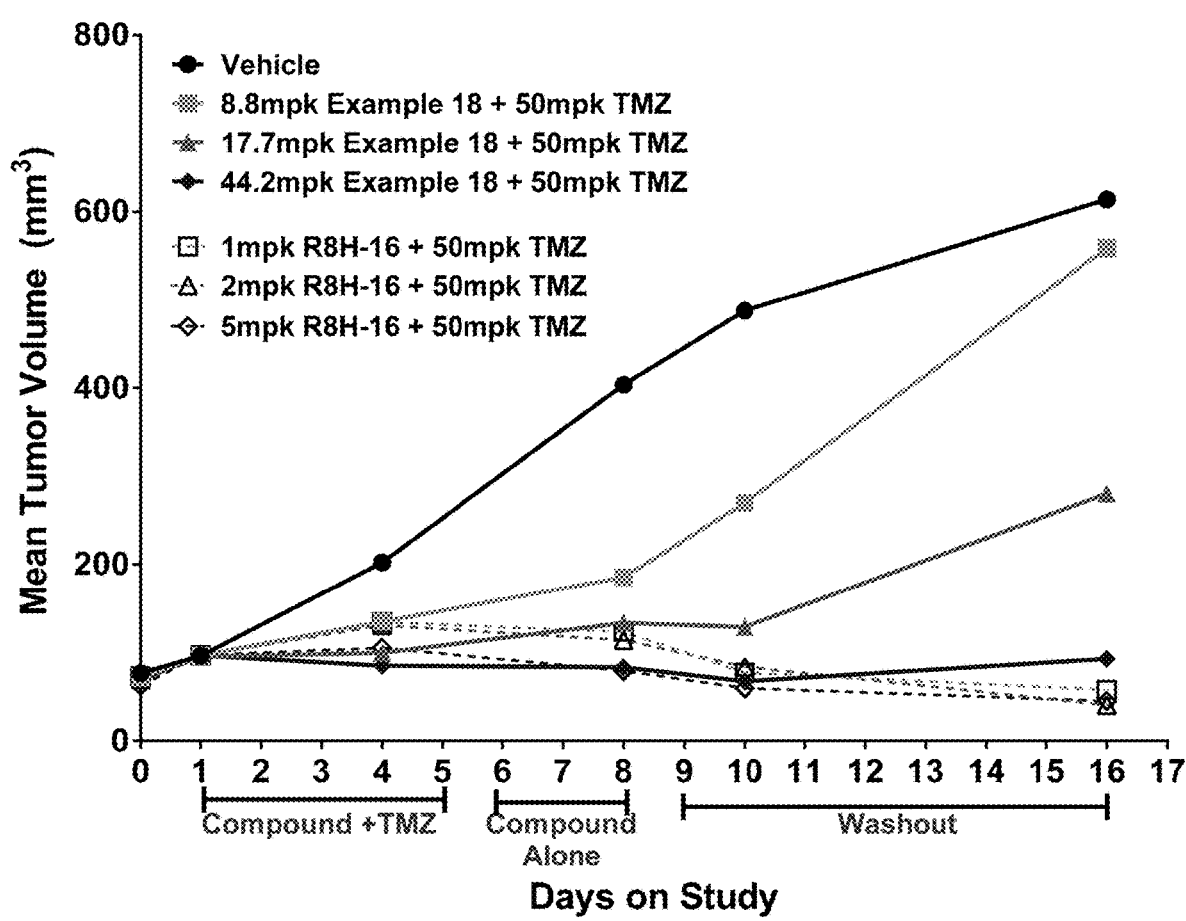
FIG. 3 shows the tumor growth delay of $R^8H$-16 and Example 18 in $BRCA^{-/-}$ Mice.

FIG. 3 shows the tumor growth delay of $R^8H$-16 and Example 18 in BRCA$^{-/-}$ Mice.

Example G. Tumor Parylation

Study Design ($R^8H$-16, Example 18)

Female Nude mice arrived at the facility at 6 weeks of age and were housed 5 per cage on Alpha-Dri bedding in a disposable IVC caging system (Innovive). Human DLD-1 BRACA2$^{-/-}$ cells were diluted 1:1 in Phenol Red-free Matrigel and subcutaneously implanted into the left flank of each mouse at a density of 5×10$^6$ cells in 100 µL. Caliper measurements were obtained twice weekly and treatment began when xenografts reached a minimal volume of 250 mm$^3$. Intraperitoneal (IP) doses of Example 18 (8.83, 17.66 or 44.15 mg/kg) or $R^8H$-16 (2 or 10 mg/kg) were administered once daily for 9 days in an 8% PEG400+2% Tween 80 vehicle. Mice were also administered an oral dose of 20% glucose. The eighth dose was administered in the evening about 12 hours before the ninth dose. Serum and tissue samples were collected 2 hours after administration of the ninth dose. Compound effect against PARylation was determined in tumor and bone marrow.

Compound Administration ($R^8H$-16, Example 18)

Example 18 was dissolved in 100% dimethyl sulfoxide (DMSO) to yield a 0.1 mg/µL stock solution. Intraperitoneal (IP) doses of 8.8, 17.7 or 44.2 mg/kg were prepared fresh daily by diluting 13, 26 or 66 µL of the stock, respectively, with 1800 µL of a vehicle comprised of 8% PEG400+2% Tween 80 in PBS. The doses were vortexed to achieve homogenous suspensions. Intraperitoneal (IP) doses of 10 mg/kg $R^8H$-16 were prepared fresh daily by suspending 5 mg of $R^8H$-16 in 6 mL of a vehicle comprised of 8% PEG400+2% Tween 80 in PBS. The doses were vortexed to achieve homogenous suspensions. IP doses of 2 mg/kg were prepared by diluting the 10 mg/kg dose 1:5 with vehicle. Intraperitoneal (IP) doses of Example 18 or R$^8$H-16 were administered once daily for 9 days at a volume of 12 mL/kg (300 µL, per 25 g mouse).

Tissue Collection (R$^8$H-16, Example 18)

Following blood collection, mice were euthanized by cervical dislocation under anesthesia. Xenograft tumors were removed, weighed, and cut into smaller pieces with a scalpel blade. Random 100 mg tumor samples were collected in cryo-tubes, snap frozen in liquid nitrogen and stored at −80° C. until processed. PARylation measurements were made in tumor homogenates.

PARylation in Tumor Homogenates (R$^8$H-16, Example 18)

Frozen tumor samples were homogenized in a RIPA buffer containing protease and phosphatase inhibitors (1 mg/mL) and 300 µL aliquots were brought up to a 1% SDS final concentration. Samples were heated at 100° C. for 5 minutes, quenched on ice and clarified by centrifugation at 14,000×g for 5 minutes. Tumor samples were diluted 1:10 in RIPA/HALT buffer for protein quantification using a Pierce Rapid Gold BCA Protein Assay kit. Samples were diluted to 200 µg/mL (10 µg/well) in sample buffer and 50 µL aliquots (10 m/well) were loaded on pre-coated/pre-blocked ELISA strip wells. Following a 16-hour incubation at 4° C., samples were washed 4× with PBST (1 L PBS+1 mL Tween 20) and incubated with 50 µL PAR detecting antibody for 2 hours at room temperature. Samples were washed 4× with PBST and incubated with 50 µL goat anti-rabbit IgG-HRP conjugate for 1 hour at room temperature. Following a final 4× wash with PBST, 100 µL of PeroxyGlow™ was added to each sample and luminescence was determined on a BioTek Cytation 5 using luminescence fiber endpoint and strip well area plate definition.

Figure 4:
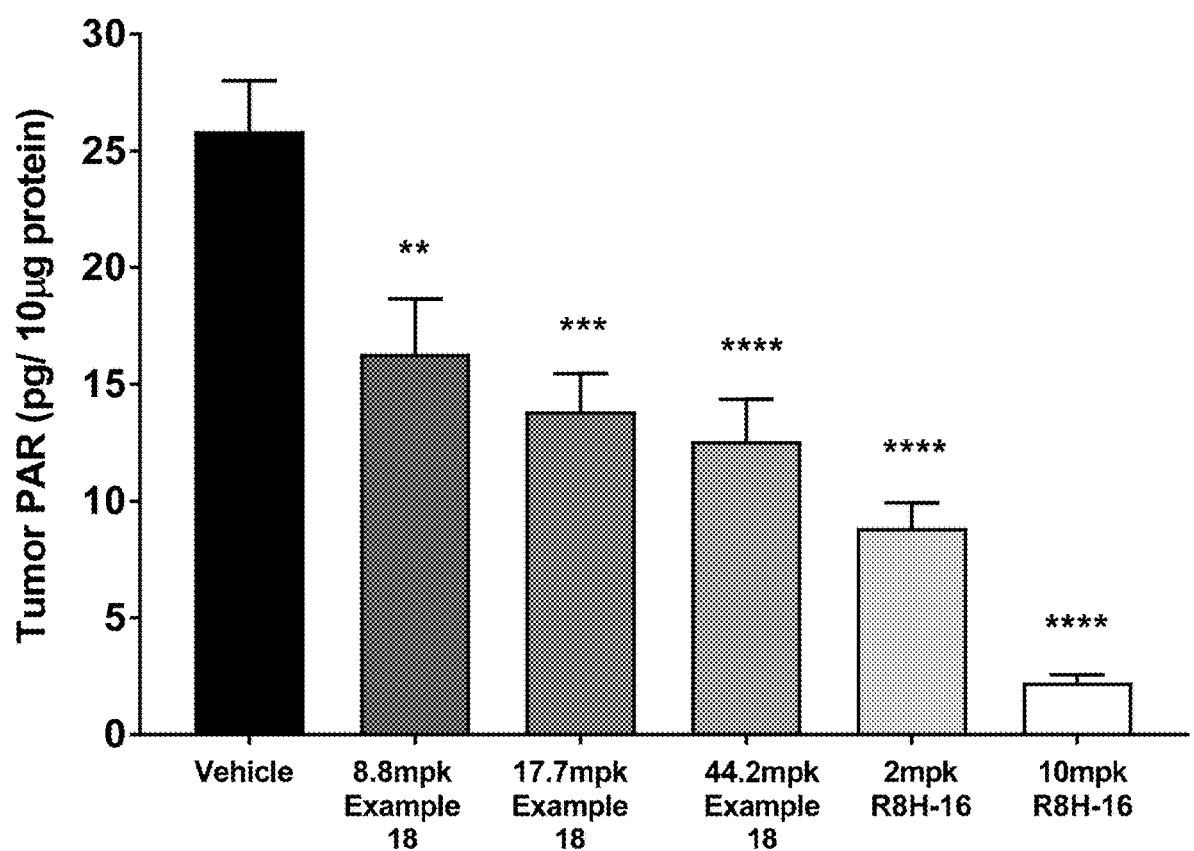
FIG. 4 shows the effect of 9-Day intraperitoneal administration of Example 18 and $R^8H$-16 on tumor PARylation in a murine DLD-1 $BRCA2^{-/-}$ xenograft model.

FIG. 4 shows the effect of 9-Day intraperitoneal administration of Example 18 and R$^8$H-16 on tumor PARylation in a murine DLD-1 BRCA2$^{-/-}$ xenograft model.

Example H. Bone Marrow Selectivity

Study Design (R$^8$H-15, Example 12)

Female Nude mice arrived at the facility at 6 weeks of age and were housed 5 per cage on Alpha-Dri bedding in a disposable IVC caging system (Innovive). After an acclimation period of 5-10 days, DLD-1 BRACA2$^{-/-}$ tumor cells were diluted 1:1 in Phenol Red-free Matrigel and subcutaneously implanted into the left flank of each mouse at a density of 5×10$^6$ cells in 100 µL. Tumor growth was monitored and caliper measurements were obtained twice weekly. When tumors reached a minimal volume of 100 mm$^3$, mice were administered an oral dose of 50 mg/kg Temozolomide (TMZ) alone or in combination with either an oral dose of 0.3 mg/kg R$^8$H-15 or an intravenous dose of 10 mg/kg Example 12, once daily for 2 days. On Day 3, fed mice were euthanized by cervical dislocation under anesthesia and tumors were removed, weighed and snap frozen in liquid nitrogen. Femurs were removed and bone marrow was extruded with PBS into 50 mL conical tubes for isolation of bone marrow cells by centrifugation. Myelotoxicity was evaluated by bone marrow cell count and by PARylation inhibition as determined by Elisa. Compound effectiveness against tumor cell viability was determined by an Elisa PARylation assay.

Study Design (R$^8$H-16, Example 18)

Female Nude mice arrived at the facility at 6 weeks of age and were housed 5 per cage on Alpha-Dri bedding in a disposable IVC caging system (Innovive). Human DLD-1 BRACA2$^{-/-}$ cells were diluted 1:1 in Phenol Red-free Matrigel and subcutaneously implanted into the left flank of each mouse at a density of 5×10$^6$ cells in 100 µL. Caliper measurements were obtained twice weekly and treatment began when xenografts reached a minimal volume of 250 mm$^3$. Intraperitoneal (IP) doses of Example 18 (8.83, 17.66 or 44.15 mg/kg) or R$^8$H-16 (2 or 10 mg/kg) were administered once daily for 9 days in an 8% PEG400+2% Tween 80 vehicle. Mice were also administered an oral dose of 20% glucose. The eighth dose was administered in the evening about 12 hours before the ninth dose. Serum and tissue samples were collected 2 hours after administration of the ninth dose. Compound effect against PARylation was determined in bone marrow.

Compound Administration (R$^8$H-15, Example 12)

5 mg of Example 12 was dissolved in 50 µL of 100% dimethyl sulfoxide (DMSO) to yield a 0.1 mg/µL stock solution. The final 10 mg/kg intravenous dose was prepared by diluting 25 µL of the stock with 2475 µL of sterile PBS. The dose was gently mixed to result in a clear injectable 1 mg/mL dosing solution. Doses were administered once daily for 2 days by tail vein injection at 10 mL/kg (200 µL per 20 g mouse). Mice were dosed in combination with an oral 50 g/kg dose of Temozolomide. An oral dose of 3 mg/kg R$^8$H-15 was prepared by suspending 1.5 mg of compound in 5 mL of a 10% Dimethyl Acetamide (DMAc)+6% Solutol+ 84% PBS vehicle. The suspension was further diluted 1:10 in the vehicle. The final 0.3 mg/kg dose was sonicated for 15 minutes until a homogenous 0.3 mg/mL suspension was achieved. Mice were orally dosed at 10 mL/kg (200 µL per 20 g mouse) once daily for 2 days in combination with an oral 50 mg/kg dose of Temozolomide.

Compound Administration (R$^8$H-16, Example 18)

Compound administration was as described in the Compound Administration (R$^8$H-16, Example 18) section of Example F.

Bone Marrow Collection (R$^8$H-15, Example 12)

Following tumor collection, femurs were removed and bone marrow was extruded into 50 mL conical tubes by flushing the bones with a 23-gauge needle fitted on a 5 cc syringe containing RPMI+2% fetal bovine serum (FBS). Bone marrow was homogenized by gentle pipetting and filtered through 100 µm nylon mesh filters. Bone marrow cells were pelleted by centrifugation at 1200 rpm for 5 minutes at 4° C. Cells were washed with 5 mL of PBE (PBS+0.2% bovine serum albumin+2 mM EDTA) and were re-pelleted by centrifugation as described above. Cells were re-suspended in 3 mL 1×RBC Lysis Buffer and incubated at room temperature for 2-5 minutes. PBE was added to a final volume of 25 mL and cells were pelleted by centrifugation. Cells were re-suspended in 5 mL PBE, passed through a 40 µm nylon mesh filter, and harvested by centrifugation. Cells were re-suspended in 1 mL PBE. Cell concentration and viability were determined using trypan blue exclusion on a TC-20 cell counter (Biorad) prior to preparation for PARylation analysis. Following cell count, 1.5 mL bone marrow cells were pelleted by centrifugation at 1200 rpm (300 rcf) for 5 minutes at 4° C. Supernatant was collected and stored at −80° C. for possible analysis of drug concentration. The remaining 2.5 mL of cells were pelleted by centrifugation at 1200 rpm (300 rcf) for 5 minutes at 4° C. Pelleted cells were lysed in RIPA buffer containing protease and phosphatase inhibitors (1004, buffer per 10$^6$ cells) and stored at −20° C. for measurement of PARylation in bone marrow cells as determined by an Elisa PARylation assay.

PARylation in Bone Marrow Cells (R⁸H-15, Example 12)

Bone marrow cells isolated from femurs on Day 3 were lysed in RIPA buffer containing protease/phosphatase inhibitors. The homogenized samples were brought to 1% SDS final concentration, heated at 100° C. for 5 minutes, quenched on ice and clarified by centrifugation at 12,000×g for 5 minutes at 4° C. PARylation analysis was performed using Trevigen's HT PARP in vivo Pharmacodynamic Assay II. Briefly, duplicate 10 µg samples were loaded on pre-coated/pre-blocked ELISA strip wells as 50 µL volumes in sample buffer and incubated for 16 hours at 4° C. in tandem with serially diluted purified PAR standards. The wells were washed 4× with PBST and incubated with 50 µL/well of PAR polyclonal detecting antibody in antibody diluent for 2 hours at room temperature. The wells were washed 4× with PBST and incubated with 50 µL/well goat anti-rabbit IgG-HRP conjugate in antibody diluent for 1 hour at room temperature. The wells were washed 4× with PBST, incubated with 100 m/well of 1:1 PARP PeroxyGlow A and PARP PeroxyGlow B and read in a BioTek Cytation 5 using the luminescence fiber endpoint. Data were plotted as PAR (pg/mL) using values calculated from the standard curve.

Bone Marrow Collection (R⁸H-16, Example 18)

Following tumor collection, femurs were removed, and bone marrow was extruded into 50 mL conical tubes by flushing the bones with a 23-gauge needle fitted on a 5 cc syringe containing PBS+2% fetal bovine serum (FBS). Bone marrow was homogenized by gentle pipetting and filtered through 100 µm nylon mesh filters and cells were pelleted by centrifugation at 1200 rpm for 5 minutes at 4° C. Red blood cells were lysed with 3 mL of lysis buffer for 2 minutes at room temperature. PBS was added to a volume of 25 mL and cells were re-pelleted by centrifugation as described above. Cell pellets were suspended in 5 mL of PBS and cell count was assessed by trypan blue exclusion on a TC-20 cell counter (BioRad). A subset of 2.5×10⁶ cells from each sample was collected into a microfuge tube for measurement of PARylation.

PARylation in Bone Marrow Cells (R⁸H-16, Example 18)

Bone marrow cells (2.5×10⁶ cells per pellet) were lysed in 500 µL of RIPA/HALT buffer and incubated on ice for 15 minutes with periodic vortexing. Cell lysates were brought up to a 1% SDS final concentration, heated at 100° C. for 5 minutes and quenched on ice. Cellular debris was removed by centrifugation at 14,000×g for 5 minutes 4° C. and pelleted cells were resuspended in buffer at a concentration of 250,000 cells/50 µL. Bone marrow cell samples were loaded on pre-coated/pre-blocked ELISA strip wells and incubated for 16 hours at 4° C. Samples were washed 4× with PBST (1 L PBS+1 mL Tween 20) and incubated with 50 µL PAR detecting antibody for 2 hours at room temperature. Samples were washed 4× with PBST and incubated with 50 µL goat anti-rabbit IgG-HRP conjugate for 1 hour at room temperature. Following a final 4× wash with PBST, 100l, of PeroxyGlow™ was added to each sample and luminescence was determined on a BioTek Cytation 5 using luminescence fiber endpoint and strip well area plate definition.

Statistical Analysis

Analysis of variance (ANOVA) was used to test for significant differences between groups. Post-hoc Bonferroni multiple comparison test analysis was used to determine significant differences among means. All statistical analysis was accomplished using Graph Pad Prism 7.03 software.

Figure 5:
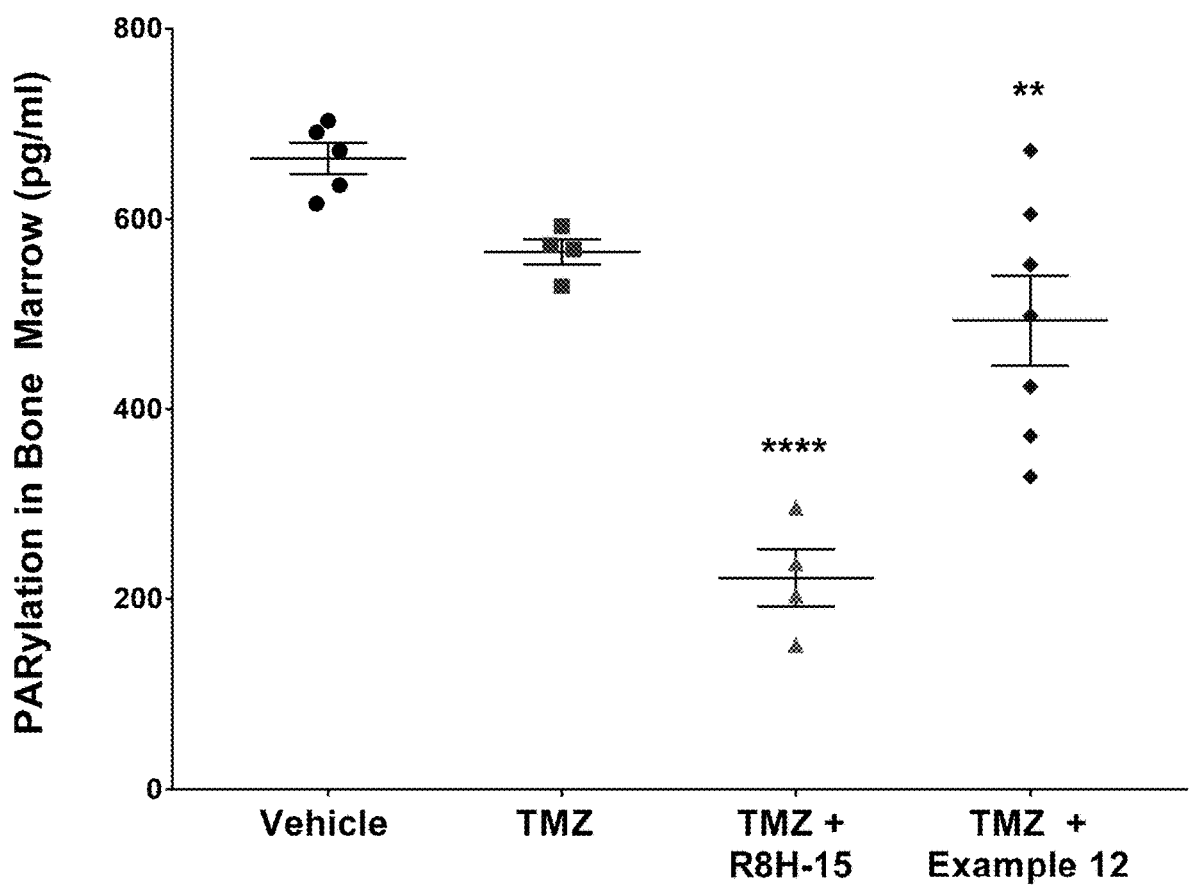
FIG. 5 shows the PARylation in bone marrow cells following intravenous administration of Example 12 or oral administration of $R^8H$-15 in combination with oral administration of temozolomide (TMZ) to nude mice.

FIG. 5 shows the PARylation in bone marrow cells following intravenous administration of Example 12 or oral administration of R⁸H-15 in combination with oral administration of temozolomide (TMZ) to nude mice.

Figure 6:
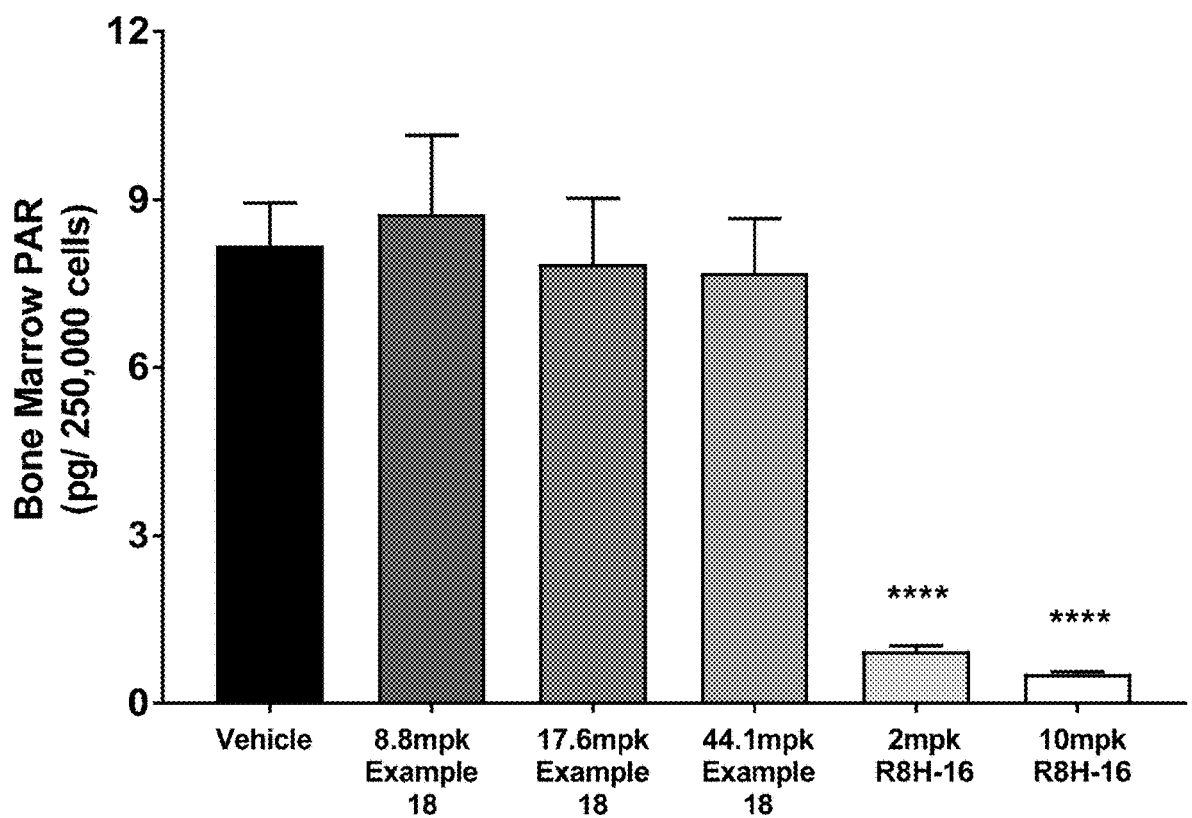
FIG. 6 shows PARylation in bone marrow cells following intraperitoneal administration of Example 18 or $R^8H$-16 to nude mice.

FIG. 6 shows PARylation in bone marrow cells following intraperitoneal administration of Example 18 or R⁸H-16 to nude mice.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound of formula (I)

R8-Q-R7    (I)

or a pharmaceutically acceptable salt thereof, wherein:

$R^7$ is a peptide;

$R^8$ is selected from the group consisting of:

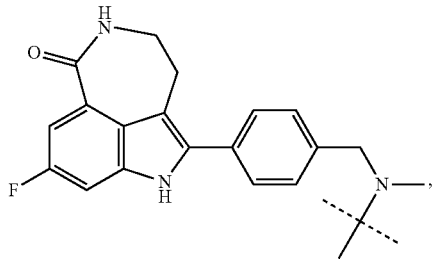

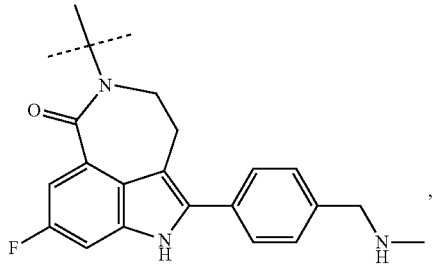

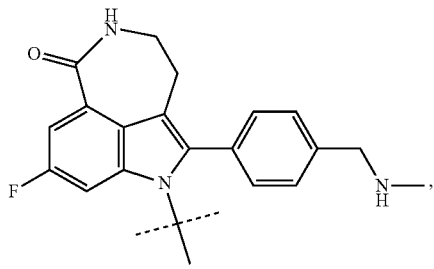

Q is selected from the group consisting of

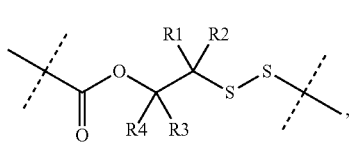

-continued

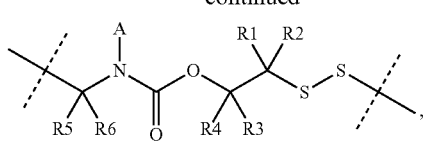

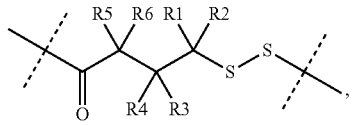

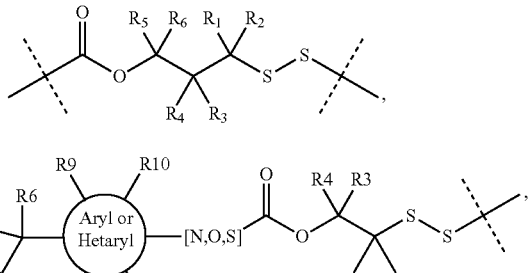

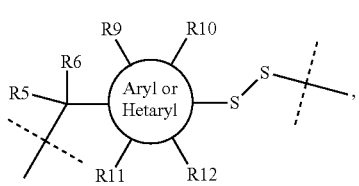

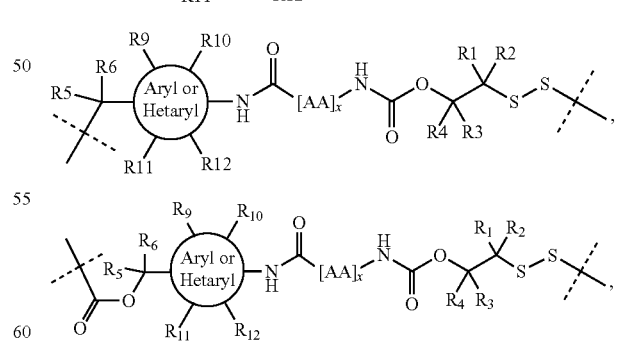

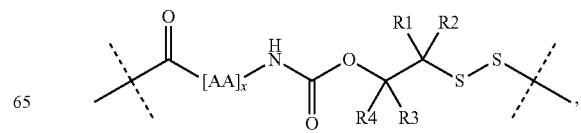

-continued

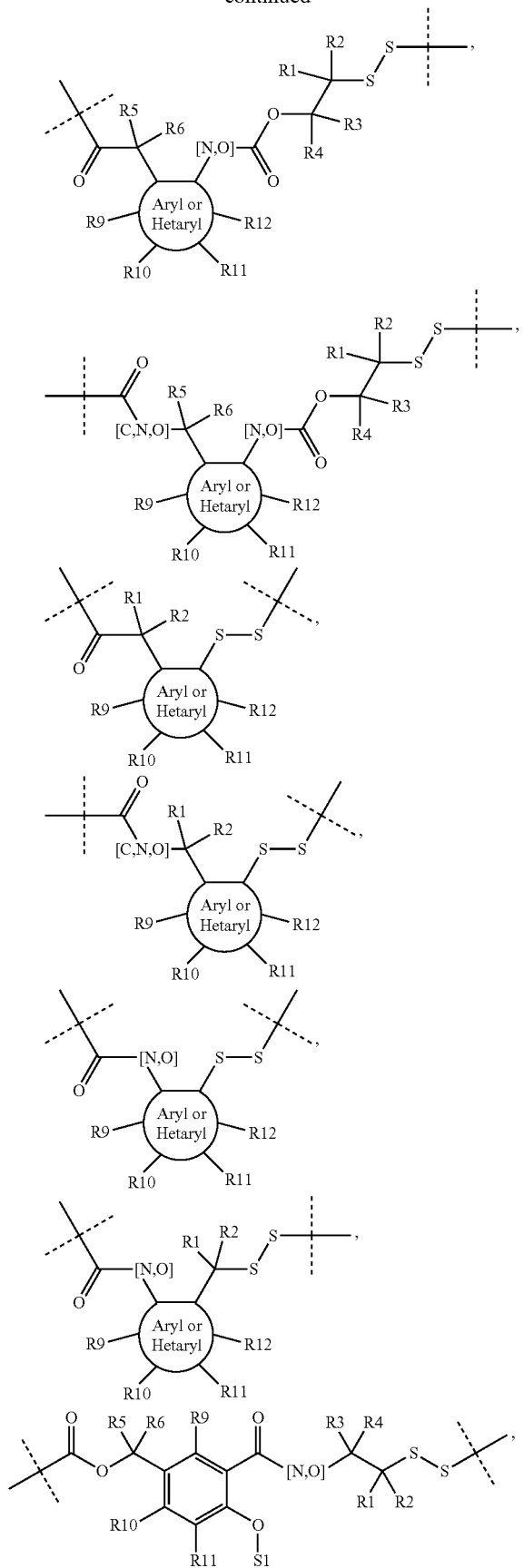
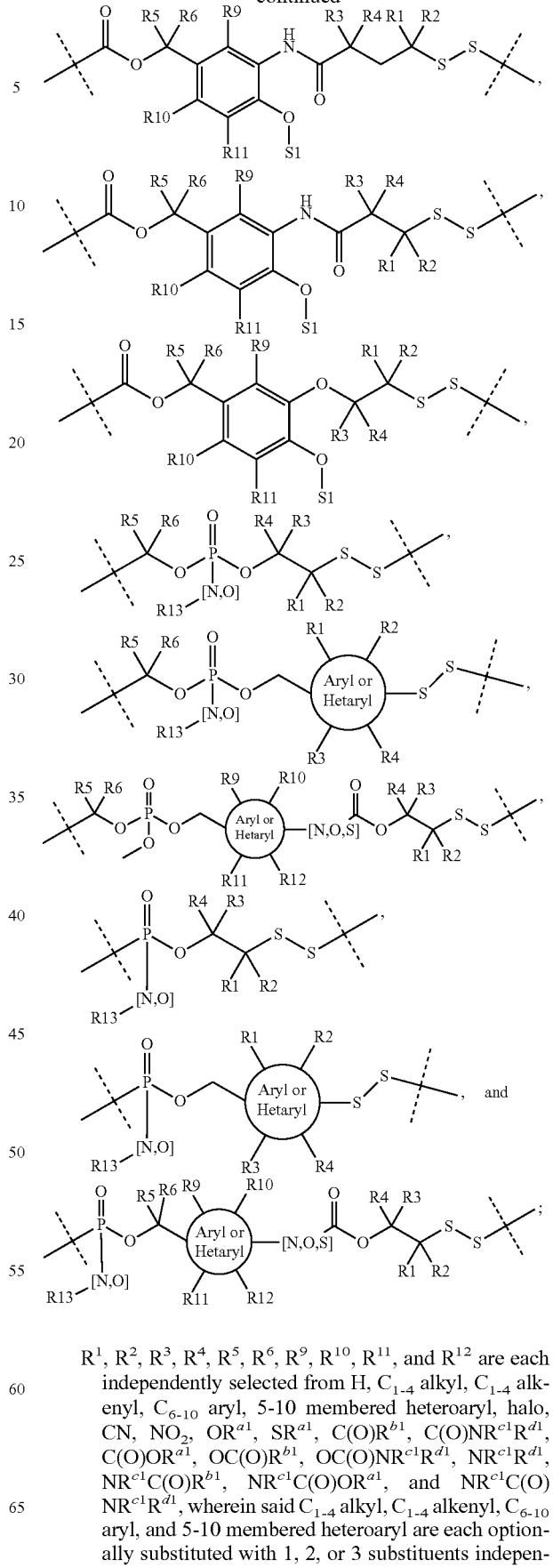

$R^1$, $R^2$, $R^3$, $R^4$, $R^5$, $R^6$, $R^9$, $R^{10}$, $R^{11}$, and $R^{12}$ are each independently selected from H, $C_{1-4}$ alkyl, $C_{1-4}$ alkenyl, $C_{6-10}$ aryl, 5-10 membered heteroaryl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$, wherein said $C_{1-4}$ alkyl, $C_{1-4}$ alkenyl, $C_{6-10}$ aryl, and 5-10 membered heteroaryl are each optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O) NR$^{c1}$R$^{d1}$;

or R$^1$ and R$^2$ together with the carbon atom to which they are attached form a C3-7 cycloalkyl group optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;

or R$^1$ and R$^3$ together with the carbon atom to which they are attached form a C$_{3-7}$ cycloalkyl group optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;

or R$^3$ and R$^4$ together with the carbon atom to which they are attached form an C$_{3-7}$ cycloalkyl group optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;

or R$^5$ and R$^6$ together with the carbon atom to which they are attached form an C$_{3-7}$ cycloalkyl group optionally substituted with 1, 2, or 3 substituents independently selected from halo, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, and NR$^{c1}$C(O)NR$^{c1}$R$^{d1}$;

R$^{13}$ is H or C$_{1-6}$ alkyl;

A is H or C$_{1-4}$ alkyl;

(Aryl or Hetaryl)

is C$_{6-10}$ aryl or 5-10 membered heteroaryl; wherein the 5-10 membered heteroaryl has at least one ring-forming carbon atom and 1, 2, 3, or 4 ring-forming heteroatoms independently selected from N, O, and S;

[N, O, S] is NH, O, or S;

[N, O] is NH or O;

[C, N, O] is CR$^X$R$^Y$, NH, or O;

each R$^X$ and R$^Y$ is independently selected from H and C$_{1-4}$ alkyl;

[AA]$_X$ is a peptide that may be cleaved by enzymatic action;

S1 is

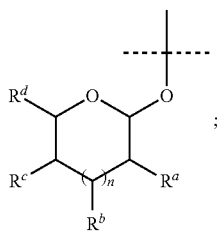

each R$^a$, R$^b$, R$^c$, and R$^d$ is independently selected from H, C$_{1-4}$ alkyl, OR$^{a2}$, CO$_2$R$^{a2}$, and OC(=O)R$^{a2}$, wherein said C$_{1-4}$ alkyl is optionally substituted with OR$^{a2}$, CO$_2$R$^{a2}$, and OC(=O)R$^{a2}$;

R$^{a1}$, R$^{b1}$, R$^{c1}$, and R$^{c1}$ are each independently selected from H, C$_{1-6}$ alkyl, C$_{2-6}$ alkenyl, C$_{2-6}$ alkynyl, C$_{1-6}$ haloalkyl, OH, CN, NO$_2$, and CO$_2$CH$_3$; wherein said C$_{1-6}$ alkyl and C$_{2-6}$ alkenyl are each optionally substituted with OH, CN, NO$_2$, or CO$_2$CH$_3$;

R$^{a2}$ is H or C1-4 alkyl; and n is 0 or 1.

2. The compound of claim 1, or a pharmaceutically acceptable salt thereof, wherein R$^7$ is a peptide capable of selectively delivering 10-across a cell membrane having an acidic or hypoxic mantle having a pH less than about 6.0.

3. The compound of claim 1, or a pharmaceutically acceptable salt thereof, wherein R$^7$ is a peptide comprising at least one of the following sequences:

```
                                        (SEQ ID NO: 1; Pv1)
ADDQNPWRAYLDLLFPTDTLLLDLLWCG;

(SEQ ID NO: 2; Pv2)
AEQNPIYWARYADWLFTTPLLLLDLALLVDADECG;

(SEQ ID NO: 3; Pv3)
ADDQNPWRAYLDLLFPTDTLLLDLLWDADECG;

(SEQ ID NO: 4; Pv4)
Ac-AAEQNPIYWARYADWLFTTPLLLLDLALLVDADEGTKCG;
and (SEQ ID No. 5; Pv5)
AAEQNPIYWARYADWLFTTPLLLLDLALLVDADEGTC;
``` and wherein R$^7$ is attached to Q through a cysteine residue of R$^7$.

4. The compound of claim 1, or a pharmaceutically acceptable salt thereof, wherein R$^7$ is a peptide comprising at least one of the following sequences:

```
                                        (SEQ ID NO: 1; Pv1)
ADDQNPWRAYLDLLFPTDTLLLDLLWCG, (SEQ ID NO: 2; Pv2)
AEQNPIYWARYADWLFTTPLLLLDLALLVDADECG,
and (SEQ ID NO: 3; Pv3)
ADDQNPWRAYLDLLFPTDTLLLDLLWDADECG,
``` and wherein R$^7$ is attached to Q through a cysteine residue of R$^7$.

5. The compound of claim 1, or a pharmaceutically acceptable salt thereof, wherein R$^7$ is a peptide comprising the sequence:

```
                                        (SEQ ID NO: 1; Pv1)
ADDQNPWRAYLDLLFPTDTLLLDLLWCG.
```

6. The compound of claim 1, or a pharmaceutically acceptable salt thereof, wherein R$^7$ is a peptide comprising the sequence:

```
                                        (SEQ ID NO: 2; Pv2)
AEQNPIYWARYADWLFTTPLLLLDLALLVDADECG.
```

7. The compound of claim 1, or a pharmaceutically acceptable salt thereof, wherein $R^7$ is a peptide comprising the sequence:

```
                            (SEQ ID NO: 3; Pv3)
ADDQNPWRAYLDLLFPTDTLLLDLLWDADECG.
```

8. The compound of claim 1, or a pharmaceutically acceptable salt thereof, wherein $R^7$ is a peptide comprising the sequence:

```
                              (SEQ ID NO: 4; Pv4)
Ac-AAEQNPIYWARYADWLFTTPLLLLDLALLVDADEGTKCG.
```

9. The compound of claim 1, or a pharmaceutically acceptable salt thereof, wherein $R^7$ is a peptide comprising the sequence:

```
                             (SEQ ID No. 5; Pv5)
AAEQNPIYWARYADWLFTTPLLLLDLALLVDADEGTC.
```

10. The compound of claim 1, or a pharmaceutically acceptable salt thereof, wherein $R^1$ and $R^2$ are each independently selected from H and methyl, and $R^3$, $R^4$, $R^5$, and $R^6$ are each H.

11. The compound of claim 1, or a pharmaceutically acceptable salt thereof, wherein $R^1$ and $R^2$ are each independently selected from H and methyl.

12. The compound of claim 1, or a pharmaceutically acceptable salt thereof, wherein $R^1$ and $R^2$ are each H.

13. The compound of claim 1, or a pharmaceutically acceptable salt thereof, wherein $R^3$ and $R^4$ are each H.

14. The compound of claim 1, or a pharmaceutically acceptable salt thereof, wherein $R^5$ and $R^6$ are each H.

15. The compound of claim 1, or a pharmaceutically acceptable salt thereof, wherein $R^9$, $R^{10}$, $R^{11}$, and $R^{12}$ are each independently selected from H and methyl.

16. The compound of claim 1, or a pharmaceutically acceptable salt thereof, wherein the enzyme capable of cleaving $[AA]_X$ is Cathepsin B, MMPXX, DPPIV, glycoprotein, peptidase, or caspase.

17. The compound of claim 1, or a pharmaceutically acceptable salt thereof, wherein $[AA]_X$ is a peptide having two to ten amino acid residues.

18. The compound of claim 1, or a pharmaceutically acceptable salt thereof, wherein S1 is a group having the following structure:

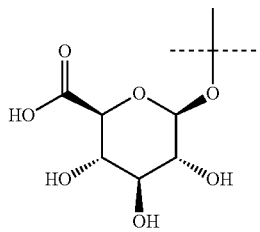

19. A pharmaceutical composition that comprises a compound of claim 1, or a pharmaceutically acceptable salt thereof.

20. The compound of claim 1, or a pharmaceutically acceptable salt thereof, wherein R8 is:

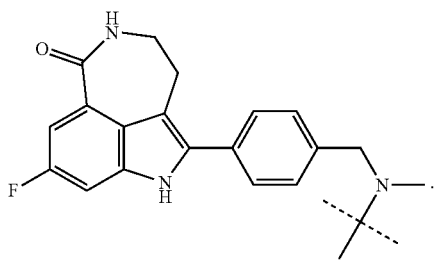

21. The compound of claim 1, or a pharmaceutically acceptable salt thereof, wherein Q is:

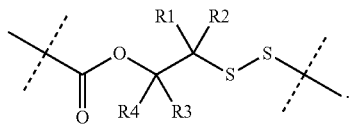

22. The compound of claim 21, or a pharmaceutically acceptable salt thereof, wherein $R^1$ and $R^2$ are each independently selected from H and methyl.

23. The compound of claim 21, or a pharmaceutically acceptable salt thereof, wherein $R^3$ and $R^4$ are each H.

24. A compound, which is:

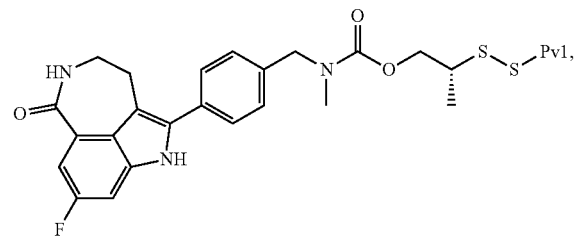

or a pharmaceutically acceptable salt thereof; wherein Pv1 is a peptide comprising the following sequence:

ADDQNPWRAYLDLLFPTDTLLLDLLWCG (SEQ ID NO: 1).

25. A compound, which is:

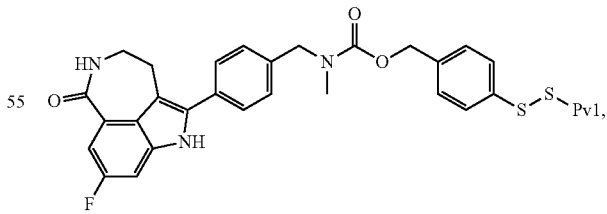

or a pharmaceutically acceptable salt thereof; wherein Pv1 is a peptide comprising the following sequence:

```
                              (SEQ ID NO: 1)
ADDQNPWRAYLDLLFPTDTLLLDLLWCG.
```

26. A compound, which is:

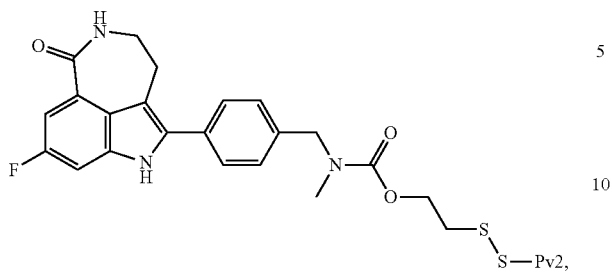

or a pharmaceutically acceptable salt thereof; wherein Pv2 is a peptide comprising the following sequence:

```
                                  (SEQ ID NO: 2)
       AEQNPIYWARYADWLFTTPLLLLDLALLVDADECG.
```

27. A pharmaceutical composition comprising a compound of claim 24, or a pharmaceutically acceptable salt thereof, and at least one pharmaceutically acceptable carrier.

28. A pharmaceutical composition comprising a compound of claim 25, or a pharmaceutically acceptable salt thereof, and at least one pharmaceutically acceptable carrier.

29. A pharmaceutical composition comprising a compound of claim 26, or a pharmaceutically acceptable salt thereof, and at least one pharmaceutically acceptable carrier.

* * * * *